(12) United States Patent
Brittain et al.

(10) Patent No.: US 9,556,133 B2
(45) Date of Patent: Jan. 31, 2017

(54) POLYCYCLIC LPA1 ANTAGONIST AND USES THEREOF

(75) Inventors: Jason Edward Brittain, El Cajon, CA (US); Thomas Jon Seiders, San Diego, CA (US); Christopher David King, Carlsbad, CA (US); Victor W. Rosso, East Windsor, NJ (US)

(73) Assignees: BRISTOL-MYERS SQUIBB COMPANY, Princeton, NJ (US); AMIRA PHARMACEUTICALS, INC., Princeton, NJ (US)

( * ) Notice: Subject to any disclaimer, the term of this patent is extended or adjusted under 35 U.S.C. 154(b) by 386 days.

(21) Appl. No.: 13/992,022

(22) PCT Filed: Dec. 7, 2011

(86) PCT No.: PCT/US2011/063817
§ 371 (c)(1),
(2), (4) Date: Jun. 6, 2013

(87) PCT Pub. No.: WO2012/078805
PCT Pub. Date: Jun. 14, 2012

(65) Prior Publication Data
US 2013/0253023 A1 Sep. 26, 2013

Related U.S. Application Data

(60) Provisional application No. 61/420,599, filed on Dec. 7, 2010.

(51) Int. Cl.
*C07D 261/14* (2006.01)
(52) U.S. Cl.
CPC ................... *C07D 261/14* (2013.01)

(58) Field of Classification Search
None
See application file for complete search history.

(56) References Cited

U.S. PATENT DOCUMENTS

| 8,058,300 B2 | 11/2011 | Hutchinson et al. |
| 8,273,780 B2 | 9/2012 | Hutchinson et al. |
| 2003/0114505 A1 | 6/2003 | Ueno et al. |

FOREIGN PATENT DOCUMENTS

| WO | WO 2010/077883 | 7/2010 |
| WO | WO 2010/141761 | 12/2010 |

OTHER PUBLICATIONS

Berge et al., Journal of Pharmaceutical Sciences, vol. 66, No. 1, Jan. 1977, pp. 1-19.*
Byrn et al.; Pharmaceutical Research; vol. 12, No. 7, pp. 945-954 (1995).

* cited by examiner

*Primary Examiner* — Alicia L Otton
(74) *Attorney, Agent, or Firm* — Hoffmann & Baron, LLP

(57) ABSTRACT

Described herein is the LPA1 antagonist 1-{4'-[3-methyl-4-((R)-1-phenyl-ethoxycarbonylamino)-isoxazol-5-yl]-biphenyl-4-yl}-cyclopropanecarboxylic acid (Compound 1), or pharmaceutically acceptable salts thereof. Also described are methods of preparing the LPA1 antagonist, or pharmaceutically acceptable salts thereof, as well as pharmaceutical compositions suitable for administration to a mammal that include the LPA1 antagonist, or pharmaceutically acceptable salt thereof, and methods of using such pharmaceutical compositions for treating LPA-dependent or LPA-mediated diseases or conditions.

2 Claims, 15 Drawing Sheets

FIG. 1 XRPD of Pattern 1 of Compound 1

FIG. 2 TGA of Pattern 1 of Compound 1

FIG. 3   DSC of Pattern 1 of Compound 1

FIG. 4  XRPD of Pattern 1 of Compound 2

FIG. 5 TGA of Pattern 1 of Compound 2

FIG. 6    DSC of Pattern 1 of Compound 2

FIG. 7    IR of Pattern 1 of Compound 2

FIG. 8    XRPD of Pattern 2 of Compound 2

FIG. 9    XRPD of Pattern 3 of Compound 2

FIG. 10  XRPD of amorphous Compound 2

FIG. 11   DSC of the amorphous Compound 2

FIG. 12    XRPD of Pattern 2 of Compound 1

FIG. 13    XRPD of Pattern 3 of Compound 1

POLYCYCLIC LPA1 ANTAGONIST AND USES THEREOF

RELATED APPLICATIONS

This application claims benefit of U.S. Provisional Application No. 61/420,599, entitled "POLYCYCLIC LPA$_1$ ANTAGONIST AND USES THEREOF" filed on Dec. 7, 2010, which is herein incorporated by reference in its entirety.

FIELD OF THE INVENTION

Described herein is the LPA receptor antagonist 1-{4'-[3-methyl-4-((R)-1-phenyl-ethoxycarbonylamino)-isoxazol-5-yl]-biphenyl-4-yl}-cyclopropanecarboxylic acid (Compound 1), pharmaceutically acceptable salts, polymorphs, amorphous phases, metabolites thereof, as well as pharmaceutical compositions thereof, and methods of use thereof in the treatment or prevention or diagnosis of diseases or conditions associated with the activity of one or more of the lysophosphatidic acid (LPA) receptors.

BACKGROUND OF THE INVENTION

Lysophospholipids are membrane-derived bioactive lipid mediators. Lysophospholipids affect fundamental cellular functions that include proliferation, differentiation, survival, migration, adhesion, invasion, and morphogenesis. These functions influence many biological processes that include, but are not limited to, neurogenesis, angiogenesis, wound healing, fibrosis, immunity, and carcinogenesis.

Lysophosphatidic acid (LPA) is a lysophospholipid that has been shown to act through sets of specific G protein-coupled receptors (GPCRs) in an autocrine and paracrine fashion. LPA binding to its cognate GPCRs (LPA$_1$, LPA$_2$, LPA$_3$, LPA$_4$, LPA$_5$, LPA$_6$) activates intracellular signaling pathways to produce a variety of biological responses. Antagonists of the LPA receptors find use in the treatment of diseases, disorders or conditions in which LPA plays a role.

SUMMARY OF THE INVENTION

Described herein is 1-{4'-[3-methyl-4-((R)-1-phenyl-ethoxycarbonylamino)-isoxazol-5-yl]-biphenyl-4-yl}-cyclopropanecarboxylic acid (Compound 1), including all pharmaceutically acceptable solvates (including hydrates), prodrugs, polymorphs, amorphous phases and metabolites thereof or a pharmaceutically acceptable salt of Compound 1 including (including hydrates), prodrugs, polymorphs, amorphous phases and metabolites thereof, and methods of uses thereof. Compound 1, as well as the pharmaceutically acceptable salts thereof, are used in the manufacture of medicaments for the treatment or prevention of LPA mediated and/or LPA dependent diseases, disorders, or conditions. Compound 1 is a LPA$_1$ antagonist.

Described herein are pharmaceutical compositions comprising Compound 1, or a pharmaceutically acceptable salt thereof (e.g. the sodium salt) as the active ingredient in the pharmaceutical composition. In some embodiments, described herein are pharmaceutical compositions comprising crystalline Compound 1, or solvate thereof. In some embodiments, described herein are pharmaceutical compositions comprising crystalline Compound 2, or solvate thereof. In some embodiments, described herein are pharmaceutical compositions comprising a hydrate of crystalline Compound 2.

In one aspect, described is 1-{4'-[3-methyl-4-((R)-1-phenyl-ethoxycarbonylamino)-isoxazol-5-yl]-biphenyl-4-yl}-cyclopropanecarboxylic acid, 1-{4'-[3-methyl-4-((S)-1-phenyl-ethoxycarbonylamino)-isoxazol-5-yl]-biphenyl-4-yl}-cyclopropanecarboxylic acid, or 1-{4'-[3-methyl-4-(1-phenyl-ethoxycarbonylamino)-isoxazol-5-yl]-biphenyl-4-yl}-cyclopropanecarboxylic acid, or a pharmaceutically acceptable salt, or solvate thereof. In another aspect, described is a pharmaceutically acceptable salt of 1-{4'-[3-methyl-4-((R)-1-phenyl-ethoxycarbonylamino)-isoxazol-5-yl]-biphenyl-4-yl}-cyclopropanecarboxylic acid, 1-{4'-[3-methyl-4-((S)-1-phenyl-ethoxycarbonylamino)-isoxazol-5-yl]-biphenyl-4-yl}-cyclopropanecarboxylic acid, or 1-{4'-[3-methyl-4-(1-phenyl-ethoxycarbonylamino)-isoxazol-5-yl]-biphenyl-4-yl}-cyclopropanecarboxylic acid, or solvate thereof. In some embodiments, the pharmaceutically acceptable salt of Compound 1 is substantially free of the S-isomer. In some embodiments, the pharmaceutically acceptable salt of Compound 1 is crystalline. In some embodiments, the pharmaceutically acceptable salt of Compound 1 is crystalline and is substantially free of the amorphous pharmaceutically acceptable salt.

In one aspect, described is a pharmaceutically acceptable salt of 1-{4'-[3-methyl-4-((R)-1-phenyl-ethoxycarbonylamino)-isoxazol-5-yl]-biphenyl-4-yl}-cyclopropanecarboxylic acid (Compound 1), or solvate thereof. In some embodiments, the pharmaceutically acceptable salt is a sodium salt, calcium salt, potassium salt, ammonium salt, L-arginine salt, L-lysine salt, or N-methyl-D-glucamine salt, or solvate thereof. In some embodiments, the pharmaceutically acceptable salt is a sodium salt, or solvate thereof. In some embodiments, the pharmaceutically acceptable salt is 1-{4'-[3-methyl-4-((R)-1-phenyl-ethoxycarbonylamino)-isoxazol-5-yl]-biphenyl-4-yl}-cyclopropanecarboxylic acid, sodium salt (Compound 2), or solvate thereof. In some embodiments, the pharmaceutically acceptable salt is amorphous. In some embodiments, the pharmaceutically acceptable salt is crystalline. In some embodiments, the pharmaceutically acceptable salt is a crystalline form of Compound 2, or solvate thereof. In some embodiments, the pharmaceutically acceptable salt is a hydrated crystalline form of Compound 2. In some embodiments, the pharmaceutically acceptable salt is an amorphous phase of Compound 2, or solvate thereof.

In one aspect, described is a crystalline form of 1-{4'-[3-methyl-4-((R)-1-phenyl-ethoxycarbonylamino)-isoxazol-5-yl]-biphenyl-4-yl}-cyclopropanecarboxylic acid, 1-{4'-[3-methyl-4-((S)-1-phenyl-ethoxycarbonylamino)-isoxazol-5-yl]-biphenyl-4-yl}-cyclopropanecarboxylic acid, or 1-{4'-[3-methyl-4-(1-phenyl-ethoxycarbonylamino)-isoxazol-5-yl]-biphenyl-4-yl}-cyclopropanecarboxylic acid, or a pharmaceutically acceptable salt, or solvate thereof. In some embodiments, the pharmaceutically acceptable salt is a sodium salt, calcium salt, potassium salt, ammonium salt, L-arginine salt, L-lysine salt, or N-methyl-D-glucamine salt, or solvate thereof. In some embodiments, the pharmaceutically acceptable salt is a sodium salt, or solvate thereof.

In some embodiments, described is a crystalline form of 1-{4'-[3-methyl-4-((R)-1-phenyl-ethoxycarbonylamino)-isoxazol-5-yl]-biphenyl-4-yl}-cyclopropanecarboxylic acid, or a pharmaceutically acceptable salt, or solvate thereof.

In some embodiments, described is a crystalline form of a pharmaceutically acceptable salt of 1-{4'-[3-methyl-4-((R)-1-phenyl-ethoxycarbonylamino)-isoxazol-5-yl]-biphenyl-4-yl}-cyclopropanecarboxylic acid, or solvate thereof.

In any of the embodiments described herein the crystalline form is hydrated. In any of the embodiments described herein the crystalline form is a monohydrate.

In some embodiments, described is a crystalline form of 1-{4'-[3-methyl-4-((R)-1-phenyl-ethoxycarbonylamino)-isoxazol-5-yl]-biphenyl-4-yl}-cyclopropanecarboxylic acid, sodium salt.

In some embodiments, described is a crystalline form of a hydrate of 1-{4'-[3-methyl-4-((R)-1-phenyl-ethoxycarbonylamino)-isoxazol-5-yl]-biphenyl-4-yl}-cyclopropanecarboxylic acid, sodium salt.

In some embodiments, the crystalline form of the hydrate of 1-{4'-[3-methyl-4-((R)-1-phenyl-ethoxycarbonylamino)-isoxazol-5-yl]-biphenyl-4-yl}-cyclopropanecarboxylic acid, sodium salt (Compound 2):

(a) has an X-ray powder diffraction (XRPD) pattern with characteristic peaks at 13.2° 2-Theta, 17.2° 2-Theta, 19.3° 2-Theta, 22.4° 2-Theta, and 25.6° 2-Theta;
(b) has an X-ray powder diffraction (XRPD) pattern substantially the same as shown in FIG. 4;
(c) has a thermo-gravimetric analysis (TGA) or a DSC substantially similar to the ones set forth in FIG. 5 and FIG. 6;
(d) has an infrared spectrum substantially similar to the one set forth in FIG. 7;
(e) was obtained from methyl ethyl ketone, acetonitrile, 1,4-dioxane/tert-butyl methyl ether, methyl ethyl ketone (MEK)/tert-butyl methyl, or ethanol/heptane;
(f) has unit cell parameters substantially equal to the following at 25° C.:

| | |
|---|---|
| a(Å) | 13.8714(2) |
| b(Å) | 7.7379(2) |
| c(Å) | 25.5253(5) |
| α° | 90 |
| β° | 103.863(1) |
| γ° | 90 |
| V(Å3) | 2659.96(9) |
| Z | 4 |
| Calculated Density | 1.305 |
| Crystal System | Monoclinic |
| SG | P2$_1$ |
| R1 | 0.0301 |
| Sol. Sites | 1H$_2$O | or
(g) combinations thereof.

In some embodiments, the hydrated crystalline form of Compound 2 has at least one of the properties selected from (a), (b), (c), (d), (e), and (f). In some embodiments, the hydrated crystalline form of Compound 2 has at least two of the properties selected from (a), (b), (c), (d), (e), and (f). In some embodiments, the hydrated crystalline form of Compound 2 has at least three of the properties selected from (a), (b), (c), (d), (e), and (f). In some embodiments, the hydrated crystalline form of Compound 2 has at least four of the properties selected from (a), (b), (c), (d), (e), and (f). In some embodiments, the hydrated crystalline form of Compound 2 has at least five of the properties selected from (a), (b), (c), (d), (e), and (f). In some embodiments, the hydrated crystalline form of Compound 2 has properties (a), (b), (c), (d), (e), and (f).

In one embodiment, described is a crystalline form of 1-{4'-[3-methyl-4-((R)-1-phenyl-ethoxycarbonylamino)-isoxazol-5-yl]-biphenyl-4-yl}-cyclopropanecarboxylic acid, sodium salt (Compound 2), or a solvate thereof.

In one embodiment, described is a crystalline form of 1-{4'-[3-methyl-4-((R)-1-phenyl-ethoxycarbonylamino)-isoxazol-5-yl]-biphenyl-4-yl}-cyclopropanecarboxylic acid, sodium salt (Compound 2):

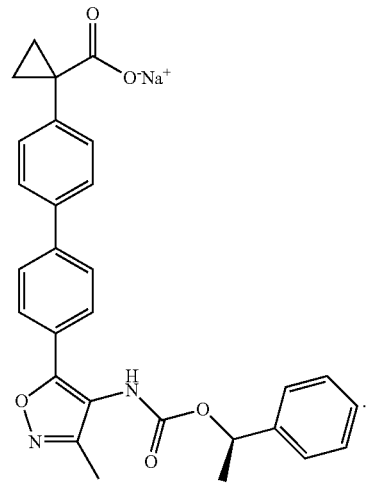

In some embodiments, the crystalline form of Compound 2 is hydrated.

In some embodiments, the crystalline form of Compound 2 has an X-ray powder diffraction (XRPD) pattern with characteristic peaks at 13.2° 2-Theta, 17.2° 2-Theta, 19.3° 2-Theta, 22.4° 2-Theta, and 25.6° 2-Theta.

In some embodiments, the crystalline form of Compound 2 has an X-ray powder diffraction (XRPD) pattern substantially the same as shown in FIG. 4.

In some embodiments, the crystalline form of Compound 2 has a DSC thermogram substantially similar to the one set forth in FIG. 6. In some embodiments, the crystalline form of Compound 2 has a thermo-gravimetric analysis (TGA) substantially similar to the one set forth in FIG. 5.

In some embodiments, the crystalline form of Compound 2 has a thermo-gravimetric analysis (TGA) or a DSC substantially similar to the ones set forth in FIG. 5 and FIG. 6.

In some embodiments, the crystalline form of Compound 2 was obtained from:
(i) methyl ethyl ketone;
(ii) methyl ethyl ketone, methyl tert-butyl ether and water;
(iii) methyl ethyl ketone, and water;
(iv) acetonitrile or acetonitrile and tetrahydrofuran;
(v) 1,4-dioxane and tert-butyl methyl ether;
(vi) methyl ethyl ketone and tert-butyl methyl; or
(vii) ethanol and heptane.

In some embodiments, the crystalline form of Compound 2 is substantially free of the S-isomer.

In some embodiments, the crystalline form of Compound 2 is substantially free of the amorphous phase of Compound 2.

In some embodiments, the crystalline form of Compound 2 has substantially the same X-ray powder diffraction (XRPD) pattern after a week's storage at elevated relative humidity.

In some embodiments, the crystalline form of Compound 2 has substantially the same X-ray powder diffraction (XRPD) pattern after a week's storage at 40° C./75% relative humidity or 25° C./95% relative humidity.

In one aspect, described herein is amorphous 1-{4'-[3-methyl-4-((R)-1-phenyl-ethoxycarbonylamino)-isoxazol-5-yl]-biphenyl-4-yl}-cyclopropanecarboxylic acid, sodium salt (Compound 2). In some embodiments, amorphous Compound 2 is substantially free of the S-isomer.

In some embodiments, the crystalline form of Compound 2 is Pattern 1. In some embodiments, the crystalline form of Compound 2 is Pattern 2. In some embodiments, the crystalline form of Compound 2 is Pattern 3.

In some embodiments, described is a crystalline form of 1-{4'-[3-methyl-4-((R)-1-phenyl-ethoxycarbonylamino)-isoxazol-5-yl]-biphenyl-4-yl}-cyclopropanecarboxylic acid (Compound 1), or solvate thereof.

In some embodiments, described is a crystalline form of a compound with the following structure:

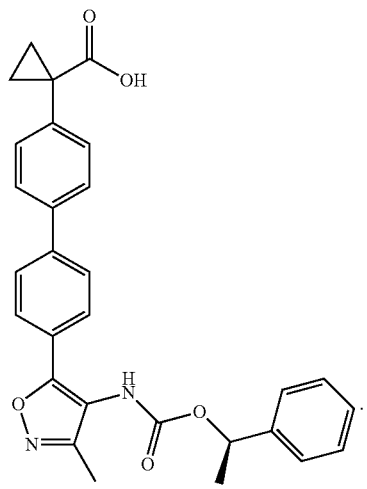 [SMILES: Cc1noc(-c2ccc(-c3ccc(C4(C(=O)O)CC4)cc3)cc2)c1NC(=O)O[C@H](C)c1ccccc1 ; "."]

In some embodiments, the crystalline form of Compound 1 is characterized as having:
(a) an X-ray powder diffraction (XRPD) pattern with characteristic peaks at 4.7° 2-Theta, 9.4° 2-Theta, 14.5° 2-Theta, and 21.0° 2-Theta;
(b) an X-ray powder diffraction (XRPD) pattern substantially the same as the XRPD shown in FIG. 1;
(c) a DSC thermogram with an endotherm at about 172° C.-176° C.;
(d) a DSC or a thermo-gravimetric analysis (TGA) substantially similar to the ones set forth in FIG. 2 and FIG. 3;
(e) substantially the same X-ray powder diffraction (XRPD) pattern post storage at 40 C/75% relative humidity for one week;
(f) unit cell parameters substantially equal to the following at 25° C.:

| | |
|---|---|
| a(Å) | 26.2070(8) |
| b(Å) | 37.700(1) |
| c(Å) | 5.0051(2) |
| α° | 90 |
| β° | 90 |
| γ° | 90 |
| V(Å3) | 4945.1(3) |
| Z | 8 |
| Calculated Density | 1.296 |
| Crystal System | Orthorhombic |
| SG | P2$_1$2$_1$2 |
| R1 | 0.0418 |
| Sol. Sites | — | or
(g) combinations thereof.

In some embodiments, the crystalline form of Compound 1 has an X-ray powder diffraction (XRPD) pattern with characteristic peaks at 4.7° 2-Theta, 9.4° 2-Theta, 14.5° 2-Theta, and 21.0° 2-Theta.

In some embodiments, the crystalline form of Compound 1 has an X-ray powder diffraction (XRPD) pattern substantially the same as the XRPD shown in FIG. 1.

In some embodiments, the crystalline form of Compound 1 has a DSC thermogram with an endotherm at about 176° C.

In some embodiments, the crystalline form of Compound 1 has a DSC or a thermo-gravimetric analysis (TGA) substantially similar to the ones set forth in FIG. 2 and FIG. 3.

In some embodiments, the crystalline form of Compound 1 has substantially the same X-ray powder diffraction (XRPD) pattern post storage at 40 C/75% relative humidity for one week.

In some embodiments, the crystalline form of Compound 1 is characterized as having:
(a) an X-ray powder diffraction (XRPD) pattern substantially the same as the XRPD shown in FIG. 12;
(b) an X-ray powder diffraction (XRPD) pattern with characteristic peaks at 6.3° 2-Theta, 12.8° 2-Theta, 16.4° 2-Theta, 17.0° 2-Theta, and 19.7° 2-Theta;
(c) unit cell parameters approximately equal to the following at a temperature of 25° C.:

| | |
|---|---|
| a(Å) | 30.3522(9) |
| b(Å) | 7.8514(3) |
| c(Å) | 22.4570(7) |
| α° | 90 |
| β° | 111.665(2) |
| γ° | 90 |
| V(Å3) | 4973.6(3) |
| Z | 8 |
| Calculated Density | 1.289 |
| Crystal System | Monoclinic |
| SG | C2 |
| R1 | 0.0298 |
| Sol. Sites | — | or
(d) combinations thereof.

In some embodiments, the crystalline form of Compound 1 is characterized as having:
(a) an X-ray powder diffraction (XRPD) pattern substantially the same as the XRPD shown in FIG. 13;
(b) an X-ray powder diffraction (XRPD) pattern with characteristic peaks at 5.5° 2-Theta, 5.9° 2-Theta, 12.6° 2-Theta, and 16.7° 2-Theta;
(c) unit cell parameters approximately equal to the following at a temperature of 25° C.:

| | |
|---|---|
| a(Å) | 32.3574(9) |
| b(Å) | 5.1057(2) |
| c(Å) | 33.148(1) |
| α° | 90 |
| β° | 114.846(2) |
| γ° | 90 |
| V(Å3) | 4969.4(3) |
| Z | 8 |

-continued

| | |
|---|---|
| Calculated Density | 1.290 |
| Crystal System | Monoclinic |
| SG | C2 |
| R1 | 0.0553 |
| Sol. Sites | — | or
(d) combinations thereof.

In some embodiments, the crystalline form of Compound 1 is substantially free of the S-isomer.

In some embodiments, the crystalline form of Compound 1 is substantially free of amorphous Compound 1.

In some embodiments, the crystalline form of Compound 1 is crystallized from ethanol, methanol, 2-methoxyethanol, ethanol, 1-propanol, 2-propanol, 1-butanol, butyl acetate, acetone, methylethyl ketone, anisole, toluene, nitromethane, acetonitrile, ethyl acetate, cumene, 1-4-dioxane, tetrahydrofuran, dichloromethane, heptane, or combinations thereof.

In some embodiments, the crystalline form of Compound 1 is Pattern 1. In some embodiments, the crystalline form of Compound 1 is Pattern 2. In some embodiments, the crystalline form of Compound 1 is Pattern 3.

In some embodiments, the pharmaceutically acceptable salt of Compound 1 includes a detectable amount of palladium that is less than 20 ppm. In some embodiments, the pharmaceutically acceptable salt of Compound 1 includes a detectable amount of palladium that is less than 15 ppm. In some embodiments, the pharmaceutically acceptable salt of Compound 1 does not include a detectable amount of palladium.

In one aspect, provided is a compound which has the following structure:

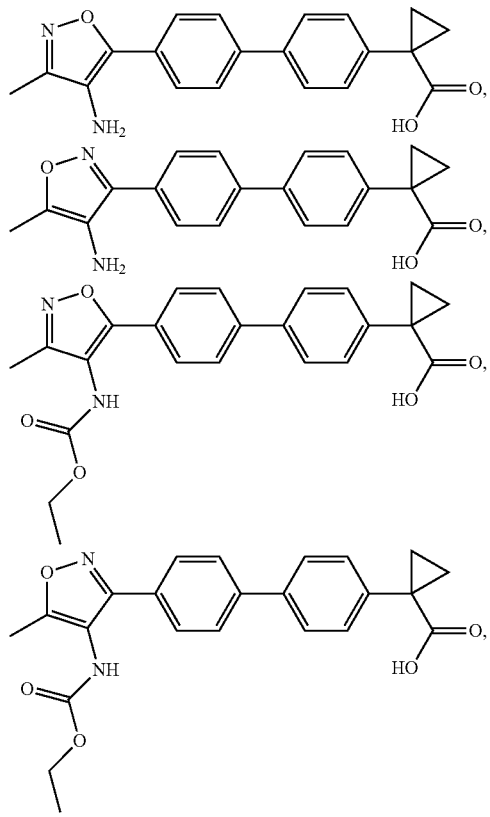

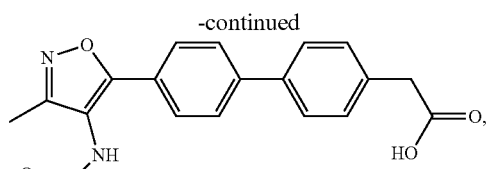

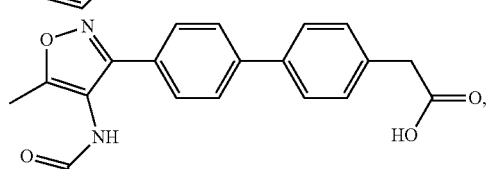

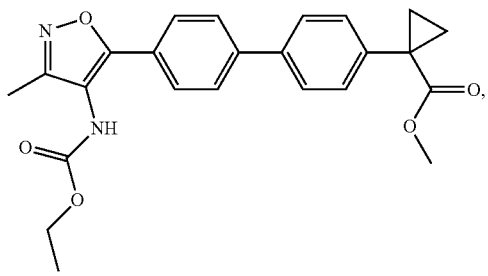

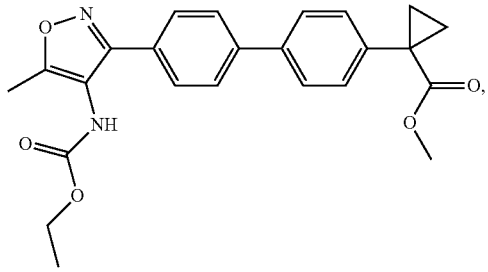

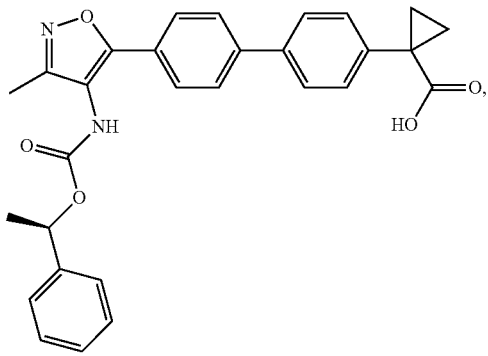

9
-continued
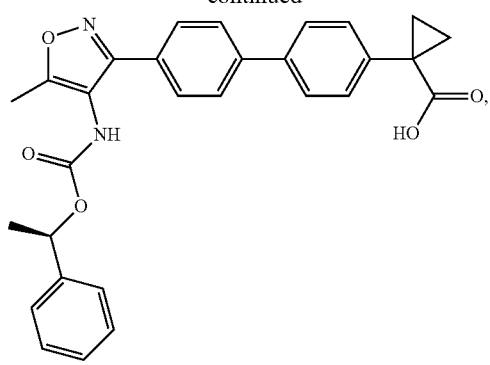
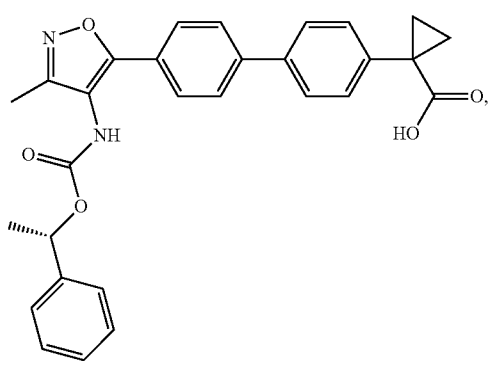
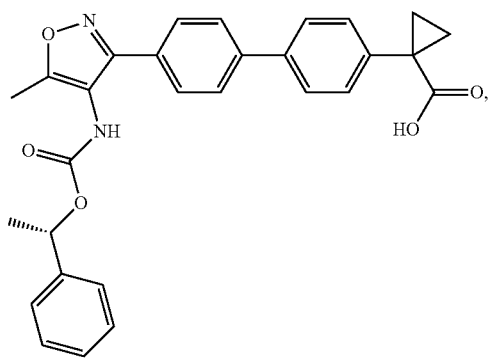
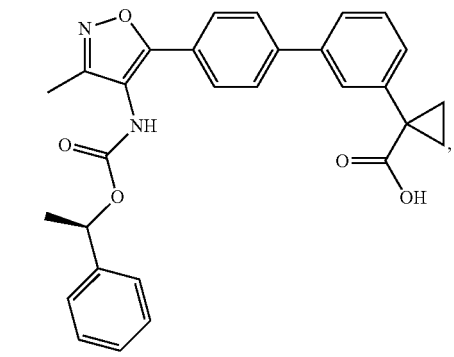
10
-continued
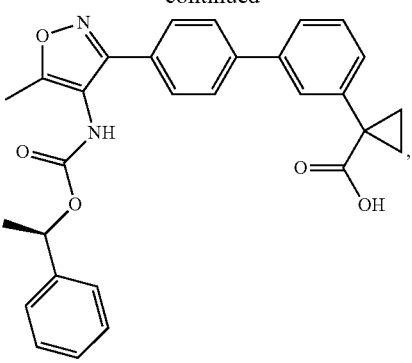
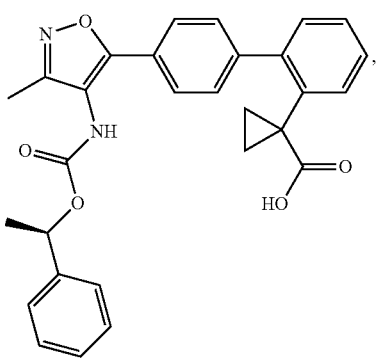
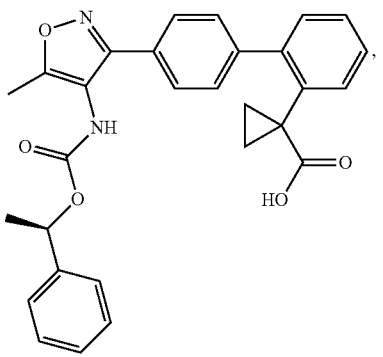
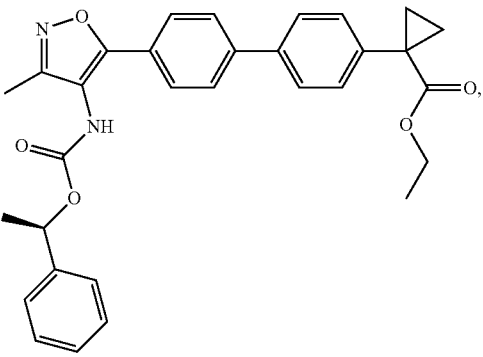

-continued

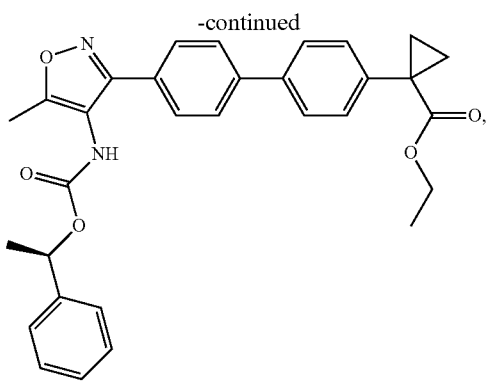

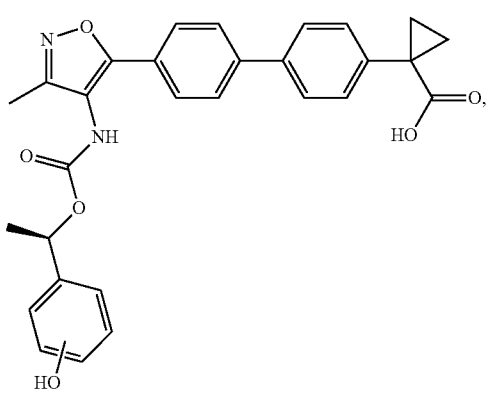

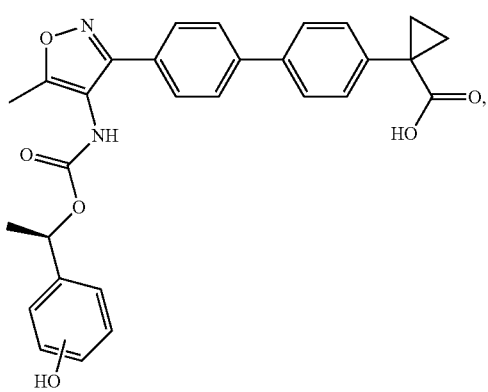

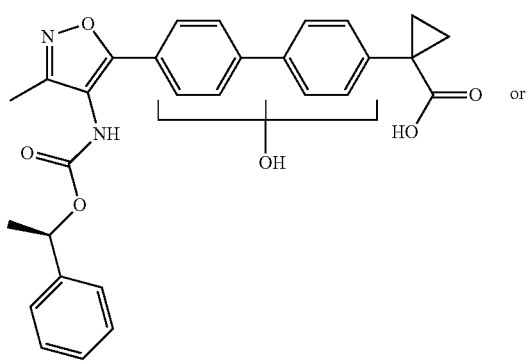

-continued

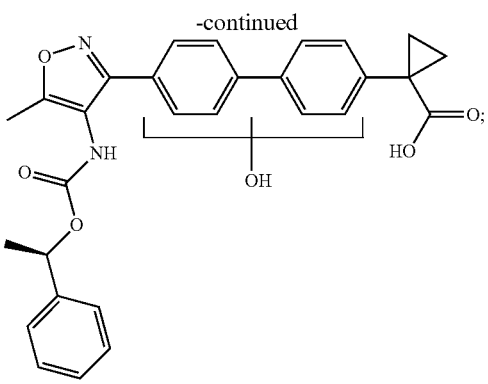

or a pharmaceutically acceptable salt thereof.

In some embodiments, described herein is a pharmaceutical composition comprising Compound 1, or a pharmaceutically acceptable salt or solvate thereof. In some embodiments, Compound 1, or the pharmaceutically acceptable salt or solvate thereof is amorphous. In some embodiments, Compound 1, or the pharmaceutically acceptable salt or solvate thereof is crystalline.

In some embodiments, described herein are pharmaceutical compositions comprising a crystalline form of Compound 1 or a pharmaceutically acceptable salt or solvate thereof. In some embodiments, described herein are pharmaceutical compositions comprising a crystalline form of Compound 2, or solvate thereof. In some embodiments, described herein are pharmaceutical compositions comprising a hydrated crystalline form of Compound 2. In some embodiments, described herein are pharmaceutical compositions comprising Compound 2 (Pattern 1).

In some embodiments, the pharmaceutical composition comprises at least inactive ingredient selected from pharmaceutically acceptable carriers, diluents and excipients.

In some embodiments, the pharmaceutical composition comprises Compound 2, or a solvate thereof.

In some embodiments, the pharmaceutical composition comprises crystalline Compound 2, or solvate thereof.

In some embodiments, Compound 2, or solvate thereof is greater than 96% pure. In some embodiments, Compound 2, or solvate thereof is greater than 97% pure. In some embodiments, Compound 2, or solvate thereof is greater than 98% pure.

In some embodiments, the pharmaceutical composition is formulated for intravenous injection, subcutaneous injection, oral administration, inhalation, nasal administration, topical administration, ophthalmic administration or otic administration.

In some embodiments, the pharmaceutical composition is a tablet, a pill, a capsule, a liquid, an inhalant, a nasal spray solution, a suppository, a suspension, a gel, a colloid, a dispersion, a suspension, a solution, an emulsion, an ointment, a lotion, an eye drop or an ear drop.

In some embodiments, the pharmaceutical composition is in a form suitable for oral administration to a mammal.

In some embodiments, the pharmaceutical composition is in the form of a pill, capsule, tablet, aqueous solution, aqueous suspension, non-aqueous solution, or non-aqueous suspension.

In some embodiments, the pharmaceutical composition is in the form of a capsule. In some embodiments, the pharmaceutical composition is in the form of an immediate release capsule or an enteric coated capsule. In some embodiments, the capsule is a hard gelatine capsule or hypromellose (HPMC) capsule. In some embodiments, the capsule comprises at least one excipient in addition to the hard gelatine capsule or hypromellose (HPMC) capsule.

In some embodiments, the pharmaceutical composition is in the form of a tablet. In some embodiments, the pharmaceutical composition is in the form of an immediate release tablet, an enteric coated tablet, or a sustained release tablet. In some embodiments, the pharmaceutical composition is in the form of a moisture barrier coated tablet.

In some embodiments, the pharmaceutical composition is in the form of an aqueous solution or aqueous suspension.

In some embodiments, a single dose of the pharmaceutical composition comprises about 10 mg to about 1500 mg of Compound 1, or a pharmaceutically acceptable salt or solvate thereof.

In some embodiments, a single dose of the pharmaceutical composition comprises about 10 mg, 15 mg, 20 mg, 25 mg, 50 mg, about 100 mg, about 150 mg, about 200 mg, about 250 mg, about 300 mg, about 350 mg, about 400 mg, about 450 mg, about 500 mg, about 600 mg, about 700 mg, about 800 mg, about 900 mg or about 1000 mg of Compound 1, or a pharmaceutically acceptable salt or solvate thereof (e.g. Compound 2).

In some embodiments, a single dose of the pharmaceutical composition comprises about 10 mg to about 1500 mg of Compound 2, or solvate thereof.

In some embodiments, a single dose of the pharmaceutical composition comprises about 10 mg, 15 mg, 20 mg, 25 mg, 50 mg, about 100 mg, about 150 mg, about 200 mg, about 250 mg, about 300 mg, about 350 mg, about 400 mg, about 450 mg, about 500 mg, about 600 mg, about 700 mg, about 800 mg, about 900 mg or about 1000 mg of Compound 2, or solvate thereof.

In some embodiments, the pharmaceutical compositions described herein comprise a detectable amount of a compound with the structure:

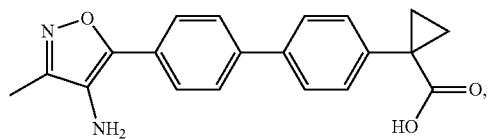

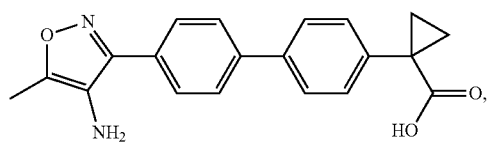

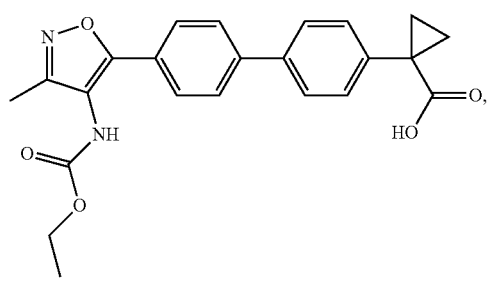

-continued

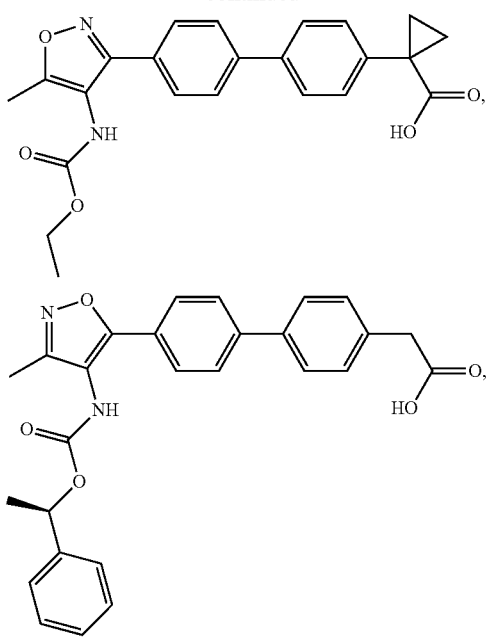

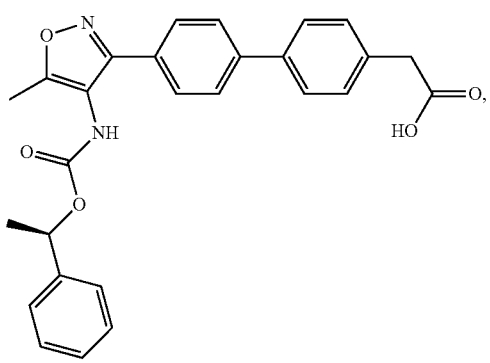

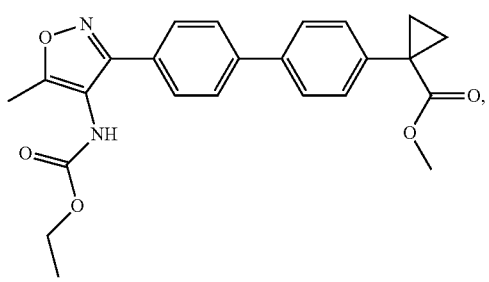

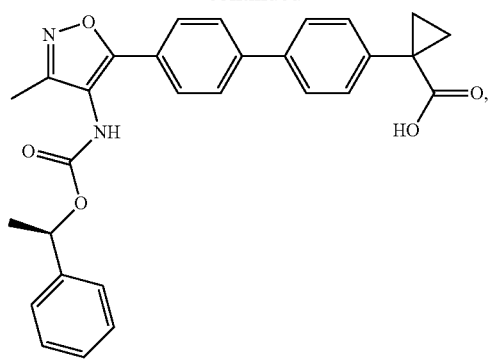
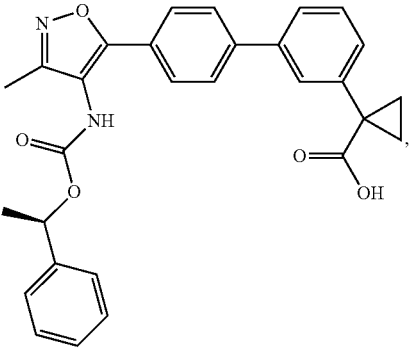
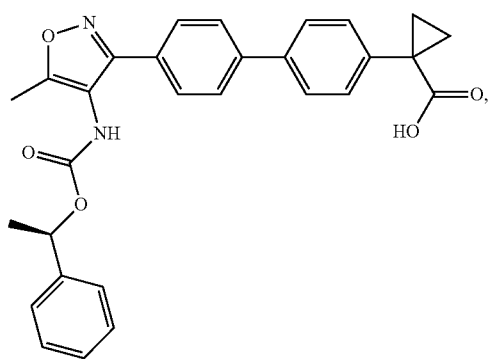
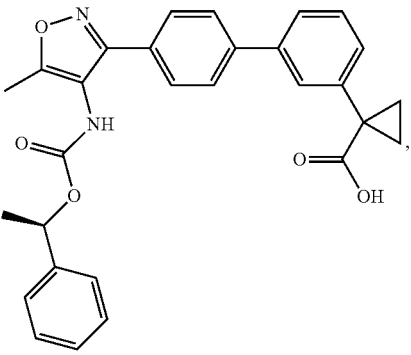
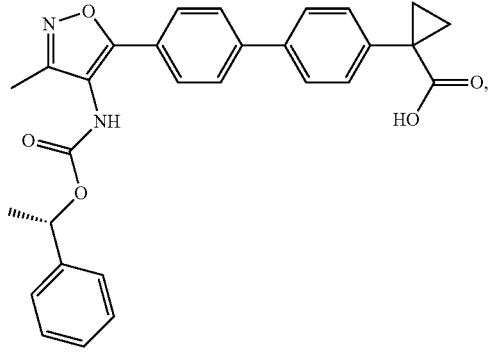
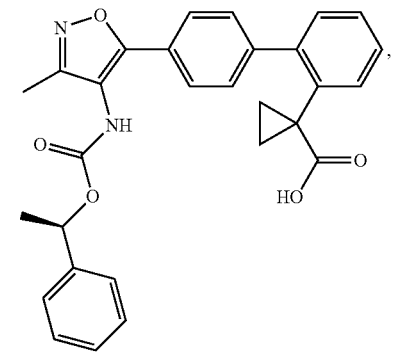
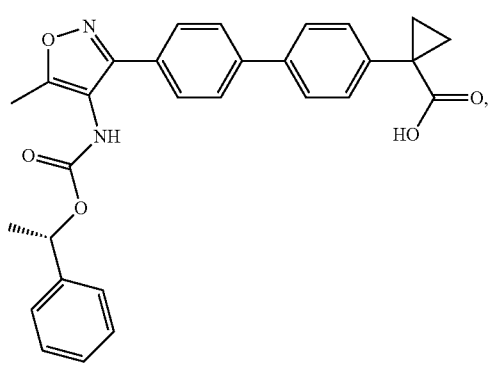
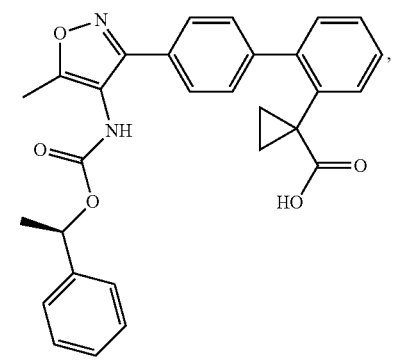

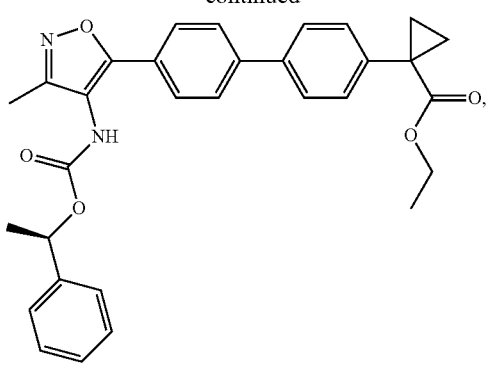
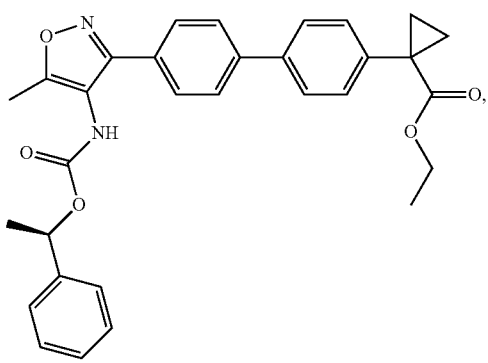
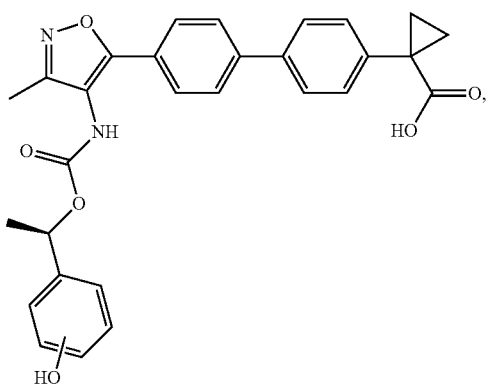
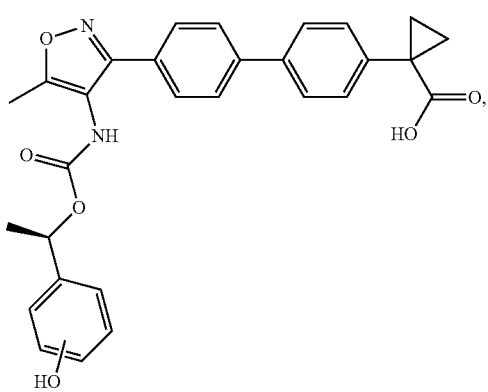
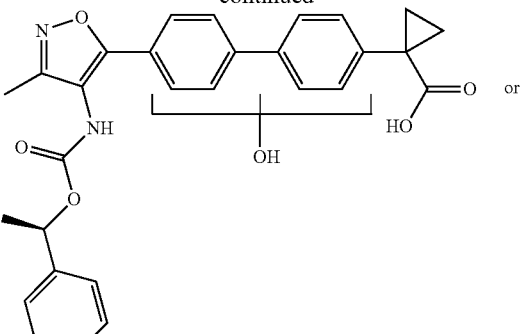
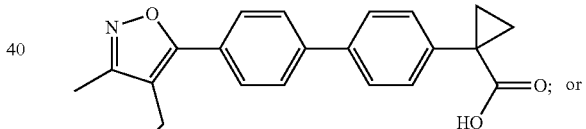
In some embodiments, described herein is a pharmaceutical composition that provides at least one metabolite of Compound 1 after administration to a mammal.
In some embodiments, the at least one metabolite is selected from among:
glucuronidation of Compound 1;
glucuronidation of Compound 1 plus oxidation;
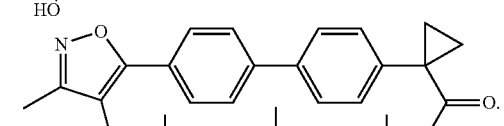
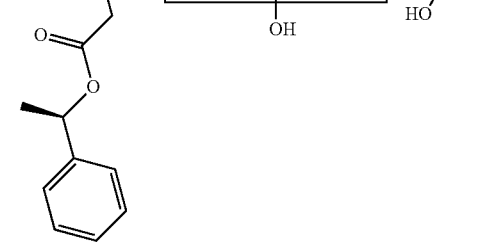

In some embodiments, described herein is a method of inhibiting the physiological activity of LPA in a mammal comprising administering Compound 1, or a pharmaceutically acceptable salt thereof (e.g. Compound 2), or a pharmaceutical composition thereof to the mammal in need thereof.

In some embodiments, described herein is a method for treating or preventing a LPA-dependent or LPA-mediated disease or condition in a mammal comprising administering Compound 1, or a pharmaceutically acceptable salt thereof (e.g. Compound 2), or a pharmaceutical composition thereof to the mammal in need thereof.

In some embodiments, the LPA-dependent or LPA-mediated disease or condition is selected from lung fibrosis, asthma, chronic obstructive pulmonary disease (COPD), renal fibrosis, acute kidney injury, chronic kidney disease, liver fibrosis, skin fibrosis, fibrosis of the gut, breast cancer, pancreatic cancer, ovarian cancer, prostate cancer, glioblastoma, bone cancer, colon cancer, bowel cancer, head and neck cancer, melanoma, multiple myeloma, chronic lymphocytic leukemia, cancer pain, tumor metastasis, transplant organ rejection, scleroderma, ocular fibrosis, age related macular degeneration (AMD), diabetic retinopathy, collagen vascular disease, atherosclerosis, Raynaud's phenomenon, or neuropathic pain.

In some embodiments, Compound 1, or a pharmaceutically acceptable salt thereof (e.g. Compound 2) is used in the treatment or prevention of fibrosis, inflammation or cancer in a mammal.

In some embodiments, described herein is a method of controlling the activation of LPA receptors in a tissue in a mammal comprising administering Compound 1, or a pharmaceutically acceptable salt thereof (e.g. Compound 2), or a pharmaceutical composition thereof to the mammal in need thereof. In some embodiments, the activation of LPA receptors in a tissue in a mammal results in fibrosis.

In some embodiments, described herein is a method for the treatment or prevention of fibrosis in a mammal comprising administering Compound 1, or a pharmaceutically acceptable salt thereof (e.g. Compound 2), or a pharmaceutical composition thereof to the mammal in need thereof. In some embodiments, the fibrosis comprises lung fibrosis, renal fibrosis, hepatic fibrosis or cutaneous fibrosis.

In some embodiments, described herein is a method of improving lung function in a mammal comprising administering Compound 1, or a pharmaceutically acceptable salt thereof (e.g. Compound 2), or a pharmaceutical composition thereof to the mammal in need thereof. In some embodiments, the mammal has been diagnosed as having lung fibrosis.

In some embodiments, described herein is a method of treating idiopathic pulmonary fibrosis in a mammal comprising administering Compound 1, or a pharmaceutically acceptable salt thereof (e.g. Compound 2), or a pharmaceutical composition thereof to the mammal in need thereof.

In some embodiments, described herein is a method of controlling an abnormal accumulation or activation of cells, fibronectin, collagen or increased fibroblast recruitment in a tissue of a mammal comprising administering Compound 1, or a pharmaceutically acceptable salt thereof (e.g. Compound 2), or a pharmaceutical composition thereof to the mammal in need thereof.

In some embodiments, the abnormal accumulation or activation of cells, fibronectin, collagen or increased fibroblast recruitment in the tissue results in fibrosis.

In some embodiments, described herein is a method for the treatment or prevention of scleroderma in a mammal comprising administering Compound 1, or a pharmaceutically acceptable salt thereof (e.g. Compound 2), or a pharmaceutical composition thereof to the mammal in need thereof.

In some embodiments, described herein is a method for reducing undesired or abnormal dermal thickening in a mammal comprising administering to mammal in need thereof. Compound 1, or a pharmaceutically acceptable salt thereof (e.g. Compound 2), or a pharmaceutical composition thereof. In some embodiments, the dermal thickening is associated with scleroderma.

In some embodiments, described herein is a method of controlling an abnormal accumulation or activation of cells, fibronectin, collagen or increased fibroblast recruitment in dermal tissues of a mammal comprising administering to mammal in need thereof. Compound 1, or a pharmaceutically acceptable salt thereof (e.g. Compound 2), or a pharmaceutical composition thereof. In some embodiments, the abnormal accumulation or activation of cells, fibronectin, collagen or increased fibroblast recruitment in the dermal tissues results in dermal fibrosis. In some embodiments, described herein is a method of reducing hydroxyproline content in dermal tissues of a mammal with cutaneous fibrosis comprising administering to mammal in need thereof. Compound 1, or a pharmaceutically acceptable salt thereof (e.g. Compound 2), or a pharmaceutical composition thereof.

In some embodiments, described herein is a method for the treatment or prevention of Raynaud's phenomenon in a mammal comprising administering Compound 1, or a pharmaceutically acceptable salt thereof (e.g. Compound 2), or a pharmaceutical composition thereof to the mammal in need thereof.

In some embodiments, the pharmaceutical composition is administered daily to the mammal. In some embodiments, the pharmaceutical composition is administered once-daily to the mammal. In some embodiments, the pharmaceutical composition is administered twice-daily to the mammal.

In some embodiments, the mammal is a human.

In some embodiments, in any of the method of treatments involving a mammal, the mammal is administered one or more additional therapeutically active agents in addition to Compound 1, or a pharmaceutically acceptable salt thereof.

In some embodiments, in any of the method of treatments involving a mammal, the mammal is administered one or more additional therapeutically active agents selected from: corticosteroids, immunosuppressant, analgesics, anti-cancer agent, anti-inflammatories, chemokine receptor antagonists, bronchodilators, leukotriene receptor antagonists, leukotriene formation inhibitors, monoacylglycerol kinase inhibitors, phospholipase $A_1$ inhibitors, phospholipase $A_2$ inhibitors, and lysophospholipase D (lysoPLD) inhibitors, autotaxin inhibitors, decongestants, antihistamines, mucolytics, anticholinergics, antitussives, expectorants, and β-2 agonists.

In some embodiments, provided is a method comprising administering Compound 1, or a pharmaceutically acceptable salt thereof (e.g. Compound 2), to a human with a LPA-dependent or LPA-mediated disease or condition. In some embodiments, the human is already being administered one or more additional therapeutically active agents other than Compound 1, or a pharmaceutically acceptable salt thereof (e.g. Compound 2). In some embodiments, the method further comprises administering one or more additional therapeutically active agents other than Compound 1, or a pharmaceutically acceptable salt thereof (e.g. Compound 2).

In some embodiments, the one or more additional therapeutically active agents other than Compound 1, or a pharmaceutically acceptable salt thereof (e.g. Compound 2), are selected from: corticosteroids, immunosuppresants, analgesics, anti-cancer agent, anti-inflammatories, chemokine receptor antagonists, bronchodilators, leukotriene receptor antagonists, leukotriene formation inhibitors, monoacylglycerol kinase inhibitors, phospholipase $A_1$ inhibitors, phospholipase $A_2$ inhibitors, and lysophospholipase D (lysoPLD) inhibitors, autotaxin inhibitors, decongestants, antihistamines, mucolytics, anticholinergics, antitussives, expectorants, and β-2 agonists.

In another aspect is the use of Compound 1, or a pharmaceutically acceptable salt thereof (e.g. Compound 2), in the treatment of a disease, disorder or condition in which the activity of at least one LPA receptor contributes to the pathology and/or symptoms of the disease or condition. In one embodiment of this aspect, the LPA receptor is selected from $LPA_1$, $LPA_2$, $LPA_3$, $LPA_4$, $LPA_5$ and $LPA_6$. In some embodiments, the LPA receptor is $LPA_1$ or $LPA_2$ or $LPA_3$. In some embodiments, the disease or condition is any of the diseases or conditions specified herein.

Also provided is a method of inhibiting the physiological activity of LPA in a mammal comprising administering a therapeutically effective amount of a compound of Compound 1, or a pharmaceutically acceptable salt thereof (e.g. Compound 2), to the mammal in need thereof.

In one aspect, is a method for treating or preventing a LPA-dependent or LPA-mediated disease or condition in a mammal comprising administering a therapeutically effective amount of Compound 1, or a pharmaceutically acceptable salt thereof (e.g. Compound 2).

In one aspect, LPA-dependent or LPA-mediated diseases or conditions include, but are not limited to, fibrosis of organs or tissues, scarring, liver diseases, dermatological conditions, cancer, cardiovascular disease, respiratory diseases or conditions, inflammatory disease, gastrointestinal tract disease, renal disease, urinary tract-associated disease, inflammatory disease of lower urinary tract, dysuria, frequent urination, pancreas disease, arterial obstruction, cerebral infarction, cerebral hemorrhage, pain, peripheral neuropathy, and fibromyalgia.

In some embodiments, the LPA-dependent or LPA-mediated disease or condition is selected from idiopathic pulmonary fibrosis; other diffuse parenchymal lung diseases of different etiologies including iatrogenic drug-induced fibrosis, occupational and/or environmental induced fibrosis, granulomatous diseases (sarcoidosis, hypersensitivity pneumonia), collagen vascular disease, alveolar proteinosis, langerhans cell granulomatosis, lymphangioleiomyomatosis, inherited diseases (Hermansky-Pudlak Syndrome, tuberous sclerosis, neurofibromatosis, metabolic storage disorders, familial interstitial lung disease); radiation induced fibrosis; chronic obstructive pulmonary disease (COPD); scleroderma; bleomycin induced pulmonary fibrosis; chronic asthma; silicosis; asbestos induced pulmonary fibrosis; acute respiratory distress syndrome (ARDS); kidney fibrosis; tubulointerstitium fibrosis; glomerular nephritis; focal segmental glomerular sclerosis; IgA nephropathy; hypertension; Alport; gut fibrosis; liver fibrosis; cirrhosis; alcohol induced liver fibrosis; toxic/drug induced liver fibrosis; hemochromatosis; nonalcoholic steatohepatitis (NASH); biliary duct injury; primary biliary cirrhosis; infection induced liver fibrosis; viral induced liver fibrosis; and autoimmune hepatitis; corneal scarring; hypertrophic scarring; Duputren disease, keloids, cutaneous fibrosis; cutaneous scleroderma; spinal cord injury/fibrosis; myelofibrosis; vascular restenosis; atherosclerosis; arteriosclerosis; Wegener's granulomatosis; Peyronie's disease, chronic lymphocytic leukemia, tumor metastasis, transplant organ rejection, endometriosis, neonatal respiratory distress syndrome and neuropathic pain.

In one aspect, is a method for treating or preventing cancer in a mammal comprising administering a therapeutically effective amount of Compound 1, or a pharmaceutically acceptable salt thereof (e.g. Compound 2), to the mammal in need thereof.

In one aspect, is a method for treating or preventing fibrosis in a mammal comprising administering a therapeutically effective amount of Compound 1, or a pharmaceutically acceptable salt thereof (e.g. Compound 2), to the mammal in need thereof.

In one aspect, is a method for treating or preventing lung fibrosis, asthma, chronic obstructive pulmonary disease (COPD), renal fibrosis, acute kidney injury, chronic kidney disease, liver fibrosis, skin fibrosis, fibrosis of the gut, breast cancer, pancreatic cancer, ovarian cancer, prostate cancer, glioblastoma, bone cancer, colon cancer, bowel cancer, head and neck cancer, melanoma, multiple myeloma, chronic lymphocytic leukemia, cancer pain, tumor metastasis, transplant organ rejection, scleroderma, ocular fibrosis, age related macular degeneration (AMD), diabetic retinopathy, collagen vascular disease, atherosclerosis, Raynaud's phenomenon, or neuropathic pain in a mammal comprising administering a therapeutically effective amount of Compound 1, or a pharmaceutically acceptable salt thereof (e.g. Compound 2), to the mammal in need thereof.

In one aspect, provided is a method for the treatment or prevention of organ fibrosis in a mammal comprising administering a therapeutically effective amount of Compound 1, or a pharmaceutically acceptable salt thereof (e.g. Compound 2), to a mammal in need thereof. In some embodiments, the organ fibrosis comprises lung fibrosis, renal fibrosis, or hepatic fibrosis.

In one aspect, provided is a method of improving lung function in a mammal comprising administering a therapeutically effective amount of Compound 1, or a pharmaceutically acceptable salt thereof (e.g. Compound 2), to the mammal in need thereof. In one aspect, the mammal has been diagnosed as having lung fibrosis.

In one aspect, Compound 1, or a pharmaceutically acceptable salt thereof (e.g. Compound 2), is used to treat idiopathic pulmonary fibrosis (usual interstitial pneumonia) in a mammal.

In one aspect, Compound 1, or a pharmaceutically acceptable salt thereof (e.g. Compound 2), is used to treat Raynaud's phenomenon. Raynaud's phenomenon comprises both Raynaud's disease (where the phenomenon is idiopathic) and Raynaud's syndrome, where it is caused by some other instigating factor.

In some embodiments, Compound 1, or a pharmaceutically acceptable salt thereof (e.g. Compound 2), is used to treat diffuse parenchymal interstitial lung diseases in mammal: iatrogenic drug induced, occupational/environmental (Farmer lung), granulomatous diseases (sarcoidosis, hypersensitivity pneumonia), collagen vascular disease (scleroderma and others), alveolar proteinosis, langerhans cell granulomatosis, lymphangioleiomyomatosis, Hermansky-Pudlak Syndrome, Tuberous sclerosis, neurofibromatosis, metabolic storage disorders, familial interstitial lung disease.

In some embodiments, Compound 1, or a pharmaceutically acceptable salt thereof (e.g. Compound 2), is used to treat post-transplant fibrosis associated with chronic rejection in a mammal (e.g. Bronchiolitis obliterans for lung transplant).

In some embodiments, Compound 1, or a pharmaceutically acceptable salt thereof (e.g. Compound 2), is used to treat cutaneous fibrosis in a mammal (e.g. cutaneous scleroderma, Dupuytren disease, keloids).

In some embodiments, Compound 1, or a pharmaceutically acceptable salt thereof (e.g. Compound 2), is used to treat hepatic fibrosis with or without cirrhosis in a mammal: toxic/drug induced (hemochromatosis), alcoholic liver disease, viral hepatitis (hepatitis B virus, hepatitis C virus, HCV), nonalcoholic liver disease (NASH), metabolic and auto-immune.

In one aspect, Compound 1, or a pharmaceutically acceptable salt thereof (e.g. Compound 2), is used to treat renal fibrosis in a mammal: tubulointerstitium fibrosis, glomerular sclerosis.

In any of the aforementioned aspects involving the treatment of LPA dependent diseases or conditions are further embodiments comprising administering at least one additional agent in addition to the administration of Compound 1, or a pharmaceutically acceptable salt thereof (e.g. Compound 2). In various embodiments, each agent is administered in any order, including simultaneously.

In any of the embodiments disclosed herein, the mammal is a human.

In some embodiments, compounds provided herein are administered to a human. In some embodiments, compounds provided herein are orally administered to a human.

In some embodiments, Compound 1, or a pharmaceutically acceptable salt thereof (e.g. Compound 2), is used for inhibiting the activity of at least one LPA receptor or for the treatment of a disease or condition that would benefit from inhibition of the activity of at least one LPA receptor. In one aspect, the LPA receptor is $LPA_1$.

In other embodiments, Compound 1, or a pharmaceutically acceptable salt thereof (e.g. Compound 2), is used for the formulation of a medicament for the inhibition of $LPA_1$ activity.

In some embodiments, Compound 1, or a pharmaceutically acceptable salt thereof (e.g. Compound 2), is used in the preparation of a medicament for use in medicine. In some embodiments, Compound 2, is used in the preparation of a medicament for use in medicine. In some embodiments, Compound 2, monohydrate is used in the preparation of a medicament for use in medicine. In some embodiments, Compound 2 (Pattern 1) is used in the preparation of a medicament for use in medicine.

Also provided is an article of manufacture comprising multiple unit doses of an oral solid dosage form pharmaceutical composition described herein in a high-density polyethylene (HDPE) bottle equipped with a high-density polyethylene (HDPE) cap.

In some embodiments, high-density polyethylene (HDPE) bottle further comprises an aluminum foil induction seal and silica gel desiccant.

In any of the aforementioned embodiments are further embodiments comprising single administrations of the effective amount of Compound 1, or a pharmaceutically acceptable salt thereof (e.g. Compound 2), including further embodiments in which Compound 1, or a pharmaceutically acceptable salt thereof (e.g. Compound 2) is (i) administered once-a-day; (ii) is administered twice-a-day; or (iii) is administered multiple times over the span of one day.

In any of the aforementioned embodiments are further embodiments comprising multiple administrations of the effective amount of the compound, including further embodiments in which (i) the compound is administered in a single dose; (ii) the time between multiple administrations is every 6 hours; (iii) the time between multiple administrations is every 8 hours; (iv) the time between multiple administrations is every 12 hours.

In some embodiments, the pharmaceutical composition is administered daily to the mammal.

In some embodiments, the pharmaceutical composition is administered in treatment cycles comprising: (a) a first period during which Compound 2 is administered daily to the mammal; and (b) a second period during which the Compound 1, or a pharmaceutically acceptable salt thereof (e.g. Compound 2) is administered to the mammal in a reduced amount as compared to (a) or not administered.

In some embodiments, the methods of treatment or prevention disclosed herein comprise a drug holiday, wherein the administration of Compound 1, or a pharmaceutically acceptable salt thereof (e.g. Compound 2) is temporarily suspended or the dose being administered is temporarily reduced; at the end of the drug holiday dosing is resumed. In some embodiments, the length of the drug holiday varies from 2 days to 1 year.

Compound 1, or a pharmaceutically acceptable salt thereof (e.g. Compound 2) for treating any of the diseases or conditions disclosed herein. In some embodiments, Compound 1 is crystalline. In some embodiments, Compound 2 is crystalline. In some embodiments, Compound 2 is amorphous.

A pharmaceutical composition comprising Compound 1, or a pharmaceutically acceptable salt thereof (e.g. Compound 2) for use in any of the uses and methods disclosed herein.

Also described herein are process for the preparation of Compound 1 and pharmaceutically acceptable salts thereof. In one aspect, the pharmaceutically acceptable salt of Compound 1 is the sodium salt (Compound 2).

In one embodiment provided is a process for preparing crystalline 1-{4'-[3-methyl-4-((R)-1-phenyl-ethoxycarbonylamino)-isoxazol-5-yl]-biphenyl-4-yl}-cyclopropanecarboxylic acid (Compound 1) comprising isolating Compound 1 from: ethanol, methanol, 2-methoxyethanol, ethanol, 1-propanol, 2-propanol, 1-butanol, butyl acetate, acetone, methylethyl ketone, anisole, toluene, nitromethane, acetonitrile, ethyl acetate, cumene, 1-4-dioxane, or tetrahydrofuran.

In one embodiment provided is a process for preparing crystalline 1-{4'-[3-methyl-4-((R)-1-phenyl-ethoxycarbonylamino)-isoxazol-5-yl]-biphenyl-4-yl}-cyclopropanecarboxylic acid, sodium salt (Compound 2) comprising isolating Compound 2 from:
 (i) methyl ethyl ketone;
 (ii) methyl ethyl ketone, methyl tert-butyl ether and water;
 (iii) methyl ethyl ketone, and water;
 (iv) acetonitrile;
 (v) 1,4-dioxane and tert-butyl methyl ether;
 (vi) methyl ethyl ketone and tert-butyl methyl; or
 (vii) ethanol and heptane.

In one embodiment provided is a process for the preparation of 1-{4'-[3-methyl-4-((R)-1-phenyl-ethoxycarbonylamino)-isoxazol-5-yl]-biphenyl-4-yl}-cyclopropanecarboxylic acid (Compound 1) comprising the steps of:
 (1) treatment of a compound of Formula XVIII with diphenylphosphoryl azide in the presence of (R)-(+)-1-phenylethanol:

XVIII

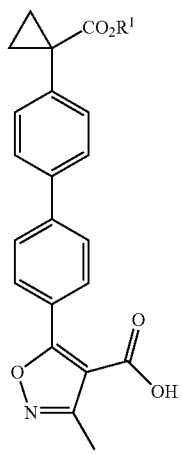

wherein,
R$^1$ is C$_1$-C$_6$alkyl;
to provide a compound of Formula X:

X

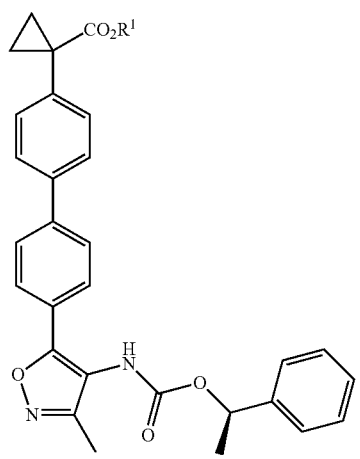

(2) hydrolysis of the ester moiety of the compound of Formula X to provide Compound 1.

In some embodiments, step (2) comprises treatment of the compound of Formula X with sodium hydroxide in a suitable solvent followed by a pH adjustment.

In one embodiment provided is a process for the preparation of 1-{4'-[3-methyl-4-((R)-1-phenyl-ethoxycarbonylamino)-isoxazol-5-yl]-biphenyl-4-yl}-cyclopropanecarboxylic acid (Compound 1) comprising the steps of:
(1) reacting a compound of Formula VII:

VII

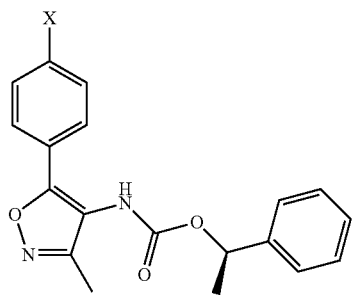

wherein,
X is a leaving group;
with a compound of Formula VIII:

VIII

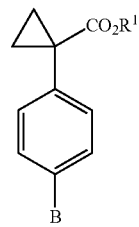

wherein,
R$^1$ is C$_1$-C$_6$ alkyl; and B is a boronic acid or boronate ester;
in the presence of a coupling catalyst, a suitable base, and in a suitable solvent, to provide a compound of Formula X:

X

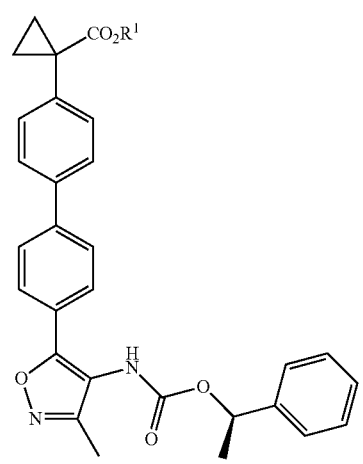

(2) hydrolysis of the ester moiety of the compound of Formula X to provide Compound 1.

In another embodiment provided is a process for the preparation of 1-{4'-[3-methyl-4-((R)-1-phenyl-ethoxycarbonylamino)-isoxazol-5-yl]-biphenyl-4-yl}-cyclopropanecarboxylic acid (Compound 1) comprising the steps of:
(1) reacting a compound of Formula IX:

IX

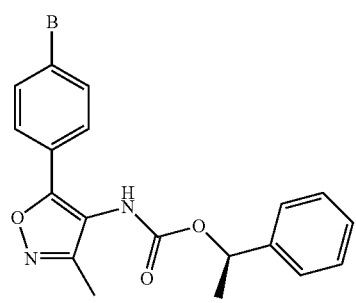

wherein,
B is a boronic acid or boronate ester;

with a compound of Formula XII:

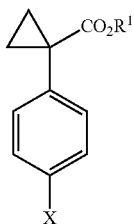

wherein,
$R^1$ is $C_1$-$C_6$ alkyl; and X is a leaving group;
in the presence of a coupling catalyst, a suitable base, and in a suitable solvent, to provide a compound of Formula X:

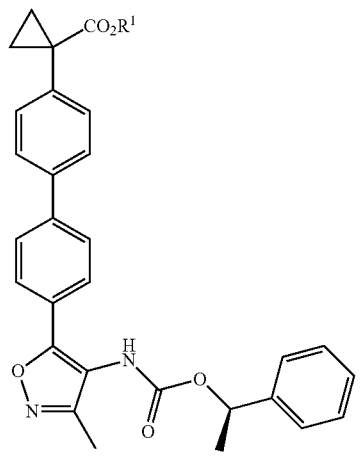

(2) hydrolysis of the ester moiety of the compound of Formula X to provide Compound 1.

In some embodiments, the coupling catalyst is a palladium catalyst. In some embodiments, the palladium catalyst is tetrakis(triphenylphosphine)palladium or (1,1'-bis(diphenylphosphino)ferrocene)-dichloropalladium(II).

In some embodiments, $R^1$ is —$CH_3$ or —$CH_2CH_3$.

In some embodiments, the suitable base is triethylamine, diisopropylethylamine, 1,2,2,6,6-pentamethylpiperidine, tributylamine, sodium bicarbonate, potassium bicarbonate, sodium carbonate, potassium carbonate, cesium carbonate, sodium acetate, potassium acetate, sodium phosphate or potassium phosphate.

In some embodiments, the suitable solvent is tetrahydrofuran, dioxane, water, or combinations thereof.

In some embodiments, X is selected from Cl, Br, I, —$OSO_2CF_3$, —$OSO_2$(4-methylphenyl), —$OSO_2$(phenyl) and —$OSO_2CH_3$. In some embodiments, X is Br.

In some embodiments, B is

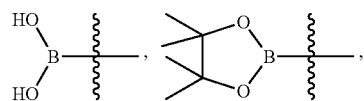

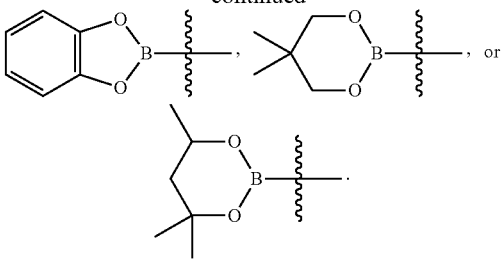

In some embodiments, B is

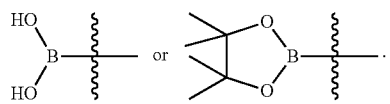

In some embodiments, B is

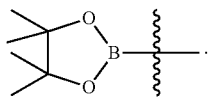

In some embodiments, step (1) further comprises isolating the compound of Formula X prior to step (2).

In some embodiments, step (1) further comprises a purification step for reducing the amount of palladium to less than 20 ppm.

The disclosed processes provide for the synthesis of Compound 1 and pharmaceutically acceptable salts thereof (e.g. Compound 2). The processes disclosed herein are particularly applicable to large scale chemical production of Compound 1 and pharmaceutically acceptable salts thereof.

In some embodiments, in any of the embodiments disclosed herein (including methods, uses, formulations, combination therapy, etc.), Compound 1, or a pharmaceutically acceptable salt or solvate thereof, is replaced with: a) Compound 1, or a pharmaceutically acceptable salt or solvate thereof, of lower chiral purity; b) 1-{4'-[3-methyl-4-((S)-1-phenyl-ethoxycarbonylamino)-isoxazol-5-yl]-biphenyl-4-yl}-cyclopropanecarboxylic acid, or a pharmaceutically acceptable salt or solvate thereof of any optical purity; or c) racemic 1-{4'-[3-methyl-4-(1-phenyl-ethoxycarbonylamino)-isoxazol-5-yl]-biphenyl-4-yl}-cyclopropanecarboxylic acid, or a pharmaceutically acceptable salt or solvate thereof.

In any of the embodiments disclosed herein (including methods, uses, formulations, combination therapy, etc.), amorphous Compound 1 is used. In any of the embodiments disclosed herein (including methods, uses, formulations, combination therapy, etc.), crystalline Compound 1 is used. In any of the embodiments disclosed herein (including methods, uses, formulations, combination therapy, etc.), crystalline Compound 1 (Pattern 1) is used. In any of the embodiments disclosed herein (including methods, uses, formulations, combination therapy, etc.), crystalline Compound 1 (Pattern 2) is used. In any of the embodiments disclosed herein (including methods, uses, formulations, combination therapy, etc.), crystalline Compound 1 (Pattern 3) is used.

In any of the embodiments disclosed herein (including methods, uses, formulations, combination therapy, etc.), amorphous Compound 2 is used. In any of the embodiments disclosed herein (including methods, uses, formulations, combination therapy, etc.), crystalline Compound 2 is used. In any of the embodiments disclosed herein (including methods, uses, formulations, combination therapy, etc.), partially crystalline Compound 2 is used. In any of the embodiments disclosed herein (including methods, uses, formulations, combination therapy, etc.), crystalline Compound 2 (Pattern 1) is used. In any of the embodiments disclosed herein (including methods, uses, formulations, combination therapy, etc.), crystalline Compound 2 (Pattern 2) is used. In any of the embodiments disclosed herein (including methods, uses, formulations, combination therapy, etc.), crystalline Compound 2 (Pattern 3) is used.

In some embodiments, in any of the embodiments disclosed herein (including methods, uses, formulations, combination therapy, etc.), Compound 1, or a pharmaceutically acceptable salt thereof, is replaced with an active metabolite of Compound 1. In some embodiments, the active metabolite is in a crystalline form. In some embodiments, the active metabolite is in an amorphous phase. In some embodiments, in any of the embodiments disclosed herein (including methods, uses, formulations, combination therapy, etc.), Compound 1, or a pharmaceutically acceptable salt thereof, is replaced with a prodrug of Compound 1, or a deuterated analog of Compound 1, or a pharmaceutically acceptable salt thereof.

Other objects, features and advantages of the methods and compositions described herein will become apparent from the following detailed description. It should be understood, however, that the detailed description and the specific examples, while indicating specific embodiments, are given by way of illustration only, since various changes and modifications within the spirit and scope of the invention will become apparent to those skilled in the art from this detailed description.

DETAILED DESCRIPTION OF THE INVENTION

Figure 1:
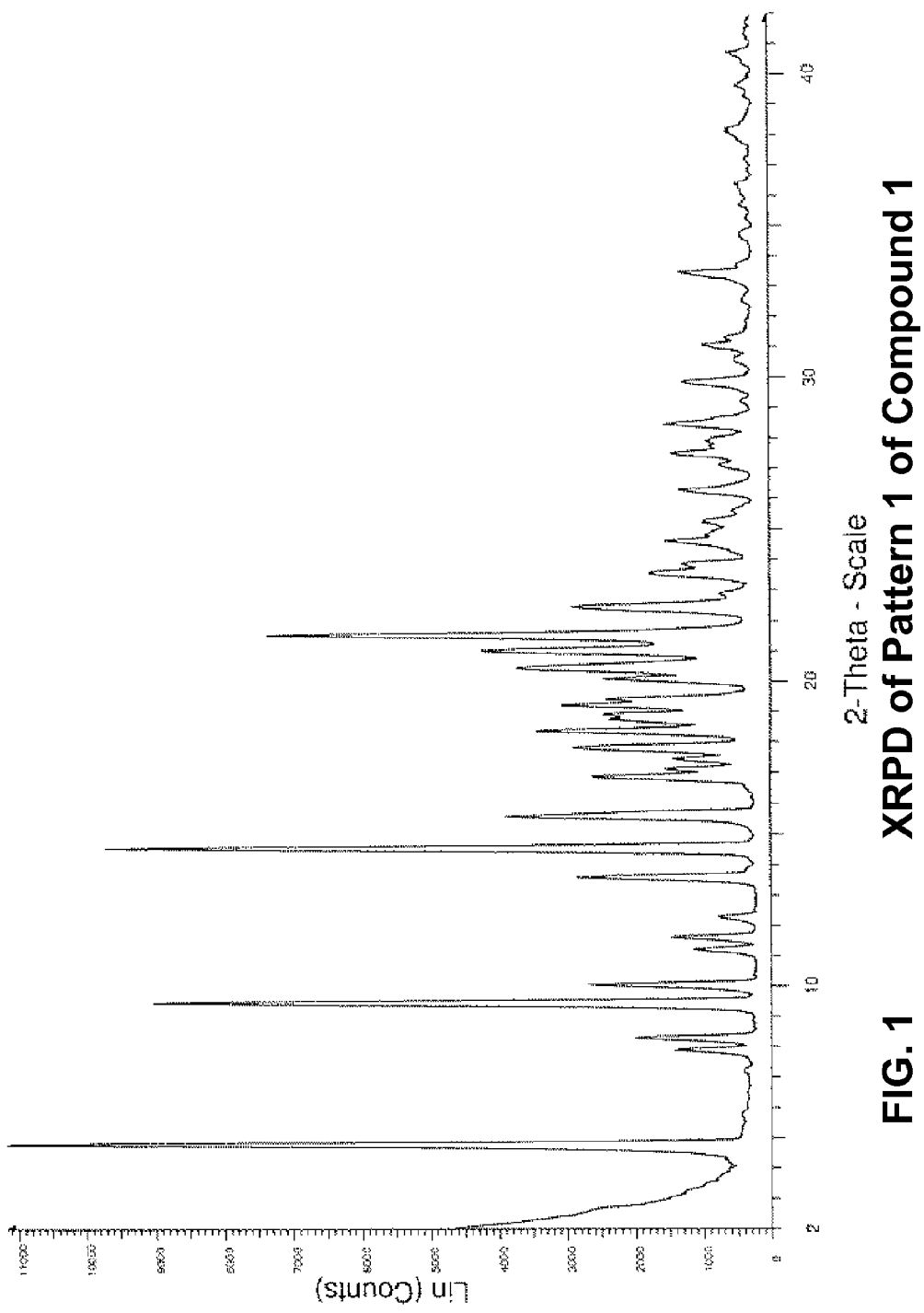
FIG. 1 illustrates the XRPD of Pattern 1 of Crystalline Compound 1.

Lysophospholipids (such as lysophosphatidic acid (LPA)) affect fundamental cellular functions that include cellular proliferation, differentiation, survival, migration, adhesion, invasion, and morphogenesis. These functions influence many biological processes that include neurogenesis, angiogenesis, wound healing, immunity, and carcinogenesis.

LPA acts through sets of specific G protein-coupled receptors (GPCRs) in an autocrine and paracrine fashion. LPA binding to its cognate GPCRs ($LPA_1$, $LPA_2$, $LPA_3$, $LPA_4$, $LPA_5$, $LPA_6$) activates intracellular signaling pathways to produce a variety of biological responses.

LPA has a role as a biological effector molecule, and has a diverse range of physiological actions such as, but not limited to, effects on blood pressure, platelet activation, and smooth muscle contraction, and a variety of cellular effects, which include cell growth, cell rounding, neurite retraction, and actin stress fiber formation and cell migration. The effects of LPA are predominantly receptor mediated.

Activation of the LPA receptors with LPA mediates a range of downstream signaling cascades. The actual pathway and realized end point are dependent on a range of variables that include receptor usage, cell type, expression level of a receptor or signaling protein, and LPA concentration. Nearly all mammalian cells, tissues and organs co-express several LPA-receptor subtypes, which indicates that LPA receptors signal in a cooperative manner $LPA_1$, $LPA_2$, and $LPA_3$ share high amino acid sequence similarity.

LPA regulates many important functions of fibroblasts in wound healing, including proliferation, migration, differentiation and contraction. Fibroblast proliferation is required in wound healing in order to fill an open wound. In contrast, fibrosis is characterized by intense proliferation and accumulation of myofibroblasts that actively synthesize ECM and proinflammatory cytokines. LPA can either increase or suppress the proliferation of cell types important in wound healing.

Tissue injury initiates a complex series of host wound-healing responses; if successful, these responses restore normal tissue structure and function. If not, these responses can lead to tissue fibrosis and loss of function.

A number of muscular dystrophies are characterized by a progressive weakness and wasting of musculature, and by extensive fibrosis. It has been shown that LPA treatment of cultured myoblasts induced significant expression of connective tissue growth factor (CTGF). CTGF subsequently induces collagen, fibronectin and integrin expression and induces dedifferentiation of these myoblasts. Treatment of a variety of cell types with LPA induces reproducible and high level induction of CTGF. CTGF is a profibrotic cytokine, signaling down-stream and in parallel with TGFβ.

LPA and $LPA_1$ play key pathogenic roles in pulmonary fibrosis. Fibroblast chemoattractant activity plays an important role in the lungs in patients with pulmonary fibrosis. Profibrotic effects of $LPA_1$-receptor stimulation is explained by $LPA_1$-receptor-mediated vascular leakage and increased fibroblast recruitment, both profibrotic events. The LPA-$LPA_1$ pathway has a role in mediating fibroblast migration and vascular leakage in IPF. The end result is the aberrant healing process that characterises this fibrotic condition.

The LPA-LPA2 pathway contributes to the activation of the TGF-β pathway in pulmonary fibrosis. In some embodiments, compounds that inhibit LPA2 show efficacy in the treatment of lung fibrosis. In some embodiments, compounds that inhibit both LPA1 and LPA2 show improved efficacy in the treatment of lung fibrosis compared to compounds which inhibit only LPA1 or LPA2.

LPA and $LPA_1$ are involved in the etiology of kidney fibrosis. In mice invalidated for the $LPA_1$ receptor ($LPA_1$ (−/−), the development of renal fibrosis was significantly attenuated. Unilateral ureteral obstruction (UUO; animal model of renal fibrosis) mice treated with the LPA receptor antagonist Ki16425 closely resembled the $LPA_1$ (−/−) mice.

LPA is implicated in liver disease and fibrosis. Plasma LPA levels and serum autotoxin are elevated in hepatitis patients and animal models of liver injury in correlation with increased fibrosis. LPA also regulates liver cell function. $LPA_1$ and $LPA_2$ receptors are expressed by mouse hepatic stellate cells and LPA stimulates migration of hepatic myofibroblasts.

LPA is in involved in wound healing in the eye. $LPA_1$ and $LPA_3$ receptors are detectable in the normal rabbit corneal epithelial cells, keratocytes and endothelial cells and $LPA_1$ and $LPA_3$ expression are increased in corneal epithelial cells following injury.

LPA is present in the aqueous humor and the lacrimal gland fluid of the rabbit eye and these levels are increased in a rabbit corneal injury model.

LPA induces actin stress fiber formation in rabbit corneal endothelial and epithelial cells and promotes contraction corneal fibroblasts. LPA also stimulates proliferation of human retinal pigmented epithelial cells.

LPA is implicated in myocardial infarction and cardiac fibrosis. Serum LPA levels are increased in patients following myocardial infarction (MI) and LPA stimulates proliferation and collagen production (fibrosis) by rat cardiac fibroblasts. Both LPA1 and LPA3 receptors are highly expressed in human heart tissue.

In one aspect, Compound 1, or a pharmaceutically acceptable salt thereof (e.g. Compound 2), is used to treat or prevent fibrosis in a mammal. In one aspect, Compound 1, or a pharmaceutically acceptable salt thereof (e.g. Compound 2), is used to treat or prevent fibrosis of an organ or tissue in a mammal.

The terms "fibrosis" or "fibrosing disorder," as used herein, refers to conditions that are associated with the abnormal accumulation of cells and/or fibronectin and/or collagen and/or increased fibroblast recruitment and include but are not limited to fibrosis of individual organs or tissues such as the heart, kidney, liver, joints, lung, pleural tissue, peritoneal tissue, skin, cornea, retina, musculoskeletal and digestive tract.

Exemplary diseases, disorders, or conditions that involve fibrosis include, but are not limited to: lung diseases associated with fibrosis, e.g., idiopathic pulmonary fibrosis, pulmonary fibrosis secondary to systemic inflammatory disease such as rheumatoid arthritis, scleroderma, lupus, cryptogenic fibrosing alveolitis, radiation induced fibrosis, chronic obstructive pulmonary disease (COPD), chronic asthma, silicosis, asbestos induced pulmonary or pleural fibrosis, acute lung injury and acute respiratory distress (including bacterial pneumonia induced, trauma induced, viral pneumonia induced, ventilator induced, non-pulmonary sepsis induced, and aspiration induced); Chronic nephropathies associated with injury/fibrosis (kidney fibrosis), e.g., glomerulonephritis secondary to systemic inflammatory diseases such as lupus and scleroderma, diabetes, glomerular nephritis, focal segmental glomerular sclerosis, IgA nephropathy, hypertension, allograft and Alport; Gut fibrosis, e.g., scleroderma, and radiation induced gut fibrosis; Liver fibrosis, e.g., cirrhosis, alcohol induced liver fibrosis, nonalcoholic steatohepatitis (NASH), biliary duct injury, primary biliary cirrhosis, infection or viral induced liver fibrosis (e.g., chronic HCV infection), and autoimmune hepatitis; Head and neck fibrosis, e.g., radiation induced; Corneal scarring, e.g., LASIK (laser-assisted in situ keratomileusis), corneal transplant, and trabeculectomy; Hypertrophic scarring and keloids, e.g., burn induced or surgical; and other fibrotic diseases, e.g., sarcoidosis, scleroderma, spinal cord injury/fibrosis, myelofibrosis, vascular restenosis, atherosclerosis, arteriosclerosis, Wegener's granulomatosis, mixed connective tissue disease, and Peyronie's disease.

In one aspect, a mammal suffering from one of the following non-limiting exemplary diseases, disorders, or conditions will benefit from therapy with Compound 1, or a pharmaceutically acceptable salt thereof (e.g. Compound 2): atherosclerosis, thrombosis, heart disease, vasculitis, formation of scar tissue, restenosis, phlobitis, COPD (chronic obstructive pulmonary disease), pulmonary hypertension, pulmonary fibrosis, pulmonary inflammation, bowel adhesions, bladder fibrosis and cystitis, fibrosis of the nasal passages, sinusitis, inflammation mediated by neutrophils, and fibrosis mediated by fibroblasts.

In one aspect, Compound 1, or a pharmaceutically acceptable salt thereof (e.g. Compound 2), is used to treat a dermatological disorders in a mammal Dermatological disorders include, but are not limited to, proliferative or inflammatory disorders of the skin such as, atopic dermatitis, bullous disorders, collagenoses, psoriasis, psoriatic lesions, scleroderma, dermatitis, contact dermatitis, eczema, urticaria, rosacea, scleroderma, wound healing, scarring, hypertrophic scarring, keloids, Kawasaki Disease, rosacea, Sjogren-Larsso Syndrome, urticaria.

LPA is released following tissue injury. $LPA_1$ plays a role in the initiation of neuropathic pain. In one aspect, Compound 1, or a pharmaceutically acceptable salt thereof (e.g. Compound 2), is used in the treatment of pain in a mammal. In one aspect, the pain is acute pain or chronic pain. In another aspect, the pain is neuropathic pain. In another aspect, the pain is cancer pain. In one aspect, Compound 1, or a pharmaceutically acceptable salt thereof (e.g. Compound 2), is used in the treatment of fibromylagia.

Lysophospholipid receptor signaling plays a role in the etiology of cancer. Lysophosphatidic acid (LPA) and its G protein-coupled receptors (GPCRs) $LPA_1$, $LPA_2$, and/or $LPA_3$ play a role in the development of several types of cancers.

LPA contributes to tumorigenesis by increasing motility and invasiveness of cells. LPA has been implicated in the initiation or progression of ovarian cancer. LPA is present at significant concentrations (2-80 µM) in the ascitic fluid of ovarian cancer patients. LPA receptors (LPA2 and LPA3) are also overexpressed in ovarian cancer cells as compared to normal ovarian surface epithelial cells. LPA has also been implicated in the initiation or progression of prostate cancer, breast cancer, melanoma, head and neck cancer, bowel cancer (colorectal cancer), thyroid cancer, glioblastoma, and other cancers.

LPA receptors mediate both migration of and invasion by pancreatic cancer cell lines: Ki16425 and $LPA_1$-specific siRNA effectively blocked in vitro migration in response to LPA and peritoneal fluid (ascites) from pancreatic cancer patients; in addition, Ki16425 blocked the LPA-induced and ascites-induced invasion activity of a highly peritoneal metastatic pancreatic cancer cell line (Yamada et al, *J. Biol. Chem.*, 279, 6595-6605, 2004).

Colorectal carcinoma cell lines show significant expression of $LPA_1$ mRNA and respond to LPA by cell migration and production of angiogenic factors. Overexpression of LPA receptors has a role in the pathogenesis of thyroid cancer. $LPA_3$ was originally cloned from prostate cancer cells, concordant with the ability of LPA to induce autocrine proliferation of prostate cancer cells.

LPA has stimulatory roles in cancer progression in many types of cancer. LPA is produced from and induces proliferation of prostate cancer cell lines. LPA induces human colon carcinoma DLD1 cell proliferation, migration, adhesion, and secretion of angiogenic factors through $LPA_1$ signalling. In other human colon carcinoma cells lines (HT29 and WiDR), LPA enhances cell proliferation and secretion of angiogenic factors. In other colon cancer cell lines, $LPA_2$ and $LPA_3$ receptor activation results in proliferation of the cells. $LPA_1$ is implicated in bone metastasis (Boucharaba et al., *Proc. Natl. Acad. Sci USA*, 103, 9643-9648, 2006).

In one aspect, Compound 1, or a pharmaceutically acceptable salt thereof (e.g. Compound 2), is used in the treatment of cancer. In one aspect, Compound 1, or a pharmaceutically acceptable salt thereof (e.g. Compound 2), is used in the treatment of malignant and benign proliferative disease. In one aspect, Compound 1, or a pharmaceutically acceptable salt thereof (e.g. Compound 2), is used to prevent or reduce proliferation of tumor cells, invasion and metastasis of carcinomas, pleural mesothelioma or peritoneal mesothelioma, cancer pain, bone metastases. In one aspect is a method of treating cancer in a mammal, the method comprising administering to the mammal Compound 1, or a pharmaceutically acceptable salt thereof (e.g. Compound 2), and a second therapeutic agent, wherein the second therapeutic agent is an anti-cancer agent. In some embodiments, radiation therapy is also used.

The types of cancer include, but is not limited to, solid tumors (such as those of the bladder, bowel, brain, breast, endometrium, heart, kidney, lung, lymphatic tissue (lymphoma), ovary, pancreas or other endocrine organ (thyroid), prostate, skin (melanoma or basal cell cancer) or hematological tumors (such as the leukemias) at any stage of the disease with or without metastases.

Additional non-limiting examples of cancers include, acute lymphoblastic leukemia, acute myeloid leukemia, adrenocortical carcinoma, anal cancer, appendix cancer, astrocytomas, basal cell carcinoma, bile duct cancer, bladder cancer, bone cancer (osteosarcoma and malignant fibrous histiocytoma), brain stem glioma, brain tumors, brain and spinal cord tumors, breast cancer, bronchial tumors, Burkitt lymphoma, cervical cancer, chronic lymphocytic leukemia, chronic myelogenous leukemia, colon cancer, colorectal cancer, craniopharyngioma, cutaneous T-Cell lymphoma, embryonal tumors, endometrial cancer, ependymoblastoma, ependymoma, esophageal cancer, ewing sarcoma family of tumors, eye cancer, retinoblastoma, gallbladder cancer, gastric (stomach) cancer, gastrointestinal carcinoid tumor, gastrointestinal stromal tumor (GIST), gastrointestinal stromal cell tumor, germ cell tumor, glioma, hairy cell leukemia, head and neck cancer, hepatocellular (liver) cancer, hodgkin lymphoma, hypopharyngeal cancer, intraocular melanoma, islet cell tumors (endocrine pancreas), Kaposi sarcoma, kidney cancer, Langerhans cell histiocytosis, laryngeal cancer, leukemia, Acute lymphoblastic leukemia, acute myeloid leukemia, chronic lymphocytic leukemia, chronic myelogenous leukemia, hairy cell leukemia, liver cancer, non-small cell lung cancer, small cell lung cancer, Burkitt lymphoma, cutaneous T-cell lymphoma, Hodgkin lymphoma, non-Hodgkin lymphoma, lymphoma, Waldenström macroglobulinemia, medulloblastoma, medulloepithelioma, melanoma, mesothelioma, mouth cancer, chronic myelogenous leukemia, myeloid leukemia, multiple myeloma, nasopharyngeal cancer, neuroblastoma, non-Hodgkin lymphoma, non-small cell lung cancer, oral cancer, oropharyngeal cancer, osteosarcoma, malignant fibrous histiocytoma of bone, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, retinoblastoma, rhabdomyosarcoma, salivary gland cancer, sarcoma, Ewing sarcoma family of tumors, sarcoma, kaposi, Sézary syndrome, skin cancer, small cell Lung cancer, small intestine cancer, soft tissue sarcoma, squamous cell carcinoma, stomach (gastric) cancer, supratentorial primitive neuroectodermal tumors, T-cell lymphoma, testicular cancer, throat cancer, thymoma and thymic carcinoma, thyroid cancer, urethral cancer, uterine cancer, uterine sarcoma, vaginal cancer, vulvar cancer, Waldenström macroglobulinemia, Wilms tumor.

In one aspect, LPA is a contributor to the pathogenesis of respiratory diseases. Proinflammatory effects of LPA include degranulation of mast cells, contraction of smooth-muscle cells and release of cytokines from dendritic cells. LPA induces the secretion of IL-8 from human bronchial epithelial cells. IL-8 is found in increased concentrations in BAL fluids from patients with asthma, chronic obstructive lung disease, pulmonary sarcoidosis and acute respiratory distress syndrome and Il-8 has been shown to exacerbate airway inflammation and airway remodeling of asthmatics. LPA1, LPA2 and LPA3 receptors have all been shown to contribute to the LPA-induced IL-8 production.

Administration of LPA in vivo induces airway hyperresponsiveness, itch-scratch responses, infiltration and activation of eosinophils and neutrophils, vascular remodeling, and nociceptive flexor responses. LPA also induces histamine release from mouse and rat mast cells. In one aspect, the effects of LPA are mediated through $LPA_1$ and/or $LPA_3$. In one aspect, Compound 1, or a pharmaceutically acceptable salt thereof (e.g. Compound 2), is used in the treatment of various allergic disorders in a mammal. In one aspect, Compound 1, or a pharmaceutically acceptable salt thereof (e.g. Compound 2), is used in the treatment of respiratory diseases, disorders or conditions in a mammal. In one aspect, Compound 1, or a pharmaceutically acceptable salt thereof (e.g. Compound 2), is used in the treatment of asthma in a mammal. In one aspect, Compound 1, or a pharmaceutically acceptable salt thereof (e.g. Compound 2), is used in the treatment of chronic asthma in a mammal.

The term "respiratory disease," as used herein, refers to diseases affecting the organs that are involved in breathing, such as the nose, throat, larynx, eustachian tubes, trachea, bronchi, lungs, related muscles (e.g., diaphram and intercostals), and nerves. Respiratory diseases include, but are not limited to, asthma, adult respiratory distress syndrome and allergic (extrinsic) asthma, non-allergic (intrinsic)

asthma, acute severe asthma, chronic asthma, clinical asthma, nocturnal asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, seasonal asthma, seasonal allergic rhinitis, perennial allergic rhinitis, chronic obstructive pulmonary disease, including chronic bronchitis or emphysema, pulmonary hypertension, interstitial lung fibrosis and/or airway inflammation and cystic fibrosis, and hypoxia.

In one aspect, presented herein is the use of Compound 1, or a pharmaceutically acceptable salt thereof (e.g. Compound 2), in the treatment or prevention of chronic obstructive pulmonary disease in a mammal comprising administering to the mammal at least once an effective amount of Compound 1, or a pharmaceutically acceptable salt thereof (e.g. Compound 2). In addition, chronic obstructive pulmonary disease includes, but is not limited to, chronic bronchitis or emphysema, pulmonary hypertension, interstitial lung fibrosis and/or airway inflammation, and cystic fibrosis.

The nervous system is a major locus for $LPA_1$ expression. In one aspect, provided is Compound 1, or a pharmaceutically acceptable salt thereof (e.g. Compound 2), for use in the treatment or prevention of a nervous system disorder in a mammal. The term "nervous system disorder," as used herein includes, but is not limited to, Alzheimer's Disease, cerebral edema, cerebral ischemia, stroke, multiple sclerosis, neuropathies, Parkinson's Disease, multiple sclerosis, retinal ischemia, post-surgical cognitive dysfunction, migraine, peripheral neuropathy/neuropathic pain, spinal cord injury, cerebral edema and head injury.

Angiogenesis, the formation of new capillary networks from pre-existing vasculature, is normally invoked in wound healing, tissue growth and myocardial angiogenesis after ischemic injury. Peptide growth factors and lysophospholipids control coordinated proliferation, migration, adhesion, differentiation and assembly of vascular endothelial cells (VECs) and surrounding vascular smooth-muscle cells (VSMCs). In one aspect, dysregulation of the processes mediating angiogenesis leads to atherosclerosis, hypertension, tumor growth, rheumatoid arthritis and diabetic retinopathy.

In one aspect, Compound 1, or a pharmaceutically acceptable salt thereof (e.g. Compound 2), is used to treat or prevent cardiovascular disease in mammal, including but not limited to: arrhythmia (atrial or ventricular or both); atherosclerosis and its sequelae; angina; cardiac rhythm disturbances; myocardial ischemia; myocardial infarction; cardiac or vascular aneurysm; vasculitis, stroke; peripheral obstructive arteriopathy of a limb, an organ, or a tissue; reperfusion injury following ischemia of the brain, heart, kidney or other organ or tissue; endotoxic, surgical, or traumatic shock; hypertension, valvular heart disease, heart failure, abnormal blood pressure; shock; vasoconstriction (including that associated with migraines); vascular abnormality, inflammation, insufficiency limited to a single organ or tissue.

In one aspect, provided herein are methods for preventing or treating vasoconstriction, atherosclerosis and its sequelae myocardial ischemia, myocardial infarction, aortic aneurysm, vasculitis and stroke comprising administering at least once to the mammal an effective amount of Compound 1, or a pharmaceutically acceptable salt thereof (e.g. Compound 2). In some embodiments, the LPA antagonist disclosed herein is used to treat Raynaud's phenomenon. Raynaud's phenomenon comprises both Raynaud's disease (where the phenomenon is idiopathic) and Raynaud's syndrome, where it is caused by some other instigating factor.

In one aspect, provided herein are methods for reducing cardiac reperfusion injury following myocardial ischemia and/or endotoxic shock comprising administering at least once to the mammal an effective amount of Compound 1, or a pharmaceutically acceptable salt thereof (e.g. Compound 2).

In one aspect, provided herein are methods for reducing the constriction of blood vessels in a mammal comprising administering at least once to the mammal an effective amount of Compound 1, or a pharmaceutically acceptable salt thereof (e.g. Compound 2).

In one aspect, provided herein are methods for lowering or preventing an increase in blood pressure of a mammal comprising administering at least once to the mammal an effective amount of Compound 1, or a pharmaceutically acceptable salt thereof (e.g. Compound 2).

LPA is associated with various inflammatory/immune diseases. In one aspect, Compound 1, or a pharmaceutically acceptable salt thereof (e.g. Compound 2), is used to treat or prevent inflammation in a mammal. In one aspect, antagonists of $LPA_1$ and/or $LPA_3$ find use in the treatment or prevention of inflammatory/immune disorders in a mammal.

Examples of inflammatory/immune disorders include psoriasis, rheumatoid arthritis, vasculitis, inflammatory bowel disease, dermatitis, osteoarthritis, asthma, inflammatory muscle disease, allergic rhinitis, vaginitis, interstitial cystitis, scleroderma, eczema, allogeneic or xenogeneic transplantation (organ, bone marrow, stem cells and other cells and tissues) graft rejection, graft-versus-host disease, lupus erythematosus, inflammatory disease, type I diabetes, pulmonary fibrosis, dermatomyositis, Sjogren's syndrome, thyroiditis (e.g., Hashimoto's and autoimmune thyroiditis), myasthenia gravis, autoimmune hemolytic anemia, multiple sclerosis, cystic fibrosis, chronic relapsing hepatitis, primary biliary cirrhosis, allergic conjunctivitis and atopic dermatitis.

In accordance with one aspect, are methods for treating, preventing, reversing, halting or slowing the progression of LPA-dependent or LPA-mediated diseases or conditions once it becomes clinically evident, or treating the symptoms associated with or related to LPA-dependent or LPA-mediated diseases or conditions, by administering to the mammal Compound 1, or a pharmaceutically acceptable salt thereof (e.g. Compound 2). In certain embodiments, the subject already has a LPA-dependent or LPA-mediated disease or condition at the time of administration, or is at risk of developing a LPA-dependent or LPA-mediated disease or condition.

In certain aspects, are methods for preventing or treating eosinophil and/or basophil and/or dendritic cell and/or neutrophil and/or monocyte and/or T-cell recruitment comprising administering at least once to the mammal an effective amount of Compound 1, or a pharmaceutically acceptable salt thereof (e.g. Compound 2).

In certain aspects, are methods for the treatment of cystitis, including, e.g., interstitial cystitis, comprising administering at least once to the mammal a therapeutically effective amount of Compound 1, or a pharmaceutically acceptable salt thereof (e.g. Compound 2).

In accordance with one aspect, methods described herein include the diagnosis or determination of whether or not a patient is suffering from a LPA-dependent or LPA-mediated disease or condition by administering to the subject a therapeutically effective amount of Compound 1, or a pharmaceutically acceptable salt thereof (e.g. Compound 2), and determining whether or not the patient responds to the treatment.

In one aspect provided herein is Compound 1, pharmaceutically acceptable salts, pharmaceutically acceptable prodrugs, and pharmaceutically acceptable solvates thereof, which is an antagonist of at least one LPA receptor (e.g. $LPA_1$, $LPA_2$, $LPA_3$) and is used to treat patients suffering from one or more LPA-dependent or LPA-mediated conditions or diseases, including, but not limited to, lung fibrosis, kidney fibrosis, liver fibrosis, scarring, scleroderma, asthma, rhinitis, chronic obstructive pulmonary disease, pulmonary hypertension, interstitial lung fibrosis, arthritis, allergy, psoriasis, inflammatory bowel disease, adult respiratory distress syndrome, myocardial infarction, aneurysm, stroke, cancer, pain, proliferative disorders and inflammatory conditions. In some embodiments, LPA-dependent conditions or diseases include those wherein an absolute or relative excess of LPA is present and/or observed.

In any of the aforementioned aspects the LPA-dependent or LPA-mediated diseases or conditions include, but are not limited to, organ fibrosis, tissue fibrosis, asthma, allergic disorders, chronic obstructive pulmonary disease, pulmonary hypertension, lung or pleural fibrosis, peritoneal fibrosis, arthritis, allergy, cancer, cardiovascular disease, adult respiratory distress syndrome, myocardial infarction, aneurysm, stroke, and cancer.

In one aspect, Compound 1, or a pharmaceutically acceptable salt thereof (e.g. Compound 2), is used to improve the corneal sensitivity decrease caused by corneal operations such as laser-assisted in situ keratomileusis (LASIK) or cataract operation, corneal sensitivity decrease caused by corneal degeneration, and dry eye symptom caused thereby.

In one aspect, presented herein is the use of Compound 1, or a pharmaceutically acceptable salt thereof (e.g. Compound 2), in the treatment or prevention of ocular inflammation and allergic conjunctivitis, vernal keratoconjunctivitis, and papillary conjunctivitis in a mammal.

In one aspect, presented herein is the use of Compound 1, or a pharmaceutically acceptable salt thereof (e.g. Compound 2), in the treatment or prevention of Sjogren disease or inflammatory disease with dry eyes in a mammal.

In one aspect, LPA and LPA receptors (e.g. $LPA_1$) are involved in the pathogenesis of osteoarthritis. In one aspect, presented herein is the use of Compound 1, or a pharmaceutically acceptable salt thereof (e.g. Compound 2), in the treatment or prevention of osteoarthritis in a mammal.

In one aspect, LPA receptors (e.g. $LPA_1$, $LPA_3$) contribute to the pathogenesis of rheumatoid arthritis. In one aspect, presented herein is the use of Compound 1, or a pharmaceutically acceptable salt thereof (e.g. Compound 2), in the treatment or prevention of rheumatoid arthritis in a mammal.

In one aspect, LPA receptors (e.g. $LPA_1$) contribute to adipogenesis. In one aspect, presented herein is the use of Compound 1, or a pharmaceutically acceptable salt thereof (e.g. Compound 2), in the promotion of adipose tissue formation in a mammal.

In one aspect, Compound 1, or a pharmaceutically acceptable salt thereof (e.g. Compound 2), is used to treat Raynaud's phenomenon in a mammal Raynaud's phenomenon comprises both Raynaud's disease (where the phenomenon is idiopathic) and Raynaud's syndrome, where it is caused by some instigating factor.

Described herein are compositions, pharmaceutical compositions, methods for treating, methods for formulating, methods for producing, methods for manufacturing, treatment strategies, pharmacokinetic strategies using Compound 1, or pharmaceutically acceptable salts thereof.

Compound 1, and Pharmaceutically Acceptable Salts Thereof

"Compound 1" or "1-{4'-[3-methyl-4-((R)-1-phenyl-ethoxycarbonylamino)-isoxazol-5-yl]-biphenyl-4-yl}-cyclopropanecarboxylic acid," "(R)-1-phenylethyl-5-(4-biphenyl-4-cyclopropanecarboxylic acid)-3-methylisoxazole-4-yl carbamate" or any other similar name refers to the compound with the following structure:

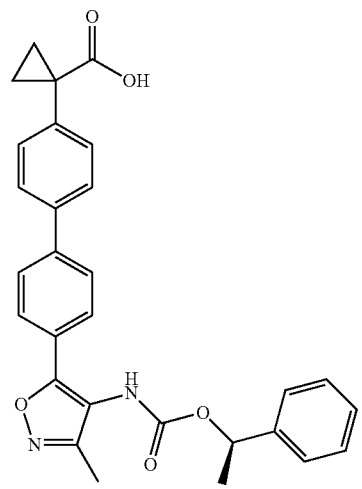 [SMILES: Cc1noc(-c2ccc(-c3ccc(C4(C(=O)O)CC4)cc3)cc2)c1NC(=O)O[C@H](C)c1ccccc1]

In some embodiments, Compound 1 is substantially free of the S-isomer.

"Substantially free" with respect to an enantiomer, means that the referenced enantiomer is not present or there is less than 5%, less than 4%, less than 3%, less than 2% or less than 1% of the referenced enantiomer.

"Compound 2" or "1-{4'-[3-methyl-4-((R)-1-phenyl-ethoxycarbonylamino)-isoxazol-5-yl]-biphenyl-4-yl}-cyclopropanecarboxylic acid, sodium salt" or "sodium 1-{4'-[3-methyl-4-((R)-1-phenyl-ethoxycarbonylamino)-isoxazol-5-yl]-biphenyl-4-yl}-cyclopropanecarboxylate" or "(R)-1-phenylethyl-5-(4-biphenyl-4-cyclopropanecarboxylic acid)-3-methylisoxazole-4-yl carbamate sodium salt" or any other similar name refers to the compound with the following structure:

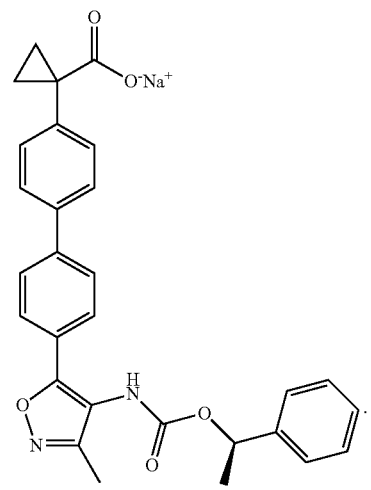

In some embodiments, Compound 2 is substantially free of the S-isomer.

A wide variety of pharmaceutically acceptable salts are formed from Compound 1 and include:

salts formed when the acidic proton of the carboxylic acid of Compound 1 is replaced by a metal ion, such as for example, an alkali metal ion (e.g. lithium, sodium, potassium), an alkaline earth ion (e.g. magnesium, or calcium), or an aluminum ion, or is replaced by an ammonium cation ($NH_4^+$);

salts formed by reacting Compound 1 with a pharmaceutically acceptable organic base, which includes alkylamines, such as choline, ethanolamine, diethanolamine, triethanolamine, tromethamine, N-methylglucamine, dicyclohexylamine, tris(hydroxymethyl)methylamine, and salts with amino acids, such as arginine, lysine, and the like.

In some embodiments, Compound 1 is treated with an amino acid to form a salt.

In other embodiments, Compound 1 is treated with choline, ethanolamine, diethanolamine, triethanolamine, tromethamine, N-methylglucamine, arginine, lysine, ammonium hydroxide, calcium hydroxide, potassium hydroxide, sodium carbonate, sodium hydroxide, and the like to form a salt.

The term "pharmaceutically acceptable salt" in reference to Compound 1 refers to a salt of Compound 1, which does not cause significant irritation to a mammal to which it is administered and does not substantially abrogate the biological activity and properties of the compound. In some embodiments, the pharmaceutically acceptable salt of Compound 1 is a lithium salt, sodium salt, potassium salt, magnesium salt, calcium salt, ammonium salt, choline salt, ethanolamine salt, diethanolamine salt, triethanolamine salt, tromethamine salt, N-methylglucamine salt, dicyclohexylamine salt, tris(hydroxymethyl)methylamine salt, arginine salt, or lysine salt. In some embodiments, the pharmaceutically acceptable salt of Compound 1 is a sodium salt.

It should be understood that a reference to a pharmaceutically acceptable salt includes the solvent addition forms (solvates). Solvates contain either stoichiometric or non-stoichiometric amounts of a solvent, and are formed during the process of product formation or isolation with pharmaceutically acceptable solvents such as water, ethanol, methyl tert-butyl ether, isopropanol, acetonitrile, heptane, and the like. In one aspect, solvates are formed using, but not limited to, Class 3 solvent(s). Categories of solvents are defined in, for example, the International Conference on Harmonization of Technical Requirements for Registration of Pharmaceuticals for Human Use (ICH), "Impurities: Guidelines for Residual Solvents, Q3C(R3), (November 2005). Hydrates are formed when the solvent is water, or alcoholates are formed when the solvent is alcohol. In one embodiment, solvates of Compound 1, or pharmaceutically acceptable salts thereof, are conveniently prepared or formed during the processes described herein. In addition, Compound 1, or pharmaceutically acceptable salts thereof, exist in unsolvated form. In some embodiments, Compound 1, or a pharmaceutically acceptable salt thereof, is hydrated. In some embodiments, Compound 2 is hydrated. In some embodiments, Compound 2 is a monohydrate.

In yet other embodiments, Compound 1, or a pharmaceutically acceptable salt thereof (e.g. Compound 2) is prepared in various forms, including but not limited to, amorphous phase, milled forms and nano-particulate forms.

Amorphous Compound 1

In some embodiments, Compound 1 is amorphous. In some embodiments, Amorphous Phase of Compound 1 has an XRPD pattern showing a lack of crystallinity.

Compound 1—Pattern 1

Figure 2:
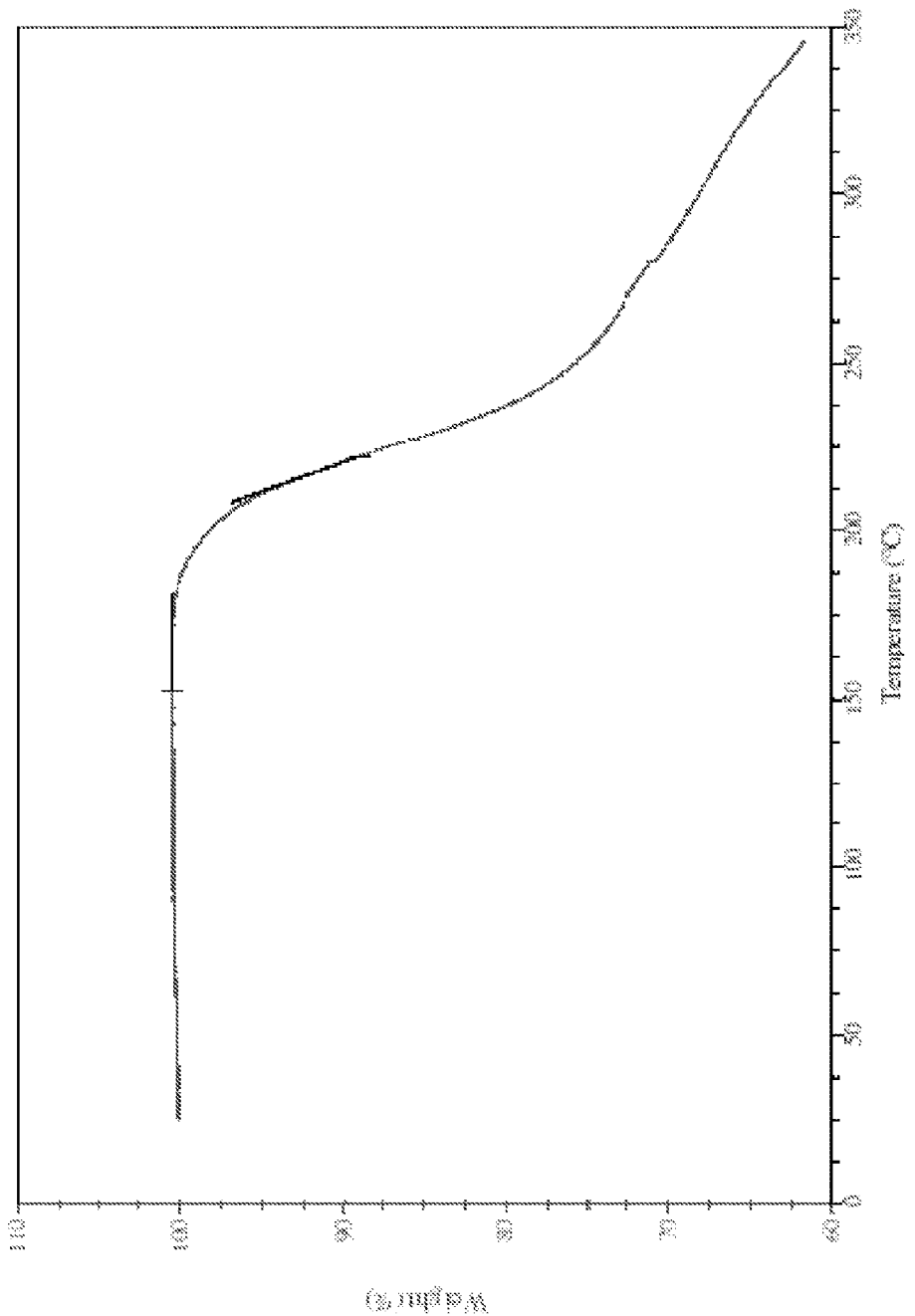
FIG. 2 illustrates the TGA of Pattern 1 of Crystalline Compound 1.
Figure 3:
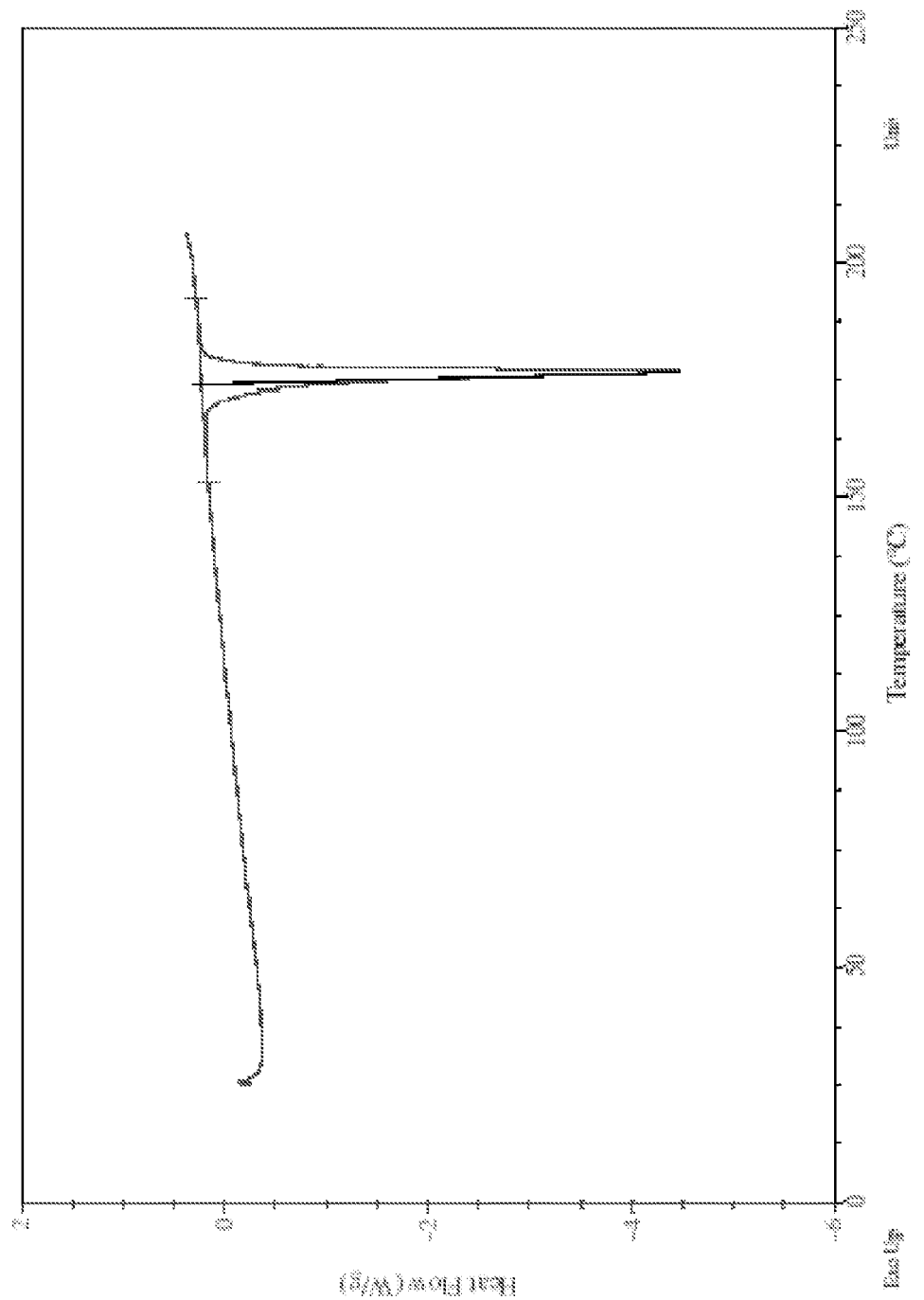
FIG. 3 illustrates the DSC of Pattern 1 of Crystalline Compound 1.

In some embodiments, Compound 1 is crystalline. In some embodiments, Compound 1 is crystalline Pattern 1. Crystalline Pattern 1 of Compound 1 is characterized as having:

(a) an X-ray powder diffraction (XRPD) pattern with characteristic peaks at 4.7° 2-Theta, 9.4° 2-Theta, 14.5° 2-Theta, and 21.0° 2-Theta;

(b) an X-ray powder diffraction (XRPD) pattern substantially the same as the XRPD shown in FIG. 1;

(c) a DSC thermogram with an endotherm at about 172-176° C.;

(d) a DSC or a thermo-gravimetric analysis (TGA) substantially similar to the ones set forth in FIG. 2 and FIG. 3;

(e) substantially the same X-ray powder diffraction (XRPD) pattern post storage at 40 C/75% relative humidity for one week;

(f) unit cell parameters substantially equal to the following at 25° C.:

| | |
|---|---|
| a(Å) | 26.2070(8) |
| b(Å) | 37.700(1) |
| c(Å) | 5.0051(2) |
| α° | 90 |
| β° | 90 |
| γ° | 90 |
| V(Å3) | 4945.1(3) |
| Z | 8 |
| Calculated Density | 1.296 |
| Crystal System | Orthorhombic |
| SG | $P2_12_12$ |
| R1 | 0.0418 |
| Sol. Sites | — | or (g) combinations thereof.

In some embodiments, the crystalline form of Compound 1 is substantially free of the S-isomer. In some embodiments, the crystalline form of Compound 1 is substantially free of amorphous Compound 1.

In some embodiments, the crystalline form of Compound 1 is crystallized from ethanol, methanol, 2-methoxyethanol, ethanol, 1-propanol, 2-propanol, 1-butanol, butyl acetate, acetone, methylethyl ketone, anisole, toluene, nitromethane, acetonitrile, ethyl acetate, cumene, 1-4-dioxane, tetrahydrofuran, dichloromethane, heptane, or combinations thereof.

In some embodiments, Crystalline Pattern 1 of Compound 1 is characterized as having at least one of the properties selected from (a) to (f). In some embodiments, Crystalline Pattern 1 of Compound 1 is characterized as having at least two of the properties selected from (a) to (f). In some embodiments, Crystalline Pattern 1 of Compound 1 is characterized as having at least three of the properties selected from (a) to (f). In some embodiments, Crystalline Pattern 1 of Compound 1 is characterized as having at least four of the properties selected from (a) to (f). In some embodiments, Crystalline Pattern 1 of Compound 1 is characterized as having at least five of the properties selected from (a) to (f). In some embodiments, Crystalline Pattern 1 of Compound 1 is characterized as having the properties (a), (b), (c), (d), (e), and (f).

In some embodiments, crystalline Compound 1 has an X-ray powder diffraction (XRPD) pattern with characteristic peaks at 4.7° 2-Theta, 9.4° 2-Theta, 14.5° 2-Theta, and 21.0° 2-Theta.

In some embodiments, crystalline Compound 1 has an X-ray powder diffraction (XRPD) pattern substantially the same as the XRPD shown in FIG. 1.

In some embodiments, crystalline Compound 1 has a DSC thermogram with an endotherm at about 172°-176° C.

In some embodiments, crystalline Compound 1 has a DSC or a thermo-gravimetric analysis (TGA) substantially similar to the ones set forth in FIG. 2 or FIG. 3.

In some embodiments, crystalline Compound 1 has substantially the same X-ray powder diffraction (XRPD) pattern post storage at 40 C/75% relative humidity for one week.

In one embodiment, Crystalline Pattern 1 of Compound 1 is characterized by unit cell parameters approximately equal to the following at a temperature of 25° C.:

| | |
|---|---|
| a(Å) | 26.2070(8) |
| b(Å) | 37.700(1) |
| c(Å) | 5.0051(2) |
| α° | 90 |
| β° | 90 |
| γ° | 90 |
| V(Å3) | 4945.1(3) |
| Z | 8 |
| Calculated Density | 1.296 |
| Crystal System | Orthorhombic |
| SG | P2$_1$2$_1$2 |
| R1 | 0.0418 |
| Sol. Sites | — |

In a further embodiment, Crystalline Pattern 1 of Compound 1 is characterized by fractional atomic coordinates substantially the same as listed in Table 2.

Compound 1—Pattern 2

Figure 12:
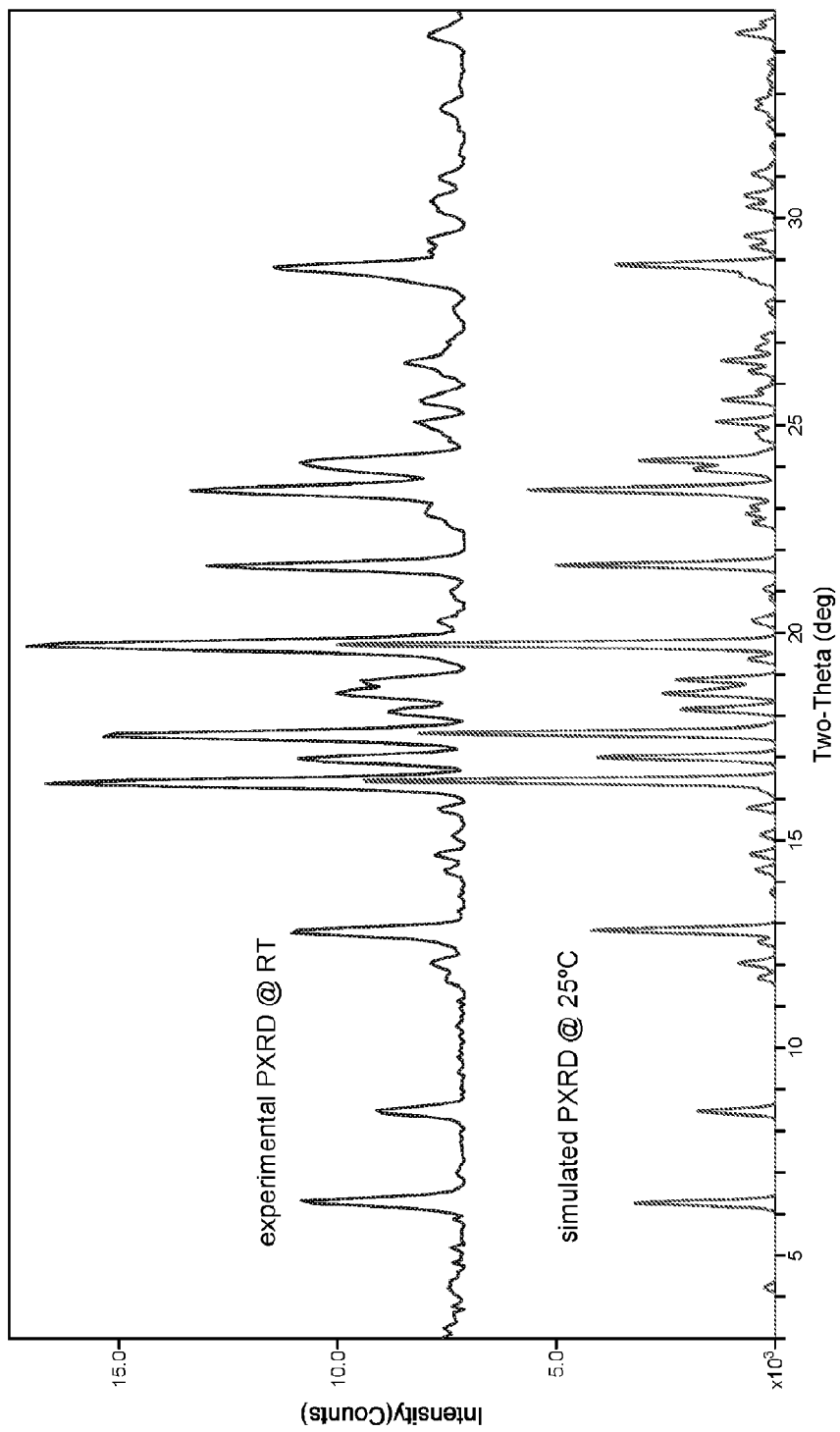
FIG. 12 illustrates the XRPD of Pattern 2 of Crystalline Compound 1.

In some embodiments, Compound 1 is crystalline. In some embodiments, Compound 1 is crystalline Pattern 2. Crystalline Pattern 2 of Compound 1 is characterized as having:

(a) an X-ray powder diffraction (XRPD) pattern substantially the same as the XRPD shown in FIG. 12;

(b) an X-ray powder diffraction (XRPD) pattern with characteristic peaks at 6.3° 2-Theta, 12.8° 2-Theta, 16.4° 2-Theta, 17.0° 2-Theta, and 19.7° 2-Theta;

(c) unit cell parameters approximately equal to the following at a temperature of 25° C.:

| | |
|---|---|
| a(Å) | 30.3522(9) |
| b(Å) | 7.8514(3) |
| c(Å) | 22.4570(7) |
| α° | 90 |
| β° | 111.665(2) |
| γ° | 90 |
| V(Å³) | 4973.6(3) |
| Z | 8 |
| Calculated Density | 1.289 |
| Crystal System | Monoclinic |
| SG | C2 |
| R1 | 0.0298 |
| Sol. Sites | — | or
(d) combinations thereof.

In some embodiments, Crystalline Pattern 2 of Compound 1 is characterized as having at least one of the properties selected from (a) to (c). In some embodiments, Crystalline Pattern 2 of Compound 1 is characterized as having at least two of the properties selected from (a) to (c). In some embodiments, Crystalline Pattern 2 of Compound 1 is characterized as having properties (a), (b), and (c).

In some embodiments, the crystalline form of Compound 1 is substantially free of the S-isomer. In some embodiments, the crystalline form of Compound 1 is substantially free of amorphous Compound 1. In some embodiments, the crystalline form of Compound 1 has an X-ray powder diffraction (XRPD) pattern substantially the same as the XRPD shown in FIG. 12. In some embodiments, the crystalline form of Compound 1 has an X-ray powder diffraction (XRPD) pattern with characteristic peaks at 6.3° 2-Theta, 12.8° 2-Theta, 16.4° 2-Theta, 17.0° 2-Theta, and 19.7° 2-Theta.

In one embodiment, Crystalline Pattern 2 of Compound 1 is characterized by unit cell parameters approximately equal to the following at a temperature of 25° C.:

| | |
|---|---|
| a(Å) | 30.3522(9) |
| b(Å) | 7.8514(3) |
| c(Å) | 22.4570(7) |
| α° | 90 |
| β° | 111.665(2) |
| γ° | 90 |
| V(Å³) | 4973.6(3) |
| Z | 8 |
| Calculated Density | 1.289 |
| Crystal System | Monoclinic |
| SG | C2 |
| R1 | 0.0298 |
| Sol. Sites | — |

In a further embodiment, Crystalline Pattern 2 of Compound 1 is characterized by fractional atomic coordinates substantially the same as listed in Table 4.

Compound 1—Pattern 3

Figure 13:
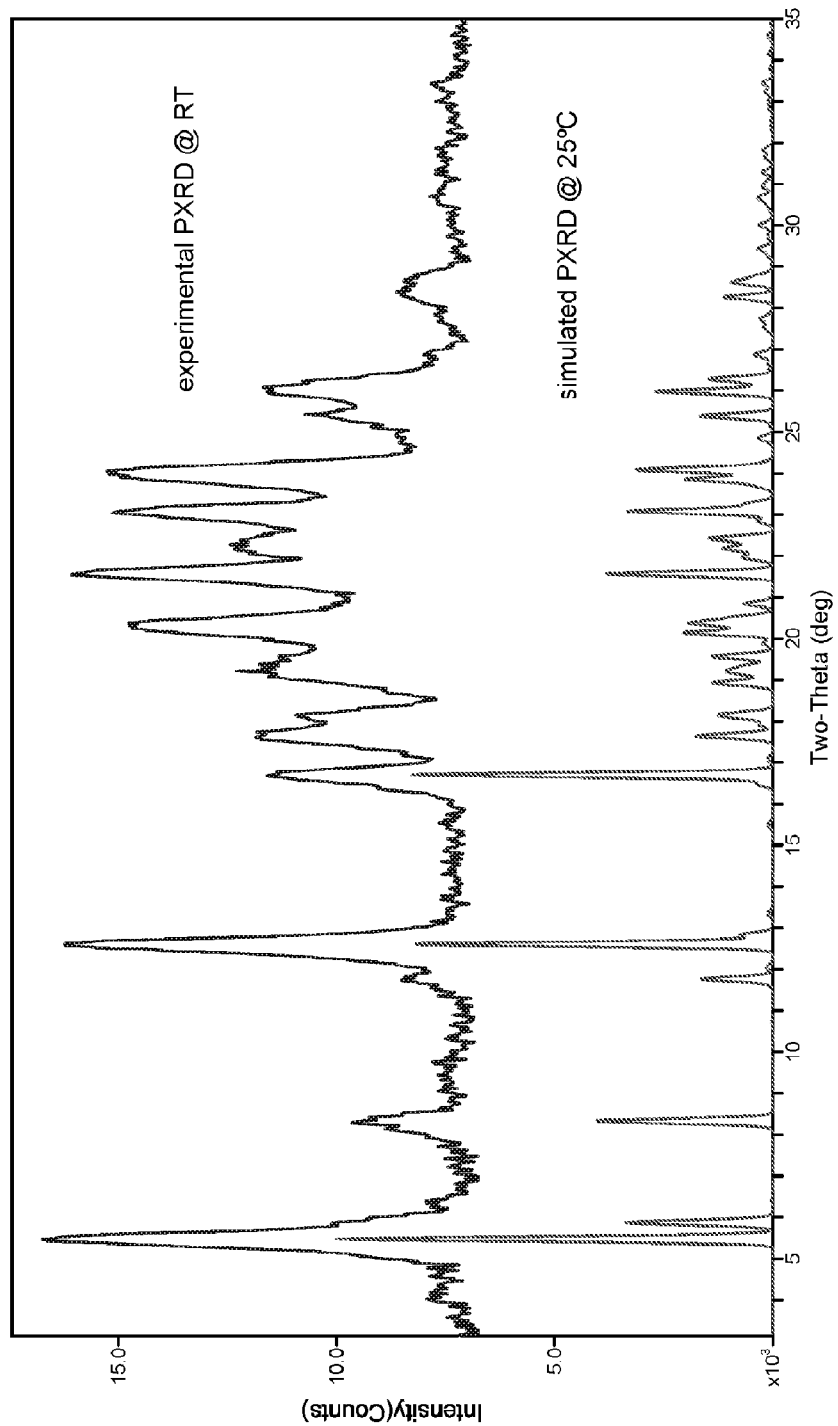
FIG. 13 illustrates the XRPD of Pattern 3 of Crystalline Compound 1.

In some embodiments, Compound 1 is crystalline. In some embodiments, Compound 1 is crystalline Pattern 3. Crystalline Pattern 3 of Compound 1 is characterized as having:

(a) an X-ray powder diffraction (XRPD) pattern substantially the same as the XRPD shown in FIG. 13;

(b) an X-ray powder diffraction (XRPD) pattern with characteristic peaks at 5.5° 2-Theta, 5.9° 2-Theta, 12.6° 2-Theta, and 16.7° 2-Theta;

(c) unit cell parameters approximately equal to the following at a temperature of 25° C.:

| | |
|---|---|
| a(Å) | 32.3574(9) |
| b(Å) | 5.1057(2) |
| c(Å) | 33.148(1) |
| α° | 90 |
| β° | 114.846(2) |
| γ° | 90 |
| V(Å³) | 4969.4(3) |
| Z | 8 |
| Calculated Density | 1.290 |
| Crystal System | Monoclinic |
| SG | C2 |
| R1 | 0.0553 |
| Sol. Sites | — | or
(d) combinations thereof.

In some embodiments, Crystalline Pattern 3 of Compound 1 is characterized as having at least one of the properties selected from (a) to (c). In some embodiments, Crystalline Pattern 3 of Compound 1 is characterized as having at least two of the properties selected from (a) to (c). In some embodiments, Crystalline Pattern 3 of Compound 1 is characterized as having properties (a), (b), and (c).

In some embodiments, the crystalline form of Compound 1 is substantially free of the S-isomer. In some embodiments, the crystalline form of Compound 1 is substantially free of amorphous Compound 1. In some embodiments, the crystalline form of Compound 1 has an X-ray powder diffraction (XRPD) pattern substantially the same as the XRPD shown in FIG. 13. In some embodiments, the crystalline form of Compound 1 has an X-ray powder diffraction (XRPD) pattern with characteristic peaks at 5.5° 2-Theta, 5.9° 2-Theta, 12.6° 2-Theta, 16.7° 2-Theta.

In one embodiment, Crystalline Pattern 3 of Compound 1 is characterized by unit cell parameters approximately equal to the following at a temperature of 25° C.:

| | |
|---|---|
| a(Å) | 32.3574(9) |
| b(Å) | 5.1057(2) |
| c(Å) | 33.148(1) |
| α° | 90 |
| β° | 114.846(2) |
| γ° | 90 |
| V(Å$^3$) | 4969.4(3) |
| Z | 8 |
| Calculated Density | 1.290 |
| Crystal System | Monoclinic |
| SG | C2 |
| R1 | 0.0553 |
| Sol. Sites | — |

In a further embodiment, Crystalline Pattern 3 of Compound 1 is characterized by fractional atomic coordinates substantially the same as listed in Table 6.

Amorphous Compound 2

Figure 10:
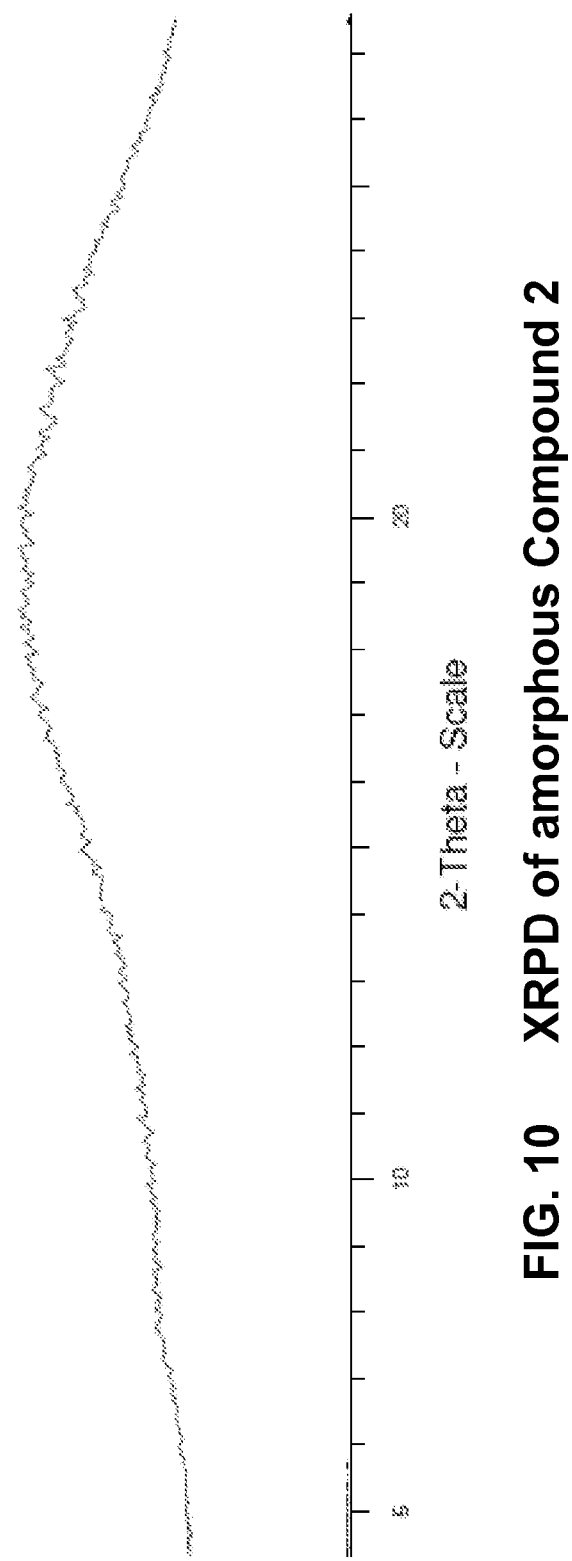
FIG. 10 illustrates the XRPD of amorphous Compound 2.

In some embodiments, Compound 2 is amorphous. In some embodiments, Amorphous Phase of Compound 2 has an XRPD pattern showing a lack of crystallinity. In some embodiments, Compound 2 is amorphous and has an X-ray powder diffraction (XRPD) pattern substantially the same as shown in FIG. 10. In some embodiments, Compound 2 is amorphous and has a DSC substantially similar to the one set forth in FIG. 11.

Compound 2—Pattern 1

In some embodiments, Compound 2 is crystalline. In some embodiments, Compound 2 is crystalline and hydrated. In some embodiments, Compound 2 is crystalline Pattern 1.

Figure 4:
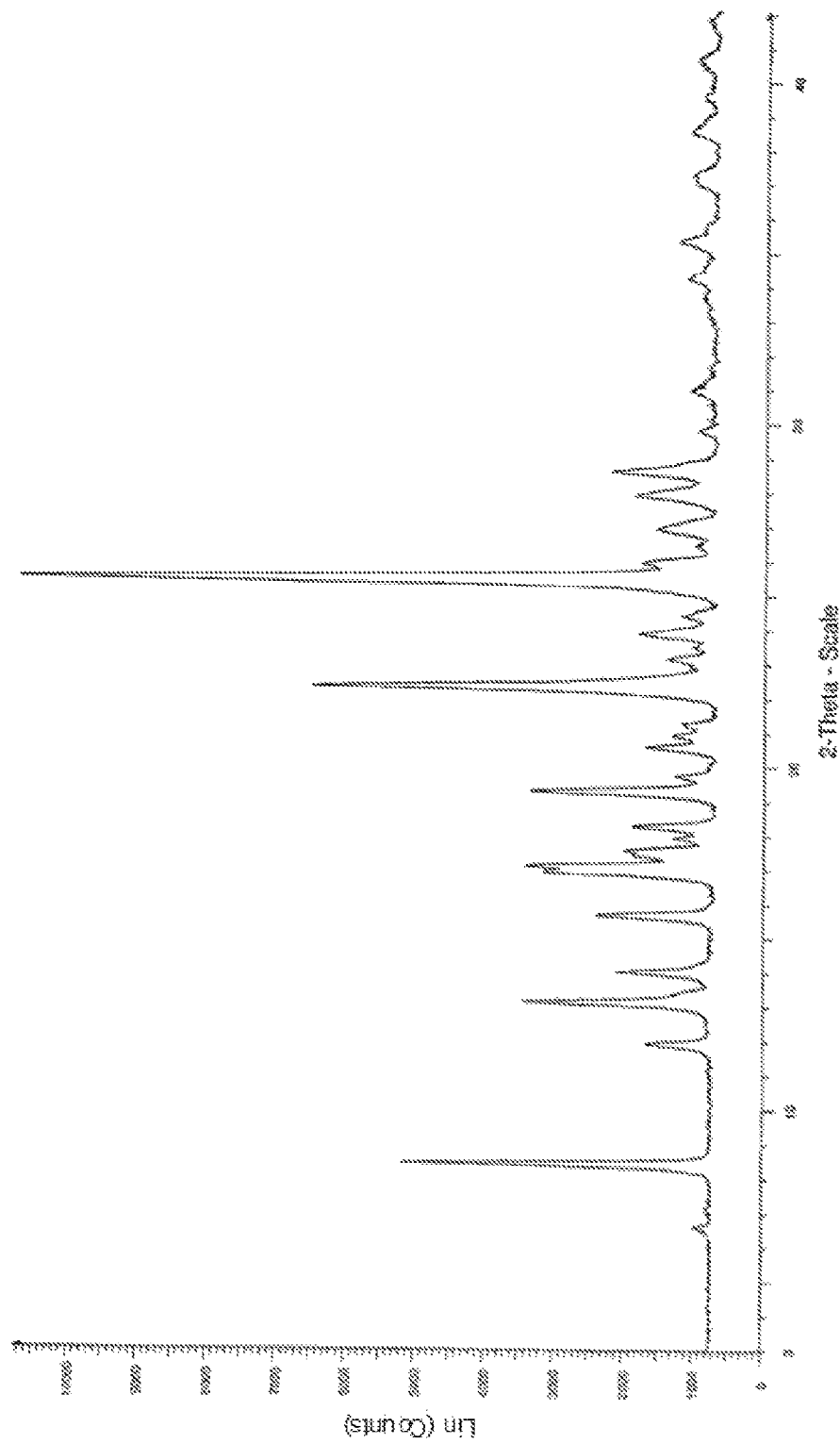
FIG. 4 illustrates the XRPD of Pattern 1 of Crystalline Compound 2.

In some embodiments, described is a hydrated crystalline form of Compound 2 (Pattern 1), wherein the hydrated crystalline form of Compound 2:
(a) has an X-ray powder diffraction (XRPD) pattern with characteristic peaks at 13.2° 2-Theta, 17.2° 2-Theta, 19.3° 2-Theta, 22.4° 2-Theta, and 25.6° 2-Theta;
(b) has an X-ray powder diffraction (XRPD) pattern substantially the same as shown in FIG. 4;
(c) has a thermo-gravimetric analysis (TGA) or a DSC substantially similar to the ones set forth in FIG. 5 and FIG. 6;
(d) has an infrared spectrum substantially similar to the one set forth in FIG. 7;
(e) was obtained from methyl ethyl ketone, acetonitrile, 1,4-dioxane/tert-butyl methyl ether, methyl ethyl ketone (MEK)/tert-butyl methyl, or ethanol/heptane;
(f) has unit cell parameters substantially equal to the following at 25° C.:

| | |
|---|---|
| a(Å) | 13.8714(2) |
| b(Å) | 7.7379(2) |
| c(Å) | 25.5253(5) |
| α° | 90 |
| β° | 103.863(1) |
| γ° | 90 |
| V(Å3) | 2659.96(9) |
| Z | 4 |
| Calculated Density | 1.305 |
| Crystal System | Monoclinic |
| SG | P2$_1$ |
| R1 | 0.0301 |
| Sol. Sites | 1H$_2$O | or
(g) combinations thereof.

In some embodiments, the hydrated crystalline form of Compound 2 (Pattern 1) is characterized as having at least one property selected from (a) to (f). In some embodiments, the hydrated crystalline form of Compound 2 (Pattern 1) is characterized as having at least two of the properties selected from (a) to (f). In some embodiments, the hydrated crystalline form of Compound 2 (Pattern 1) is characterized as having at least three of the properties selected from (a) to (f). In some embodiments, the hydrated crystalline form of Compound 2 (Pattern 1) is characterized as having at least three of the properties selected from (a) to (f).

In some embodiments, crystalline Compound 2 (Pattern 1) has an X-ray powder diffraction (XRPD) pattern with characteristic peaks at 13.2° 2-Theta, 17.2° 2-Theta, 19.3° 2-Theta, 22.4° 2-Theta, and 25.6° 2-Theta.

In some embodiments, crystalline Compound 2 (Pattern 1) has an X-ray powder diffraction (XRPD) pattern substantially the same as shown in FIG. 4.

Figure 5:
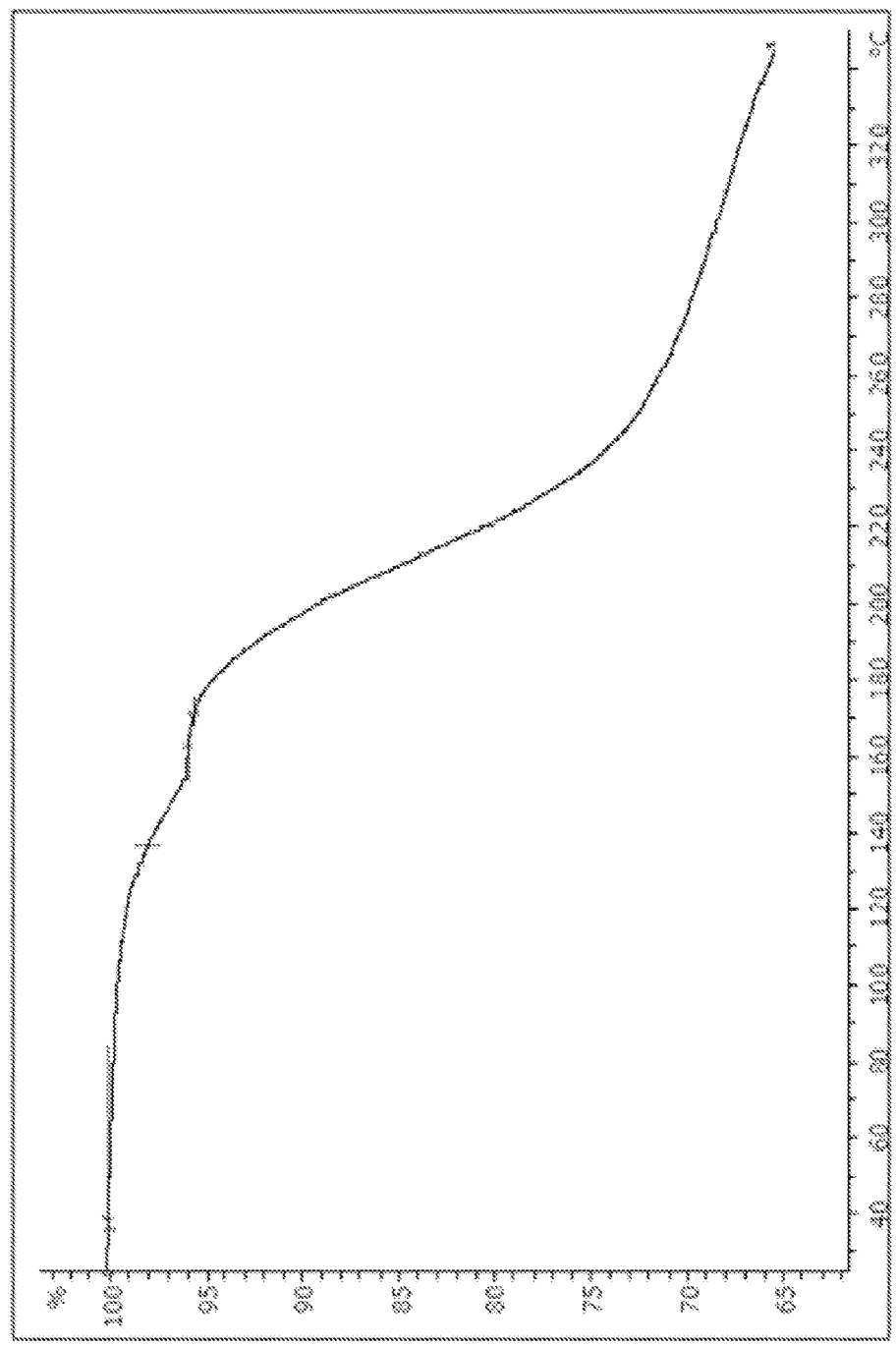
FIG. 5 illustrates the TGA of Pattern 1 of Crystalline Compound 2.
Figure 6:
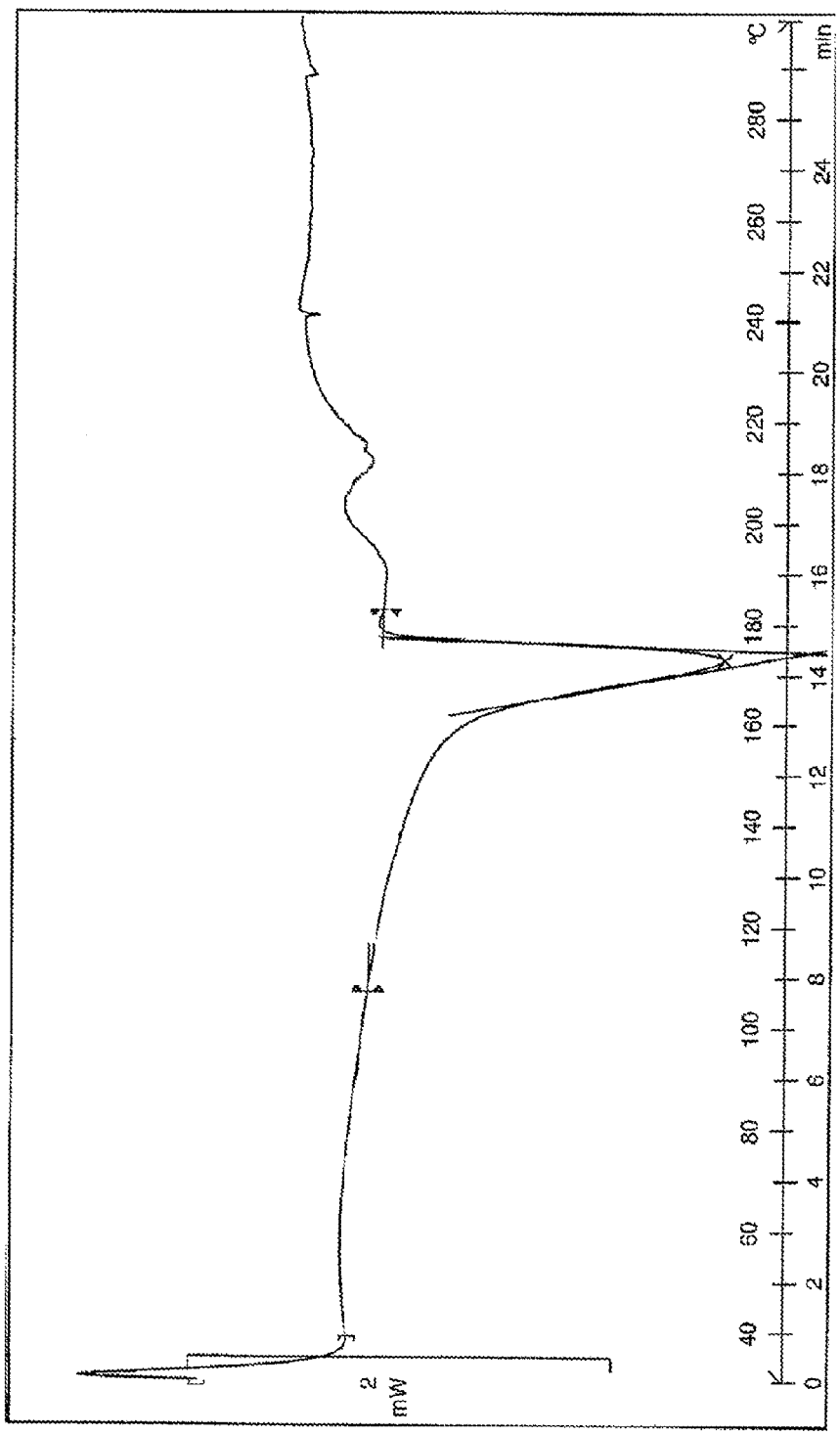
FIG. 6 illustrates the DSC of Pattern 1 of Crystalline Compound 2.

In some embodiments, crystalline Compound 2 (Pattern 1) has a thermo-gravimetric analysis (TGA) or a DSC substantially similar to the ones set forth in FIG. 5 and FIG. 6. In some embodiments, crystalline Compound 2 (Pattern 1) has a thermo-gravimetric analysis (TGA) substantially similar to the one set forth in FIG. 5. In some embodiments, crystalline Compound 2 (Pattern 1) has a DSC substantially similar to the one set forth in FIG. 6.

Figure 7:
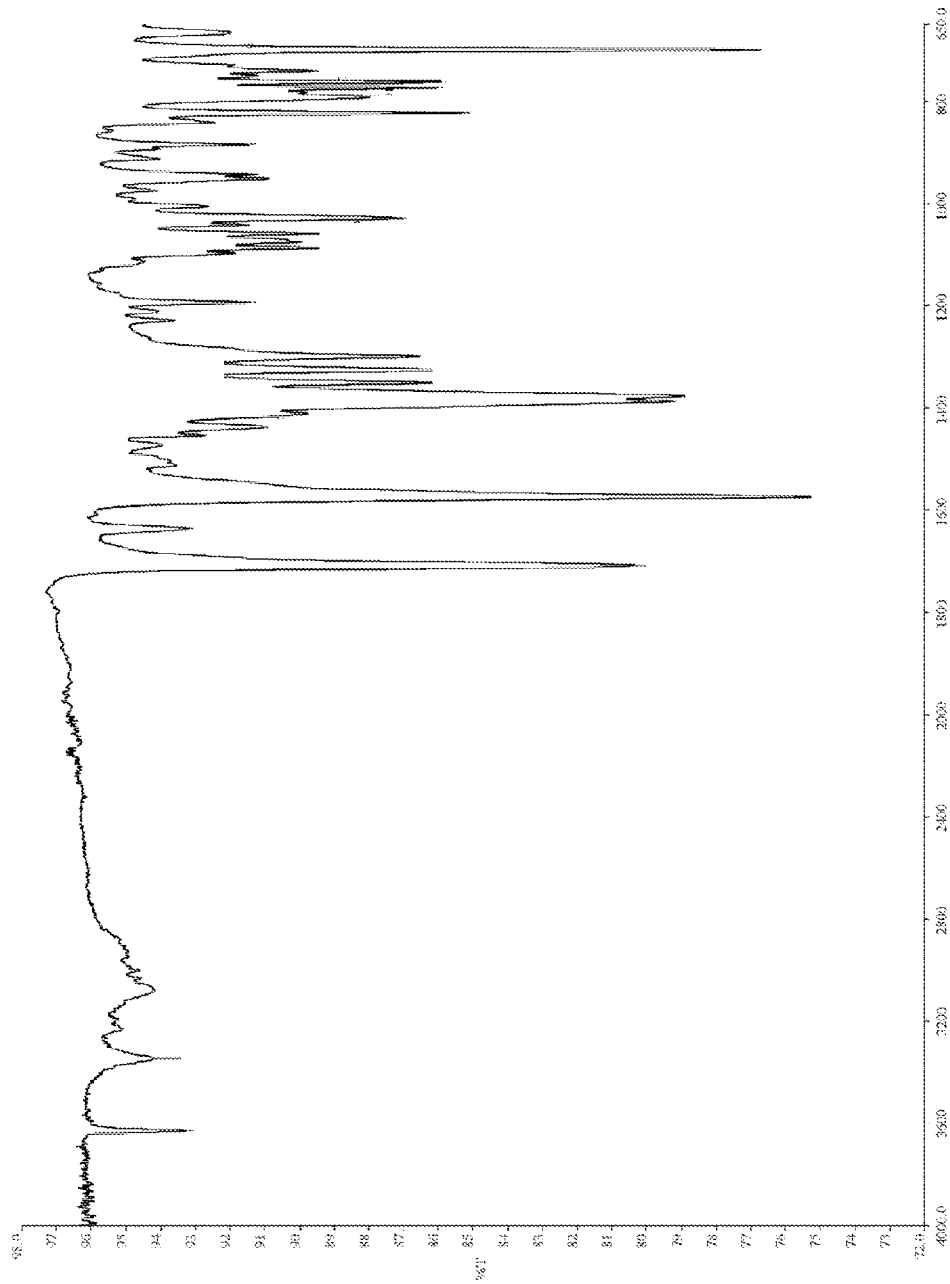
FIG. 7 illustrates the IR spectrum of Pattern 1 of Crystalline Compound 2.

In some embodiments, crystalline Compound 2 (Pattern 1) has an infrared spectrum substantially similar to the one set forth in FIG. 7.

In some embodiments, crystalline Compound 2 (Pattern 1) was obtained from methyl ethyl ketone, acetonitrile, 1,4-dioxane/tert-butyl methyl ether, methyl ethyl ketone (MEK)/tert-butyl methyl, or ethanol/heptanes.

In some embodiments, Crystalline Pattern 1 of Compound 2 is obtained from:
(i) methyl ethyl ketone;
(ii) methyl ethyl ketone, methyl tert-butyl ether and water;
(iii) methyl ethyl ketone, and water;
(iv) acetonitrile;
(v) 1,4-dioxane and tert-butyl methyl ether;
(vi) methyl ethyl ketone and tert-butyl methyl; or
(vii) ethanol and heptane.

In one embodiment, Crystalline Pattern 1 of Compound 2 is characterized by unit cell parameters approximately equal to the following at a temperature of 25° C.:

| | |
|---|---|
| a(Å) | 13.8714(2) |
| b(Å) | 7.7379(2) |
| c(Å) | 25.5253(5) |
| α° | 90 |
| β° | 103.863(1) |

-continued

| | |
|---|---|
| γ° | 90 |
| V(Å3) | 2659.96(9) |
| Z | 4 |
| Calculated Density | 1.305 |
| Crystal System | Monoclinic |
| SG | P2₁ |
| R1 | 0.0301 |
| Sol. Sites | 1H₂O |

In a further embodiment, Crystalline Pattern 1 of Compound 2 is characterized by fractional atomic coordinates substantially the same as listed in Table 8.

Compound 2—Pattern 2

Figure 8:
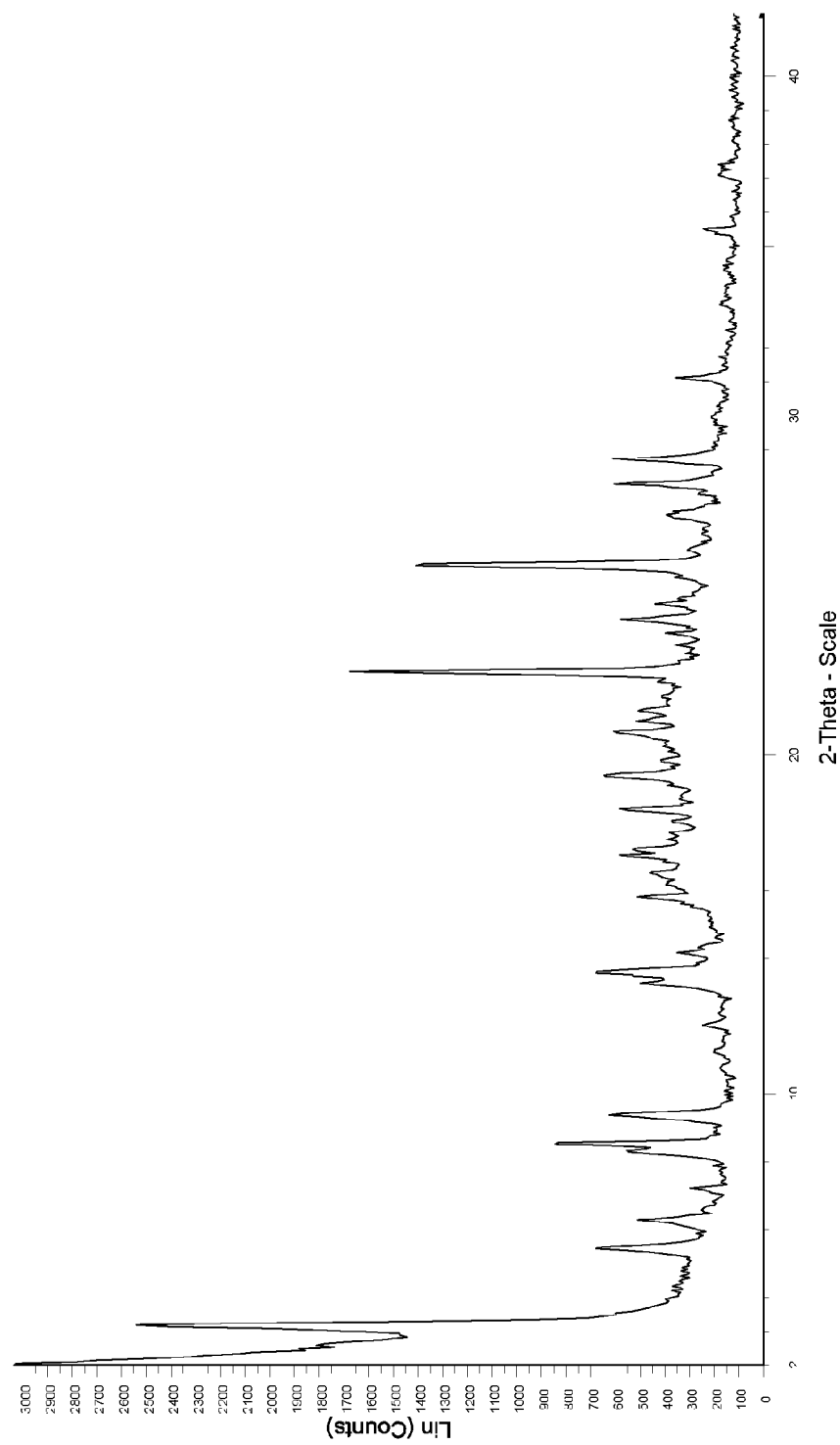
FIG. 8 illustrates the XRPD of Pattern 2 of Crystalline Compound 2.

In some embodiments, Compound 2 is crystalline. In some embodiments, Compound 2 is crystalline Pattern 2. In some embodiments, Compound 2 is crystalline and has an X-ray powder diffraction (XRPD) pattern substantially the same as shown in FIG. 8.

Compound 2—Pattern 3

Figure 9:
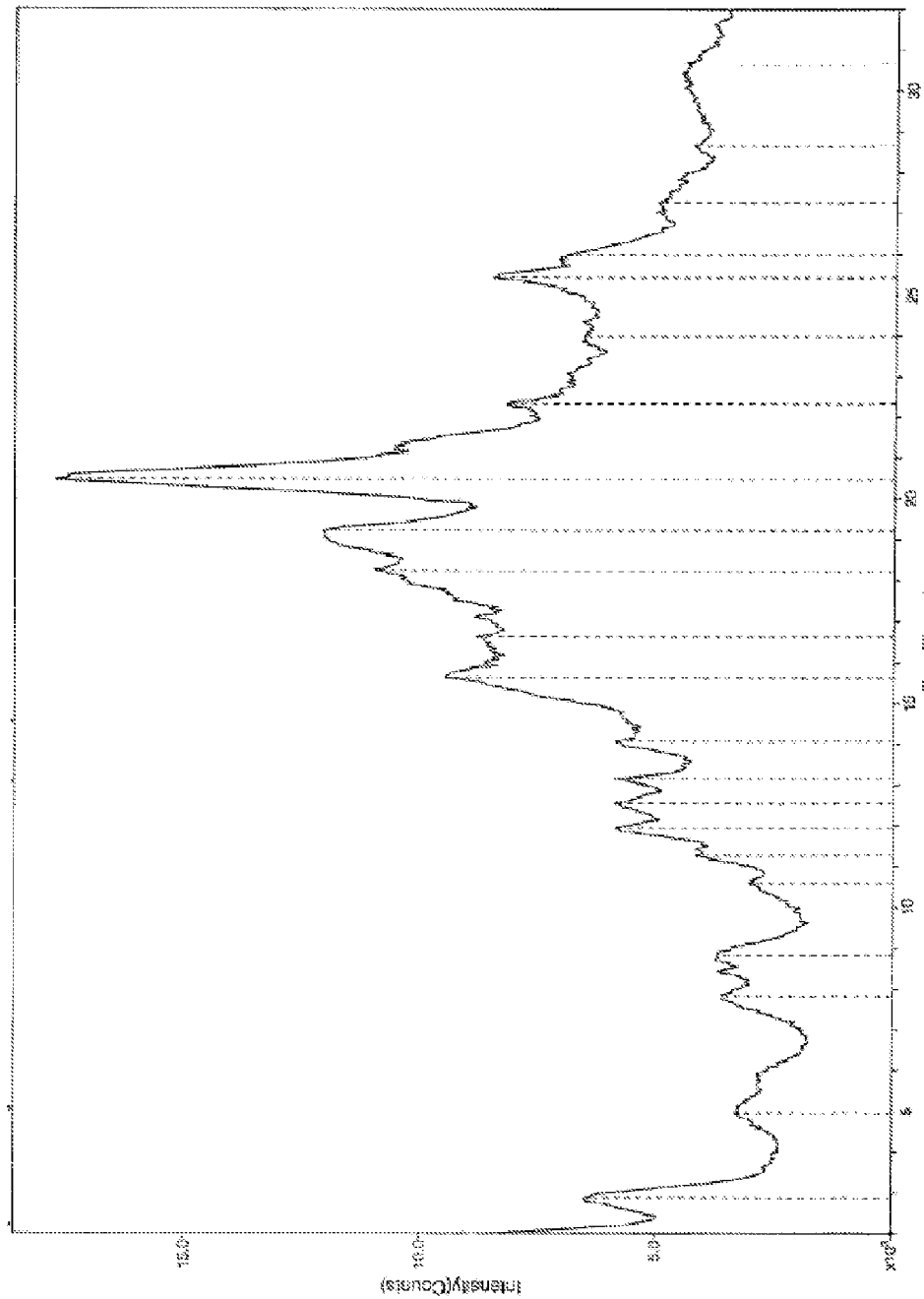
FIG. 9 illustrates the XRPD of Pattern 3 of Crystalline Compound 2.

In some embodiments, Compound 2 is crystalline. In some embodiments, Compound 2 is crystalline Pattern 3. In some embodiments, Compound 2 is crystalline and has an X-ray powder diffraction (XRPD) pattern substantially the same as shown in FIG. 9.

Prodrugs of Compound 1

In some embodiments, Compound 1 is prepared as a prodrug.

A "prodrug of Compound 1" refers to a compound that is converted into Compound 1 in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. In some embodiments, prodrugs facilitate transmittal across a cell membrane where water solubility is detrimental to mobility but which then is metabolically hydrolyzed to the carboxylic acid, the active entity, once inside the cell where water-solubility is beneficial. An example, without limitation, of a prodrug would be an ester of Compound 1 (the "prodrug"). A further example of a prodrug might be a short peptide (polyaminoacid) bonded to an acid group where the peptide is metabolized to reveal the active moiety.

Prodrugs are generally drug precursors that, following administration to a subject and subsequent absorption, are converted to an active, or a more active species via some process, such as conversion by a metabolic pathway. Some prodrugs have a chemical group present on the prodrug that renders it less active and/or confers solubility or some other property to the drug. Once the chemical group has been cleaved and/or modified from the prodrug the active drug is generated. Prodrugs are often useful because, in some situations, they are easier to administer than the parent drug. In certain embodiments, the prodrug of Compound 1 increases the bioavailability of Compound 1 when orally administered. In some embodiments, the prodrug of Compound 1 has improved solubility in pharmaceutical compositions over Compound 1.

In some embodiments, a prodrug of Compound 1 is an alkyl ester of Compound 1, such as, for example, methyl ester, ethyl ester, n-propyl ester, iso-propyl ester, n-butyl ester, sec-butyl ester, or tert-butyl ester.

Non-limiting examples of prodrugs of Compound 1 include:

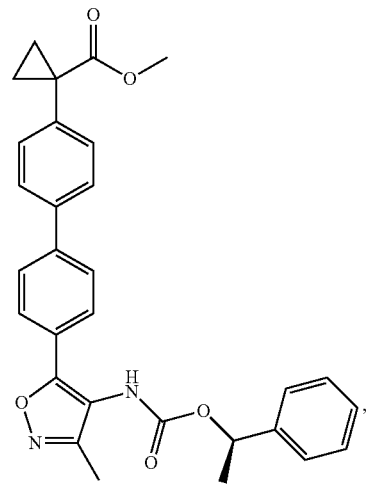

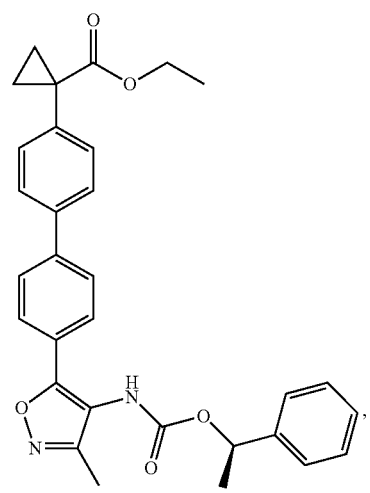

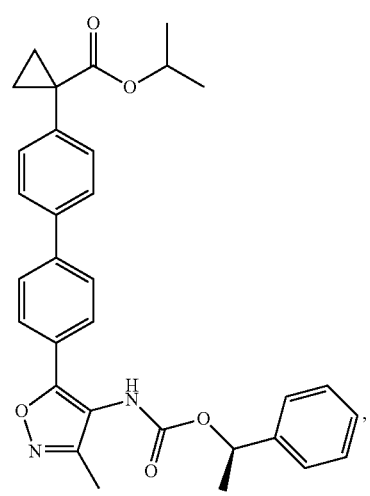

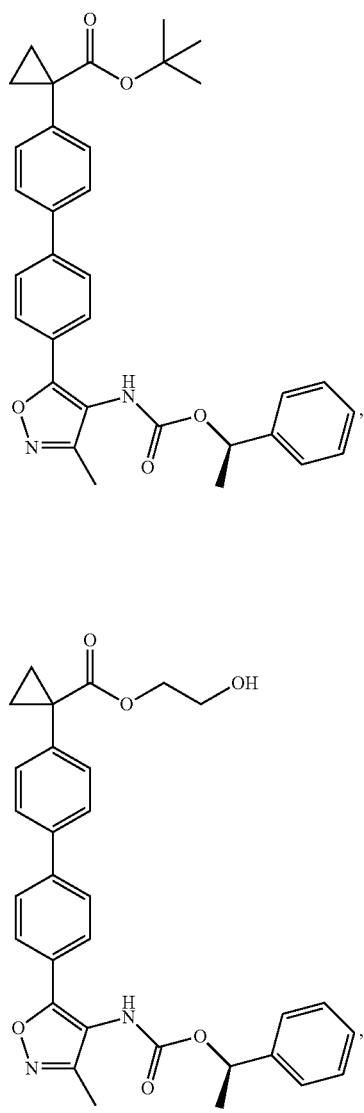

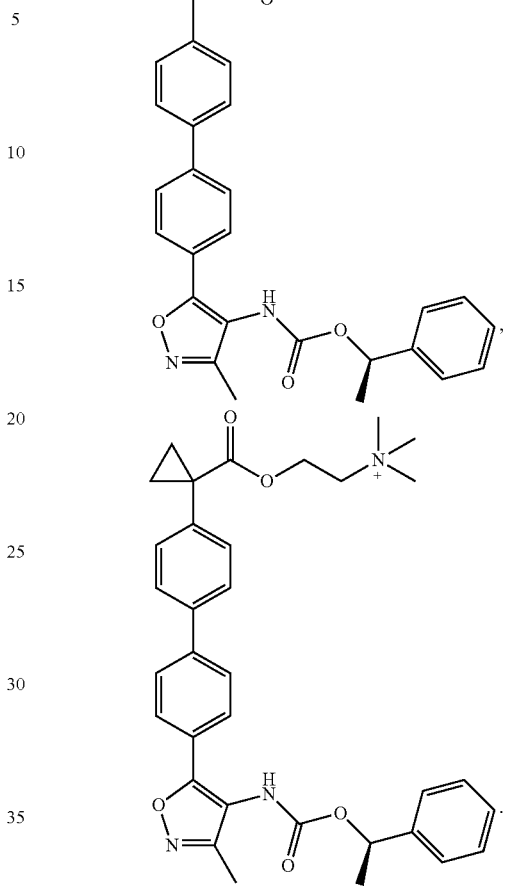

Metabolites of Compound 1

Compound 1 metabolites formed during incubation of Compound 1 with: rat, dog, monkey, and human liver microsomes; rat, dog, and human hepatocytes; as well as those generated in vivo and isolated from rat bile and rat and dog plasma were investigated. The following metabolites of Compound 1 were observed:

| Metabolite | Structure | Metabolite Description |
|---|---|---|
| M1 | 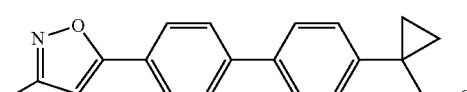 | Glucuronidation of Compound 1 |

-continued

| Metabolite | Structure | Metabolite Description |
|---|---|---|
| M2 | 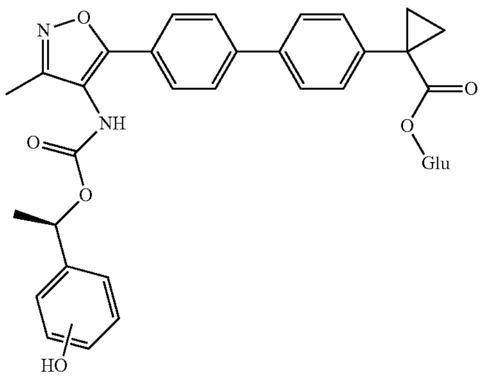 | Glucuronidation of Compound 1 plus oxidation |
| M3 | 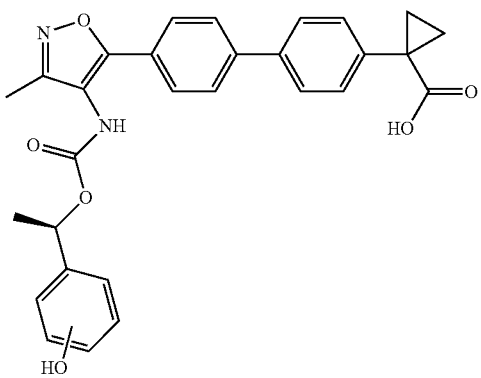 | Oxidation of phenyl ring of benzyl group. |
| M4 | 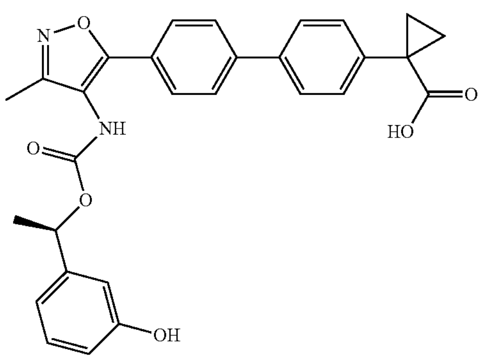 [SMILES: Cc1noc(-c2ccc(-c3ccc(C4(C(=O)O)CC4)cc3)cc2)c1NC(=O)O[C@H](C)c1cccc(O)c1] | Oxidation of phenyl ring of benzyl group. |
| M5 | 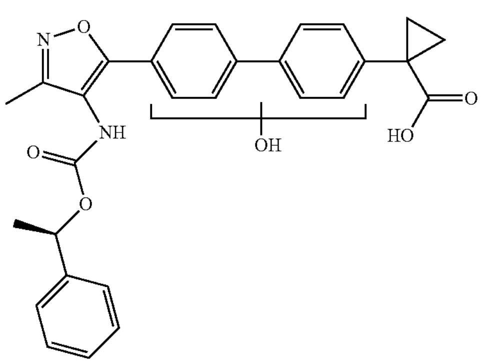 | Oxidation of biphenyl |

In some embodiments, sites on Compound 1 are susceptible to various metabolic reactions. Therefore incorporation of appropriate substituents on Compound 1 will reduce, minimize or eliminate this metabolic pathway. In specific embodiments, the appropriate substituent to decrease or eliminate the susceptibility of the aromatic ring to metabolic reactions is, by way of example only, a halogen, deuterium or an alkyl group (e.g. methyl, ethyl).

In some embodiments, Compound 1 is isotopically labeled (e.g. with a radioisotope) or by another other means, including, but not limited to, the use of chromophores or fluorescent moieties, bioluminescent labels, or chemiluminescent labels. In some embodiments, Compound 1 is isotopically-labeled, which is identical to Compound 1 but for the fact that one or more atoms are replaced by an atom having an atomic mass or mass number different from the atomic mass or mass number usually found in nature. In some embodiments, one or more hydrogen atoms are replaced with deuterium. In some embodiments, metabolic sites on Compound 1 are deuterated. In some embodiments, substitution with deuterium affords certain therapeutic advantages resulting from greater metabolic stability, such as, for example, increased in vivo half-life or reduced dosage requirements.

In one aspect, described is a compound with the following structure:

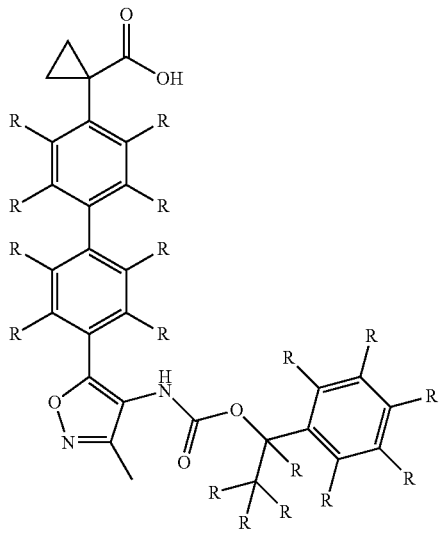

wherein,
each R is independently selected from hydrogen or deuterium,
or a pharmaceutically acceptable salt thereof.

In some embodiments, the pharmaceutically acceptable salt of the compound is a sodium salt.

Synthesis of Compound 1, and Pharmaceutically Acceptable Salts Thereof

Compound 1, and pharmaceutically acceptable salts thereof (e.g. Compound 2), are synthesized as described herein. In additions, solvents, temperatures and other reaction conditions presented herein may vary.

The starting materials used for the synthesis are either synthesized or obtained from commercial sources, such as, but not limited to, Sigma-Aldrich, Fluka, Acros Organics, Alfa Aesar, VWR Scientific, and the like. General methods for the preparation of compounds can be modified by the use of appropriate reagents and conditions for the introduction of the various moieties found in the structures as provided herein.

In one aspect, the preparation of Compound 1, or pharmaceutically acceptable salts thereof (e.g. sodium salt) begins with the steps outlined in Scheme 1.

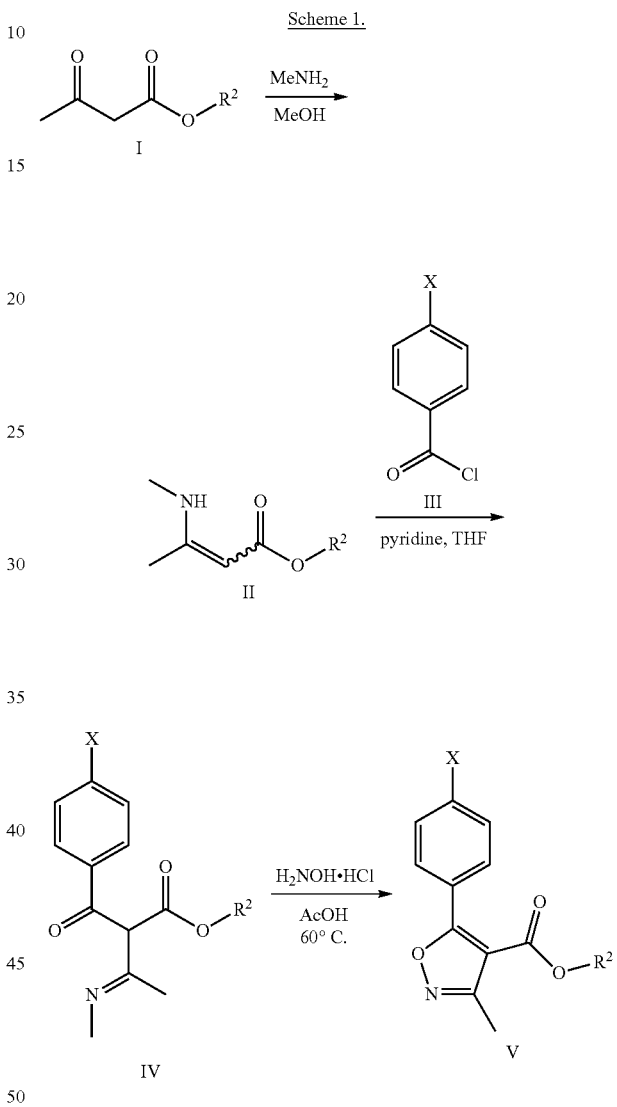

In one aspect, the synthesis of Compound 1 begins with the reaction of an alkyl acetoacetate with methylamine to provide a compound of structure II. Compounds of structure II are reacted with a 4-substituted-benzoyl chloride (structure III) to provide compounds of structure IV. X is halide, triflate or any other suitable leaving group for use in a Suzuki coupling reaction. In some embodiments, X is —Cl, —Br, —I, —OSO$_2$CF$_3$, —OSO$_2$(4-methylphenyl), and —OSO$_2$CH$_3$. In some embodiments, X is a halide. In some embodiments, X is —Br. R$^1$ is an alkyl or benzyl. In some embodiments, R$^2$ is methyl, ethyl, propyl, or benzyl. Other alkyl acetoacetates contemplated include, ethyl acetoacetate, isopropyl acetoacetate, benzyl acetoacetate. Treatment of compounds of structure IV with hydroxyl amine and acetic acid provides isoxazoles of structure V. Isoxazoles of structure V are utilized as outlined in scheme 2.

Scheme 2

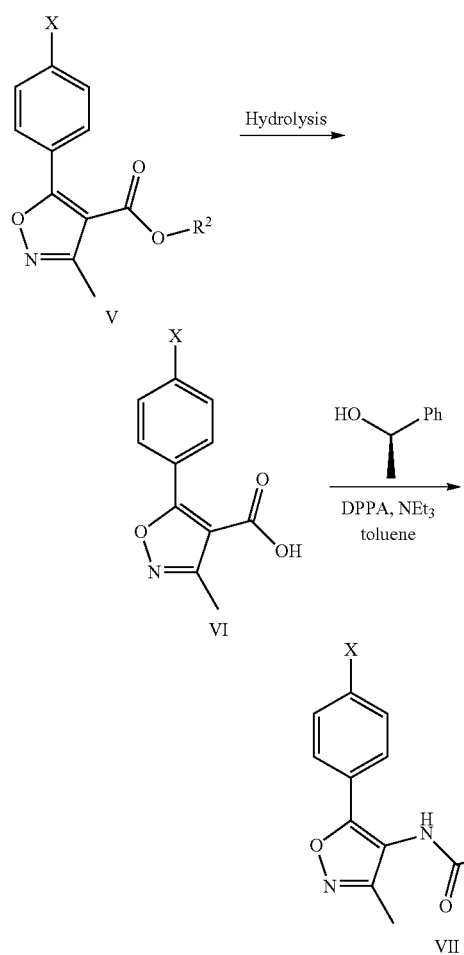

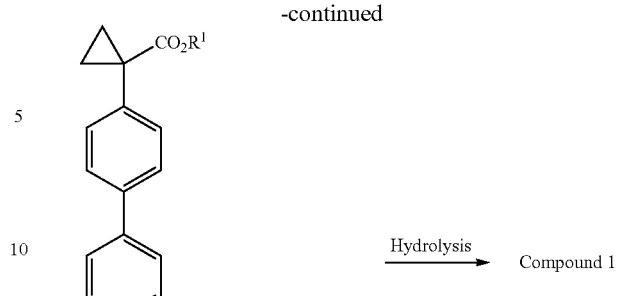

Hydrolysis of the ester group of isoxazoles of structure V provides carboxylic acids of structure VI. Hydrolysis can also be accomplished with the use of suitable bases, such as lithium hydroxide or sodium hydroxide. Suitable solvents for the hydrolysis include water, methanol, ethanol, tetrahydrofuran, or combinations thereof. A Curtius rearrangement of carboxylic acids of structure VI in the presence of (R)-1-phenylethyl alcohol provides carbamate compounds of structure VII.

Scheme 3.

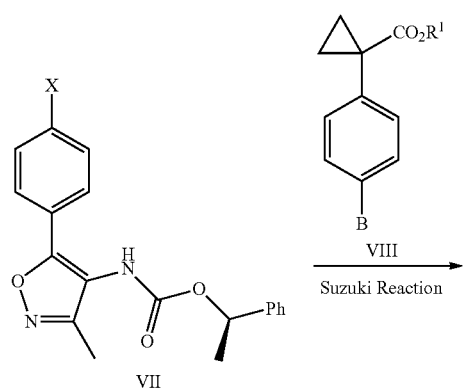

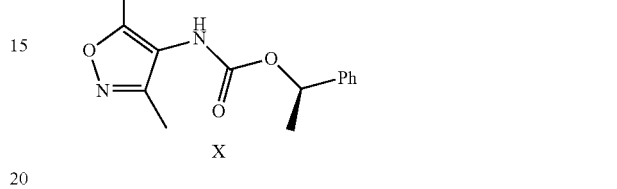

In some embodiments, a Suzuki reaction between compounds of structure VII and compounds of structure VIII is used to provide compounds of structure X. In some embodiments, $R^1$ is an alkyl. In some embodiments, B is boronic acid or boronic ester. In some embodiments, X is

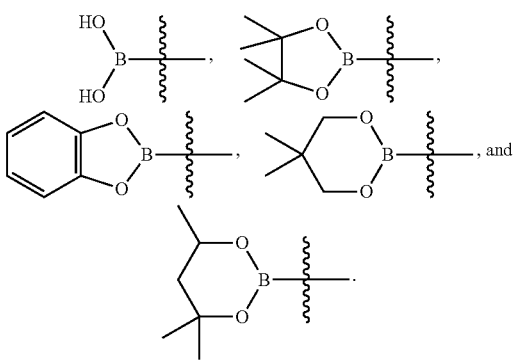

In some embodiments,

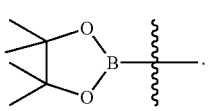

In some embodiments, X is —Cl, —Br, —I, —OSO$_2$CF$_3$, —OSO$_2$(4-methylphenyl), and —OSO$_2$CH$_3$. In some embodiments, X is a halide. In some embodiments, X is —Br. In some embodiments, the Suzuki reaction includes the use of a palladium catalyst, a suitable base and a suitable solvent. In some embodiments, the palladium catalyst is a phosphine containing palladium catalyst. In some embodiments, the palladium catalyst is Pd(PPh$_3$)$_4$ or Pd(dppf)Cl$_2$. In some embodiments, the suitable base for the Suzuki reaction is an inorganic base. In some embodiments, the suitable base for the Suzuki reaction is triethylamine, diisopropylethylamine, 1,2,2,6,6-pentamethylpiperidine, tributylamine, sodium bicarbonate, Na$_2$CO$_3$, K$_2$CO$_3$, Cs$_2$CO$_3$, NaOAc, KOAc, Na$_3$PO$_4$ or K$_3$PO$_4$. Other metal mediated coupling reactions are known for the preparation of compounds of structure X.

Other metal mediated coupling reactions to form biaryls include, but are not limited to Suzuki reactions, Stille cross couplings, Negishi couplings, Kumada couplings, Ullmann reactions, Hiyama Coupling, and variants thereof (Metal-Catalyzed Cross-Coupling Reactions, Armin de Meijere (Editor), François Diederich (Editor), John Wiley & Sons; 2nd edition, 2004; Özdemir, et al., *Tetrahedron*, 2005, 61, 9791-9798; Ackermann, et al., *Org. Lett.*, 2006, 8, 3457-3460; Blakey, et al., *J. Am. Chem. Soc.*, 2003, 125, 6046-6047; Dai, et al., *Org. Lett.*, 2004, 6, 221-224; Yoshikai, et al, *J. Am. Chem. Soc.*, 2005, 127, 17978-17979; Tang, et al, *J. Org. Chem.*, 2006, 71, 2167-2169; Murata, et al., *Synthesis*, 2001, 2231-2233).

In some embodiments, compounds of structure VIII are prepared as outlined in Scheme 4.

Scheme 4.

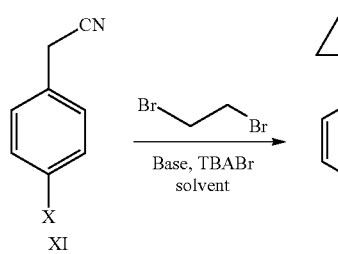

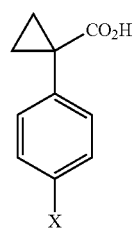

In some embodiments, compounds of structure XI are treated with a dihalo alkyl compound, such as 1,2-dibromoethane, to form a cycloalkyl group. The cyano group is hydrolysed to the acid and an ester is formed from the acid to provide tricyclic compounds of structure XII. In some embodiments, compounds of structure XII are reacted with a borylating agent using transition metal mediated reaction conditions to form boronate compounds of structure VII. In some embodiments, $R^1$ is ethyl. In some embodiments, X is a halide. In some embodiments, X is —Br.

Scheme 5.

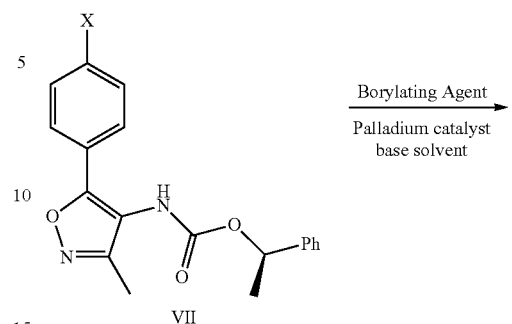

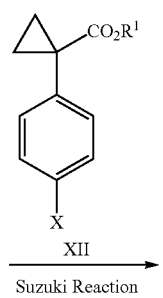

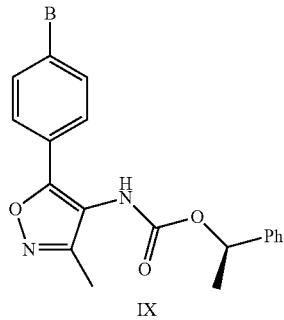

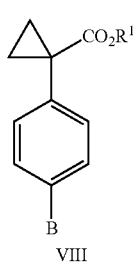

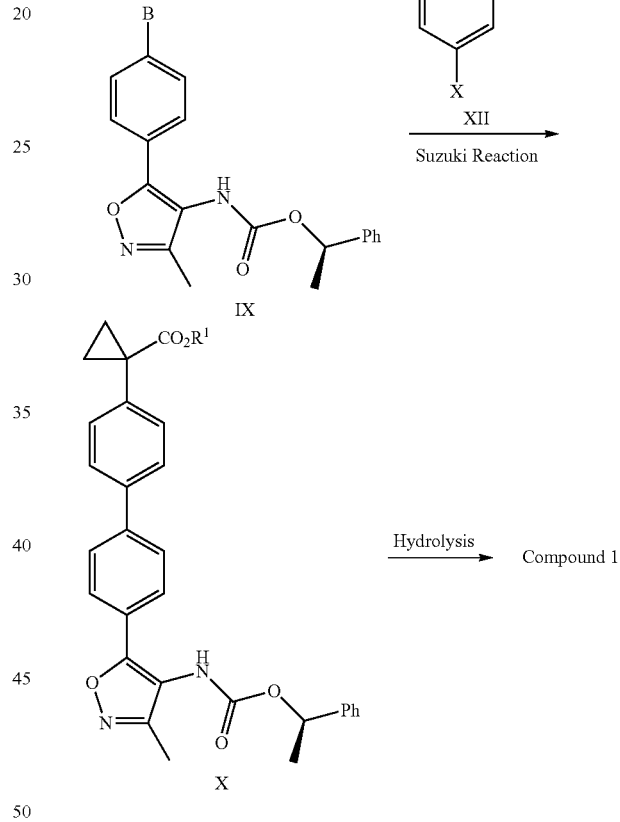

In some embodiments, compounds of structure VII are reacted with a borylating agent using transition metal mediated reaction conditions to form boronate compounds of structure IX. In some embodiments, the borylating reaction to form IX includes the use of a palladium catalyst, such as Pd(PPh$_3$)$_4$ or Pd(dppf)Cl$_2$, in the presence of a suitable base, such as potassium acetate. In some embodiments, the borylation reagent is selected from among pinacolborane, catecholborane, bis(neopentyl glycolato)diboron, bis(pinacolato)diboron, bis(hexylene glycolato)diboron, and bis(catecholato)diboron. In some embodiments, the borylation reagent is bis(pinacolato)diboron. In some embodiments, the borylation reaction is performed with heating. Boronate compounds of structure IX are reacted with compounds of structure XII under palladium mediated coupling conditions (Suzuki reaction conditions) to form compounds of structure X.

In some embodiments, Compound 1 is prepared as described in Scheme 6.

An additional alternative route to the synthesis of compound X is outlined in Scheme 7.

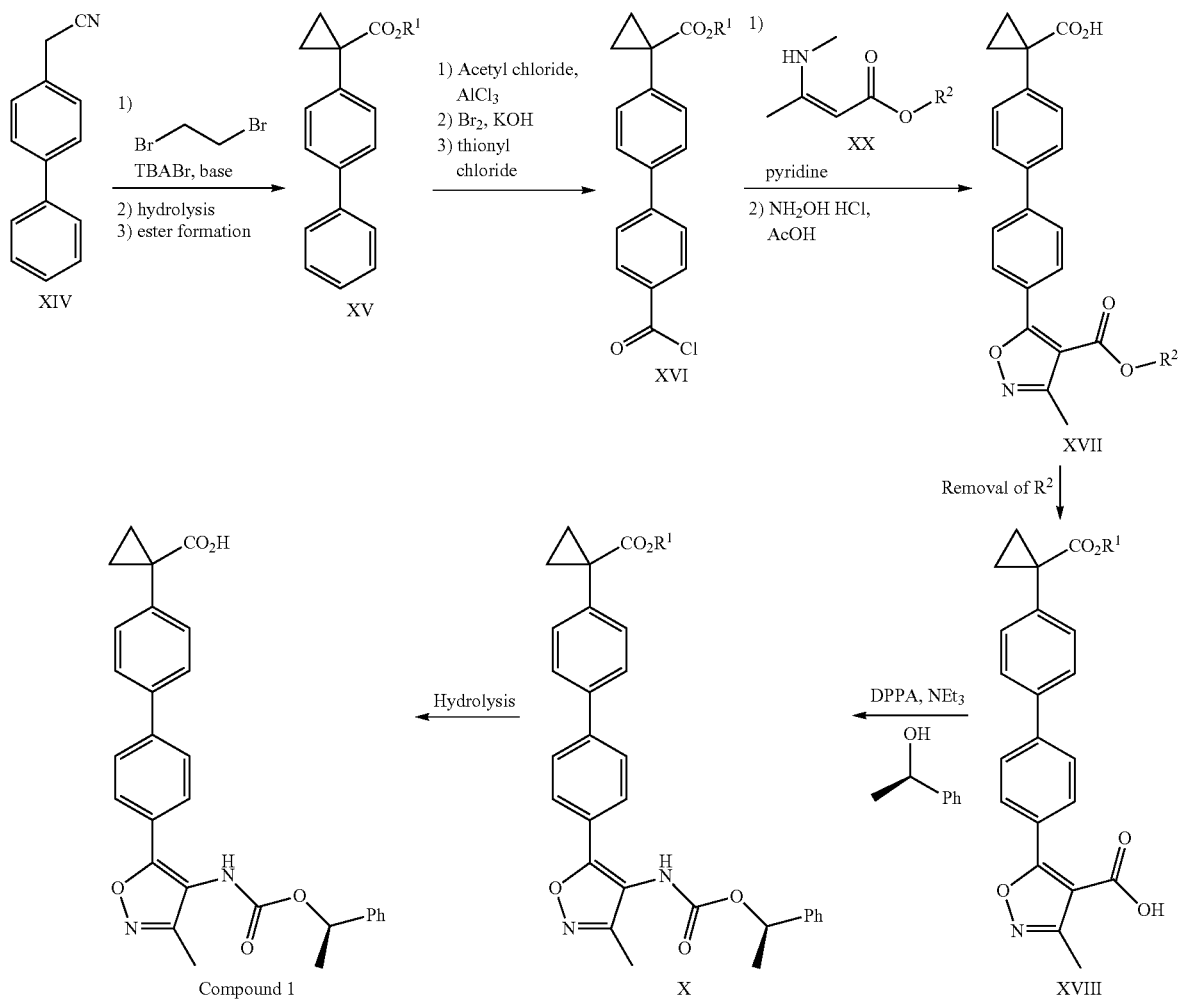

Scheme 6.

In some embodiments, biphenyl compounds of structure XIV are elaborated into the polycyclic Compound 1 as shown in scheme 6. Biphenyl compounds of structure XIV are treated with a dihalo alkyl compound, such as 1,2-dibromoethane, to form a cycloalkyl group. The cyano group is hydrolysed to the acid and an ester is formed from the acid to provide tricyclic compounds of structure XV. In some embodiments, $R^1$ is ethyl. In some embodiments, $R^1$ is isopropyl. Tricyclic compounds of structure XV are then treated with acetyl chloride in the presence of a suitable Lewis acid, follow by conversion of the acetyl group to the carboxylic acid and treatment of the carboxylic acid with thionyl chloride to provide acid chlorides of structure XVI. Acid chlorides of structure XVI are then used to prepare isoxazoles of structure XVII as described in Scheme 1. In some embodiments, $R^2$ is an alkyl group. In some embodiments, $R^2$ is methyl and $R^2$ is removed from isoxazoles of structure XVII under hydrolysis conditions. In some embodiments, $R^2$ is benzyl and $R^2$ is removed from isoxazoles of structure XVII under hydrogenation conditions (e.g. $H_2$, Pd/C). A Curtius rearrangement of carboxylic acids of structure XVIII in the presence of (R)-1-phenylethyl alcohol provides carbamate compounds of structure X.

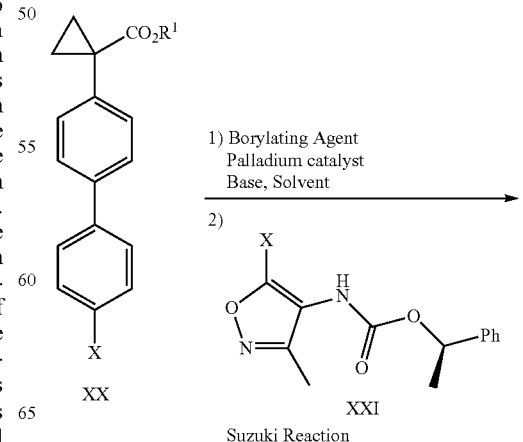

Scheme 7.

Suzuki Reaction

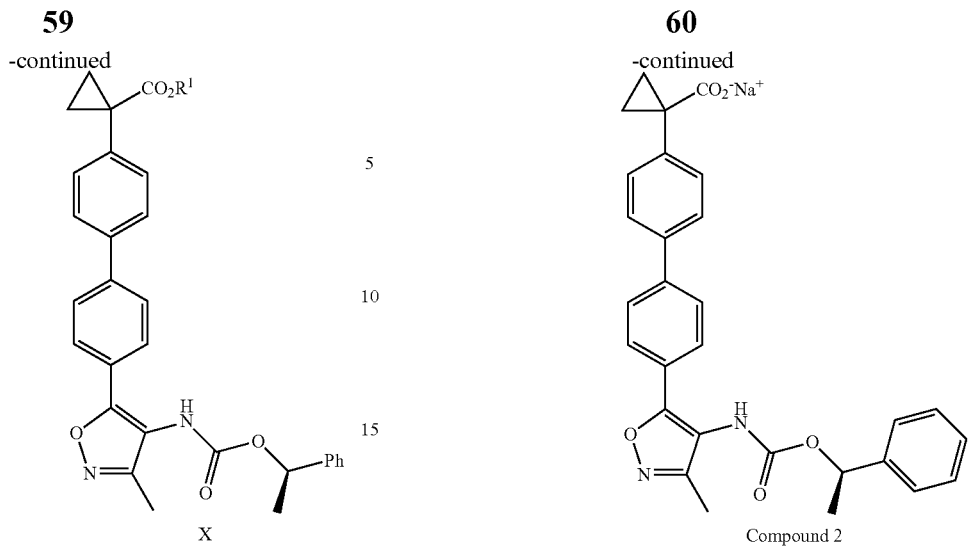

Conversion of the X group in biphenyl compound XX to a boronic acid or boronate ester produces a coupling partner for compound XXI in a Suzuki reaction that provides compound X.

The hydrolysis of the ester group in compound X to provide Compound 1 and Compound 2 is outlined in Scheme 8.

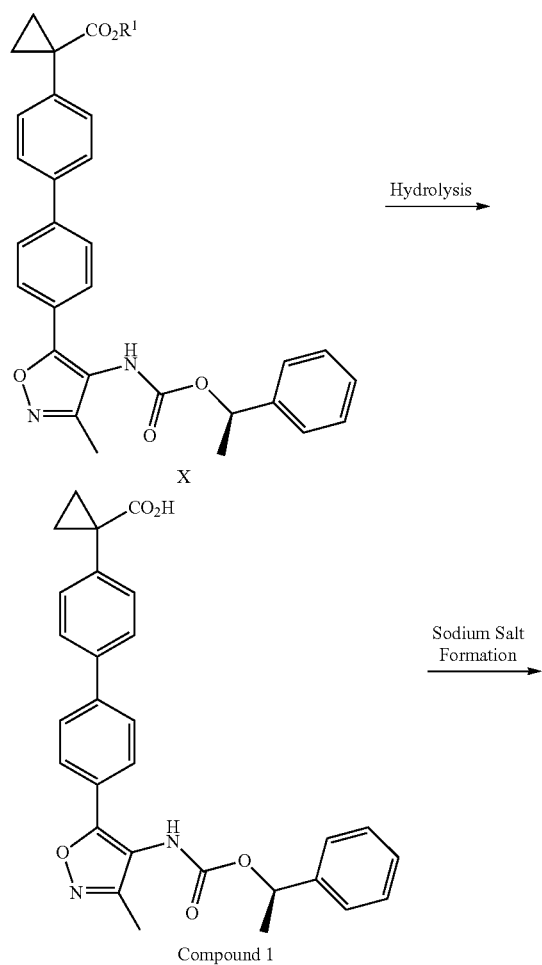

Hydrolysis of alkyl esters of structure X with a suitable base in a suitable solvent yields Compound 1 after pH adjustment. Suitable bases for the hydrolysis include, but are not limited to, lithium hydroxide and sodium hydroxide. Suitable solvents for the hydrolysis include, but are not limited to, water, methanol, ethanol, tetrahydrofuran, or combinations thereof. Compound 1 is then treated with sodium hydroxide in tetrahydrofuran, methanol and water to furnish Compound 2.

In some embodiments, Compound 2 is prepared from compound X by performing a one-step hydrolysis and salt forming reaction. In some embodiments, the one-step hydrolysis and salt forming reaction includes treatment of compound X with sodium hydroxide in a suitable solvent.

In some embodiments, Compound 1 is treated with potassium hydroxide in a solvent to form Compound 1, potassium salt. In some embodiments, Compound 1 is treated with lithium hydroxide in a solvent to form Compound 1, lithium salt. In some embodiments, Compound 1 is treated with calcium hydroxide in a solvent to form Compound 1, calcium salt.

In some embodiments, Compound 1 is treated with dicyclohexylamine in a solvent to form the corresponding salt. In some embodiments, Compound 1 is treated with N-methyl-D-glucamine in a solvent to form the corresponding salt. In some embodiments, Compound 1 is treated with choline in a solvent to form the corresponding salt. In some embodiments, Compound 1 is treated with tris(hydroxymethyl) methylamine in a solvent to form the corresponding salt.

In some embodiments, Compound 1 is treated with arginine in a solvent to form the corresponding salt. In some embodiments, Compound 1 is treated with lysine in a solvent to form the corresponding salt.

In some embodiments, due to the fact that that synthetic methods described above utilize a transition metal catalyst, purification steps are performed to reduce the amount of palladium in the product. Purification steps to reduce the amount of palladium in a product are conducted so that active pharmaceutical ingredients meet palladium specification guidelines. ("Guideline on the Specification Limits for Residues of Metal Catalysts" European Medicines Agency *Pre-authorisation Evaluation of Medicines for Human Use*, London, January 2007, Doc. Ref. CPMP/SWP/QWP/4446/00 corr.). In some embodiments, purification steps to reduce the amount of palladium in a product includes, but is not limited to, treatment with solid trimercaptotriazine (TMT), polystyrene-bound TMT, mercapto-porous polystyrene-bound TMT, polystyrene-bound ethylenediamine, activated carbon, glass bead sponges, Smopex™, silicon dioxide, silica bound scavengers, thiol-derivatized silica gel, N-acetylcysteine, n-Bu$_3$P, crystallization, extraction, 1-cysteine, n-Bu$_3$P/lactic acid. (Garrett et al., Adv. Synth. Catal. 2004, 346, 889-900). In some embodiments, activated carbon includes but is not limited to DARCO® KB-G, DARCO® KB-WJ. In one aspect silica bound scavengers include but are not limited to

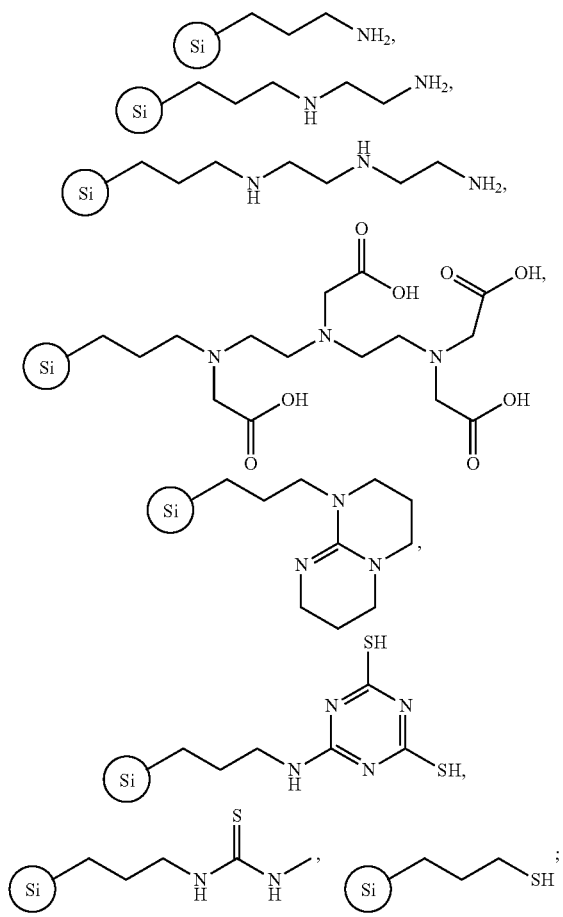

where

denotes silica gel. In some embodiments, the purification steps to reduce the amount of palladium include the use of activated carbon, silica gel, derivatized silica gel (e.g. thiol derivatized silica gel), or combinations thereof.

Although the foregoing schemes exemplified the synthesis with (R)-1-phenylethyl alcohol, the same synthetic procedures could be performed with (S)-1-phenylethyl alcohol or (R/S)-1-phenylethyl alcohol in place of (R)-1-phenylethyl alcohol. In some embodiments, (R)-1-phenylethyl alcohol is optically pure. In some embodiments, (R)-1-phenylethyl alcohol has an enantiomeric excess that of at least 97%, at least 98%, or at least 99%.

In one aspect, Compound 1 is prepared as outlined in the Examples. In one aspect, Compound 2 is prepared as outlined in the Examples Suitable Solvents Therapeutic agents that are administrable to mammals, such as humans, must be prepared by following regulatory guidelines. Such government regulated guidelines are referred to as Good Manufacturing Practice (GMP). GMP guidelines outline acceptable contamination levels of active therapeutic agents, such as, for example, the amount of residual solvent in the final product. Preferred solvents are those that are suitable for use in GMP facilities and consistent with industrial safety concerns. Categories of solvents are defined in, for example, the International Conference on Harmonization of Technical Requirements for Registration of Pharmaceuticals for Human Use (ICH), "Impurities: Guidelines for Residual Solvents, Q3C(R3), (November 2005).

Solvents are categorized into three classes. Class 1 solvents are toxic and are to be avoided. Class 2 solvents are solvents to be limited in use during the manufacture of the therapeutic agent. Class 3 solvents are solvents with low toxic potential and of lower risk to human health. Data for Class 3 solvents indicate that they are less toxic in acute or short-term studies and negative in genotoxicity studies.

Class 1 solvents, which are to be avoided, include: benzene; carbon tetrachloride; 1,2-dichloroethane; 1,1-dichloroethene; and 1,1,1-trichloroethane.

Examples of Class 2 solvents are: acetonitrile, chlorobenzene, chloroform, cyclohexane, 1,2-dichloroethene, dichloromethane, 1,2-dimethoxyethane, N,N-dimethylacetamide, N,N-dimethylformamide, 1,4-dioxane, 2-ethoxyethanol, ethyleneglycol, formamide, hexane, methanol, 2-methoxyethanol, methylbutyl ketone, methylcyclohexane, N-methylpyrrolidine, nitromethane, pyridine, sulfolane, tetralin, toluene, 1,1,2-trichloroethene and xylene.

Class 3 solvents, which possess low toxicity, include: acetic acid, acetone, anisole, 1-butanol, 2-butanol, butyl acetate, tert-butylmethyl ether (MTBE), cumene, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, methylisobutyl ketone, 2-methyl-1-propanol, pentane, 1-pentanol, 1-propanol, 2-propanol, propyl acetate, and tetrahydrofuran.

Residual solvents in active pharmaceutical ingredients (APIs) originate from the manufacture of API. In some cases, the solvents are not completely removed by practical manufacturing techniques. Appropriate selection of the solvent for the synthesis of APIs may enhance the yield, or determine characteristics such as crystal form, purity, and solubility. Therefore, the solvent is a critical parameter in the synthetic process.

In some embodiments, compositions comprising salts of Compound 1 comprise an organic solvent(s). In some embodiments, compositions comprising salts of Compound 1 comprise a residual amount of an organic solvent(s). In some embodiments, compositions comprising salts of Compound 1 comprise a residual amount of a Class 3 solvent. In some embodiments, the organic solvent is a Class 3 solvent. In some embodiments, the Class 3 solvent is selected from the group consisting of acetic acid, acetone, anisole, 1-butanol, 2-butanol, butyl acetate, tert-butylmethyl ether, cumene, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, methylisobutyl ketone, 2-methyl-1-propanol, pentane, 1-pentanol, 1-propanol, 2-propanol, propyl acetate, and tetrahydrofuran. In some embodiments, the Class 3 solvent is selected from ethyl acetate, isopropyl acetate, tert-butylmethylether, heptane, isopropanol, and ethanol.

In some embodiments, the compositions comprising a salt of Compound 1 include a detectable amount of an organic solvent. In some embodiments, the salt of Compound 1 is a sodium salt (i.e. Compound 2). In some embodiments, the organic solvent is a Class 3 solvent.

In one aspect, the salt of Compound 1 is a sodium salt, potassium salt, lithium salt, calcium salt, magnesium salt, ammonium salt, choline salt, protonated dicyclohexylamine salt, protonated N-methyl-D-glucamine salt, protonated tris(hydroxymethyl)methylamine salt, arginine salt, or lysine salt. In one aspect, the salt of Compound 1 is a sodium salt.

In other embodiments are compositions comprising Compound 2, wherein the composition comprises a detectable amount of solvent that is less than about 1%, wherein the solvent is selected from acetone, 1,2-dimethoxyethane, acetonitrile, ethyl acetate, tetrahydrofuran, methanol, ethanol, heptane, and 2-propanol. In a further embodiment are compositions comprising Compound 2, wherein the composition comprises a detectable amount of solvent which is less than about 5000 ppm. In yet a further embodiment are compositions comprising Compound 2, wherein the detectable amount of solvent is less than about 5000 ppm, less than about 4000 ppm, less than about 3000 ppm, less than about 2000 ppm, less than about 1000 ppm, less than about 500 ppm, or less than about 100 ppm.

Certain Terms

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Unless otherwise indicated, conventional methods of mass spectroscopy, NMR, HPLC, protein chemistry, organic synthesis, biochemistry, recombinant DNA techniques and pharmacology, within the skill of the art are employed. In this application, the use of "or" means "and/or" unless stated otherwise. Furthermore, use of the term "including" as well as other forms, such as "include", "includes," and "included," is not limiting.

The term "pharmaceutically acceptable excipient," as used herein, refers to a material, such as a carrier, diluent, stabilizer, dispersing agent, suspending agent, thickening agent, etc. which allows processing the active pharmaceutical ingredient (API) into a form suitable for administration to a mammal. In one aspect, the mammal is a human. Pharmaceutically acceptable excipients refer to materials which do not substantially abrogate the desired biological activity or desired properties of the compound (i.e. API), and is relatively nontoxic, i.e., the material is administered to an individual without causing undesirable biological effects or interacting in a deleterious manner with any of the components of the composition in which it is contained.

"Active pharmaceutical ingredient" or API refers to a compound that possesses a desired biological activity or desired properties. In some embodiments, an API is Compound 1. In some embodiments, an API is Compound 2. Provided herein is an active pharmaceutical ingredient (API), Compound 1, or pharmaceutically acceptable salt thereof (e.g. Compound 2), with a purity of greater than 80%, greater than 85%, greater than 90%, greater than 95%, greater than 96%, greater than 97%, greater than 98%, greater than 98%, or greater than 99%. In specific embodiments, provided herein is an active pharmaceutical ingredient (API), Compound 2, with a purity of greater than 80%, greater than 85%, greater than 90%, greater than 95%, greater than 96%, greater than 97%, greater than 98%, or greater than 99%.

The term "pharmaceutical combination" as used herein, means a product that results from the mixing or combining of more than one active ingredient and includes both fixed and non-fixed combinations of the active ingredients. The term "fixed combination" means that the active ingredients, e.g. Compound 1 or a pharmaceutically acceptable salt, and a co-agent, are both administered to a patient simultaneously in the form of a single entity or dosage. The term "non-fixed combination" means that the active ingredients, e.g. Compound 1 or a pharmaceutically acceptable salt, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The term "pharmaceutical composition" refers to a mixture of Compound 1, or pharmaceutically acceptable salt and/or solvate thereof, with other chemical components, such as carriers, stabilizers, diluents, dispersing agents, suspending agents, thickening agents, excipients, etc. The pharmaceutical composition facilitates administration of the compound to a mammal.

Administration of a combination of agents, as used herein, includes administration of the agents described in a single composition or in a combination therapy wherein one or more agent is administered separately from at least one other agent.

An "alkyl" group refers to an aliphatic hydrocarbon group. The alkyl moiety is branched, straight chain, or cyclic. The alkyl group may be designated as "$C_1$-$C_6$alkyl". In one aspect, an alkyl is selected from methyl, ethyl, propyl, isopropyl, butyl, isobutyl, tert-butyl, pentyl, neopentyl, hexyl, ethenyl, propenyl, allyl, butenyl, cyclopropyl, cyclobutyl, cyclopentyl, cyclohexyl, and the like.

"Detectable amount" refers to an amount that is measurable using standard analytic methods (e.g. ion chromatography, mass spectrometry, NMR, HPLC, gas chromatography, elemental analysis, IR spectroscopy, inductively coupled plasma atomic emission spectrometry, USP<231>Method II, etc) (ICH guidances, *Q2A Text on Validation of Analytical Procedures* (March 1995) and *Q2B Validation of Analytical Procedures: Methodology* (November 1996)).

The term "acceptable" with respect to a formulation, composition or ingredient, as used herein, means having no persistent detrimental effect on the general health of the subject being treated.

The terms "effective amount" or "therapeutically effective amount," as used herein, refer to a sufficient amount of an agent being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. The term "therapeutically effective amount" includes, for example, a prophylactically effective amount. The effective amount will be selected based on the particular patient and the disease level. It is understood that "an effect amount" or "a therapeutically effective amount" varies from subject to subject, due to variation in metabolism of drug, age, weight, general condition of the subject, the condition being treated, the severity of the condition being treated, and the judgment of the prescribing physician. In one embodiment, an appropriate "effective" amount in any individual case is determined using techniques, such as a dose escalation study.

The terms "co-administration" or the like, as used herein, are meant to encompass administration of the selected therapeutic agents to a single patient, and are intended to include treatment regimens in which the agents are administered by the same or different route of administration or at the same or different time.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The terms "kit" and "article of manufacture" are used as synonyms.

A "metabolite" of a compound disclosed herein is a derivative of that compound that is formed when the compound is metabolized. The term "active metabolite" refers to a biologically active derivative of a compound that is formed when the compound is metabolized (biotransformed). The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases (UGT) catalyze the transfer of an activated glucuronic-acid molecule to aromatic alcohols, aliphatic alcohols, carboxylic acids, amines and free sulphydryl groups (e.g. conjugation reactions). In some embodiments, compounds disclosed herein are metabolite to provide taurine metabolites. Further information on metabolism is available in The Pharmacological Basis of Therapeutics, 9th Edition, McGraw-Hill (1996). In one embodiment, metabolites of the compounds disclosed herein are identified either by administration of compounds to a host and analysis of tissue samples from the host, or by incubation of compounds with hepatic cells in vitro and analysis of the resulting compounds.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator," as used herein, refers to a molecule that interacts with a target either directly or indirectly. The interactions include, but are not limited to, the interactions of an agonist and an antagonist.

The term "agonist," as used herein, refers to a molecule such as a compound, a drug, an enzyme activator or a hormone modulator that binds to a specific receptor and triggers a response in the cell. An agonist mimics the action of an endogenous ligand (such as prostaglandin, hormone or neurotransmitter) that binds to the same receptor.

The term "antagonist," as used herein, refers to a molecule such as a compound, which diminishes, inhibits, or prevents the action of another molecule or the activity of a receptor site.

The term "LPA-dependent", as used herein, refers to conditions or disorders that would not occur, or would not occur to the same extent, in the absence of LPA.

The term "LPA-mediated", as used herein, refers to refers to conditions or disorders that might occur in the absence of LPA but can occur in the presence of LPA.

The term "subject" or "patient" encompasses mammals. In one aspect, the mammal is a human. In another aspect, the mammal is a non-human primate such as chimpanzee, and other apes and monkey species. In one aspect, the mammal is a farm animal such as cattle, horse, sheep, goat, or swine. In one aspect, the mammal is a domestic animal such as rabbit, dog, or cat. In one aspect, the mammal is a laboratory animal, including rodents, such as rats, mice and guinea pigs, and the like.

"Bioavailability" refers to the percentage of the weight of Compound 1, or a pharmaceutically acceptable salt and/or solvate thereof, dosed that is delivered into the general circulation of the animal or human being studied. The total exposure ($AUC_{(0-\infty)}$) of a drug when administered intravenously is usually defined as 100% Bioavailable (F %). "Oral bioavailability" refers to the extent to which Compound 1, or a pharmaceutically acceptable salt and/or solvate thereof, is absorbed into the general circulation when the pharmaceutical composition is taken orally as compared to intravenous injection.

"Blood plasma concentration" refers to the concentration Compound 1, in the plasma component of blood of a mammal. It is understood that the plasma concentration of Compound 1 may vary significantly between subjects, due to variability with respect to metabolism and/or interactions with other therapeutic agents. In one aspect, the blood plasma concentration of Compound 1 varies from subject to subject. Likewise, values such as maximum plasma concentration ($C_{max}$) or time to reach maximum plasma concentration ($T_{max}$), or total area under the plasma concentration time curve ($AUC_{(0-\infty)}$) vary from subject to subject. Due to this variability, in one embodiment, the amount necessary to constitute "a therapeutically effective amount" of Compound 1 varies from subject to subject.

"Drug absorption" or "absorption" typically refers to the process of movement of drug from site of administration of a drug across a barrier into a blood vessel or the site of action, e.g., a drug moving from the gastrointestinal tract into the portal vein or lymphatic system.

"Serum concentration" or "Plasma concentration" describes the blood serum or blood plasma concentration, typically measured in mg, μg, or ng of therapeutic agent per ml, dl, or l of blood serum, absorbed into the bloodstream after administration. Plasma concentrations are typically measured in ng/ml or μg/ml.

"Pharmacodynamics" refers to the factors which determine the biologic response observed relative to the concentration of drug at a site of action.

"Pharmacokinetics" refers to the factors which determine the attainment and maintenance of the appropriate concentration of drug at a site of action.

"Steady state," as used herein, is when the amount of drug administered is equal to the amount of drug eliminated within one dosing interval resulting in a plateau or constant plasma drug exposure.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Pharmaceutical Compositions/Formulations

Pharmaceutical compositions are formulated in a conventional manner using one or more physiologically acceptable carriers comprising excipients and auxiliaries which facilitate processing of the active compounds into preparations which are used pharmaceutically. Suitable techniques, carriers, and excipients include those found within, for example, *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999), herein incorporated by reference in their entirety.

A pharmaceutical composition, as used herein, refers to a mixture of a compound of Formula (I) with other chemical components (i.e. pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. The pharmaceutical composition facilitates administration of the compound to an organism.

Pharmaceutical formulations described herein are administerable to a subject in a variety of ways by multiple administration routes, including but not limited to, oral, parenteral (e.g., intravenous, subcutaneous, intramuscular, intramedullary injections, intrathecal, direct intraventricular, intraperitoneal, intralymphatic, intranasal injections), intranasal, buccal, topical or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

In some embodiments, Compound 1, or a pharmaceutically acceptable salt thereof (e.g. Compound 2), is administered orally.

In some embodiments, Compound 1, or a pharmaceutically acceptable salt thereof (e.g. Compound 2), is administered topically. In such embodiments, Compound 1, or a pharmaceutically acceptable salt thereof (e.g. Compound 2), is formulated into a variety of topically administrable compositions, such as solutions, suspensions, lotions, gels, pastes, shampoos, scrubs, rubs, smears, medicated sticks, medicated bandages, balms, creams or ointments. In one aspect, Compound 1, or a pharmaceutically acceptable salt thereof (e.g. Compound 2), is administered topically to the skin.

In another aspect, Compound 1, or a pharmaceutically acceptable salt thereof (e.g. Compound 2), is administered by inhalation.

In another aspect, Compound 1, or a pharmaceutically acceptable salt thereof (e.g. Compound 2), is formulated for intranasal administration. Such formulations include nasal sprays, nasal mists, and the like.

In another aspect, Compound 1, or a pharmaceutically acceptable salt thereof (e.g. Compound 2), is formulated as eye drops.

In any of the aforementioned aspects are further embodiments in which the effective amount of Compound 1, or a pharmaceutically acceptable salt thereof (e.g. Compound 2), is: (a) systemically administered to the mammal; and/or (b) administered orally to the mammal; and/or (c) intravenously administered to the mammal; and/or (d) administered by inhalation to the mammal; and/or (e) administered by nasal administration to the mammal; or and/or (f) administered by injection to the mammal; and/or (g) administered topically to the mammal; and/or (h) administered by ophthalmic administration; and/or (i) administered rectally to the mammal; and/or (j) adminstered non-systemically or locally to the mammal.

In any of the aforementioned aspects are further embodiments comprising single administrations of the effective amount of the compound, including further embodiments in which (i) the compound is administered once; (ii) the compound is administered to the mammal multiple times over the span of one day; (iii) continually; or (iv) continuously.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

In certain embodiments, a compound as described herein is administered in a local rather than systemic manner.

In some embodiments, the compound described herein is administered topically. In some embodiments, the compound described herein is administered systemically.

In some embodiments, for oral administration, Compound 1, or a pharmaceutically acceptably salt thereof (e.g. Compound 2), are formulated by combining the active compound with pharmaceutically acceptable carriers or excipients. Such carriers enable Compound 1, or a pharmaceutically acceptably salt thereof (e.g. Compound 2) to be formulated as tablets, powders, pills, dragees, capsules, liquids, gels, syrups, elixirs, slurries, suspensions and the like, for oral ingestion by a patient to be treated. In some embodiments, for oral administration, Compound 1, or a pharmaceutically acceptably salt thereof (e.g. Compound 2), is formulated without combining the active compound with pharmaceutically acceptable carriers or excipients and is placed directly into a capsule for administration to a mammal.

In some embodiments, the pharmaceutical compositions will include at least one pharmaceutically acceptable carrier, diluent or excipient and Compound 1 as an active ingredient in free-acid or free-base form, or in a pharmaceutically acceptable salt form. In some embodiments, the pharmaceutical compositions will include at least one pharmaceutically acceptable carrier, diluent or excipient and Compound 2.

The pharmaceutical compositions described herein include Compound 1, or a pharmaceutically acceptable salt thereof (e.g. Compound 2). In some embodiments, the pharmaceutical compositions described herein include Compound 1. In some embodiments, the pharmaceutical compositions described herein include amorphous Compound 1. In some embodiments, the pharmaceutical compositions described herein include crystalline Compound 1. In some embodiments, the pharmaceutical compositions described herein include Compound 2. In some embodiments, the pharmaceutical compositions described herein include amorphous Compound 2. In some embodiments, the pharmaceutical compositions described herein include crystalline Compound 2.

In some embodiments, the pharmaceutical compositions described herein include: (a) Compound 1, or a pharmaceutically acceptable salt thereof (e.g. Compound 2); and one or more of the following: (b) binders; (c) disintegrants; (d) fillers (diluents); (e) lubricants; (f) glidants (flow enhancers); (g) compression aids; (h) colors; (i) sweeteners; (j) preservatives; (k) suspending/dispersing agents; (l) film formers/coatings; (m) flavors; (o) printing inks; (p) solubilizers; (q) alkalizing agents; (r) buffering agents; (s) antioxidants; (t) effervescent agents.

In some embodiments, the pharmaceutical compositions described herein include: (a) Compound 1, or a pharmaceutically acceptable salt thereof (e.g. Compound 2); and (b) a capsule shell.

In some embodiments, pharmaceutical compositions described herein include one or more of the following in addition to Compound 1, or a pharmaceutically acceptable salt thereof (e.g. Compound 2): (a) magnesium stearate; (b) lactose; (c) microcrystalline cellulose; (d) silicified microcrystalline cellulose; (e) mannitol; (f) starch (corn); (g) silicon dioxide; (h) titanium dioxide; (i) stearic acid; (j) sodium starch glycolate; (k) gelatin; (l) talc; (m) sucrose; (n) aspartame; (o) calcium stearate; (p) povidone; (q) pregelatinized starch; (r) hydroxy propyl methylcellulose; (s) OPA products (coatings & inks); (t) croscarmellose; (u) hydroxy propyl cellulose; (v) ethylcellulose; (w) calcium phosphate (dibasic); (x) crospovidone; (y) shellac (and glaze); (z) sodium carbonate; (aa) hypromellose.

In one embodiment, pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, silicified microcrystalline cellulose, hydroxypropylmethylcellulose, sodium carboxymethylcellulose; or others such as: polyvinylpyrrolidone (PVP or povidone) or calcium phosphate. If desired, disintegrating agents are added, such as the cross-linked croscarmellose sodium, polyvinylpyrrolidone, agar, or alginic acid or a salt thereof such as sodium alginate.

In one embodiment, the pharmaceutical compositions described herein are formulated into any suitable dosage form, including but not limited to, aqueous oral dispersions, solid oral dosage forms, fast melt formulations, effervescent formulations, lyophilized formulations, tablets, capsules, pills, controlled release formulations, enteric coated tablets, inhaled powder, inhaled dispersion, IV formulations.

In further embodiments, the pharmaceutical compositions provided herein may be provided as compressed tablets, tablet triturates, rapidly dissolving tablets, multiple compressed tablets, or enteric-coated tablets, sugar-coated, or film-coated tablets.

Pharmaceutical dosage forms can be formulated in a variety of methods and can provide a variety of drug release profiles, including immediate release, sustained release, and delayed release. In some cases it may be desirable to prevent drug release after drug administration until a certain amount of time has passed (i.e. timed release), to provide substantially continuous release over a predetermined time period (i.e. sustained release) or to provide release immediately following drug administration (i.e., immediate release).

In some embodiments, formulations provide a therapeutically effective amount of Compound 1, or a pharmaceutically acceptable salt thereof (e.g. Compound 2), enabling, for example, once a week, twice a week, three times a week, four times a week, five times a week, once every other day, once-a-day, twice-a-day (b.i.d.), or three times a day (t.i.d.) administration if desired. In one embodiment, the formulation provides a therapeutically effective amount of Compound 1, or a pharmaceutically acceptable salt thereof (e.g. Compound 2) enabling once-a-day administration.

In one embodiment, Compound 1, or a pharmaceutically acceptable salt thereof (e.g. Compound 2) is formulated into an immediate release form that provides for once-a-day administration. Generally speaking, one will desire to administer an amount of Compound 1, or a pharmaceutically acceptable salt thereof (e.g. Compound 2) that is effective to achieve a plasma level commensurate with the concentrations found to be effective in vivo for a period of time effective to elicit a therapeutic effect.

In some embodiments, Compound 1, or a pharmaceutically acceptable salt thereof (e.g. Compound 2) and one or more excipients are dry blended and compressed into a mass, such as a tablet, having a hardness sufficient to provide a pharmaceutical composition that substantially disintegrates within less than about 10 minutes, less than about 15 minutes, less than about 20 minutes, less than about 25 minutes, less than about 30 minutes, less than about 35 minutes, or less than about 40 minutes, after oral administration, thereby releasing the Compound 1, or a pharmaceutically acceptable salt thereof (e.g. Compound 2) formulation into the gastrointestinal fluid.

In some embodiments, the pharmaceutical compositions provided herein in an immediate release dosage form are capable of releasing not less than 75% of the therapeutically active ingredient or combination and/or meet the disintegration or dissolution requirements for immediate release tablets of the particular therapeutic agents or combination included in the tablet core, as set forth in USP XXII, 1990 (The United States Pharmacopeia) Immediate release pharmaceutical compositions include capsules, tablets, pills, oral solutions, powders, beads, pellets, particles, and the like.

Excipients used in pharmaceutical compositions should be selected on the basis of compatibility with Compound 1, or a pharmaceutically acceptable salt thereof (e.g. Compound 2) and the release profile properties of the desired dosage form. Exemplary excipients include, e.g., binders, suspending agents, disintegration agents, filling agents, surfactants, solubilizers, stabilizers, lubricants, wetting agents, diluents, and the like.

Binders impart cohesiveness to solid oral dosage form formulations: for powder filled capsule formulation, they aid in plug formation that is filled into soft or hard shell capsules and for tablet formulation, they ensure the tablet remaining intact after compression and help assure blend uniformity prior to a compression or fill step.

In some embodiments, the binder(s) are selected from starches, sugars, povidone, cellulose or modified cellulose such as microcrystalline cellulose, hydroxypropyl methyl cellulose, lactose, or sugar alcohols like xylitol, sorbitol or maltitol. In some embodiments, the binder is hydroxypropyl methyl cellulose. In some embodiments, the binder is hypromellose (e.g., Methocel E5).

In general, binder levels of 20-70% are used in powder-filled gelatin capsule formulations. Binder usage level in tablet formulations varies whether direct compression, wet granulation, roller compaction, or usage of other excipients such as fillers which itself acts as moderate binder.

Dispersing agents, and/or viscosity modulating agents include materials that control the diffusion and homogeneity of a drug through liquid media or a granulation method or blend method. In some embodiments, these agents also facilitate the effectiveness of a coating or eroding matrix.

Diluents increase bulk of the composition to facilitate compression or create sufficient bulk for homogenous blend for capsule filling.

The term "disintegrate" includes both the dissolution and dispersion of the dosage form when contacted with gastrointestinal fluid. "Disintegration agents or disintegrants" facilitate the breakup or disintegration of a substance. In some embodiments, one aspect, solid oral dosage forms include up to 15% w/w of disintegrant. In some embodiments, the disintegrant is croscarmellose sodium. In another aspect, the disintegrant is sodium starch glycolate or crospovidone.

Filling agents include compounds such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

In one aspect, the filler is lactose (e.g. monohydrate). In another aspect, the filler is mannitol, or dicalcium phosphate. In another aspect, the filler is mannitol, microcrystalline cellulose, dicalcium phosphate or sorbitol.

Gastrointestinal fluid is the fluid of stomach secretions of a subject or the saliva of a subject after oral administration of a composition described herein, or the equivalent thereof. An "equivalent of stomach secretion" includes, e.g., an in vitro fluid having similar content and/or pH as stomach secretions such as a 1% sodium dodecyl sulfate solution or 0.1N HCl solution in water. In addition, simulated intestinal fluid (USP) is an aqueous phosphate buffer system at pH 6.8.

Lubricants and glidants are compounds that prevent, reduce or inhibit adhesion or friction of materials. In one aspect, solid oral dosage forms include about 0.25% w/w to about 2.5% w/w of lubricant. In another aspect solid oral dosage forms include about 0.5% w/w to about 1.5% w/w of lubricant.

In some embodiments, the solid dosage forms described herein are in the form of a tablet, (including an immediate release tablet, an extended release tablet, a sustained release tablet, a enteric coated tablet, a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder), a capsule (including both soft or hard capsules, e.g., capsules made from animal-derived gelatin or plant-derived HPMC, or "sprinkle capsules"), solid dispersion, multiparticulate dosage forms, pellets, or granules.

In other embodiments, the pharmaceutical formulation is in the form of a powder. In still other embodiments, the pharmaceutical formulation is in the form of a tablet, including but not limited to, an immediate release tablet. Additionally, pharmaceutical formulations described herein are administered as a single dosage or in multiple dosages. In some embodiments, the pharmaceutical formulation is administered in two, or three, or four tablets.

In some embodiments, solid dosage forms, e.g., tablets, effervescent tablets, and capsules, are prepared by mixing Compound 1, or a pharmaceutically acceptable salt thereof (e.g. Compound 2) with one or more pharmaceutical excipients to form a bulk blend composition. When referring to these bulk blend compositions as homogeneous, it is meant that the Compound 1, or a pharmaceutically acceptable salt thereof (e.g. Compound 2) particles are dispersed evenly throughout the composition so that the composition is capable of being readily subdivided into equally effective unit dosage forms, such as tablets, pills, or capsules. In one embodiment, the individual unit dosages also include film coatings, which disintegrate upon oral ingestion or upon contact with diluent. In one embodiment, these formulations are manufactured by conventional techniques.

Conventional techniques include, e.g., one or a combination of methods: (1) dry mixing, (2) direct compression, (3) milling, (4) dry or non-aqueous granulation, (5) wet granulation, or (6) fusion. See, e.g., Lachman et al., *The Theory and Practice of Industrial Pharmacy* (1986). Other methods include, e.g., spray drying, pan coating, melt granulation, granulation, fluidized bed spray drying or coating (e.g., wurster coating), tangential coating, top spraying, tableting, extruding and the like.

Compressed tablets are solid dosage forms prepared by compacting the bulk blend formulations described above. In various embodiments, compressed tablets which are designed to dissolve in the mouth will include one or more flavoring agents. In other embodiments, the compressed tablets will include a film surrounding the final compressed tablet. In some embodiments, the film coating aids in patient compliance (e.g., Opadry® coatings or sugar coating). Film coatings comprising Opadry® typically range from about 1% to about 5% of the tablet weight. In other embodiments, the compressed tablets include one or more excipients.

Provided herein are pharmaceutical compositions in film-coated dosage forms, which comprise a combination of an active ingredient, or a pharmaceutically acceptable salt, solvate, or prodrug thereof; and one or more tabletting excipients to form a tablet core using conventional tabletting processes and subsequently coating the core. The tablet cores can be produced using conventional granulation methods, for example wet or dry granulation, with optional comminution of the granules and with subsequent compression and coating.

Further provided herein are pharmaceutical compositions in enteric coated dosage forms, which comprise a combination of an active ingredient, or a pharmaceutically acceptable salt, solvate, or prodrug thereof; and one or more release controlling excipients for use in an enteric coated dosage form. The pharmaceutical compositions also comprise non-release controlling excipients.

Enteric-coatings are coatings that resist the action of stomach acid but dissolve or disintegrate in the intestine.

In one aspect, the oral solid dosage form disclosed herein include an enteric coating(s). Enteric coatings include one or more of the following: cellulose acetate phthalate; methyl acrylate-methacrylic acid copolymers; cellulose acetate succinate; hydroxy propyl methyl cellulose phthalate; hydroxy propyl methyl cellulose acetate succinate (hypromellose acetate succinate); polyvinyl acetate phthalate (PVAP); methyl methacrylate-methacrylic acid copolymers; methacrylic acid copolymers, cellulose acetate (and its succinate and phthalate version); styrol maleic acid co-polymers; polymethacrylic acid/acrylic acid copolymer; hydroxyethyl ethyl cellulose phthalate; hydroxypropyl methyl cellulose acetate succinate; cellulose acetate tetrahydrophtalate; acrylic resin; shellac.

An enteric coating is a coating put on a tablet, pill, capsule, pellet, bead, granule, particle, etc. so that it doesn't dissolve until it reaches the small intestine.

Sugar-coated tablets are compressed tablets surrounded by a sugar coating, which may be beneficial in covering up objectionable tastes or odors and in protecting the tablets from oxidation.

Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets. In some embodiments, tablets are coated with water soluble, pH independent film coating which allows for immediate disintegration for fast, active release (e.g. Opadry products).

In some embodiments, the pharmaceutical compositions provided herein are in the form of a controlled release dosage form. As used herein, the term "controlled release" refers to a dosage form in which the rate or place of release of the active ingredient(s) is different from that of an immediate dosage form when orally administered. Controlled release dosage forms include delayed-, extended-, prolonged-, sustained-, pulsatile-, modified-, targeted-, programmed-release. The pharmaceutical compositions in controlled release dosage forms are prepared using a variety of modified release devices and methods including, but not limited to, matrix controlled release devices, osmotic controlled release devices, multiparticulate controlled release devices, ion-exchange resins, enteric coatings, multilayered coatings, and combinations thereof. The release rate of the active ingredient(s) can also be modified by varying the particle sizes.

In contrast to immediate release compositions, controlled release compositions allow delivery of an agent to a human over an extended period of time according to a predetermined profile. Such release rates can provide therapeutically effective levels of agent for an extended period of time and thereby provide a longer period of pharmacologic response. Such longer periods of response provide for many inherent benefits that are not achieved with the corresponding immediate release preparations. In one aspect, controlled release compositions of Compound 1, or a pharmaceutically acceptable salt thereof, provide therapeutically effective levels of Compound 1 for an extended period of time and thereby provide a longer period of pharmacologic response.

Delayed release as used herein refers to the delivery so that the release can be accomplished at some generally predictable location in the intestinal tract more distal to that which would have been accomplished if there had been no delayed release alterations. In some embodiments the method for delay of release is coating. Any coatings should be applied to a sufficient thickness such that the entire coating does not dissolve in the gastrointestinal fluids at pH below about 5, but does dissolve at pH about 5 and above.

In some embodiments, the pharmaceutical compositions provided herein is in a modified release dosage form that is fabricated using a matrix controlled release device (see, Takada et al in "Encyclopedia of Controlled Drug Delivery," Vol. 2, Mathiowitz ed., Wiley, 1999).

In one embodiment, the pharmaceutical compositions provided herein in a modified release dosage form is formulated using an erodible matrix device, which is water-swellable, erodible, or soluble polymers, including synthetic polymers, and naturally occurring polymers and derivatives, such as polysaccharides and proteins.

In some embodiments, a matrix controlled release system includes an enteric coating so that no drug is released in the stomach.

The pharmaceutical compositions provided herein may be provided in unit-dosage forms or multiple-dosage forms. Unit-dosage forms, as used herein, refer to physically discrete units suitable for administration to human and animal subjects and packaged individually as is known in the art. Each unit-dose contains a predetermined quantity of the active ingredient(s) sufficient to produce the desired therapeutic effect, in association with the required pharmaceutical carriers or excipients. Examples of unit-dosage forms include individually packaged tablets and capsules. Unit-dosage forms may be administered in fractions or multiples thereof. A multiple-dosage form is a plurality of identical unit-dosage forms packaged in a single container to be administered in segregated unit-dosage form. Examples of multiple-dosage forms include bottles of tablets or capsules.

In other embodiments a powder comprising the Compound 1, or a pharmaceutically acceptable salt thereof (e.g. Compound 2) formulations described herein are formulated to include one or more pharmaceutical excipients and flavors. Additional embodiments also comprise a suspending agent and/or a wetting agent. This bulk blend is uniformly subdivided into unit dosage packaging or multi-dosage packaging units. The term "uniform" means the homogeneity of the bulk blend is substantially maintained during the packaging process.

In still other embodiments, effervescent powders are prepared. Effervescent salts have been used to disperse medicines in water for oral administration. Effervescent salts are granules or coarse powders containing a medicinal agent in a dry mixture, usually composed of sodium bicarbonate, citric acid and/or tartaric acid.

The method of preparation of the effervescent granules described herein employs three basic processes: wet granulation, dry granulation and fusion. The fusion method is used for the preparation of most commercial effervescent powders. It should be noted that, although these methods are intended for the preparation of granules, the formulations of effervescent salts described herein, in one embodiment, are also prepared as tablets, according to technology for tablet preparation.

In one embodiment, pharmaceutical preparations which are used orally include push-fit capsules made of gelatin, as well as soft, sealed capsules made of gelatin and a plasticizer, such as glycerol or sorbitol. In one embodiment, the push-fit capsules contain the active ingredients in admixture with filler such as lactose, binders such as starches, and/or lubricants such as talc or magnesium stearate and, optionally, stabilizers. In one embodiment, the push-fit capsules contain the active ingredient only without additional inactive ingredients. In one embodiment, in soft capsules, the active compounds are dissolved or suspended in suitable liquids, such as fatty oils, liquid paraffin, or liquid polyethylene glycols. In addition, in one embodiment, stabilizers are added. In other embodiments, the formulation is placed in a sprinkle capsule, wherein the capsule is swallowed whole or the capsule is opened and the contents sprinkled on food prior to eating.

All formulations for oral administration should be in dosages suitable for such administration.

In some embodiments, pharmaceutical formulations are provided comprising Compound 1, or a pharmaceutically acceptable salt thereof (e.g. Compound 2) and at least one dispersing agent or suspending agent for oral administration to a subject. In one embodiment, the formulation is a powder and/or granules for suspension, and upon admixture with water, a substantially uniform suspension is obtained.

A suspension is "substantially uniform" when it is mostly homogenous, that is, when the suspension is composed of approximately the same concentration of Compound 1, or a pharmaceutically acceptable salt thereof (e.g. Compound 2) at any point throughout the suspension (USP Chapter 905).

Liquid formulation dosage forms for oral administration are aqueous suspensions or non-aqueous suspensions.

Liquid formulation dosage forms for oral administration are aqueous suspensions selected from, but not limited to, pharmaceutically acceptable aqueous oral dispersions, emulsions, solutions, and syrups. See, e.g., Singh et al., *Encyclopedia of Pharmaceutical Technology*, $2^{nd}$ Ed., pp. 754-757 (2002). In addition to including Compound 1, or a pharmaceutically acceptable salt thereof (e.g. Compound 2), the liquid dosage forms include additives, such as: (a) disintegrating agents; (b) dispersing agents; (c) wetting agents; (d) preservatives; (e) viscosity enhancing agents; (f) sweetening agents; (g) flavoring agents; (h) solibizing agents (bioavailability enhancers).

In one embodiment, the aqueous suspensions and dispersions described herein remain in a homogenous state, as defined above by USP Chapter 905, for at least 4 hours.

Liquid compositions illustratively take the form of a liquid where the agent (e.g. Compound 1, or a pharmaceutically acceptable salt thereof (e.g. Compound 2)) is present in solution, in suspension or both. In one embodiment, the liquid composition is aqueous.

Liquid compositions illustratively take the form of a liquid where the agent (e.g. Compound 1, or a pharmaceutically acceptable salt thereof (e.g. Compound 2)) is present in solution, in suspension or both. In one embodiment, the liquid composition is non-aqueous.

In one embodiment, the aqueous suspension also contains one or more polymers as suspending agents. Useful polymers include water-soluble polymers such as cellulosic polymers, e.g., hydroxypropyl methylcellulose, and water-insoluble polymers such as cross-linked carboxyl-containing polymers. In one embodiment, useful compositions also comprise an mucoadhesive polymer, selected for example from carboxymethylcellulose, carbomer (acrylic acid polymer), poly(methylmethacrylate), polyacrylamide, polycarbophil, acrylic acid/butyl acrylate copolymer, sodium alginate and dextran.

In one embodiment, pharmaceutical compositions also include one or more pH adjusting agents or buffering agents, including acids such as acetic, boric, citric, lactic, phosphoric and hydrochloric acids; bases such as sodium hydroxide, sodium phosphate, sodium borate, sodium carbonate, sodium citrate, sodium acetate, sodium lactate and tris-hydroxymethylaminomethane; and buffers such as citrate/dextrose, sodium carbonate, sodium bicarbonate and ammonium chloride. Such acids, bases and buffers are included in an amount required to maintain pH of the composition in an acceptable range.

In one embodiment, liquid pharmaceutical compositions also include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

In one embodiment, pharmaceutical compositions also include one or more preservatives to inhibit microbial activity.

Still other compositions include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Still other compositions include one or more antioxidants to enhance chemical stability where required. Suitable antioxidants include, by way of example only, ascorbic acid, tocopherol, and sodium metabisulfite.

In one embodiment, aqueous compositions are packaged in single-dose non-reclosable containers. Alternatively, multiple-dose reclosable containers are used, in which case it is typical to include a preservative in the composition.

In some embodiments, aqueous pharmaceutical compositions do not include a preservative and are used within 24 hours of preparation.

In some embodiments, aqueous pharmaceutical compositions include one or more solubilizers which aid in enhancing the bioavailability of the active pharmaceutical ingredient. In some embodiments, the solubilizer is selected from Labrasol, Lutrol (macrogels, poloxamers), and others known in the art.

The oral pharmaceutical solutions described herein are beneficial for the administration to infants (less than 2 years old), children under 10 years of age and any patient group that is unable to swallow or ingest solid oral dosage forms.

For buccal or sublingual administration, in one embodiment, the compositions take the form of tablets, lozenges, or gels formulated in a conventional manner (see e.g. U.S. Pat. Nos. 4,229,447, 4,596,795, 4,755,386, and 5,739,136).

In one embodiment, dragee cores are prepared with suitable coatings. For this purpose, concentrated sugar solutions are used, which optionally contain gum arabic, talc, polyvinylpyrrolidone, carbopol gel, polyethylene glycol, and/or titanium dioxide, lacquer solutions, and suitable organic solvents or solvent mixtures. In one embodiment, dyestuffs or pigments are added to the tablets or dragee coatings for identification or to characterize different combinations of active compound doses.

It should be understood that many carriers and excipients may serve several functions, even within the same formulation.

In some embodiments, Compound 1, or a pharmaceutically acceptable salt thereof (e.g. Compound 2) is formulated in the form of a pharmaceutical composition that is suitable for inhalation/nasal delivery. In some embodiments, the pharmaceutical composition is in the form of a solution, suspension, emulsion, colloidal dispersion, spray, dry powder, aerosol, or combinations thereof. In some embodiments, the pharmaceutical composition comprises at least one pharmaceutically acceptable excipient that is commonly used in nasal/inhalable pharmaceutical compositions. In some embodiments, the pharmaceutical composition is administered with an atomizer, an insufflator, a nebulizer, a vaporizer, or a metered dose inhaler. In some embodiments, the pharmaceutical composition is inhaled nasally or orally. In some embodiments, crystalline Compound 1 is used in the pharmaceutical composition. In some embodiments, crystalline Compound 2 is used in the pharmaceutical composition. In some embodiments, amorphous Compound 1 is used in the pharmaceutical composition. In some embodiments, amorphous Compound 2 is used in the pharmaceutical composition.

Representative nasal/inhalation formulations are described in, for example, Ansel, H. C. et al., Pharmaceutical Dosage Forms and Drug Delivery Systems, Sixth Ed. (1995); REMINGTON: THE SCIENCE AND PRACTICE OF PHARMACY, 21st edition, 2005.

In some embodiments, Compound 1, or a pharmaceutically acceptable salt thereof (e.g. Compound 2) is formulated in the form of a nasal spray, nasal mist, and the like.

For administration by inhalation, Compound 1, or a pharmaceutically acceptable salt thereof (e.g. Compound 2) is formulated for use as an aerosol, a mist or a powder.

In some embodiments, pharmaceutical compositions suitable for nasal/inhalation administration are conveniently delivered in the form of an aerosol spray presentation from pressurized packs or a nebuliser, with the use of a suitable propellant. Capsules and cartridges for use in an inhaler or insufflator may be formulated containing a powder mix of the compound described herein and a suitable powder base such as lactose or starch.

In some embodiments, the pharmaceutical composition is in the form of a powder for nasal/inhalation delivery to a mammal. In some embodiments, powders comprise micronized and/or nano-sized particles of Compound 1, or a pharmaceutically acceptable salt thereof (e.g. Compound 2), blended with larger carrier particles that prevent aggregation. For example, in one embodiment a dry powder formulation is prepared as follows: Compound 1 or a pharmaceutically acceptable salt thereof (e.g. Compound 2) is jet milled. Lactose is jet milled and the two ingredients are mixed and the final mixture is packaged in sterile insufflators. In some instances powder inhalable formulations described herein comprise crystalline particles of Compound 1. In some instances powder inhalable formulations described herein comprise crystalline particles of Compound 2. In some embodiments, powder inhalable formulations described herein comprise amorphous particles of Compound 1. In some embodiments, powder inhalable formulations described herein comprise amorphous particles of Compound 2.

In some embodiments, Compound 1, or a pharmaceutically acceptable salt thereof (e.g. Compound 2), is prepared as transdermal dosage forms. In one embodiment, the transdermal formulations described herein include at least three components: (1) a formulation of Compound 1, or a pharmaceutically acceptable salt thereof (e.g. Compound 2); (2) a penetration enhancer; and (3) an aqueous adjuvant. In some embodiments the transdermal formulations include additional components such as, but not limited to, gelling agents, creams and ointment bases, and the like. In some embodiments, the transdermal formulation further include a woven or non-woven backing material to enhance absorption and prevent the removal of the transdermal formulation from the skin. In other embodiments, the transdermal formulations described herein can maintain a saturated or supersaturated state to promote diffusion into the skin.

In one aspect, formulations suitable for transdermal administration of compounds described herein employ transdermal delivery devices and transdermal delivery patches and can be lipophilic emulsions or buffered, aqueous solutions, dissolved and/or dispersed in a polymer or an adhesive. In one aspect, such patches are constructed for continuous, pulsatile, or on demand delivery of pharmaceutical agents. Still further, transdermal delivery of the compounds described herein can be accomplished by means of iontophoretic patches and the like. In one aspect, transdermal patches provide controlled delivery of the active compound. In one aspect, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

In one aspect, Compound 1, or a pharmaceutically acceptable salt thereof (e.g. Compound 2), is formulated into a pharmaceutical composition suitable for intramuscular, subcutaneous, or intravenous injection. In one aspect, formulations suitable for intramuscular, subcutaneous, or intravenous injection include physiologically acceptable sterile aqueous or non-aqueous solutions, dispersions, suspensions or emulsions, and sterile powders for reconstitution into sterile injectable solutions or dispersions. Proper fluidity can be maintained, for example, by the use of a coating such as lecithin, by the maintenance of the required particle size in the case of dispersions, and by the use of surfactants. In some embodiments, formulations suitable for subcutaneous injection also contain additives such as preserving, wetting, emulsifying, and dispensing agents. In some cases it is desirable to include isotonic agents, such as sugars, sodium chloride, and the like. Prolonged absorption of the injectable pharmaceutical form can be brought about by the use of agents delaying absorption, such as aluminum monostearate and gelatin.

For intravenous injections, compounds described herein are formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art. For other parenteral injections, appropriate formulations include aqueous or nonaqueous solutions, preferably with physiologically compatible buffers or excipients. Such excipients are known.

Parenteral injections may involve bolus injection or continuous infusion. Formulations for injection may be presented in unit dosage form, e.g., in ampoules or in multi-dose containers, with an added preservative. The pharmaceutical composition described herein may be in a form suitable for parenteral injection as a sterile suspensions, solutions or emulsions in oily or aqueous vehicles, and may contain formulatory agents such as suspending, stabilizing and/or dispersing agents. In one aspect, the active ingredient is in powder form for constitution with a suitable vehicle, e.g., sterile pyrogen-free water, before use.

In some embodiments, Compound 1, or a pharmaceutically acceptable salt thereof (e.g. Compound 2), is administered topically and can be formulated into a variety of topically administrable compositions, such as solutions, suspensions, lotions, gels, pastes, medicated sticks, balms, creams or ointments. Such pharmaceutical compounds can contain solubilizers, stabilizers, tonicity enhancing agents, buffers and preservatives.

In some embodiments, Compound 1, or a pharmaceutically acceptable salt thereof (e.g. Compound 2), is administered topically and can be formulated into a variety of topically administrable compositions, such as solutions, suspensions, lotions, gels, pastes, medicated sticks, balms, creams or ointments.

Dose Amounts of Compound 1 or a Pharmaceutically Acceptable Salt Thereof (e.g. Compound 2)

In certain embodiments, the effective amount of Compound 1, or a pharmaceutically acceptable salt thereof (e.g. Compound 2) is about 1 mg to about 2 g per dose, about 1 mg to about 1.5 g per dose, about 5 mg to about 1500 mg per dose or about 10 mg to about 1500 mg per dose. In some embodiments, the effective amount of Compound 1, or a pharmaceutically acceptable salt thereof (e.g. Compound 2) is about 1 mg to about 5 g per day, about 5 mg to about 2 g per day, about 5 mg to about 1.5 g per day, about 10 mg to about 1.5 g per day, or about 10 mg to about 1 g per day.

In one embodiment, the effective amount of Compound 1, or a pharmaceutically acceptable salt thereof (e.g. Compound 2) is about 5 mg per dose, about 10 mg per dose, about 15 mg per dose, about 20 mg per dose, about 25 mg per dose, about 50 mg per dose, about 100 mg per dose, about 150 mg per dose, about 200 mg per dose, about 250 mg per dose, about 300 mg per dose, about 350 mg per dose, about 400 mg per dose, about 450 mg per dose, about 500 mg per dose, about 550 mg per dose, about 600 mg per dose, about 650 mg per dose, about 700 mg per dose, about 750 mg per dose, about 800 mg per dose, about 850 mg per dose, about 900 mg per dose, about 1000 mg per dose or about 1500 mg per dose.

In some embodiments, oral pharmaceutical solutions include about 0.0.01 mg/ml to about 10 mg/ml of Compound 2. In some embodiments, oral pharmaceutical solutions include about 1 mg/ml to about 10 mg/ml of Compound 2.

In one aspect, immediate release tablets include about 5% w/w to about 50% w/w of Compound 1, or a pharmaceutically acceptable salt thereof (e.g. Compound 2). In some embodiments, immediate release tablets include about 5% w/w to about 40% w/w, or about 5% w/w to about 30% w/w of Compound 1, or a pharmaceutically acceptable salt thereof (e.g. Compound 2). In some embodiments, immediate release tablets include about 5% w/w, about 10% w/w, about 15% w/w, about 20% w/w, about 25% w/w, about 30% w/w, about 33% w/w, about 35% w/w, about 40% w/w of Compound 1, or a pharmaceutically acceptable salt thereof (e.g. Compound 2).

In one aspect, immediate release capsules include about 1.25% w/w to about 50% w/w of Compound 1, or a pharmaceutically acceptable salt thereof (e.g. Compound 2). In some embodiments, immediate release capsules include Compound 1, or a pharmaceutically acceptable salt thereof (e.g. Compound 2) and the capsule shell only.

Methods of Dosing and Treatment Regimens

In one embodiment, the pharmaceutical compositions including Compound 1, or a pharmaceutically acceptable salt thereof (e.g. Compound 2), described herein is administered for prophylactic and/or therapeutic treatments. In therapeutic applications, the compositions are administered to a patient already suffering from a disease or condition, in an amount sufficient to cure or at least partially arrest at least one of the symptoms of the disease or condition. In certain embodiments, amounts effective for this use depend on the severity and course of the disease or condition, previous therapy, the patient's health status, weight, and response to the drugs, and/or the judgment of the treating physician.

In prophylactic applications, compositions containing Compound 1, or a pharmaceutically acceptable salt thereof (e.g. Compound 2), described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in a patient, effective amounts for this use will depend on the severity and course of the disease, disorder or condition, previous therapy, the patient's health status and response to the drugs, and the judgment of the treating physician.

In certain embodiments, administration of the compound, compositions or therapies as described herein includes chronic administration. In certain embodiments, chronic administration includes administration for an extended period of time, including, e.g., throughout the duration of the patient's life in order to ameliorate or otherwise control or limit the symptoms of the patient's disease or condition. In some embodiments, chronic administration includes daily administration.

In some embodiments, administration of the compounds, compositions or therapies described herein is given continuously. In alternative embodiments, the dose of drug being administered is temporarily reduced or temporarily suspended for a certain length of time (i.e., a "drug holiday"). The length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, and 365 days. The dose reduction during a drug holiday is from 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

In some embodiments, Compound 1, or a pharmaceutically acceptable salt thereof (e.g. Compound 2) is administered once a day to a mammal in need thereof. In some embodiments, Compound 1, or a pharmaceutically acceptable salt thereof (e.g. Compound 2) is administered twice a day to a mammal in need thereof. In some embodiments, Compound 1, or a pharmaceutically acceptable salt thereof (e.g. Compound 2) is administered three times a day to a mammal in need thereof.

In some embodiments, the compounds, compositions or therapies described herein are administered in at least one priming dose, followed by at least one maintenance dose. In certain embodiments, a priming dose of the agent(s) is administered until the symptoms of the disorder, disease or condition treated have been reduced (e.g., to a satisfactory level). Upon reduction, a maintenance dose of the compounds, compositions or therapies described herein is administered if desired or if necessary. In some embodiments, the maintenance dose comprises administration of the agent(s) described herein in an amount sufficient to at least partially maintain the reduction achieved by administration of the priming dose. In various embodiments, the maintenance dose, compared to the priming dose, includes a decrease in dosage and/or frequency of administration of the agent or one or more of the agents administered in the method. In certain embodiments, however, intermittent treatment with increased frequency and/or dosage amounts may be necessary upon any recurrence of symptoms.

In certain embodiments, the amount of a given agent that corresponds to a priming or maintenance amount varies depending upon factors including, by way of non-limiting example, the specific agent(s) utilized, the disease condition and its severity, the identity (e.g., weight) of the subject or host in need of treatment, and/or the route of administration. In various embodiments, the desired dose is conveniently presented in a single dose or in divided doses administered simultaneously (or over a short period of time) or at appropriate intervals, for example as two, three, four or more sub-doses per day.

Pharmacokinetic and Pharmacodynamic Analysis

In one embodiment, any standard pharmacokinetic protocol is used to determine blood plasma concentration profile in humans following administration of a formulation described herein (that include Compound 1, or a pharmaceutically acceptable salt thereof (e.g. Compound 2)). For example, a randomized single-dose crossover study is performed using a group of healthy adult human subjects. The number of subjects is sufficient to provide adequate control of variation in a statistical analysis, and is typically about 10 or greater, although for certain purposes a smaller group suffices. Each subject receives administration at time zero a single dose of a formulation of Compound 1, or a pharmaceutically acceptable salt thereof (e.g. Compound 2), normally at around 8 am following an overnight fast. The subjects continue to fast and remain in an upright position for about 2 hours after administration of the formulation. Blood samples are collected from each subject prior to administration (e.g., 15 minutes) and at several intervals after administration. In certain instances, several samples are taken within the first hour and taken less frequently thereafter. Illustratively, blood samples are collected at 0 (pre-dose), 0.25, 0.5, 1, 2, 3, 4, 6, 8, 12, and 16 hours after administration and, 24, 36, 48, 60 and 72 hours after administration. If the same subjects are to be used for study of a second test formulation, a period of at least 10 days should elapse before administration of the second formulation. Plasma is separated from the blood samples by centrifugation and the separated plasma is analyzed for Compound 1 by a validated high performance liquid chromatography/tandem weight spectrometry (LC/APCI-MS/MS) procedure such as, for example, Ramu et al., *Journal of Chromatography B*, 751 (2001) 49-59).

Any formulation giving the desired pharmacokinetic profile is suitable for administration according to the present methods.

Patient Selection

In any of the aforementioned aspects involving the prevention or treatment of LPA-mediated diseases or conditions are further embodiments comprising identifying patients by screening for LPA receptor gene SNPs. A SNP located in the promoter region of $LPA_1$ showed significant association with knee osteoarthritis in two independent populations (Mototani et al. *Hum. Mol. Genetics*, vol. 17, no. 12, 2008). Patients can be further selected based on increased LPA receptor expression in the tissue of interest. For example, chronic lymphocytic leukemia (CLL) is characterized by the accumulation of CD19+/CD5+ B-lymphocytes in the peripheral blood, bone marrow and lymphoid organs which occurs as a result of a block in B-lymphocyte apoptosis. LPA can protect some CLL cells from apoptosis and the cells that are protected by LPA have high levels of $LPA_1$ mRNA. In some embodiments, CLL patients are selected based on the expression of the LPA1R. LPA receptor expression are determined by methods including, but not limited to, northern blotting, western blotting, quantitative PCR (qPCR), flow cytometry, autoradiography (using a small molecule radioligand or PET ligand). In some embodiments, patients are selected based on the concentration of serum or tissue LPA measured by mass spectrometry. LPA concentrations are high in ovarian cancer ascites and in some breast cancer effusions. In some embodiments, patients are selected based on a combination of the above markers (increased LPA concentrations and increased LPA receptor expression).

Combination Therapies

In certain instances, it is appropriate to administer Compound 1, or a pharmaceutically acceptable salt thereof (e.g. Compound 2) in combination with another therapeutic agent. By way of example only, if one of the side effects experienced by a patient upon receiving one of the compounds herein is inflammation, then it may be appropriate to administer an anti-inflammatory agent in combination with the initial therapeutic agent.

Or, in one embodiment, the therapeutic effectiveness of one of the compounds described herein is enhanced by administration of an adjuvant (i.e., by itself the adjuvant may have minimal therapeutic benefit, but in combination with another therapeutic agent, the overall therapeutic benefit to the patient is enhanced). Or, in some embodiments, the benefit experienced by a patient is increased by administering one of the compounds described herein with another therapeutic agent (which also includes a therapeutic regimen) that also has therapeutic benefit.

In one specific embodiment, Compound 1, or a pharmaceutically acceptable salt thereof (e.g. Compound 2) is co-administered with a second therapeutic agent, wherein Compound 1, or a pharmaceutically acceptable salt thereof (e.g. Compound 2) and the second therapeutic agent modulate different aspects of the disease, disorder or condition being treated, thereby providing a greater overall benefit than administration of either therapeutic agent alone.

In any case, regardless of the disease, disorder or condition being treated, the overall benefit experienced by the patient may simply be additive of the two therapeutic agents or the patient may experience a synergistic benefit.

In certain embodiments, different therapeutically-effective dosages of the compounds disclosed herein will be utilized in formulating pharmaceutical composition and/or in treatment regimens when the compounds disclosed herein are administered in combination with one or more additional agent, such as an additional therapeutically effective drug, an adjuvant or the like. Therapeutically-effective dosages of drugs and other agents for use in combination treatment regimens can be determined by means similar to those set forth hereinabove for the actives themselves. Furthermore, the methods of prevention/treatment described herein encompasses the use of metronomic dosing, i.e., providing more frequent, lower doses in order to minimize toxic side effects. In some embodiments, a combination treatment regimen encompasses treatment regimens in which administration of Compound 1, or a pharmaceutically acceptable salt thereof (e.g. Compound 2) is initiated prior to, during, or after treatment with a second agent described herein, and continues until any time during treatment with the second agent or after termination of treatment with the second agent. It also includes treatments in which Compound 1, or a pharmaceutically acceptable salt thereof (e.g. Compound 2) and the second agent being used in combination are administered simultaneously or at different times and/or at decreasing or increasing intervals during the treatment period. Combination treatment further includes periodic treatments that start and stop at various times to assist with the clinical management of the patient.

Compositions and methods for combination therapy are provided herein. In accordance with one aspect, the pharmaceutical compositions disclosed herein are used to treat LPA-dependent or LPA-mediated conditions.

It is understood that the dosage regimen to treat, prevent, or ameliorate the condition(s) for which relief is sought, is modified in accordance with a variety of factors. These factors include the disease, disorder or condition from which the subject suffers, as well as the age, weight, sex, diet, and medical condition of the subject. Thus, in some instances, the dosage regimen actually employed varies and, in some embodiments, deviates from the dosage regimens set forth herein.

For combination therapies described herein, dosages of the co-administered compounds vary depending on the type of co-drug employed, on the specific drug employed, on the disease or condition being treated and so forth. In additional embodiments, when co-administered with one or more other therapeutic agents, the compound provided herein is administered either simultaneously with the one or more other therapeutic agents, or sequentially.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills). In one embodiment, one of the therapeutic agents is given in multiple doses, and in another, two (or more if present) are given as multiple doses. In some embodiments of non-simultaneous administration, the timing between the multiple doses vary from more than zero weeks to less than four weeks. In addition, the combination methods, compositions and formulations are not to be limited to the use of only two agents; the use of multiple therapeutic combinations is also envisioned.

Compound 1, or a pharmaceutically acceptable salt thereof (e.g. Compound 2) and combination therapies are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject. For example, in specific embodiments, a compound described herein or a formulation containing the compound is administered for at least 2 weeks, about 1 month to about 5 years.

By way of example, therapies which combine Compound 1, or a pharmaceutically acceptable salt thereof (e.g. Compound 2) with inhibitors of LPA synthesis or LPA receptor antagonists, either acting at the same or other points in the LPA synthesis or signalling pathway, are encompassed herein for treating LPA-dependent or LPA-mediated diseases or conditions.

In another embodiment described herein, methods for treatment of LPA-dependent or LPA-mediated conditions or diseases, such as proliferative disorders, including cancer, comprises administration to a mammal Compound 1, or a pharmaceutically acceptable salt thereof (e.g. Compound 2) in combination with at least one additional agent selected, by way of example only, alemtuzumab, arsenic trioxide, asparaginase (pegylated or non-), bevacizumab, cetuximab, platinum-based compounds such as cisplatin, cladribine, daunorubicin/doxorubicin/idarubicin, irinotecan, fludarabine, 5-fluorouracil, gemtuzumab, methotrexate, Paclitaxel™, taxol, temozolomide, thioguanine, or classes of drugs including hormones (an antiestrogen, an antiandrogen, or gonadotropin releasing hormone analogues, interferons such as alpha interferon, nitrogen mustards such as busulfan or melphalan or mechlorethamine, retinoids such as tretinoin, topoisomerase inhibitors such as irinotecan or topotecan, tyrosine kinase inhibitors such as gefinitinib or imatinib, or agents to treat signs or symptoms induced by such therapy including allopurinol, filgrastim, granisetron/ondansetron/palonosetron, dronabinol.

In one aspect, Compound 1, or a pharmaceutically acceptable salt thereof (e.g. Compound 2) is administered or formulated in combination with one or more anti-cancer agents. In some embodiments, one or more of the anti-cancer agents are proapoptotic agents. Examples of anti-cancer agents include, but are not limited to, any of the following: gossypol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib, geldanamycin, 17-N-Allylamino-17-Demethoxygeldanamycin (17-AAG), flavopiridol, LY294002, bortezomib, trastuzumab, BAY 11-7082, PKC412, or PD184352, Taxol™ (paclitaxel), and analogs of Taxol™, such as Taxotere™. Compounds that have the basic taxane skeleton as a common structure feature, have also been shown to have the ability to arrest cells in the G2-M phases due to stabilized microtubules and may be useful for treating cancer in combination with the compounds described herein.

Further examples of anti-cancer agents for use in combination with Compound 1, or a pharmaceutically acceptable salt thereof (e.g. Compound 2) include inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; mTOR inhibitors; and antibodies (e.g., rituxan).

Other anti-cancer agents for use in combination with Compound 1, or a pharmaceutically acceptable salt thereof (e.g. Compound 2) include one or more of the following: abiraterone; abarelix; adriamycin; aactinomycin; acivicin; aclarubicin; acodazole hydrochloride; acronine; adozelesin; aldesleukin; alemtuzumab; allopurinol; alitretinoin; altretamine; ambomycin; ametantrone acetate; aminoglutethimide; aminolevulinic acid; amifostine; amsacrine; anastrozole; anthramycin; aprepitant; arsenic trioxide; asparaginase; asperlin; azacitidine; azetepa; azotomycin; batimastat; bendamustine hydrochloride; benzodepa; bevacizumab; bexarotene; bicalutamide; bisantrene hydrochloride; bisnafide dimesylate; bizelesin; bleomycin; bleomycin sulfate; bortezomib; brequinar sodium; bropirimine; busulfan; cactinomycin; calusterone; caracemide; carbetimer; carboplatin; carmustine; carubicin hydrochloride; carzelesin; capecitabine; cedefingol; cetuximab; chlorambucil; cirolemycin; cisplatin; cladribine; clofarabine; crisnatol mesylate; cyclophosphamide; cytarabine; dacarbazine; dasatinib; daunorubicin hydrochloride; dactinomycin; darbepoetin alfa; decitabine; degarelix; denileukin diftitox; dexormaplatin; dexrazoxane hydrochloride; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; eltrombopag olamine; enloplatin; enpromate; epipropidine; epirubicin hydrochloride; epoetin alfa; erbulozole; erlotinib hydrochloride; esorubicin hydrochloride; estramustine; estramustine phosphate sodium; etanidazole; etoposide; etoposide phosphate; etoprine; everolimus; exemestane; fadrozole hydrochloride; fazarabine; fenretinide; filgrastim; floxuridine; fludarabine phosphate; fluorouracil; fluorocitabine; fosquidone; fostriecin sodium; fulvestrant; gefitinib; gemcitabine; gemcitabine hydrochloride; gemcitabine-cisplatin; gemtuzumab ozogamicin; goserelin acetate; histrelin acetate; hydroxyurea; idarubicin hydrochloride; ifosfamide; iimofosine; ibritumomab tiuxetan; idarubicin; ifosfamide; imatinib mesylate; imiquimod; interleukin II (including recombinant interleukin II, or rIL2), interferon alfa-2a; interferon alfa-2b; interferon alfa-n1; interferon alfa-n3; interferon beta-1a; interferon gamma-1b; iproplatin; irinotecan hydrochloride; ixabepilone; lanreotide acetate; lapatinib; lenalidomide; letrozole; leuprolide acetate; leucovorin calcium; leuprolide acetate; levamisole; liposomal cytarabine; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; methoxsalen; metoprine; meturedepa; mitindomide; mitocarcin; mitocromin; mitogillin; mitomalcin; mitomycin C; mitosper; mitotane; mitoxantrone hydrochloride; mycophenolic acid; nandrolone phenpropionate; nelarabine; nilotinib; nocodazoie; nofetumomab; nogalamycin; ofatumumab; oprelvekin; ormaplatin; oxaliplatin; oxisuran; paclitaxel; palifermin; palonosetron hydrochloride; pamidronate; pegfilgrastim; pemetrexed disodium; pentostatin; panitumumab; pazopanib hydrochloride; pemetrexed disodium; plerixafor; pralatrexate; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; quinacrine; raloxifene hydrochloride; rasburicase; recombinant HPV bivalent vaccine; recombinant HPV quadrivalent vaccine; riboprine; rogletimide; rituximab; romidepsin; romiplostim; safingol; safingol hydrochloride; sargramostim; semustine; simtrazene; sipuleucel-T; sorafenib; sparfosate sodium; sparsomycin; spirogermanium hydrochloride; spiromustine; spiroplatin; streptonigrin; streptozocin; sulofenur; sunitinib malate; talisomycin; tamoxifen citrate; tecogalan sodium; tegafur; teloxantrone hydrochloride; temozolomide; temoporfin; temsirolimus; teniposide; teroxirone; testolactone; thalidomide; thiamiprine; thioguanine; thiotepa; tiazofurin; tirapazamine; topotecan hydrochloride; toremifene; tositumomab; tositumomab and I 131 Iodine tositumomab; trastuzumab; trestolone acetate; tretinoin; triciribine phosphate; trimetrexate; trimetrexate glucuronate; triptorelin; tubulozole hydrochloride; uracil mustard; uredepa; valrubicin; vapreotide; verteporfin; vinblastine; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorinostat; vorozole; zeniplatin; zinostatin; zoledronic acid; zorubicin hydrochloride.

Yet other anticancer agents for use in combination include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, ete.), or triazenes (decarbazine, etc.). Examples of antimetabolites include but are not limited to folic acid analog (e.g., methotrexate), or pyrimidine analogs (e.g., Cytarabine), purine analogs (e.g., mercaptopurine, thioguanine, pentostatin).

Examples of natural products for use in combination with Compound 1, or a pharmaceutically acceptable salt thereof (e.g. Compound 2) include but are not limited to vinca alkaloids (e.g., vinblastin, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents for use in combination with Compound 1, or a pharmaceutically acceptable salt thereof (e.g. Compound 2) include, but are not limited to, nitrogen mustards (e.g., mechloroethamine, cyclophosphamide, chlorambucil, meiphalan, etc.), ethylenimine and methylmelamines (e.g., hexamethylmelamine, thiotepa), alkyl sulfonates (e.g., busulfan), nitrosoureas (e.g., carmustine, lomusitne, semustine, streptozocin, etc.), or triazenes (decarbazine, ete.). Examples of antimetabolites include, but are not limited to folic acid analog (e.g., methotrexate), or pyrimidine analogs (e.g., fluorouracil, floxouridine, Cytarabine), purine analogs (e.g., mercaptopurine, thioguanine, pentostatin.

Examples of hormones and antagonists for use in combination with Compound 1, or a pharmaceutically acceptable salt thereof (e.g. Compound 2) include, but are not limited to, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), gonadotropin releasing hormone analog (e.g., leuprolide). Other agents that can be used in the methods and compositions described herein for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

Examples of anti-cancer agents which act by arresting cells in the G2-M phases due to stabilized microtubules include without limitation the following marketed drugs and drugs in development: Erbulozole, Dolastatin 10, Mivobulin isethionate, Vincristine, NSC-639829, Discodermolide, ABT-751, Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride, Epothilones (such as Epothilone A, Epothilone B, Epothilone C, Epothilone D, Epothilone E, Epothilone F, Epothilone B N-oxide, Epothilone A N-oxide, 16-aza-epothilone B, 21-aminoepothilone B, 21-hydroxyepothilone D, 26-fluoroepothilone, Auristatin PE, Soblidotin, Vincristine sulfate, Cryptophycin 52, Vitilevuamide, Tubulysin A, Canadensol, Centaureidin, Oncocidin A1 Fijianolide B, Laulimalide, Narcosine, Nascapine, Hemiasterlin, Vanadocene acetylacetonate, Indanocine Eleutherobins (such as Desmethyleleutherobin, Desaetyleleutherobin, lsoeleutherobin A, and Z-Eleutherobin), Caribaeoside, Caribaeolin, Halichondrin B, Diazonamide A, Taccalonolide A, Diozostatin, (−)-Phenylahistin, Myoseverin B, Resverastatin phosphate sodium.

In one aspect, Compound 1, or a pharmaceutically acceptable salt thereof (e.g. Compound 2) is co-administered with thrombolytic agents (e.g., alteplase anistreplase, streptokinase, urokinase, or tissue plasminogen activator), heparin, tinzaparin, warfarin, dabigatran (e.g., dabigatran etexilate), factor Xa inhibitors (e.g., fondaparinux, draparinux, rivaroxaban, DX-9065a, otamixaban, LY517717, or YM150), ticlopidine, clopidogrel, CS-747 (prasugrel, LY640315), ximelagatran, or BIBR 1048.

In some embodiments, Compound 1, or a pharmaceutically acceptable salt thereof (e.g. Compound 2) is used in combination with anti-emetic agents to treat nausea or emesis. Anti-emetic agents include, but are not limited to: neurokinin-1 receptor antagonists, 5HT3 receptor antagonists (such as ondansetron, granisetron, tropisetron, Palonosetron, and zatisetron), $GABA_B$ receptor agonists (such as baclofen), corticosteroids (such as dexamethasone, prednisone, prednisolone, or others), dopamine antagonists (such as, but not limited to, domperidone, droperidol, haloperidol, chlorpromazine, promethazine, prochlorperazine, metoclopramide), antihistamines (H1 histamine receptor antagonists, such as but not limited to, cyclizine, diphenhydramine, dimenhydrinate, meclizine, promethazine, hydroxyzine), cannabinoids (such as but not limited to, cannabis, marinol, dronabinol), and others (such as, but not limited to, trimethobenzamide; ginger, emetrol, propofol).

In some embodiments, Compound 1, or a pharmaceutically acceptable salt thereof (e.g. Compound 2) is used in combination with an agent useful in the treatment of anemia. Such an anemia treatment agent is, for example, a continuous eythropoiesis receptor activator (such as epoetin-α).

In some embodiments, Compound 1, or a pharmaceutically acceptable salt thereof (e.g. Compound 2) is used in combination with an agent useful in the treatment of neutropenia. Examples of agents useful in the treatment of neutropenia include, but are not limited to, a hematopoietic growth factor which regulates the production and function of neutrophils such as a human granulocyte colony stimulating factor, (G-CSF). Examples of a G-CSF include filgrastim.

In some embodiments, Compound 1, or a pharmaceutically acceptable salt thereof (e.g. Compound 2) is used in combination with radiation therapy (or radiotherapy). Radiation therapy is the treatment of cancer and other diseases with ionizing radiation. Radiation therapy can be used to treat localized solid tumors, such as cancers of the skin, tongue, larynx, brain, breast, prostate, colon, uterus and/or cervix. It can also be used to treat leukemia and lymphoma (cancers of the blood-forming cells and lymphatic system, respectively).

A technique for delivering radiation to cancer cells is to place radioactive implants directly in a tumor or body cavity. This is called internal radiotherapy (brachytherapy, interstitial irradiation, and intracavitary irradiation are types of internal radiotherapy.) Using internal radiotherapy, the radiation dose is concentrated in a small area, and the patient stays in the hospital for a few days. Internal radiotherapy is frequently used for cancers of the tongue, uterus, prostate, colon, and cervix.

The term "radiotherapy" or "ionizing radiation" include all forms of radiation, including but not limited to $\alpha$, $\beta$, and $\gamma$ radiation and ultraviolet light.

In one aspect, Compound 1, or a pharmaceutically acceptable salt thereof (e.g. Compound 2) is used to treat or reduce fibrosis in a mammal. In one aspect, Compound 1, or a pharmaceutically acceptable salt thereof (e.g. Compound 2) is administered in combination with one or more immunosuppresants. Immunosuppressive therapy is clinically used to treat or prevent the rejection of transplanted organs and tissues (e.g. bone marrow, heart, kidney, liver); treatment of autoimmune diseases or diseases that are most likely of autoimmune origin (e.g. rheumatoid arthritis, myasthenia gravis, systemic lupus erythematosus, Crohn's disease, and ulcerative colitis); and treatment of some other non-autoimmune inflammatory diseases (e.g. long term allergic asthma control), and in the treatment of fibrotic conditions.

In some embodiments, Compound 1, or a pharmaceutically acceptable salt thereof (e.g. Compound 2) is administered with corticosteroids. In some embodiments, Compound 1, or a pharmaceutically acceptable salt thereof (e.g. Compound 2) is administered with an a therapeutic agent selected from among: Calcineurin inhibitors (such as, but not limited to, cyclosporin, tacrolimus); mTOR inhibitors (such as, but not limited to, sirolimus, everolimus); anti-proliferatives (such as, but not limited to, azathioprine, mycophenolic acid); corticosteroids (such as, but not limited to, prednisone, cortisone acetate, prednisolone, methylprednisolone, dexamethasone, betamethasone, triamcinolone, beclometasone, fludrocortisone acetate, deoxycorticosterone acetate, aldosterone, hydrocortisone); antibodies (such as, but not limited to, monoclonal anti-IL-2Rα receptor antibodies (basiliximab, daclizumab), polyclonal anti-T-cell antibodies (anti-thymocyte globulin (ATG), anti-lymphocyte globulin (ALG)), B-cell antagonists, rituximab, natalizumab.

Other therapeutic agents include, but are not limited to: cyclophosphamide, penicillamine, cyclosporine, nitrosoureas, cisplatin, carboplatin, oxaliplatin, methotrexate, azathioprine, mercaptopurine, pyrimidine analogues, protein synthesis inhibitors, dactinomycin, anthracyclines, mitomycin C, bleomycin, mithramycin, Atgam®, Thymoglobuline®, OKT3®, basiliximab, daclizumab, cyclosporin, tacrolimus, sirolimus, Interferons (IFN-β, IFN-γ), opioids, TNF binding proteins (infliximab, etanercept, adalimumab, golimumab), leflunomide, gold thioglucose, gold thiomalate, aurofin, sulfasalazine, hydroxychloroquinine, minocycline, rapamicin, mycophenolic acid, mycophenolate mofetil, FTY720, as well as those listed in U.S. Pat. No. 7,060,697.

In one embodiment, Compound 1, or a pharmaceutically acceptable salt thereof (e.g. Compound 2) is administered in combination with Cyclosporin A (CsA) or tacrolimus (FK506). In one embodiment, Compound 1, or a pharmaceutically acceptable salt thereof (e.g. Compound 2) is administered to a mammal in combination with an anti-inflammatory agent including, but not limited to, non-steroidal anti-inflammatory drugs (NSAIDs) and corticosteroids (glucocorticoids).

NSAIDs include, but are not limited to: aspirin, salicylic acid, gentisic acid, choline magnesium salicylate, choline salicylate, choline magnesium salicylate, choline salicylate, magnesium salicylate, sodium salicylate, diflunisal, carprofen, fenoprofen, fenoprofen calcium, fluorobiprofen, ibuprofen, ketoprofen, nabutone, ketolorac, ketolorac tromethamine, naproxen, oxaprozin, diclofenac, etodolac, indomethacin, sulindac, tolmetin, meclofenamate, meclofenamate sodium, mefenamic acid, piroxicam, meloxicam, COX-2 specific inhibitors (such as, but not limited to, celecoxib, rofecoxib, valdecoxib, parecoxib, etoricoxib, lumiracoxib, CS-502, JTE-522, L-745,337 and NS398).

Corticosteroids, include, but are not limited to: betamethasone, prednisone, alclometasone, aldosterone, amcinonide, beclometasone, betamethasone, budesonide, ciclesonide, clobetasol, clobetasone, clocortolone, cloprednol, cortisone, cortivazol, deflazacort, deoxycorticosterone, desonide, desoximetasone, desoxycortone, dexamethasone, diflorasone, diflucortolone, difluprednate, fluclorolone, fludrocortisone, fludroxycortide, flumetasone, flunisolide, fluocinolone acetonide, fluocinonide, fluocortin, fluocortolone, fluorometholone, fluperolone, fluprednidene, fluticasone, formocortal, halcinonide, halometasone, hydrocortisone/cortisol, hydrocortisone aceponate, hydrocortisone buteprate, hydrocortisone butyrate, loteprednol, medrysone, meprednisone, methylprednisolone, methylprednisolone aceponate, mometasone furoate, paramethasone, prednicarbate, prednisone/prednisolone, rimexolone, tixocortol, triamcinolone, and ulobetasol.

In one embodiment, Compound 1, or a pharmaceutically acceptable salt thereof (e.g. Compound 2) is administered in combination with leukotriene receptor antagonists.

In another embodiment described herein, methods for treatment of LPA-dependent or LPA-mediated conditions or diseases, such as atherosclerosis, comprises administration to a patient compounds, pharmaceutical compositions, or medicaments described herein in combination with at least one additional agent selected, by way of example only, HMG-CoA reductase inhibitors (e.g., statins in their lactonized or dihydroxy open acid forms and pharmaceutically acceptable salts and esters thereof, including but not limited to lovastatin; simvastatin; dihydroxy open-acid simvastatin, particularly the ammonium or calcium salts thereof; pravastatin, particularly the sodium salt thereof; fluvastatin, particularly the sodium salt thereof; atorvastatin, particularly the calcium salt thereof; nisvastatin, also referred to as NK-104; rosuvastatin); agents that have both lipid-altering effects and other pharmaceutical activities; HMG-CoA synthase inhibitors; cholesterol absorption inhibitors such as ezetimibe; cholesterol ester transfer protein (CETP) inhibitors, for example JTT-705 and CP529, 414; squalene epoxidase inhibitors; squalene synthetase inhibitors (also known as squalene synthase inhibitors); acyl-coenzyme A: cholesterol acyltransferase (ACAT) inhibitors including selective inhibitors of ACAT-1 or ACAT-2 as well as dual inhibitors of ACAT-1 and -2; microsomal triglyceride transfer protein (MTP) inhibitors; probucol; niacin; bile acid sequestrants; LDL (low density lipoprotein) receptor inducers; platelet aggregation inhibitors, for example glycoprotein IIb/IIIa fibrinogen receptor antagonists and aspirin; human peroxisome proliferator activated receptor gamma (PPARγ) agonists, including the compounds commonly referred to as glitazones, for example troglitazone, pioglitazone and rosiglitazone and including those compounds included within the structural class known as thiazolidinediones as well as those PPARγ agonists outside the thiazolidinedione structural class; PPARα agonists such as clofibrate, fenofibrate including micronized fenofibrate, and gemfibrozil; PPAR dual α/γ agonists such as 5-[(2,4-dioxo-5-thiazolidinyl)methyl]-2-methoxy-N-[[4-(trifluoromethyl)phenyl]methyl]-benzamide, known as KRP-297; vitamin B6 (also known as pyridoxine) and the pharmaceutically acceptable salts thereof such as the HCl salt; vitamin B12 (also known as cyanocobalamin); folic acid or a pharmaceutically acceptable salt or ester thereof such as the sodium salt and the methylglucamine salt; anti-oxidant vitamins such as vitamin C and E and beta carotene; beta-blockers; angiotensin II antagonists such as losartan; angiotensin converting enzyme inhibitors such as enalapril and captopril; calcium channel blockers such as nifedipine and diltiazam; endothelian antagonists; agents that enhance ABC1 gene expression; FXR and LXR ligands including both inhibitors and agonists; bisphosphonate compounds such as alendronate sodium; and cyclooxygenase-2 inhibitors such as rofecoxib and celecoxib.

In another embodiment described herein, methods for treatment of LPA-dependent or LPA-mediated conditions or diseases, such as the therapy of stroke, comprises administration to a patient compounds, pharmaceutical compositions, or medicaments described herein in combination with at least one additional agent selected from, by way of example only, COX-2 inhibitors; nitric oxide synthase inhibitors, such as N-(3-(aminomethyl)benzyl) acetamidine; Rho kinase inhibitors, such as fasudil; angiotension II type-1 receptor antagonists, including candesartan, losartan, irbesartan, eprosartan, telmisartan and valsartan; glycogen synthase kinase 3 inhibitors; sodium or calcium channel blockers, including crobenetine; p38 MAP kinase inhibitors, including SKB 239063; thromboxane AX-synthetase inhibitors, including isbogrel, ozagrel, ridogrel and dazoxiben; statins (HMG CoA reductase inhibitors), including lovastatin, simvastatin, dihydroxy open-acid simvastatin, pravastatin, fluvastatin, atorvastatin, nisvastatin, and rosuvastatin; neuroprotectants, including free radical scavengers, calcium channel blockers, excitatory amino acid antagonists, growth factors, antioxidants, such as edaravone, vitamin C, TROLOX™, citicoline and minicycline, and reactive astrocyte inhibitors, such as (2R)-2-propyloctanoic acid; beta andrenergic blockers, such as propranolol, nadolol, timolol, pindolol, labetalol, metoprolol, atenolol, esmolol and acebutolol; NMDA receptor antagonists, including memantine; NR2B antagonists, such as traxoprodil; 5-HT1A agonists; receptor platelet fibrinogen receptor antagonists, including tirofiban and lamifiban; thrombin inhibitors; antithrombotics, such as argatroban; antihypertensive agents, such as enalapril; vasodilators, such as cyclandelate; nociceptin antagonists; DPIV antagonists; GABA 5 inverse agonists; and selective androgen receptor modulators.

In another embodiment described herein, methods for treatment of LPA-dependent or LPA-mediated conditions or diseases, such as the therapy of interstitial cystitis, comprises administration to a patient compounds, pharmaceutical compositions, or medicaments described herein in combination with at least one additional agent selected from, by way of example only, dimethylsulfoxide, omalizumab, and pentosan polysulfate.

In yet another embodiment described herein, methods for treating LPA-dependent or LPA-mediated conditions or diseases, such as the therapy of respiratory disorders (e.g., asthma, COPD and rhinitis), comprises administration to a patient compounds, pharmaceutical compositions, or medicaments described herein in combination with at least one agent used in the treatment of respiratory conditions. Agents used in the treatment of respiratory conditions include, but are not limited to, bronchodilators (e.g., sympathomimetic agents and xanthine derivatives), leukotriene receptor antagonists, leukotriene formation inhibitors, leukotriene modulators, nasal decongestants, respiratory enzymes, lung surfactants, antihistamines (e.g., mepyramine (pyrilamine), antazoline, diphenhydramine, carbinoxamine, doxylamine, clemastine, dimenhydrinate, pheniramine, chlorphenamine (chlorpheniramine), dexchlorpheniramine, brompheniramine, triprolidine, cetirizine, cyclizine, chlorcyclizine, hydroxyzine, meclizine, loratadine, desloratidine, promethazine, alimemazine (trimeprazine), cyproheptadine, azatadine, ketotifen, acrivastine, astemizole, cetirizine, mizolastine, terfenadine, azelastine, levocabastine, olopatadine, levocetirizine, fexofenadine), mucolytics, corticosteroids, anticholinergics, antitussives, analgesics, expectorants, albuterol, ephedrine, epinephrine, fomoterol, metaproterenol, terbutaline, budesonide, ciclesonide, dexamethasone, flunisolide, fluticasone propionate, triamcinolone acetonide, ipratropium bromide, pseudoephedrine, theophylline, montelukast, zafirlukast, ambrisentan, bosentan, enrasentan, sitaxsentan, tezosentan, iloprost, treprostinil, pirfenidone, 5-lipoxygenase-activating protein (FLAP) inhibitors, FLAP modulators and 5-LO inhibitors.

In a specific embodiment described herein, methods for treating LPA-dependent or LPA-mediated conditions or diseases, such as the therapy of asthma and/or COPD, comprises administration to a patient anti-inflammatory agents. In certain embodiments, methods for treating LPA-dependent or LPA-mediated conditions or diseases, such as the therapy of asthma and/or COPD, comprise administration to a patient compounds, pharmaceutical compositions, or medicaments described herein in combination with at least one additional agent selected from, but not limited to, epinephrine, isoproterenol, orciprenaline, bronchodilators, glucocorticoids, leukotriene modifiers, mast-cell stabilizers, xanthines, anticholinergics, β-2 agonists, FLAP inhibitors, FLAP modulators or 5-LO inhibitors. β-2 agonists include, but are not limited to, short-acting β-2 agonists (e.g., salbutamol (albuterol), levalbuterol, terbutaline, pirbuterol, procaterol, metaproterenol, fenoterol and bitolterol mesylate) and long-acting β-2 agonists (e.g., salmeterol, formoterol, bambuterol and clenbuterol). FLAP inhibitors and/or FLAP modulators include, but are not limited to, 3-[3-tert-butylsulfanyl-1-[4-(6-methoxy-pyridin-3-yl)-benzyl]-5-(pyridin-2-ylmethoxy)-1H-indol-2-yl]-2,2-dimethyl-propionic acid, 3-[3-tert-butylsulfanyl-1-[4-(6-ethoxy-pyridin-3-yl)-benzyl]-5-(5-methyl-pyridin-2-ylmethoxy)-1H-indol-2-yl]-2,2-dimethyl-propionic acid, MK-886, MK-0591, BAY-x1005 and compounds found in US 2007/0225285, US 2007/0219206, US 2007/0173508, US 2007/0123522 and US 2007/0105866 (each of which are hereby incorporated by reference). Glucocorticoids include, but are not limited to, beclometasone, budesonide, ciclesonide, fluticasone and mometasone. Anticholinergics include, but are not limited to, ipratropium and tiotropium. Mast cell stabilizers include, but are not limited to, cromoglicate and nedocromil. Xanthines include, but are not limited to, amminophylline, theobromine and theophylline. Leukotriene antagonists include, but are not limited to, montelukast, tomelukast, pranlukast and zafirlukast. 5-LO inhibitors include, but are not limited to, zileuton, VIA-2291 (ABT761), AZ-4407 and ZD-2138 and compounds found in US 2007/0149579, WO2007/016784.

In another specific embodiment described herein, methods for treating LPA-dependent or LPA-mediated conditions or diseases, such as the therapy of allergic diseases or conditions, comprises administration to a patient compounds, pharmaceutical compositions, or medicaments described herein in combination with at least one additional agent selected from, by way of example only, antihistamines, leukotriene antagonists, corticosteroids and decongestants. Leukotriene antagonists include, but are not limited to, montelukast, tomelukast, pranlukast and zafirlukast.

In one aspect, LPA receptor antagonists described herein are administered in combination with one or more agents used to treat used to treat asthma, including, but not limited to: combination inhalers (fluticasone and salmeterol oral inhalation (e.g. Advair)); inhaled Beta-2 agonists (albuterol inhaler; albuterol nebulizer solution; formoterol; isoproterenol oral inhalation; levalbuterol; metaproterenol inhalation; pirbuterol acetate oral inhalation; salmeterol aerosol inhalation; salmeterol powder inhalation; terbutaline inhaler); inhaled corticosteroids (beclomethasone oral inhalation; budesonide inhalation solution; budesonide inhaler; flunisolide oral inhalation; fluticasone inhalation aerosol; fluticasone powder for oral inhalation; mometasone inhalation powder; triamcinolone oral inhalation); leukotriene modifiers (montelukast; zafirlukast; zileuton); mast cell stabilizers (cromolyn inhaler; nedocromil oral inhalation); monoclonal antibodies (omalizumab); oral Beta-2 agonists (albuterol oral syrup; albuterol oral tablets; metaproterenol; terbutaline); bronchodilator (aminophylline; oxtriphylline; theophylline).

In one aspect, LPA receptor antagonists described herein are administered in combination with one or more agents used to treat allergy, including, but not limited to: antihistamine and decongestant combinations (cetirizine and pseudoephedrine; desloratadine and pseudoephedrine ER; fexofenadine and pseudoephedrine; loratadine and pseudoephedrine); antihistamines (azelastine nasal spray; brompheniramine; brompheniramine oral suspension; carbinoxamine; cetirizine; chlorpheniramine; clemastine; desloratadine; dexchlorpheniramine ER; dexchlorpheniramine oral syrup; diphenhydramine oral; fexofenadine; loratadine; promethazine); decongestants (pseudoephedrine); leukotriene modifiers (montelukast; montelukast granules); nasal anticholinergics (ipratropium); nasal corticosteroids (beclomethasone nasal inhalation; budesonide nasal inhaler; flunisolide nasal inhalation; fluticasone nasal inhalation; mometasone nasal spray; triamcinolone nasal inhalation; triamcinolone nasal spray); nasal decongestants (phenylephrine); nasal mast cell stabilizers (cromolyn nasal spray).

In one aspect, LPA receptor antagonists described herein are administered in combination with one or more agents used to treat chronic obstructive pulmonary disease (COPD), including, but not limited to: anticholinergics—ipratropium bromide oral inhalation); combination Inhalers (albuterol and ipratropium (e.g. Combivent, DuoNeb); fluticasone and salmeterol oral inhalation (e.g. Advair)); corticosteroids (dexamethasone tablets; fludrocortisone acetate; hydrocortisone tablets; methylprednisolone; prednisolone liquid; prednisone oral; triamcinolone oral); inhaled Beta-2 Agonists (albuterol inhaler; albuterol nebulizer solution; formoterol; isoproterenol oral inhalation; levalbuterol; metaproterenol inhalation; pirbuterol acetate oral inhalation; salmeterol aerosol inhalation; salmeterol powder inhalation; terbutaline inhaler); inhaled Corticosteroids (beclomethasone oral inhalation; budesonide inhalation solution; budesonide inhaler; flunisolide oral inhalation; fluticasone inhalation aerosol; fluticasone powder for oral inhalation; triamcinolone oral inhalation); mukolytics (guaifenesin); oral Beta-2 agonists (albuterol oral syrup; albuterol oral tablets; metaproterenol; terbutaline); bronchodilator (aminophylline; oxtriphylline; theophylline).

In one embodiment, Compound 1, or a pharmaceutically acceptable salt thereof (e.g. Compound 2) is administered to a patient in combination with inhaled corticosteroids.

In one embodiment, Compound 1, or a pharmaceutically acceptable salt thereof (e.g. Compound 2) is administered to a patient in combination with beta2-adrenergic receptor agonists. In one embodiment, Compound 1, or a pharmaceutically acceptable salt thereof (e.g. Compound 2) is administered to a patient in combination with short acting beta2-adrenergic receptor agonists. In one embodiment, Compound 1, or a pharmaceutically acceptable salt thereof (e.g. Compound 2) is administered to a patient in combination with long-acting beta2-adrenergic receptor agonists.

In one embodiment, Compound 1, or a pharmaceutically acceptable salt thereof (e.g. Compound 2) is combined with or administered in combination with one or more agents that are inhibitors of UDP-glucuronosyltransferase (UGT). UGT inhibitors include those described in U.S. 2003/0215462; U.S. 2004/0014648. In some embodiments, co-administration of a UGT inhibitor allows for lower doses of Compound 1, or a pharmaceutically acceptable salt thereof (e.g. Compound 2) to be administered.

The individual compounds of such combinations are administered either sequentially or simultaneously in separate or combined pharmaceutical formulations. In one embodiment, the individual compounds will be administered simultaneously in a combined pharmaceutical formulation. Appropriate doses of known therapeutic agents will be appreciated by those skilled in the art.

The combinations referred to herein are conveniently presented for use in the form of a pharmaceutical compositions together with a pharmaceutically acceptable diluent(s) or carrier(s).

Kits/Articles of Manufacture

For use in the therapeutic methods of use described herein, kits and articles of manufacture are also described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

The articles of manufacture provided herein contain packaging materials. Packaging materials for use in packaging pharmaceutical products include, e.g., U.S. Pat. Nos. 5,323,907, 5,052,558 and 5,033,252. Examples of pharmaceutical packaging materials include, but are not limited to, blister packs, bottles, tubes, bags, containers, bottles, and any packaging material suitable for a selected formulation and intended mode of administration and treatment. A wide array of formulations of the compounds and compositions provided herein are contemplated as are a variety of treatments for any disease, disorder, or condition that would benefit by antagonism of LPA receptors.

For example, the container(s) include Compound 1, or a pharmaceutically acceptable salt thereof (e.g. Compound 2), optionally in a composition or in combination with another agent as disclosed herein. Such kits optionally include an identifying description or label or instructions relating to its use in the methods described herein.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

In certain embodiments, the pharmaceutical compositions are presented in a pack or dispenser device which contains one or more unit dosage forms containing a compound provided herein. The pack, for example, contains metal or plastic foil, such as a blister pack. In one embodiment, the pack or dispenser device is accompanied by instructions for administration. In one embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In one embodiment, compositions containing a compound provided herein formulated in a compatible pharmaceutical carrier are also prepared, placed in an appropriate container, and labeled for treatment of an indicated condition.

It is to be understood that as used herein, pharmaceutical compositions described as comprising a pharmaceutically acceptable salt described herein, e.g., liquid solutions, encompass pharmaceutical compositions comprising the associated and/or disassociated forms of the salt. Thus, for example, a pharmaceutical composition described herein comprising an aqueous solution of Compound 2 encompasses a composition comprising a population of sodium cations and a population of 1-{4'-[3-methyl-4-((R)-1-phenyl-ethoxycarbonylamino)-isoxazol-5-yl]-biphenyl-4-yl}-cyclopropanecarboxylate anions.

EXAMPLES

The following ingredients, formulations, processes and procedures for practicing the methods disclosed herein correspond to that described above. The procedures below describe with particularity illustrative, non-limiting embodiment of formulations that include a Compound 1, or a pharmaceutically acceptable salt and/or solvate thereof, and pharmacokinetic profiles and pharmacodynamic effects thereof. By way of example only, Compound 1 is optionally prepared as outlined in U.S. patent application Ser. No. 12/793,440, or as outlined herein.

Example 1

Synthesis of 1-{4'-[3-Methyl-4-((R)-1-phenyl-ethoxycarbonylamino)-isoxazol-5-yl]-biphenyl-4-yl}-cyclopropanecarboxylic acid (Compound 1)

Step 1: 3-Methylamino-but-2-enoic acid methyl ester

To a solution of methyl acetoacetate (29.4 g, 253 mmol) in MeOH (30 mL) was added methylamine (33 wt % in EtOH; 48 mL, 385 mmol) dropwise at room temperature. The reaction was stirred for 1 hour, and then concentrated and dried to give the title compound as a white crystalline solid.

Step 2: 2-(4-Bromo-benzoyl)-3-oxo-butyric acid methyl ester

To 3-methylamino-but-2-enoic acid methyl ester (5.0 g, 39.1 mmol) in THF (70 mL) was added pyridine (3.7 mL). The mixture was cooled to 0° C., and 4-bromobenzoyl chloride (8.55 g, 39.1 mmol) in THF (30 mL) was added dropwise over 2 minutes. The reaction was warmed to room temperature over 1 hour and then stirred at room temperature overnight. Aqueous work-up gave the title compound.

Step 3: 5-(4-Bromo-phenyl)-3-methyl-isoxazole-4-carboxylic acid methyl ester 2-(4-Bromo-benzoyl)-3-oxo-butyric acid methyl ester (11 g, 39 mmol) and hydroxylamine hydrochloride (2.66 g, 39 mmol) were combined in acetic acid (50 mL), and the reaction was stirred at 115° C. for 1 hour. After cooling, aqueous work-up gave the title compound.

Step 4: 5-(4-Bromo-phenyl)-3-methyl-isoxazole-4-carboxylic acid

Lithium hydroxide (2 g, 47.7 mmol) was added to a solution of 5-(4-bromo-phenyl)-3-methyl-isoxazole-4-carboxylic acid methyl ester (7 g, 23.6 mmol) in MeOH (50 mL) and $H_2O$ (10 mL), and the reaction was stirred at 60° C. for 1 hour. Acidic work-up the title compound.

Step 5: [5-(4-Bromo-phenyl)-3-methyl-isoxazol-4-yl]-carbamic acid (R)-1-phenyl-ethyl ester 5-(4-Bromo-phenyl)-3-methyl-isoxazole-4-carboxylic acid (2.0 g, 7.09 mmol) and triethylamine (0.99 mL, 7.09 mmol) were dissolved in toluene (50 mL). Diphenylphosphoryl azide (1.5 mL, 7.09 mmol) was added, followed by (R)-(+)-1-phenylethyl alcohol (0.865 g, 7.09 mmol; commercially available or prepared using procedures described herein or in the literature: e.g. E. J. Corey et al. *J. Am. Chem.* 1987, 109, 5551-5553), and the reaction was stirred at 80° C. for 4 hours. The mixture was concentrated, and the residue was purified by silica gel chromatography to give the title compound.

Step 6: 1-{4'-[3-Methyl-4-((R)-1-phenyl-ethoxycarbonylamino)-isoxazol-5-yl]-biphenyl-4-yl}-cyclopropanecarboxylic acid

[5-(4-Bromo-phenyl)-3-methyl-isoxazol-4-yl]-carbamic acid (R)-1-phenyl-ethyl ester (0.248 g, 0.62 mmol), 4-(1'-carboxyl-cyclopropyl)phenylboronic acid (0.160 g, 0.62 mmol), and sodium carbonate (0.155 g, 1.85 mmol) were combined in 2:1 DME:$H_2O$. The solution was purged with $N_2$ for 10 minutes, and then bis(triphenylphosphine)palladium(II) dichloride (0.047 g, 0.06 mmol) was added. The reaction was purged with $N_2$ for an additional 10 minutes, and then stirred in a sealed tube at 80° C. for 2 hours. The mixture was partitioned between EtOAc and $H_2O$, and the aqueous layer was extracted with EtOAc. The combined organic layers were dried over $MgSO_4$, filtered, and concentrated, and the residue was purified by silica gel chromatography to give the title compound. Mass spec. data (M+H)=483.

Example 2

Alternate synthesis of 1-{4'-[3-Methyl-4-((R)-1-phenyl-ethoxycarbonylamino)-isoxazol-5-yl]-biphenyl-4-yl}-cyclopropanecarboxylic acid (Compound 1)

Step 1: 1-(biphenyl-4-yl)cyclopropanecarbonitrile 4-phenyl-phenylacetonitrile (VWR scientific, 100 g, 518 mmol) was added to a solution of KOH (174 g, 3.1 mol) in water (175 mL) and toluene (500 mL) at room temperature. Tetrabutyl ammonium bromide (8.33 g, 26 mmol) followed by 1,2 dibromoethane (116.3 g, 622 mmol) were added and the solution was heated to 60° C. for 4 hours. Add 10 mL dibromoethane and continue heating at 60° C. for another 20 hours. Reaction is approximately 50% complete. Add KOH (116 g, 622 mmol), dibromoethane (20 mL) and tetrabutyl ammonium bromide (8.33 g, 26 mmol) and heat to 80° C. for an additional 24 hours. Reaction complete by TLC (20% EtOAc/hex). The organic layer was extracted with water (500 mL) one time and dilute hydrochloric acid (500 mL, pH ~3) one time. The organic layer was evaporated to yield product.

Step 2: 1-(Biphenyl-4-yl)cyclopropanecarboxylic acid 1-(Biphenyl-4-yl)cyclopropanecarbonitrile (112 g, 511 mmol), KOH (114 g, 2.04 mol) and ethylene glycol (400 mL) were heated to 170° C. for 3 hours. The solution was cooled to room temperature, poured into water (900 mL) and the solution acidified with ~150 mL conc. HCl (slowly) to precipitate the product. The product was filtered and washed with 500 mL water. The solid was resuspended in water (800 mL), stirred for ~15 minutes and filtered. The resulting wet solid was dried in a vacuum over overnight at 80° C. to yield product.

Step 3: 1-(Biphenyl-4-yl)cyclopropanecarboxylic acid ethyl ester 1-(Biphenyl-4-yl)cyclopropanecarboxylic acid (116 g, 487 mmol), ethanol (400 mL) and sulfuric acid (50 mL) were heated to reflux for 16 hours. The product was extracted with $CH_2Cl_2$ (500 mL) and water (800 mL) dried, filtered and evaporated to yield product.

Step 4: 1-(4'-Acetylbiphenyl-4-yl)cyclopropanecarboxylic acid ethyl ester

To 1-(biphenyl-4-yl)cyclopropanecarboxylic acid ethyl ester (90 g, 376 mmol) in $CH_2Cl_2$ (450 mL) was added acetyl chloride (31.7 g, 406 mmol) followed by aluminum chloride (94.5 g, 710 mmol) over ~30 minutes. The solution was stirred at room temperature for 2 hours. The reaction was slowly poured into 1 M HCl (500 mL) and the organic layer separated. The organic layer was washed 2 times with water (500 mL), dried ($MgSO_4$), filtered and evaporated to yield product.

Step 5: 4'-(1-(Ethoxycarbonyl)cyclopropyl)biphenyl-4-carboxylic acid

To 1-(4'-acetylbiphenyl-4-yl)cyclopropanecarboxylic acid ethyl ester (10.1 g, 33 mmol) in dioxane (200 mL) at 10° C. was added a solution of bromine (26.4 g, 165 mmol), sodium hydroxide (22.4 g, 561 mmol) in water (150 mL). The solution was stirred at room temperature for 30 minutes, poured into water (500 mL) and acidified with dilute hydrochloric acid. Sodium metabisulfite was added until the brown bromine color dissipated. The product was filtered and dried in a vacuum over overnight at 40° C. to yield 10 g of 4'-(1-(ethoxycarbonyl)cyclopropyl)biphenyl-4-carboxylic acid.

Step 6: 3-Methylamino-but-2-enoic acid benzyl ester

To benzyl acetoacetate (29 g, 151 mmol) in ethanol (30 mL) was added methyl amine (33% in ethanol, 7.02 g, 226 mmol). The solution was stirred for 2 hours at room temperature followed by evaporation to yield a yellow oil.

Step 7: Ethyl 1-(4'-(2-(benzyloxycarbonyl)-3-(methylamino)but-2-enoyl)biphenyl-4-yl)cyclopropanecarboxylate 4'-(1-(Ethoxycarbonyl)cyclopropyl)biphenyl-4-carboxylic acid (80 g, 258 mmol), dichloroethane (400 mL), DMF (0.1 mL), thionyl chloride (2.3 mL, 32 mmol) were heated to 80° C. for 1.5 hours. (acid chloride formation was monitored by adding small aliquot (100 µL) to a solution of benzyl amine in acetonitrile and analyzing for the benzyl amide by LCMS; no starting material was observed by LCMS). The solution was evaporated on a rotavap to a dark oil and a solution of enamine (68.4 g, 335 mmol), pyridine (44.8 g, 568 mmol) in THF (400 mL) was added. The solution was stirred at 50° C. for 2 hours then the volatiles were evaporated using a rotavap to yield the crude product as a dark semi-solid.

Step 8: Benzyl 5-(4'-(1-(ethoxycarbonyl)cyclopropyl)biphenyl-4-yl)-3-methylisoxazole-4-carboxylate To the crude material from the previous reaction was added hydroxylamine hydrochloride (26.7 g, 387 mmol) and acetic acid (400 mL). The solution was heated to 95° C. for 1 hour cooled to room temperature, extracted with $CH_2Cl_2$ and water 3 times, dried, evaporated. The crude product is purified by running through a plug of silica (~200 grams of SiO2) eluting with CH2Cl2, then recrystallized in ethanol to yield product.

Step 9: 5-(4'-(1-(ethoxycarbonyl)cyclopropyl)biphenyl-4-yl)-3-methylisoxazole-4-carboxylic acid The benzyl ester (54 g, 112 mmol) in THF (300 mL) was degassed with nitrogen for 20 minutes. 10% Palladium on activated carbon (1.2 g, 1.1 mmol) was added and the solution was sparged with hydrogen via balloon. The balloon of hydrogen was maintained on the head space and the solution stirred for 20 hours. The reaction was filtered through celite and evaporated to dryness. The solid was triturated with a 1/1 solution of hexane/ethyl acetate (~300 mL) and filtered to yield product. Evaporation of the mother liquor followed by trituration of the solid with 1/1 hexanes ethyl acetate yielded further product.

Step 10: 1-{4'-[3-Methyl-4-((R)-1-phenyl-ethoxycarbonylamino)-isoxazol-5-yl]-biphenyl-4-yl}-cyclopropanecarboxylic acid ethyl ester To the acid from Step 9 (0.5 g, 1.28 mmol) in toluene (5 mL) was added (R)-1-phenyl ethanol (0.16 g, 1.34 mmol), triethyl amine (0.26 g, 2.56 mmol) and diphenyl phosphoryl azide (0.39 g, 1.4 mmol). The solution was heated to 80° C. for 1 hour, cooled to room temperature and extracted with water 3 times. The organic layer wad dried and evaporated to yield 0.61 g. The product was further purified by column 0 to 40% EtOAc/hex to yield product.

Step 11: 1-{4'-[3-Methyl-4-((R)-1-phenyl-ethoxycarbonylamino)-isoxazol-5-yl]-biphenyl-4-yl}-cyclopropanecarboxylic acid To ethyl ester (22.7 g, 44 mmol) in methanol (300 mL) was added lithium hydroxide (9.1 g, 222 mmol). The solution was heated to 65° C. for 2 hours, extracted into methylene chloride and washed with diluted hydrochloric acid. The organic layer was dried and evaporated to yield product.

Example 3

Alternate synthesis of 1-{4'-[3-Methyl-4-((R)-1-phenyl-ethoxycarbonylamino)-isoxazol-5-yl]-biphenyl-4-yl}-cyclopropanecarboxylic acid (Compound 1)

Step 1: 1-(Biphenyl-4-yl)cyclopropanecarboxylic acid isopropyl ester 1-(Biphenyl-4-yl)cyclopropanecarboxylic acid (10 g, 42 mmol), isopropanol (100 mL), thionyl chloride (6.8 mL, 92 mmol) were heated to 65° C. for 4 hours. Sulfuric acid (20 mL) was added and heated at 65° C. overnight. The product is extracted with $CH_2Cl_2$ and water (2×) dried and evaporated to yield product.

Step 2: 1-(4'-Acetylbiphenyl-4-yl)cyclopropanecarboxylic acid isopropyl ester

To 1-(biphenyl-4-yl)cyclopropanecarboxylic acid isopropyl ester (10.2 g, 36 mmol) in $CH_2Cl_2$ (100 mL) was added aluminum chloride (10.2 g, 76.5 mmol) followed by acetyl chloride (5.97 g, 76.5 mmol). The solution was stirred at room temperature for 1.5 hours then slowly poured into water. The organic layer was separated and extracted 1 time with sodium potassium tartrate solution (20 g in 250 mL water). The organic layer was dried and evaporated to yield product.

Step 3: 4'-(1-(isopropoxycarbonyl)cyclopropyl)biphenyl-4-carboxylic acid

To 1-(4'-acetylbiphenyl-4-yl)cyclopropanecarboxylic acid isopropyl ester (11.6 g, 36 mmol) in dioxane (200 mL) at ~10° C. was added a solution of bromine (28.8 g, 180 mmol), sodium hydroxide (24.5 g, 612 mmol) in water (150 mL). The solution was stirred at room temperature for 30 minutes poured into water (500 mL) and acidified with dilute hydrochloric acid. Sodium metabisulfite was added until the brown bromine color dissipated. The product was filtered and dried in a vacuum over overnight at 40° C. to yield product.

Step 4: Isopropyl 1-(4'-(2-(benzyloxycarbonyl)-3-(methylamino)but-2-enoyl)biphenyl-4-yl)cyclopropanecarboxylate 4'-(1-(Isopropoxycarbonyl)cyclopropyl)biphenyl-4-carboxylic acid (9.2 g, 28 mmol), dichloroethane (50 mL), DMF (0.1 mL), thionyl chloride (5.5 mL, 62 mmol) were heated to 75° C. for 1.5 hours. (acid chloride formation was monitored by adding small aliquot (100 mL) to a solution of benzyl amine in acetonitrile and analyzing for the benzyl amide by LCMS; no starting material was observed by LCMS). The solution was evaporated on a rotavap and THF (10 mL) was added. The solution of the acid chloride in THF was added via syringe to a solution of 3-methylamino-but-2-enoic acid methyl ester (4.0 g, 31.2 mmol) and pyridine (5.5 mL, 70 mmol) in THF (50 mL). The solution was stirred at room temperature overnight. The volatiles were evaporated on a rotavap to yield the crude product.

Step 5: Methyl 5-(4'-(1-(isopropoxycarbonyl)cyclopropyl)biphenyl-4-yl)-3-methylisoxazole-4-carboxylate To the crude material from the previous reaction was added hydroxylamine hydrochloride (2.9 g, 42 mmol) and acetic acid (50 mL). The solution was heated to 100° C. for 30 minutes cooled to room temperature, extracted with $CH_2Cl_2$ and water (4 times, second and third time made basic with sodium bicarbonate). The organic phase was dried, evaporated and purified on column (220 g silica; 0 to 20% EtOAc/hexanes) to yield product.

Step 6: 5-(4'-(1-(propoxycarbonyl)cyclopropyl)biphenyl-4-yl)-3-methylisoxazole-4-carboxylic acid To the methyl ester from Step 5 (5.2 g, 12.4 mmol) in THF (100 mL) and ethanol (20 mL) was added a solution of sodium hydroxide (1.5 g, 37.2 mmol) in water (40 mL). The solution was stirred at room temperature 3 hours. ~50 mL solvent evaporated and 200 mL water added. The product was precipitated out of solution with dilute hydrochloric acid to pH 2. The product was isolated by filtration to yield product.

Step 7: 1-{4'-[3-Methyl-4-((R)-1-phenyl-ethoxycarbonylamino)-isoxazol-5-yl]-biphenyl-4-yl}-cyclopropanecarboxylic acid isopropyl ester To the acid from Step 6 (4.0 g, 10 mmol) in toluene (50 mL) was added R-1-phenyl ethanol (1.33 g, 11 mmol), triethyl amine (2.02 g, 20 mmol) and diphenyl phosphoryl azide (3.16 g, 11.5 mmol). The solution was heated to 80° C. for 1 hour cooled to room temperature and extracted with water 3 times. The organic layer wad dried and evaporated to yield product.

Step 8: 1-{4'-[3-Methyl-4-((R)-1-phenyl-ethoxycarbonylamino)-isoxazol-5-yl]-biphenyl-4-yl}-cyclopropanecarboxylic acid To the isopropyl ester from Step 7 (5.2 g, 10 mmol) in THF (30 mL), MeOH (10 mL) was added NaOH (2 g, 50 mmol) in water (10 mL). The solution is heated to 65° C. for 5 hours. The solution was cooled to room temperature, extracted with methylene chloride and dilute hydrochloric acid. The organic was dried and evaporated and the product was purified by column chromatography (0 to 60% EtOAc/hexanes) to yield product.

Example 4

Synthesis of 1-[4-(4,4,5,5-Tetramethyl-[1,3,2]dioxaborolan-2-yl)-phenyl]-cyclopropanecarboxylic acid ethyl ester Step 1:
1-(4-Bromo-phenyl)-cyclopropanecarbonitrile Potassium hydroxide (14.3 g, 255 mmol) was dissolved in $H_2O$ (5 mL) and toluene (40 mL). 4-Bromophenylacetonitrile (5.0 g, 25.5 mmol) and tetrabutylammonium bromide (0.41 g, 1.3 mmol) was added, followed by 1,2-dibromoethane (3.25 mL, 38 mmol) dropwise over 10 minutes. The reaction was stirred at room temperature for 2 hours and then worked-up to give the title compound.

Step 2: 1-(4-Bromo-phenyl)-cyclopropanecarboxylic acid 1-(4-Bromo-phenyl)-cyclopropanecarbonitrile (5 g, 22.5 mmol) and potassium hydroxide (5 g, 89.3 mmol) were combined in ethylene glycol (70 mL), and the reaction was stirred at 180° C. for 4 hours. The mixture was poured into $H_2O$, acidified, and filtered to give the title compound.

Step 3: 1-(4-Bromo-phenyl)-cyclopropanecarboxylic acid ethyl ester 1-(4-Bromo-phenyl)-cyclopropanecarboxylic acid (5 g, 20.7 mmol) in EtOH (50 mL) was treated with sulfuric acid (2 mL), and the reaction was stirred at 75° C. for 1 hour. The mixture was worked up to give the title compound.

Step 4: 1-[4-(4,4,5,5-Tetramethyl-[1,3,2]dioxaborolan-2-yl)-phenyl]-cyclopropanecarboxylic acid ethyl ester 1-(4-Bromo-phenyl)-cyclopropanecarboxylic acid ethyl ester (3.6 g, 13.4 mmol), bis(pinacolato)diboron (3.37 g, 16.1 mmol), and potassium acetate (2.8 g, 29 mmol) were combined in 1,4-dioxane (30 mL). The solution was purged with $N_2$ for 10 minutes, and then (1,1'-bis(diphenylphosphino)ferrocene)-dichloropalladium(II) (0.50 g, 0.65 mmol) was added and the reaction was heated to 80° C. for 2 hours. Aqueous work-up, followed by silica gel chromatography (0-30% EtOAc in hexanes), gave the title compound.

Example 5

Synthesis of 1-{4'-[3-Methyl-4-((S)-1-phenyl-ethoxycarbonylamino)-isoxazol-5-yl]-biphenyl-4-yl}-cyclopropanecarboxylic acid Step 1: (S)-[5-(4-Bromo-phenyl)-3-methyl-isoxazol-4-yl]-carbamic acid 1-phenyl-ethyl ester Prepared according to the procedure described in Example 1, Step 5 using the following starting materials: 5-(4-bromo-phenyl)-3-methyl-isoxazole-4-carboxylic acid and (S)-(−)-1-phenylethanol (commercially available or prepared using procedures described herein or in the literature: e.g. E. J. Corey et al. *J. Am. Chem.* 1987, 109, 5551-5553).

Step 2: 1-{4'-[3-Methyl-4-((S)-1-phenyl-ethoxycarbonylamino)-isoxazol-5-yl]-biphenyl-4-yl}-cyclopropanecarboxylic acid ethyl ester Prepared according to the procedure described in Example 1, Step 6 using the following starting materials: (S)-[5-(4-bromo-phenyl)-3-methyl-isoxazol-4-yl]-carbamic acid 1-phenyl-ethyl ester and 1-[4-(4,4,5,5-tetramethyl-[1,3,2]dioxaborolan-2-yl)-phenyl]-cyclopropanecarboxylic acid ethyl ester.

Step 3: 1-{4'-[3-Methyl-4-((S)-1-phenyl-ethoxycarbonylamino)-isoxazol-5-yl]-biphenyl-4-yl}-cyclopropanecarboxylic acid To 1-{4'-[3-methyl-4-((S)-1-phenyl-ethoxycarbonylamino)-isoxazol-5-yl]-biphenyl-4-yl}-cyclopropanecarboxylic acid ethyl ester (1 equivalent) in 2:1 MeOH:$H_2O$ was added lithium hydroxide (3-10 equivalents), and the reaction was stirred at room temperature until no starting material was seen by analytical LCMS. The mixture was acidified with 1N aqueous HCl and extracted with EtOAc. The combined organic layers were dried, filtered, and concentrated to give the title compound. Mass spec. data (M+H)=483.

Example 6

Synthesis of racemic 1-{4'-[3-Methyl-4-(1-phenyl-ethoxycarbonylamino)-isoxazol-5-yl]-biphenyl-4-yl}-cyclopropanecarboxylic acid Prepared in a similar manner to the procedures described in Example 1 using (R/S)-1-phenyl-ethanol in place of (R)-1-phenyl-ethanol. Mass spec. data (M+H)=483.

Example 7

Synthesis of 1-{4'-[3-Methyl-4-(1-phenyl-ethoxy-d9-carbonylamino)-isoxazol-5-yl]-biphenyl-4-yl}-cyclopropanecarboxylic acid Step 1: 1-{4'-[3-Methyl-4-(1-phenyl-ethoxy-d9-carbonylamino)-isoxazol-5-yl]-biphenyl-4-yl}-cyclopropanecarboxylic acid ethyl ester Prepared according to the procedure described in Example 1, Step 5 using the following starting materials: 5-[4'-(1-ethoxycarbonyl-cyclopropyl)-biphenyl-4-yl]-3-methyl-isoxazole-4-carboxylic acid and 1-phenylethanol-d9 (obtained from Carbocore).

Step 2: 1-{4'-[3-Methyl-4-(1-phenyl-ethoxy-d9-carbonylamino)-isoxazol-5-yl]-biphenyl-4-yl}-cyclopropanecarboxylic acid To 1-{4'-[3-methyl-4-(1-phenyl-ethoxy-d9-carbonylamino)-isoxazol-5-yl]-biphenyl-4-yl}-cyclopropanecarboxylic acid ethyl ester (1 equivalent) in 2:1 MeOH:H$_2$O was added lithium hydroxide (3-10 equivalents), and the reaction was stirred at room temperature until no starting material was seen by analytical LCMS. The mixture was acidified with 1N aqueous HCl and extracted with EtOAc. The combined organic layers were dried, filtered, and concentrated to give the title compound. Mass spec. data (M+H)=492.

In some embodiments, Mass spectrometric data (mass spec. data) is obtained on with a Shimadzu LCMS 2010A.

Example 8

Preparation of Crystalline 1-{4'-[3-Methyl-4-((R)-1-phenyl-ethoxycarbonylamino)-isoxazol-5-yl]-biphenyl-4-yl}-cyclopropanecarboxylic acid (Compound 1)

20 mg of Compound 1 was weighed into a HPLC vial. 40 µL of ethanol was added and the vial was heated to reflux with a hot air gun. The solution was cooled to ambient temperature and the solids were filtered off. Crystalline Compound 1 (Pattern 1) was obtained as determined by XRPD. In the same manner as described from ethanol, the following solvents also provided crystalline Compound 1 (Pattern 1): methanol, 2-methoxyethanol, ethanol, 1-propanol, 2-propanol, 1-butanol, butyl acetate, acetone, methyl-ethyl ketone, anisole, toluene. 5 Volumes (i.e. 100 µL) of the following solvents with heating also provided crystalline Compound 1 (Pattern 1): nitromethane, acetonitrile, ethyl acetate, cumene.

Compound 1 dissolved in 2 volumes (i.e. 40 µL) of the following solvents at ambient temperature: 1-4-dioxane, tetrahydrofuran. The vials were uncapped and allowed to slowly evaporate. This provided crystalline Compound 1 (Pattern 1).

In another embodiment, 4.6 mg of Compound 1 was dissolved in 0.2 ml acetonitrile and 0.1 ml H$_2$O. The resulting solution was covered and slowly evaporated at 50° C. Need-shaped crystals were obtained from the solution after 5 days. This provided crystalline Compound 1 (Pattern 1).

In another embodiment, 4.9 mg of Compound 1 was dissolved in 0.2 ml isopropyl alcohol and 0.1 ml H$_2$O. The resulting solution was covered and slowly evaporated at 50° C. Need-shaped crystals were obtained from the solution after 3 days. This provided crystalline Compound 1 (Pattern 1).

In one embodiment, 4.5 mg of Compound 1 was dissolved in 0.2 ml methanol and 0.05 ml H$_2$O. The resulting solution was covered and slowly evaporated at 50° C. Need-shaped crystals were obtained from the solution after 3 days. This provided crystalline Compound 1 (Pattern 2). In another embodiment, 115 mg of Compound 1 was dissolved in 0.98 mL of methanol and 0.12 mL of tetrahydrofuran. The solution was evaporated to dryness and then the following was charged: a) 1 mL of acetonitrile and 1 mL of water; or b) 0.5 mL of ethanol, 0.5 mL of propylene glycol and 1 mL of heptanes; or c) 1 mL of ethyl acetate and 1 mL of heptanes; or d) 1 mL of methyl isobutyl ketone and 1 mL of heptanes. The crystallization was then stirred for 72 hours. This provided Compound 1 (Pattern 2).

In another embodiment, 305 mg of Compound 2 was dissolved in 10.0 ml THF. This solution was dispensed to a high throughput crystallization plate and test solvents were added. Needle-shaped crystals were recovered from the well which consisted of the solvent mixture of 1:2 THF and H$_2$O. This provided crystalline Compound 1 (Pattern 3).

In another embodiment, 2.2 mg of Compound 1 was dissolved in 0.15 ml methanol and 0.05 ml H$_2$O. The resulting solution was covered and stored at ambient conditions. Need-shaped crystals were obtained from the solution after 2 days. This provided crystalline Compound 1 (Pattern 3).

Compound 1 exhibits good solubility in a range of solvents, with only water and highly non-polar solvents (e.g. cyclohexane, heptane) proving unsuitable.

Example 9

Preparation of Compound 2 from Compound 1

Compound 1 was suspended in 10 volumes of ethanol and 1.0 equivalent 50 wt. % sodium hydroxide was added. Then heptane (20 vol.) was added over a 2-4 hour period. The ethanol was removed in vacuum and solvent exchanged with heptane. The solid was collected under nitrogen by vacuum filtration and the product was dried at about 60° C.-100° C. in a vacuum oven. This procedure gave Compound 2 in high purity.

Example 10

Preparation of Crystalline Compound 2

Maturation of Compound 2

100 mg of Compound 2 was weighed into five vials. To each vial was added a separate solvent: 1000 µL of nitromethane; 1000 µL of acetonitrile; 500 µL of 2-propanol; 500 µL of 1-butanol; 1000 µL of anisole. The vials were then cycled between ambient and 50° C., with 4 hour periods at each temperature, for 4 days. Any solids present at this time were filtered off and analysed by XRPD. Solids were then dried under vacuum at 50° C. for 2 days and reanalysed by XRPD. Amorphous material was obtained from nitromethane. Partially crystalline material was obtained from 2-propanol, 1-butanol and anisole. Crystalline compound 2 (Pattern 1) was isolated from acetonitrile.

The solids obtained from 1-butanol were noted to contain ⅔ of an equivalent of 1-butanol by $^1$H NMR. TGA analysis was also performed and a mass loss observed up to 160° C., when taken with the $^1$H NMR data, indicate that a 1-butanol solvate of the sodium salt was obtained. A 12.43% mass loss in the TGA equates to 0.92 equivalents of 1-butanol being present in the sample.

Anti-Solvent Mediated Conditions 20 mg of Compound 2 was weighed into HPLC vials. To each vial 100 uL of a 1:1 mixture of a solvent:anti-solvent was added. The vials were then agitated at 30° C. for a period of 12 days. After this period any solids were filtered off and analysed by XRPD.

Experiments using 1,4-dioxane/tert-butyl methyl ether and methyl ethyl ketone (MEK)/tert-butyl methyl ether produced crystalline compound 2 (Pattern 1) with the same diffraction pattern as that isolated from the acetonitrile maturation experiment. Partially crystalline material was obtained from ethyl acetate/tert-butyl methyl ether and anisole/tert-butyl methyl ether.

Preparation of Hydrated Crystalline Compound 2 (Pattern 1)

16.5 g of amorphous Compound 2, 83 ml (5 vol) of methyl ethyl ketone (MEK) and 4.1 ml (0.25 vol) of water slurried at 60° C. for 30 mins 165 ml (10 vol) of MEK added and the slurry seeded with ca. 15 mg of Compound 2 (Pattern 1). Slurry cooled to 50° C. for 6 hours and then further cooled to 15° C. over 6 hrs and stirred at ambient for a further 10 hrs. Filtered and dried in-vacuo for 21 hours. Recovery=15.7 g (91%). This procedure provided the hydrated crystalline Compound 2 (Pattern 1) with no significant amorphous content. At least 97% pure.

In an alternative procedure, 4.8 mg of Compound 2 was dissolved in 0.2 ml acetonitrile and 0.2 ml tetrahydrofuran. The resulting solution was slowly evaporated at 50° C. Plate-shaped single crystals were recovered after 3 days.

Preparation of Crystalline Compound 2 (Pattern 2)

1 g of Compound 1 was added into methyl ethyl ketone (MEK) (5 mL, 5 vol). Sodium hydroxide (83 mg) and water (213 mg, 0.21 vol) were added. The solution was heated to 60° C. and MEK (10 ml, 10 vol) was slowly added to the solution at 60° C. The reaction mixture was seeded with 10 mg of the hydrate crystalline Compound 2 and agitated at 50° C. for 2 hours. The cloudy solution was then cooled down to 20° C. over 2 hours. The solid was collected and dried under vacuum at 40° C. for 24 hours.

Preparation of Crystalline Compound 2 (Pattern 3)

Charged to a 50 L multi-neck round bottom flask 31 L methanol (MeOH), 3.1 kg Compound 1, and 514.0 g of 50% sodium hydroxide and agitated until a complete solution was obtained. Distilled the reactor contents until ~10 L remained maintaining a jacket temperature of about 45° C. Charged 25.0 kg ethanol to the reactor and distilled until ~15 L remained. Charged 25.0 kg ethanol to the reactor and distilled until ~15 L remained. Charged 12.1 kg ethanol to the reactor and agitated with a jacket temperature of 20° C. for at least 20 minutes. Charged 42.1 kg heptane to the reactor over a period of at least 4 hr. The reactor was agitated for 4 hr before distilling until ~45 L remained in the reactor. 32.0 kg of heptane was charged and distilled two (2) times before charging 32.1 kg heptane and filtering the reactor contents. The filter cake was washed with 16.0 kg heptane and the cake blown dry. The filter cake was dried in the oven maintaining a temperature of about 65 C. The dry Compound 2 was charged to the reactor with a pre-made solution of 12.6 kg methyl ethyl ketone (MEK), 45.9 kg methyl t-butyl ether (MTBE), and 0.31 kg water. The reactor was agitated at 45±5 C for 16 hr. The reactor contents were agitated an additional 21.5 hours. 60 g of Compound 2 seed crystals slurried in 1552 g MTBE. The reactor was agitated for 52.3 hours. 150 mL water was added. The reactor was agitated for 11 hr. Total time from start of crystallization to crystallization deemed complete was 7 days. The reactor was agitated at 20±5 C for 1 hr before the reactor contents were filtered. The filter cake was not washed. The filter cake was dried in the oven maintaining a temperature of about 65 C.

The Compound 2 was screened using a 20 mesh screen and returned to the oven to be dried at a temperature of about 85° C. Compound 2 was held in oven for 4 hours.

Example 11

Additional Salts of Compound 1

The free acid (Compound 1; 20 mg) was placed in a HPLC vial and treated with acetonitrile (200 µL), ethanol (200 µL), ethyl acetate (200 µL) or toluene (400 µL). The vial was capped, warmed and shaken until complete dissolution was achieved. One equivalent of base was added. Base solutions included 10M KOH (water); 5M L-arginine (water); 10M L-Lysine (water); 2M NH$_4$OH (28% aqueous solution); or 1M N-Me-glucamine (water). Vials were capped and allowed to stand at room temperature for six days. Any solids formed were filtered off.

Using this procedure, salts of Compound 1 with L-lysine, ammonium and N-methyl-D-glucamine salts were isolated.

Crystalline L-lysine salt of Compound 1 was obtained in ethanol and ethyl acetate.

Crystalline ammonium salt of Compound 1 was obtained in toluene.

Crystalline N-methyl-D-glucamine salt of Compound 1 was obtained in acetonitrile.

Example 12

X-Ray Characterization

The crystalline forms were analyzed using one or more of the testing methods described below. It is understood that slight variations in the coordinates and peak data for the X-ray measurements are possible and are considered to be within the scope of the present disclosure. In some embodiments, 2-Theta peak values that are provided for the XRPD are within ±0.1° 2-Theta.

X-Ray Powder Diffraction (XRPD)

X-Ray powder diffraction patterns were collected on a Bruker AXS C2 GADDS or Bruker AXS D8 Advance diffractometer.

Bruker AXS C2 GADDS

X-Ray Powder Diffraction patterns were collected on a Bruker AXS C2 GADDS diffractometer using Cu Kα radiation (40 kV, 40 mA), automated XYZ stage, laser video microscope for auto-sample positioning and a HiStar 2-dimensional area detector. X-ray optics consisted of a single Gael multilayer mirror coupled with a pinhole collimator of 0.3 mm. The beam divergence, i.e. the effective size of the X-ray beam on the sample, was approximately 4 mm. A θ-θ continuous scan mode was employed with a sample—detector distance of 20 cm which gives an effective 2θ range of 3.2°-29.7°. Typically the sample would be exposed to the X-ray beam for 120 seconds. The software used for data collection was GADDS for WNT 4.1.16 and the data were analyzed and presented using Diffrac Plus EVA v 9.0.0.2 or v 13.0.0.2.

Ambient Conditions

Samples run under ambient conditions were prepared as flat plate specimens using powder as received without grinding. Approximately 1-2 mg of the sample was lightly pressed on a glass slide to obtain a flat surface.

Non-Ambient Conditions

Samples run under non-ambient conditions were mounted on a silicon wafer with heat-conducting compound. The sample was then heated to the appropriate temperature at ca. 10° C. min$^{-1}$ and subsequently held isothermally for ca 2 minutes before data collection was initiated.

Bruker AXS D8 Advance

X-Ray Powder Diffraction patterns were collected on a Bruker D8 diffractometer using Cu Kα radiation (40 kV, 40 mA), θ-2θ goniometer, and divergence of V4 and receiving slits, a Ge monochromator and a Lynxeye detector. The instrument was performance checked using a certified Corundum standard (NIST 1976). The software used for data collection was Diffrac Plus XRD Commander v2.5.0 and the data were analyzed and presented using Diffrac Plus EVA v 11.0.0.2 or v 13.0.0.2. Samples were run under ambient conditions as flat plate specimens using powder. Approximately 5 mg of the sample was gently packed into a cavity cut into polished, zero-background (510) silicon wafer. The sample was rotated in its own plane during analysis. The details of the data collection are:

Angular range: 2 to 42° 2θ
Step size: 0.05° 2θ
Collection time: 0.5 s·step$^{-1}$ XRPD on Pattern 1 Free Acid (Compound 1)

The X-Ray powder diffraction pattern for Pattern 1 of the free acid (Compound 1) is displayed in FIG. 1. Characteristic peaks include 4.7° 2-Theta, 9.4° 2-Theta, 14.5° 2-Theta, and 21.0° 2-Theta. No form change was noted by XRPD after either GVS analysis or storage at 40° C./75% RH for one week.

XRPD on Hydrated Crystalline Compound 2 (Pattern 1)

The X-Ray powder diffraction pattern for Pattern 1 of the sodium salt (Compound 2) is displayed in FIG. 4. Characteristic peaks include 8.5° 2-Theta, 13.2° 2-Theta, 17.2° 2-Theta, 19.3° 2-Theta, 22.4° 2-Theta, and 25.6° 2-Theta.

XRPD on Crystalline Compound 2 (Pattern 2)

The X-Ray powder diffraction pattern for Pattern 2 of the sodium salt (Compound 2) is displayed in FIG. 8.

XRPD on Crystalline Compound 2 (Pattern 3)

The X-Ray powder diffraction pattern for Pattern 3 of the sodium salt (Compound 2) is displayed in FIG. 9.

XRPD on Amorphous Compound 2

The X-Ray powder diffraction pattern for amorphous sodium salt (Compound 2) is displayed in FIG. 10.

XRPD on Crystalline Compound 1 (Pattern 2)

X-ray powder diffraction (XPRD) data were obtained using a Bruker C2 GADDS. The radiation was Cu Kα (40 KV, 40 mA). The sample-detector distance was 15 cm. Powder samples were placed in sealed glass capillaries of 1 mm or less in diameter; the capillary was rotated during data collection. Data were collected for 3≤2θ≤35° with a sample exposure time of at least 1000 seconds. The resulting two-dimensional diffraction arcs were integrated to create a traditional 1-dimensional XPRD pattern with a step size of 0.02 degrees 2θ in the range of 3 to 35 degrees 2θ.

The X-Ray powder diffraction pattern for Pattern 2 of the free acid (Compound 1) is displayed in FIG. 12. Characteristic peaks include 6.3° 2-Theta, 12.8° 2-Theta, 16.4° 2-Theta, 17.0° 2-Theta, 19.7° 2-Theta.

XRPD on Crystalline Compound 1 (Pattern 3)

The powder diffraction data were obtained with a Bruker D8 GADDS diffractometer (Bruker-AXS, Karlsruhe, Germany) which was equipped with a monochromated CuKα source operating at a tube load of 40 kV and 40 mA. Powder samples were placed in sealed glass capillaries of 0.5 mm or 0.6 mm in diameter; the capillary was rotated during data collection. The sample-detector distance was 15 cm. Data were collected for 3≤2θ≤35° with a sample exposure time of at least 1200 seconds. The resulting two-dimensional diffraction arcs were integrated to create a traditional 1-dimensional PXRD pattern with a step size of 0.02 degrees 2θ in the range of 3 to 35 degrees 2θ.

The X-Ray powder diffraction pattern for Pattern 3 of the free acid (Compound 1) is displayed in FIG. 13. Characteristic peaks include 5.5° 2-Theta, 5.9° 2-Theta, 12.6° 2-Theta, 16.7° 2-Theta.

Single Crystal Data

Data were collected on a Bruker X8 APEX2 CCD diffractometer (Bruker AXS, Inc, Madison, Wis.). Intensities were measured using Cu Kα radiation (λ=1.5418 Å) at a constant temperature with φ and ω variable scan technique and were corrected only for Lorentz-polarization factors. Indexing and processing of the measured intensity data were carried out with the APEX2 software package/program suite. Alternately, single crystal data were collected on a Bruker-Nonius Kappa CCD 2000 system using Cu Kα radiation (λ=1.5418 Å). Indexing and processing of the measured intensity data were carried out with the HKL2000 software package (Otwinowski, Z. & Minor, W. (1997) in *Macromolecular Crystallography*, eds. Carter, W. C. Jr & Sweet, R. M. (Academic, NY), Vol. 276, pp. 307-326) in the Collect program suite (Collect Data collection and processing user interface: Collect: Data collection software, R. Hooft, Nonius B. V., 1998). When indicated, crystals were cooled in the liquid nitrogen cold stream of an Oxford cryosystem (Oxford Cryosystems Cryostream cooler: J. Cosier and A. M. Glazer, J. Appl. Cryst., 1986, 19, 105) during data collection.

The structures were solved by direct methods and refined on the basis of observed reflections using either the SDP (SDP, Structure Determination Package, Enraf-Nonius, Bohemia N.Y. 11716) software package with minor local modifications or the crystallographic packages MAXUS (maXus solution and refinement software suite: S. Mackay, C. J. Gilmore, C. Edwards, M. Tremayne, N. Stewart, K. Shankland. maXus: a computer program for the solution and refinement of crystal structures from diffraction data) or SHELXTL (SHELXTL: Bruker-AXS, 5465 East Cheryl Parkway, Madison, Wis., 53711, USA).

The derived atomic parameters (coordinates and temperature factors) were refined through full matrix least-squares. The function minimized in the refinements was $\Sigma_w(|F_o|-|F_c|)^2$. R is defined as $\Sigma||F_o|-|F_c||/\Sigma|F_o|$ while $R_w=[\Sigma_w(|F_o|-|F_c|)^2/\Sigma_w|F_o|^2]^{1/2}$ where w is an appropriate weighting function based on errors in the observed intensities. Difference maps were examined at all stages of refinement. Hydrogens were introduced in idealized positions with isotropic temperature factors, but no hydrogen parameters were varied.

The single crystal X-ray measurements for Compound 1 (Pattern 1) are shown in Table 1 and Table 2. For Compound 1 (Pattern 1), when single crystals are unstable at room temperature, X-ray diffraction experiments would typically be conducted at a lower temperature to help stabilize the crystal and to obtain diffraction data sufficient for the structure solution and refinement. Low temperature data collection also has the advantage of increasing signal/background ratios and thus improves diffraction intensities and the resolution in general. In this case, the crystal structure was first solved with software program SHELXTL (Bruker-AXS, 2008, Madison, Wis.) using a complete dataset collected at 203K. A short data collection of 20 minutes was then carried out at room temperature to determine the room temperature unit cell parameters via software APEX 2 (Bruker-AXS, 2010, Madison, Wis.). The crystal structure at room temperature was then generated by refining the atomic coordinates using the LT intensity data and the unit cell parameters obtained at RT using software SHELXTL. A room temperature powder X-ray pattern was calculated from the temperature-adjusted atomic coordinates and unit cell parameters using software Lattice View, and the simulated pattern matched the bulk PXRD collected at RT. This procedure can be applied when there is no phase transition within the temperature range and the iso-structures are neat.

TABLE 1

Crystal Data of Compound 1 (Pattern 1) at 25° C.

| | |
|---|---|
| a(Å) | 26.2070(8) |
| b(Å) | 37.700(1) |
| c(Å) | 5.0051(2) |
| α° | 90 |
| β° | 90 |
| γ° | 90 |
| V(Å3) | 4945.1(3) |
| Z | 8 |
| Calculated Density | 1.296 |
| Crystal System | Orthorhombic |
| SG | $P2_12_12$ |
| R1 | 0.0418 |
| Sol. Sites | — |

TABLE 2

Fractional Atomic Coordinates for Compound 1 (Pattern 1) at 25° C.

| Atom | x | y | z |
|---|---|---|---|
| O1 | 0.2368 | 0.8973 | 0.6933 |
| O2 | 0.2386 | 0.8401 | 0.5701 |
| H2A | 0.2617 | 0.8474 | 0.4743 |
| O3 | 0.0273 | 0.5978 | 0.4093 |
| O4 | 0.1763 | 0.5542 | 0.1454 |
| O5 | 0.2241 | 0.5349 | 0.4986 |
| N1 | 0.0212 | 0.5620 | 0.3259 |
| N2 | 0.1500 | 0.5615 | 0.5784 |
| H2 | 0.1599 | 0.5632 | 0.7419 |
| C1 | 0.2189 | 0.8662 | 0.6972 |
| C2 | 0.1723 | 0.8581 | 0.8574 |
| C3 | 0.1644 | 0.8804 | 1.1107 |
| H3A | 0.1478 | 0.8692 | 1.2617 |
| H3B | 0.1909 | 0.8973 | 1.1577 |
| C4 | 0.1330 | 0.8881 | 0.8707 |
| H4A | 0.1403 | 0.9097 | 0.7723 |
| H4B | 0.0972 | 0.8816 | 0.8762 |
| C5 | 0.1542 | 0.8201 | 0.8423 |
| C6 | 0.1176 | 0.8102 | 0.6565 |
| H6 | 0.1012 | 0.8276 | 0.5560 |
| C7 | 0.1051 | 0.7749 | 0.6186 |
| H7 | 0.0808 | 0.7692 | 0.4901 |
| C8 | 0.1274 | 0.7476 | 0.7649 |
| C9 | 0.1621 | 0.7580 | 0.9599 |
| H9 | 0.1769 | 0.7407 | 1.0675 |
| C10 | 0.1752 | 0.7932 | 0.9992 |
| H10 | 0.1984 | 0.799 | 1.1326 |
| C11 | 0.1146 | 0.7098 | 0.7087 |
| C12 | 0.0793 | 0.7011 | 0.5088 |
| H12 | 0.0639 | 0.7192 | 0.4122 |
| C13 | 0.0665 | 0.6662 | 0.4502 |
| H13 | 0.0425 | 0.6615 | 0.3178 |
| C14 | 0.0889 | 0.6384 | 0.5860 |
| C15 | 0.1243 | 0.6465 | 0.7876 |
| H15 | 0.1396 | 0.6282 | 0.8831 |
| C16 | 0.1367 | 0.6815 | 0.8462 |
| H16 | 0.1604 | 0.6861 | 0.9802 |
| C17 | 0.0756 | 0.6020 | 0.5125 |
| C18 | 0.0643 | 0.5464 | 0.3846 |
| C19 | 0.0725 | 0.5077 | 0.3186 |
| H19A | 0.0414 | 0.4948 | 0.3492 |
| H19B | 0.0990 | 0.4982 | 0.4303 |
| H19C | 0.0822 | 0.5054 | 0.1345 |
| C20 | 0.0991 | 0.5703 | 0.5047 |
| C21 | 0.1831 | 0.5502 | 0.3847 |
| C22 | 0.2633 | 0.5211 | 0.3136 |
| H22 | 0.2716 | 0.5395 | 0.1823 |
| C23 | 0.2440 | 0.4882 | 0.1668 |
| H23A | 0.2164 | 0.4947 | 0.0508 |
| H23B | 0.2323 | 0.4710 | 0.2944 |
| H23C | 0.2713 | 0.4782 | 0.0629 |
| C24 | 0.3100 | 0.5150 | 0.4952 |
| C25 | 0.3297 | 0.5435 | 0.6389 |
| H25 | 0.3148 | 0.5658 | 0.6209 |
| C26 | 0.3710 | 0.5392 | 0.8083 |
| H26 | 0.3839 | 0.5584 | 0.9034 |
| C27 | 0.3932 | 0.5058 | 0.8349 |
| H27 | 0.4209 | 0.5027 | 0.9487 |
| C28 | 0.3743 | 0.4776 | 0.6936 |
| H28 | 0.3895 | 0.4554 | 0.7105 |
| C29 | 0.3324 | 0.4818 | 0.5248 |
| H29 | 0.3194 | 0.4624 | 0.4321 |
| O11 | 0.3128 | 0.8572 | 0.2537 |
| O12 | 0.3166 | 0.9142 | 0.3767 |
| H12A | 0.2926 | 0.9081 | 0.4708 |
| O13 | 0.5345 | 0.6293 | −0.3192 |
| O14 | 0.3763 | 0.6325 | −0.3003 |
| O15 | 0.3344 | 0.6304 | −0.6979 |
| N11 | 0.5380 | 0.5933 | −0.4024 |
| N12 | 0.4180 | 0.6211 | −0.6935 |
| H12B | 0.4147 | 0.6179 | −0.8627 |
| C31 | 0.3350 | 0.8862 | 0.2512 |
| C32 | 0.3840 | 0.8912 | 0.1076 |
| C33 | 0.4171 | 0.9226 | 0.1868 |
| H33A | 0.4058 | 0.9370 | 0.3365 |
| H33B | 0.4538 | 0.9199 | 0.1722 |
| C34 | 0.3876 | 0.9250 | −0.0628 |
| H34A | 0.4062 | 0.9236 | −0.2299 |
| H34B | 0.3583 | 0.9407 | −0.0655 |
| C35 | 0.4071 | 0.8572 | 0.0081 |
| C36 | 0.4501 | 0.8421 | 0.1226 |
| H36 | 0.4675 | 0.8542 | 0.2566 |
| C37 | 0.4674 | 0.8090 | 0.0384 |
| H37 | 0.4964 | 0.7995 | 0.1185 |
| C38 | 0.4431 | 0.7896 | −0.1606 |

TABLE 2-continued

Fractional Atomic Coordinates for Compound 1 (Pattern 1) at 25° C.

| Atom | x | y | z |
|---|---|---|---|
| C39 | 0.4003 | 0.8057 | −0.2798 |
| H39 | 0.3832 | 0.7941 | −0.4169 |
| C40 | 0.3832 | 0.8386 | −0.1964 |
| H40 | 0.3549 | 0.8485 | −0.2795 |
| C41 | 0.4586 | 0.7529 | −0.2356 |
| C42 | 0.5056 | 0.6984 | −0.1486 |
| H42 | 0.5292 | 0.6862 | −0.045 |
| C43 | 0.4948 | 0.7336 | −0.0908 |
| H43 | 0.5121 | 0.7447 | 0.0482 |
| C44 | 0.4813 | 0.6813 | −0.3607 |
| C45 | 0.4465 | 0.7006 | −0.5135 |
| H45 | 0.4304 | 0.6899 | −0.6578 |
| C46 | 0.4358 | 0.7355 | −0.4529 |
| H46 | 0.4127 | 0.7478 | −0.5591 |
| C47 | 0.4915 | 0.6438 | −0.4254 |
| C48 | 0.4975 | 0.5878 | −0.5550 |
| C49 | 0.4884 | 0.5527 | −0.6848 |
| H49A | 0.5124 | 0.5357 | −0.6172 |
| H49B | 0.4926 | 0.5550 | −0.8746 |
| H49C | 0.4543 | 0.5449 | −0.6461 |
| C50 | 0.4669 | 0.6186 | −0.5731 |
| C51 | 0.3764 | 0.6286 | −0.5416 |
| C52 | 0.2903 | 0.6492 | −0.5923 |
| H52 | 0.2884 | 0.6459 | −0.3984 |
| C53 | 0.2435 | 0.6324 | −0.7266 |
| H53A | 0.2415 | 0.6078 | −0.6790 |
| H53B | 0.2465 | 0.6346 | −0.9170 |
| H53C | 0.2131 | 0.6444 | −0.6675 |
| C54 | 0.2947 | 0.6885 | −0.6562 |
| C55 | 0.2676 | 0.7132 | −0.5051 |
| H55 | 0.2474 | 0.7053 | −0.3642 |
| C56 | 0.2700 | 0.7492 | −0.5600 |
| H56 | 0.2513 | 0.7653 | −0.4585 |
| C57 | 0.3005 | 0.7610 | −0.7671 |
| H57 | 0.3030 | 0.7851 | −0.8036 |
| C58 | 0.3273 | 0.7366 | −0.9201 |
| H58 | 0.3475 | 0.7445 | −1.0606 |
| C59 | 0.3242 | 0.7008 | −0.8664 |
| H59 | 0.3422 | 0.6848 | −0.9719 |

A simulated XRPD obtained from the single crystal data for Compound 1 (Pattern 1) matched the experimental XRPD.

The single crystal X-ray measurements for Compound 1 (Pattern 2) are shown in Table 3 and Table 4.

TABLE 3

Crystal Data of Compound 1 (Pattern 2) at 25° C.

| a(Å) | 30.3522(9) |
|---|---|
| b(Å) | 7.8514(3) |
| c(Å) | 22.4570(7) |
| α° | 90 |
| β° | 111.665(2) |
| γ° | 90 |
| V(Å$^3$) | 4973.6(3) |
| Z | 8 |
| Calculated Density | 1.289 |
| Crystal System | Monoclinic |
| SG | C2 |
| R1 | 0.0298 |
| Sol. Sites | — |

TABLE 4

Fractional Atomic Coordinates for Compound 1 (Pattern 2) at 25° C.

| Atom | x | y | z |
|---|---|---|---|
| O1A | 0.4270 | 0.2955 | 0.8458 |
| O2A | 0.3936 | 0.3803 | 0.7425 |
| O3A | 0.2474 | 0.2796 | 0.6497 |
| O4A | 0.3113 | −0.8496 | 0.4058 |
| H4OA | 0.2947 | −0.9101 | 0.3763 |
| O5A | 0.3678 | −0.9522 | 0.3764 |
| N1A | 0.3520 | 0.2317 | 0.7904 |
| H1NA | 0.3536 | 0.1616 | 0.8206 |
| N2A | 0.2455 | 0.4272 | 0.6847 |
| C1A | 0.4836 | 0.8847 | 0.8164 |
| H1A | 0.486 | 0.9997 | 0.8081 |
| C2A | 0.4490 | 0.8319 | 0.8373 |
| H2A | 0.4285 | 0.9105 | 0.8442 |
| C3A | 0.4447 | 0.6587 | 0.8481 |
| H3A | 0.4213 | 0.6220 | 0.8626 |
| C4A | 0.4748 | 0.5422 | 0.8377 |
| C5A | 0.5098 | 0.6023 | 0.8171 |
| H5A | 0.5306 | 0.5254 | 0.8097 |
| C6A | 0.5144 | 0.7727 | 0.8074 |
| H6A | 0.5386 | 0.8110 | 0.7948 |
| C7A | 0.4732 | 0.3557 | 0.8491 |
| H7A | 0.4824 | 0.2940 | 0.8175 |
| C8A | 0.5065 | 0.3071 | 0.9156 |
| H8A | 0.5066 | 0.1855 | 0.9202 |
| H8B | 0.4960 | 0.3592 | 0.9467 |
| H8C | 0.5379 | 0.3456 | 0.922 |
| C9A | 0.3915 | 0.3095 | 0.7889 |
| C10A | 0.3084 | 0.2691 | 0.7412 |
| C11A | 0.2818 | 0.4188 | 0.7385 |
| C12A | 0.2925 | 0.5557 | 0.7873 |
| H12A | 0.3185 | 0.6233 | 0.7859 |
| H12B | 0.3009 | 0.5058 | 0.8291 |
| H12C | 0.2651 | 0.6266 | 0.7786 |
| C13A | 0.2863 | 0.1884 | 0.6849 |
| C14A | 0.2963 | 0.0390 | 0.6532 |
| C15A | 0.3254 | −0.0908 | 0.6873 |
| H15A | 0.3374 | −0.0878 | 0.7319 |
| C16A | 0.3371 | −0.2254 | 0.6561 |
| H16A | 0.3561 | −0.3131 | 0.6798 |
| C17A | 0.3205 | −0.2305 | 0.5894 |
| C18A | 0.2905 | −0.1011 | 0.5557 |
| H18A | 0.2784 | −0.1041 | 0.5112 |
| C19A | 0.2783 | 0.0314 | 0.5864 |
| H19A | 0.2580 | 0.1161 | 0.5627 |
| C20A | 0.3360 | −0.3652 | 0.5546 |
| C21A | 0.3417 | −0.5332 | 0.5743 |
| H21A | 0.335 | −0.565 | 0.6100 |
| C22A | 0.3570 | −0.6542 | 0.5419 |
| H22A | 0.3599 | −0.7669 | 0.5556 |
| C23A | 0.3682 | −0.6111 | 0.4896 |
| C24A | 0.3622 | −0.4441 | 0.4694 |
| H24A | 0.369 | −0.4130 | 0.4338 |
| C25A | 0.3462 | −0.3214 | 0.5010 |
| H25A | 0.3422 | −0.2096 | 0.4863 |
| C26A | 0.3879 | −0.7421 | 0.4571 |
| C27A | 0.4357 | −0.8181 | 0.4939 |
| H27A | 0.4517 | −0.7817 | 0.5380 |
| H27B | 0.4407 | −0.9366 | 0.4859 |
| C28A | 0.4317 | −0.6961 | 0.4438 |
| H28A | 0.4341 | −0.7387 | 0.4046 |
| H28B | 0.4452 | −0.5838 | 0.4567 |
| C29A | 0.3555 | −0.8585 | 0.4099 |
| O1B | 0.4377 | −0.2507 | 0.3549 |
| O2B | 0.4102 | −0.4137 | 0.2659 |
| O3B | 0.2606 | −0.3039 | 0.1508 |
| O4B | 0.3053 | 0.8448 | −0.0891 |
| H4OB | 0.2891 | 0.8813 | −0.1247 |
| O5B | 0.3592 | 1.0126 | −0.1017 |
| N1B | 0.3614 | −0.2468 | 0.2959 |
| H1NB | 0.3593 | −0.1765 | 0.3241 |
| N2B | 0.2589 | −0.4546 | 0.1844 |
| C1B | 0.5329 | 0.2266 | 0.3192 |
| H1B | 0.5434 | 0.3320 | 0.3108 |
| C2B | 0.4877 | 0.2084 | 0.3179 |
| H2B | 0.4672 | 0.3014 | 0.3082 |

TABLE 4-continued

Fractional Atomic Coordinates for
Compound 1 (Pattern 2) at 25° C.

| Atom | x | y | z |
|---|---|---|---|
| C3B | 0.4722 | 0.0515 | 0.3311 |
| H3B | 0.4415 | 0.0405 | 0.3301 |
| C4B | 0.5017 | −0.0872 | 0.3456 |
| C5B | 0.5478 | −0.0661 | 0.3465 |
| H5B | 0.5685 | −0.1581 | 0.3565 |
| C6B | 0.5625 | 0.0896 | 0.3329 |
| H6B | 0.5930 | 0.1015 | 0.333 |
| C7B | 0.4864 | −0.2622 | 0.3584 |
| H7B | 0.4880 | −0.3413 | 0.3255 |
| C8B | 0.5159 | −0.3299 | 0.4230 |
| H8D | 0.5070 | −0.4455 | 0.4267 |
| H8E | 0.5109 | −0.2617 | 0.4554 |
| H8F | 0.5488 | −0.3258 | 0.4284 |
| C9B | 0.4038 | −0.3123 | 0.3020 |
| C10B | 0.3201 | −0.2928 | 0.2434 |
| C11B | 0.2947 | −0.4451 | 0.2392 |
| C12B | 0.3045 | −0.5818 | 0.2877 |
| H12D | 0.2986 | −0.5405 | 0.3243 |
| H12E | 0.3371 | −0.6162 | 0.3007 |
| H12F | 0.2844 | −0.6776 | 0.2697 |
| C13B | 0.2984 | −0.2109 | 0.1873 |
| C14B | 0.3079 | −0.0562 | 0.1578 |
| C15B | 0.3415 | 0.0597 | 0.1925 |
| H15B | 0.3572 | 0.0427 | 0.2363 |
| C16B | 0.3522 | 0.2009 | 0.1639 |
| H16B | 0.3753 | 0.2767 | 0.1886 |
| C17B | 0.3293 | 0.2316 | 0.0989 |
| C18B | 0.2950 | 0.1181 | 0.0647 |
| H18B | 0.2787 | 0.1369 | 0.0212 |
| C19B | 0.2838 | −0.0235 | 0.0929 |
| H19B | 0.2601 | −0.0973 | 0.0684 |
| C20B | 0.3416 | 0.3837 | 0.0688 |
| C21B | 0.3521 | 0.5360 | 0.1009 |
| H21B | 0.351 | 0.5437 | 0.1417 |
| C22B | 0.3643 | 0.6776 | 0.0743 |
| H22B | 0.3708 | 0.7792 | 0.0972 |
| C23B | 0.3672 | 0.6726 | 0.0147 |
| C24B | 0.3570 | 0.5200 | −0.0175 |
| H24B | 0.3590 | 0.5123 | −0.0577 |
| C25B | 0.3438 | 0.3773 | 0.0083 |
| H25B | 0.3364 | 0.2766 | −0.0151 |
| C26B | 0.3823 | 0.8252 | −0.0134 |
| C27B | 0.4147 | 0.9571 | 0.0303 |
| H27C | 0.4101 | 1.0750 | 0.0165 |
| H27D | 0.4243 | 0.9405 | 0.0761 |
| C28B | 0.4342 | 0.8400 | −0.0049 |
| H28C | 0.4557 | 0.7516 | 0.0194 |
| H28D | 0.4415 | 0.8862 | −0.0402 |
| C29B | 0.3486 | 0.9014 | −0.0728 |

A simulated XRPD obtained from the single crystal data for Compound 1 (Pattern 2) is displayed in FIG. 12.

The single crystal X-ray measurements for Compound 1 (Pattern 3) are shown in Table 5 and Table 6.

TABLE 5

Crystal Data of Compound 1
(Pattern 3) at 25° C.

| | |
|---|---|
| a(Å) | 32.3574(9) |
| b(Å) | 5.1057(2) |
| c(Å) | 33.148(1) |
| α° | 90 |
| β° | 114.846(2) |
| γ° | 90 |
| V(Å$^3$) | 4969.4(3) |
| Z | 8 |
| Calculated Density | 1.290 |
| Crystal System | Monoclinic |
| SG | C2 |
| R1 | 0.0553 |
| Sol. Sites | — |

TABLE 6

Fractional Atomic Coordinates for
Compound 1 (Pattern 3) at 25° C.

| Atom | x | y | z |
|---|---|---|---|
| O1 | 0.1645 | 1.6687 | 0.7626 |
| O2 | 0.1196 | 1.8240 | 0.6962 |
| H2A | 0.1105 | 1.9124 | 0.7115 |
| O3 | 0.4706 | 0.3023 | 0.8618 |
| O4 | 0.4183 | 0.5185 | 0.9547 |
| O5 | 0.3861 | 0.1933 | 0.9771 |
| N1 | 0.5029 | 0.1165 | 0.8877 |
| N2 | 0.4213 | 0.0950 | 0.9346 |
| H2 | 0.4133 | −0.0632 | 0.9369 |
| C1 | 0.1537 | 1.6790 | 0.7220 |
| C2 | 0.1783 | 1.5407 | 0.7005 |
| C3 | 0.1817 | 1.6969 | 0.6629 |
| H3A | 0.1686 | 1.8713 | 0.6573 |
| H3B | 0.2093 | 1.6782 | 0.6584 |
| C4 | 0.1515 | 1.4832 | 0.6515 |
| H4A | 0.1598 | 1.3284 | 0.6397 |
| H4B | 0.1191 | 1.5215 | 0.6386 |
| C5 | 0.2169 | 1.3620 | 0.7273 |
| C6 | 0.2519 | 1.3129 | 0.7160 |
| H6 | 0.2525 | 1.4003 | 0.6916 |
| C7 | 0.2863 | 1.1405 | 0.7387 |
| H7 | 0.3091 | 1.1133 | 0.7291 |
| C8 | 0.2881 | 1.0073 | 0.7753 |
| C9 | 0.2529 | 1.0501 | 0.7870 |
| H9 | 0.2526 | 0.9599 | 0.8113 |
| C10 | 0.2179 | 1.2214 | 0.7644 |
| H10 | 0.1947 | 1.2446 | 0.7736 |
| C11 | 0.3260 | 0.8265 | 0.8007 |
| C12 | 0.3678 | 0.8417 | 0.7985 |
| H12 | 0.3719 | 0.9683 | 0.7804 |
| C13 | 0.4037 | 0.6776 | 0.8222 |
| H13 | 0.4311 | 0.6947 | 0.8197 |
| C14 | 0.3989 | 0.4867 | 0.8497 |
| C15 | 0.3570 | 0.4654 | 0.8518 |
| H15 | 0.3527 | 0.3365 | 0.8695 |
| C16 | 0.3216 | 0.6341 | 0.8279 |
| H16 | 0.2940 | 0.6173 | 0.8302 |
| C17 | 0.4360 | 0.3115 | 0.8747 |
| C18 | 0.4879 | 0.0253 | 0.9154 |
| C19 | 0.5138 | −0.1823 | 0.9479 |
| H19A | 0.5361 | −0.2572 | 0.9393 |
| H19B | 0.4932 | −0.3164 | 0.9482 |
| H19C | 0.5287 | −0.1069 | 0.9770 |
| C20 | 0.4461 | 0.1449 | 0.9092 |
| C21 | 0.4095 | 0.2913 | 0.9558 |
| C22 | 0.3667 | 0.3783 | 0.9973 |
| H22 | 0.3847 | 0.5400 | 1.0041 |
| C23 | 0.3719 | 0.2503 | 1.0408 |
| H23A | 0.4030 | 0.1984 | 1.0574 |
| H23B | 0.3526 | 0.0989 | 1.0344 |
| H23C | 0.3634 | 0.3729 | 1.0579 |
| C24A | 0.3174 | 0.4369 | 0.9600 |
| C25A | 0.2892 | 0.2301 | 0.9360 |
| H25A | 0.2994 | 0.0587 | 0.943 |
| C26A | 0.2468 | 0.2743 | 0.9024 |
| H26A | 0.2288 | 0.1355 | 0.8864 |
| C27A | 0.2314 | 0.5309 | 0.8929 |
| H27A | 0.2026 | 0.5649 | 0.8706 |
| C28A | 0.2590 | 0.7367 | 0.9167 |
| H28A | 0.2487 | 0.9084 | 0.9103 |
| C29A | 0.3020 | 0.6860 | 0.9500 |

TABLE 6-continued

Fractional Atomic Coordinates for Compound 1 (Pattern 3) at 25° C.

| Atom | x | y | z |
|---|---|---|---|
| H29A | 0.3205 | 0.8246 | 0.9656 |
| C24B | 0.3186 | 0.4368 | 0.9689 |
| C25B | 0.2986 | 0.4076 | 0.9229 |
| H25B | 0.3156 | 0.3433 | 0.9084 |
| C26B | 0.2532 | 0.4745 | 0.8987 |
| H26B | 0.2398 | 0.4550 | 0.8679 |
| C27B | 0.2277 | 0.5706 | 0.9204 |
| H27B | 0.1973 | 0.6153 | 0.9041 |
| C28B | 0.2477 | 0.5997 | 0.9663 |
| H28B | 0.2307 | 0.6640 | 0.9808 |
| C29B | 0.2932 | 0.5329 | 0.9906 |
| H29B | 0.3066 | 0.5524 | 1.0213 |
| O11 | 0.5855 | −0.3790 | 0.7389 |
| O12 | 0.6296 | −0.5381 | 0.8053 |
| H12A | 0.6393 | −0.6256 | 0.7904 |
| O13 | 0.2850 | 1.0407 | 0.6414 |
| O14 | 0.3349 | 1.5830 | 0.5527 |
| O15 | 0.3640 | 1.2869 | 0.5212 |
| N3 | 0.2519 | 1.2154 | 0.6127 |
| N4 | 0.3300 | 1.1471 | 0.5621 |
| H4 | 0.3369 | 0.9966 | 0.5549 |
| C31 | 0.5959 | −0.3928 | 0.7792 |
| C32 | 0.5705 | −0.2559 | 0.8006 |
| C33 | 0.5664 | −0.4182 | 0.8373 |
| H33A | 0.5385 | −0.4026 | 0.8413 |
| H33B | 0.5797 | −0.5922 | 0.8426 |
| C34 | 0.5967 | −0.2012 | 0.8499 |
| H34A | 0.6291 | −0.2382 | 0.8632 |
| H34B | 0.5880 | −0.0487 | 0.8619 |
| C35 | 0.5326 | −0.0721 | 0.7736 |
| C36 | 0.4979 | −0.0179 | 0.7855 |
| H36 | 0.497 | −0.1041 | 0.8099 |
| C37 | 0.4639 | 0.1609 | 0.7626 |
| H37 | 0.4414 | 0.1940 | 0.7724 |
| C38 | 0.4626 | 0.2888 | 0.7263 |
| C39 | 0.4972 | 0.2384 | 0.7136 |
| H39 | 0.4975 | 0.3244 | 0.6890 |
| C40 | 0.5316 | 0.0621 | 0.7366 |
| H40 | 0.5546 | 0.0328 | 0.7273 |
| C41 | 0.4251 | 0.4749 | 0.7008 |
| C42 | 0.3839 | 0.4726 | 0.7041 |
| H42 | 0.3795 | 0.3514 | 0.7230 |
| C43 | 0.3493 | 0.6423 | 0.6808 |
| H43 | 0.3221 | 0.6343 | 0.684 |
| C44 | 0.3543 | 0.8260 | 0.6524 |
| C45 | 0.3958 | 0.8349 | 0.6494 |
| H45 | 0.4003 | 0.9590 | 0.6311 |
| C46 | 0.4304 | 0.6626 | 0.6730 |
| H46 | 0.4578 | 0.6725 | 0.6703 |
| C47 | 0.3177 | 1.0047 | 0.6270 |
| C48 | 0.2656 | 1.2775 | 0.5823 |
| C49 | 0.2379 | 1.4597 | 0.5459 |
| H49A | 0.2094 | 1.4936 | 0.5475 |
| H49B | 0.2322 | 1.3818 | 0.5177 |
| H49C | 0.2541 | 1.6212 | 0.5490 |
| C50 | 0.3070 | 1.1500 | 0.5896 |
| C51 | 0.3423 | 1.3576 | 0.5461 |
| C52 | 0.3836 | 1.4958 | 0.5041 |
| H52 | 0.3667 | 1.6577 | 0.5027 |
| C53 | 0.3743 | 1.4176 | 0.4576 |
| H53A | 0.3424 | 1.3812 | 0.4413 |
| H53B | 0.3916 | 1.2637 | 0.4582 |
| H53C | 0.3829 | 1.5576 | 0.4434 |
| C54A | 0.4328 | 1.5290 | 0.5409 |
| C55A | 0.4615 | 1.3163 | 0.5609 |
| H55A | 0.4510 | 1.1470 | 0.552 |
| C56A | 0.5049 | 1.3533 | 0.5933 |
| H56A | 0.5235 | 1.2105 | 0.6066 |
| C57A | 0.5205 | 1.6071 | 0.6059 |
| H57A | 0.5499 | 1.6351 | 0.6275 |
| C58A | 0.4923 | 1.8191 | 0.5861 |
| H58A | 0.5028 | 1.9889 | 0.5945 |
| C59A | 0.4484 | 1.7772 | 0.5537 |
| H59A | 0.4296 | 1.9195 | 0.5407 |
| C54B | 0.4328 | 1.5319 | 0.5311 |

TABLE 6-continued

Fractional Atomic Coordinates for Compound 1 (Pattern 3) at 25° C.

| Atom | x | y | z |
|---|---|---|---|
| C55B | 0.4607 | 1.5550 | 0.5089 |
| H55B | 0.4484 | 1.5408 | 0.4781 |
| C56B | 0.5071 | 1.5994 | 0.5328 |
| H56B | 0.5258 | 1.6148 | 0.5180 |
| C57B | 0.5256 | 1.6207 | 0.5788 |
| H57B | 0.5566 | 1.6504 | 0.5948 |
| C58B | 0.4976 | 1.5976 | 0.6010 |
| H58B | 0.5099 | 1.6119 | 0.6318 |
| C59B | 0.4512 | 1.5532 | 0.5772 |
| H59B | 0.4325 | 1.5378 | 0.5920 |

A simulated XRPD obtained from the single crystal data for Compound 1 (Pattern 3) is displayed in FIG. 13.

The single crystal X-ray measurements for Compound 2 (Pattern 1) are shown in Table 7 and Table 8.

TABLE 7

Crystal Data of Compound 2 (Pattern 1) at 25° C.

| | |
|---|---|
| a(Å) | 13.8714(2) |
| b(Å) | 7.7379(2) |
| c(Å) | 25.5253(5) |
| α° | 90 |
| β° | 103.863(1) |
| γ° | 90 |
| V(Å3) | 2659.96(9) |
| Z | 4 |
| Calculated Density | 1.305 |
| Crystal System | Monoclinic |
| SG | P2$_1$ |
| R1 | 0.0301 |
| Sol. Sites | 1H$_2$O |

TABLE 8

Fractional Atomic Coordinates for Compound 2 (Pattern 1) at 25° C.

| Atom | x | y | z |
|---|---|---|---|
| Na1 | 0.5534 | 0.5155 | 0.7376 |
| Na2 | 0.4268 | 0.1578 | 0.7661 |
| O1 | 0.5791 | 0.6272 | 0.8275 |
| O2 | 0.4955 | 0.3834 | 0.8159 |
| O3 | 0.9547 | 0.9797 | 0.8944 |
| O4 | 0.7250 | 0.4863 | 0.7547 |
| O5 | 0.8692 | 0.6302 | 0.7635 |
| O11 | 0.4860 | 0.2928 | 0.6884 |
| O12 | 0.4095 | 0.0426 | 0.6759 |
| O13 | −0.0533 | −0.8204 | 0.4086 |
| O14 | −0.2536 | −0.3596 | 0.2463 |
| O15 | −0.1150 | −0.5250 | 0.2643 |
| N1 | 0.8774 | 1.0896 | 0.8666 |
| N2 | 0.7799 | 0.6684 | 0.8247 |
| H2A | 0.7369 | 0.6305 | 0.8411 |
| N11 | −0.1310 | −0.9306 | 0.3820 |
| N12 | −0.2104 | −0.5182 | 0.3228 |
| H12A | −0.2539 | −0.4666 | 0.3362 |
| C1 | 0.5492 | 0.4898 | 0.8454 |
| C2 | 0.5797 | 0.4598 | 0.9052 |
| C3 | 0.4988 | 0.3880 | 0.9302 |
| H3A | 0.4986 | 0.4245 | 0.9665 |
| H3B | 0.4336 | 0.3698 | 0.9066 |
| C4 | 0.5795 | 0.2744 | 0.9234 |
| H4A | 0.5637 | 0.186 | 0.8957 |
| H4B | 0.6287 | 0.2407 | 0.9556 |
| C5 | 1.3459 | 0.0837 | 1.0622 |
| C6 | 1.3747 | 0.2412 | 1.0465 |

TABLE 8-continued

Fractional Atomic Coordinates for Compound 2 (Pattern 1) at 25° C.

| Atom | x | y | z |
|---|---|---|---|
| H6 | 1.4415 | 0.2714 | 1.0560 |
| C7 | 1.3071 | 0.3555 | 1.0170 |
| H7 | 1.3291 | 0.4614 | 1.0072 |
| C8 | 1.2061 | 0.3160 | 1.0015 |
| C9 | 1.1770 | 0.1582 | 1.0172 |
| H9 | 1.1102 | 0.1277 | 1.0076 |
| C10 | 1.2455 | 0.0434 | 1.0473 |
| H10 | 1.2237 | −0.0621 | 1.0575 |
| C11 | 1.1333 | 0.4415 | 0.9706 |
| C12 | 1.1456 | 0.6172 | 0.9799 |
| H12 | 1.1993 | 0.6559 | 1.0066 |
| C13 | 1.0812 | 0.7356 | 0.9508 |
| H13 | 1.0925 | 0.8527 | 0.9579 |
| C14 | 0.9995 | 0.6851 | 0.9111 |
| C15 | 0.9854 | 0.5090 | 0.9018 |
| H15 | 0.9309 | 0.4708 | 0.8755 |
| C16 | 1.0508 | 0.3897 | 0.9310 |
| H16 | 1.0396 | 0.2725 | 0.9240 |
| C17 | 0.9295 | 0.8131 | 0.8832 |
| C18 | 0.8097 | 0.9856 | 0.8392 |
| C19 | 0.7147 | 1.0541 | 0.8044 |
| H19A | 0.7093 | 1.1752 | 0.8113 |
| H19B | 0.6596 | 0.9937 | 0.8124 |
| H19C | 0.7146 | 1.0373 | 0.7671 |
| C20 | 0.8390 | 0.8108 | 0.8477 |
| C21 | 0.7864 | 0.5881 | 0.7789 |
| C22 | 0.8734 | 0.5694 | 0.7100 |
| H22 | 0.8543 | 0.4473 | 0.7061 |
| C23 | 0.9804 | 0.5886 | 0.7073 |
| H23A | 1.0223 | 0.5267 | 0.7367 |
| H23B | 0.9983 | 0.7087 | 0.7098 |
| H23C | 0.9887 | 0.5425 | 0.6738 |
| C24 | 0.8038 | 0.6735 | 0.6678 |
| C25 | 0.8000 | 0.8512 | 0.6713 |
| H25 | 0.8405 | 0.9078 | 0.7006 |
| C26 | 0.7367 | 0.9449 | 0.6320 |
| H26 | 0.7344 | 1.0646 | 0.6348 |
| C27 | 0.6772 | 0.8642 | 0.5888 |
| H27 | 0.6343 | 0.9287 | 0.5624 |
| C28 | 0.6801 | 0.6930 | 0.5843 |
| H28 | 0.6395 | 0.6381 | 0.5546 |
| C29 | 0.7438 | 0.5963 | 0.6238 |
| H29 | 0.7455 | 0.4768 | 0.6202 |
| C31 | 0.4410 | 0.1780 | 0.6584 |
| C32 | 0.4204 | 0.2015 | 0.5979 |
| C33 | 0.4254 | 0.3816 | 0.5778 |
| H33A | 0.3815 | 0.4114 | 0.5433 |
| H33B | 0.4374 | 0.4742 | 0.6041 |
| C34 | 0.5076 | 0.2623 | 0.5774 |
| H34A | 0.5699 | 0.2814 | 0.6037 |
| H34B | 0.5140 | 0.2186 | 0.5428 |
| C35 | 0.3483 | 0.0785 | 0.5641 |
| C36 | 0.3786 | −0.0804 | 0.5489 |
| H36 | 0.4453 | −0.1107 | 0.5597 |
| C37 | 0.3122 | −0.1948 | 0.5183 |
| H37 | 0.3350 | −0.3003 | 0.5087 |
| C38 | 0.1813 | 0.0035 | 0.5165 |
| H38 | 0.1147 | 0.0343 | 0.5057 |
| C39 | 0.2112 | −0.1555 | 0.5014 |
| C40 | 0.2480 | 0.1178 | 0.5473 |
| H40 | 0.2252 | 0.2232 | 0.5571 |
| C41 | 0.1393 | −0.2825 | 0.4702 |
| C42 | 0.1502 | −0.4561 | 0.4816 |
| H42 | 0.2045 | −0.4932 | 0.5081 |
| C43 | 0.0831 | −0.5762 | 0.4551 |
| H43 | 0.0927 | −0.6926 | 0.4640 |
| C44 | 0.0018 | −0.5265 | 0.4155 |
| C45 | −0.0105 | −0.3529 | 0.4038 |
| H45 | −0.0648 | −0.316 | 0.3772 |
| C46 | 0.0569 | −0.2331 | 0.4310 |
| H46 | 0.0465 | −0.1165 | 0.4228 |
| C47 | −0.0718 | −0.6564 | 0.3900 |
| C48 | −0.1921 | −0.8294 | 0.3485 |
| C49 | −0.2850 | −0.9024 | 0.3122 |
| H49A | −0.2753 | −1.0228 | 0.3059 |
| H49B | −0.2995 | −0.8416 | 0.2784 |
| H49C | −0.3394 | −0.8894 | 0.3291 |
| C50 | −0.1585 | −0.6569 | 0.3520 |
| C51 | −0.1972 | −0.4595 | 0.2751 |
| C52 | −0.0952 | −0.4900 | 0.2111 |
| H52 | −0.0361 | −0.5577 | 0.2100 |
| C53 | −0.0661 | −0.3036 | 0.2074 |
| H53A | −0.0165 | −0.2728 | 0.2392 |
| H53B | −0.1234 | −0.2313 | 0.2045 |
| H53C | −0.0400 | −0.2880 | 0.1762 |
| C54 | −0.1780 | −0.5628 | 0.1670 |
| C55 | −0.2312 | −0.4637 | 0.1244 |
| H55 | −0.2167 | −0.347 | 0.1222 |
| C56 | −0.3051 | −0.5386 | 0.0854 |
| H56 | −0.3410 | −0.4712 | 0.0572 |
| C57 | −0.3266 | −0.7096 | 0.0874 |
| H57 | −0.3763 | −0.7582 | 0.0603 |
| C58 | −0.2751 | −0.8119 | 0.1294 |
| H58 | −0.2896 | −0.9287 | 0.1315 |
| C59 | −0.2012 | −0.7330 | 0.1681 |
| H59 | −0.1655 | −0.8002 | 0.1964 |
| O21 | 0.5365 | 0.7582 | 0.6857 |
| H21A | 0.5740 | 0.7620 | 0.6607 |
| H21B | 0.5040 | 0.8610 | 0.6889 |
| O22 | 0.4576 | −0.0839 | 0.8173 |
| H22A | 0.4060 | −0.1190 | 0.8329 |
| H22B | 0.5040 | −0.1760 | 0.8212 |

A simulated XRPD obtained from the single crystal data for Compound 2 (Pattern 1) matched the experimental XRPD.

Example 13

Differential Scanning Calorimetry (DSC) and Thermogravimetric Analysis (TGA)

DSC data were collected on a TA Instruments Q2000 equipped with a 50 position auto-sampler. The calibration for thermal capacity was carried out using sapphire and the calibration for energy and temperature was carried out using certified indium. Typically 0.5-3 mg of each sample, in a pin-holed aluminum pan, was heated at 10° C. min$^{-1}$ from 25° C. to 250° C. A purge of dry nitrogen at 50 ml min$^{-1}$ was maintained over the sample. The instrument control software was Advantage for Q Series v2.8.0.392 and Thermal Advantage v4.8.3 and the data were analyzed using Universal Analysis v4.3A.

TGA data were collected on a TA Instruments Q500 TGA, equipped with a 16 position auto-sampler. The instrument was temperature calibrated using certified Alumel. Typically 5-30 mg of each sample was loaded onto a pre-tared platinum crucible and aluminum DSC pan, and was heated at 10° C.·min$^{-1}$ from ambient temperature to 350° C. A nitrogen purge at 60 ml·min$^{-1}$ was maintained over the sample. The instrument control software was Advantage for Q Series v2.8.0.392 and Thermal Advantage v4.8.3.

Pattern 1 Free Acid (Compound 1)

A sample of the free acid (Compound 1) were analyzed by TGA and DSC and the thermograms are shown in FIG. 2 and FIG. 3. No mass loss is noted in the TGA up to 150° C. and a sharp endotherm, attributed to a melt, is observed at around onset 172° C.-176° C. in the DSC.

Amorphous Compound 2

Figure 11:
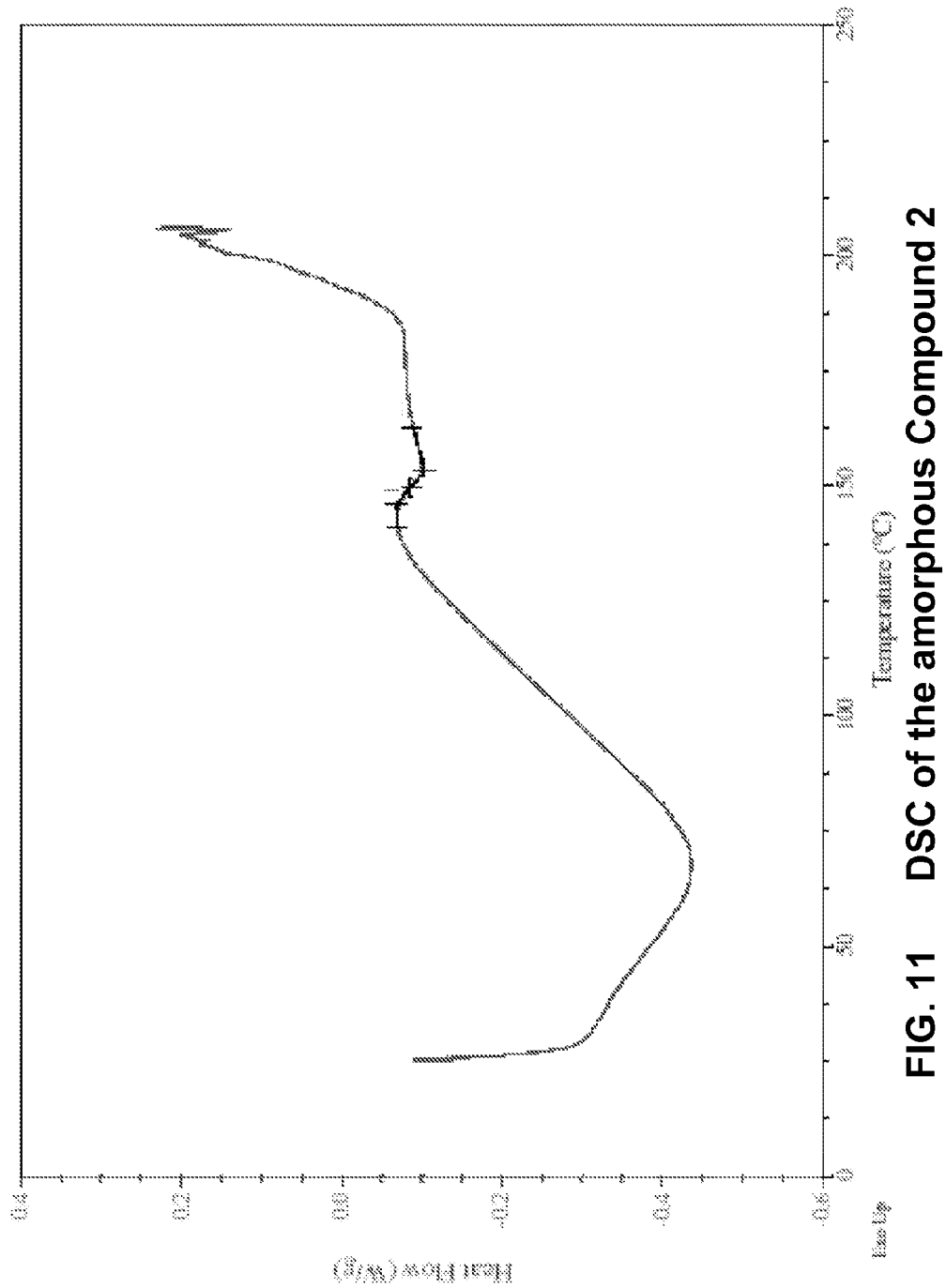
FIG. 11 illustrates the DSC of amorphous Compound 2.

A sample of the amorphous sodium salt acid (Compound 2) were analyzed by TGA and DSC. A 2.79% mass loss is observed in the TGA up to 150° C., likely attributable to loss of ethanol and water. A DSC thermogram is shown in FIG. 11.

Crystalline Compound 2 (Pattern 1)

A sample of the hydrated crystalline sodium salt (Compound 2) were analyzed by TGA and DSC and the thermograms are shown in FIG. 5 and FIG. 6.

Example 14

Water Determination by Karl Fischer Titration (KF)

The water content of each sample was measured on a Mettler Toledo DL39 Coulometer using Hydranal Coulomat AG reagent and an argon purge. Weighed solid samples were introduced into the vessel on a platinum TGA pan which was connected to a subaseal to avoid water ingress. Approx 10 mg of sample was used per titration and duplicate determinations were made.

The water content of the crystalline Compound 2 (Pattern 1) was determined as 4.1% m/m by Karl Fisher titration, which correlates with the mass loss observed in the TGA and calculates as 1.2 mol of water per mol of API. All the data is consistent with crystalline Compound 2 (Pattern 1) being a hydrated crystalline form.

Example 15

Gravimetric Vapour Sorption (GVS)

In some embodiments, sorption isotherms were obtained using a SMS DVS Intrinsic moisture sorption analyzer, controlled by SMS Analysis Suite software. The sample temperature was maintained at 25° C. by the instrument controls. The humidity was controlled by mixing streams of dry and wet nitrogen, with a total flow rate of 200 ml·min−1 The relative humidity was measured by a calibrated Rotronic probe (dynamic range of 1.0-100% RH), located near the sample. The weight change (mass relaxation) of the sample as a function of % RH was constantly monitored by the microbalance (accuracy±0.005 mg). Typically 5-20 mg of sample was placed in a tared mesh stainless steel basket under ambient conditions. The sample was loaded and unloaded at 40% RH and 25° C. (typical room conditions). A moisture sorption isotherm was performed as outlined below (2 scans giving 1 complete cycle). The standard isotherm was performed at 25° C. at 10% RH intervals over a 0.5-90% RH range.

TABLE 9

Method Parameters for SMS DVS Intrinsic Experiments

| Parameters | Values |
| --- | --- |
| Adsorption - Scan 1 | 40-90 |
| Desorption/Adsorption - Scan 2 | 85-Dry, Dry-40 |
| Intervals (% RH) | 10 |
| Number of Scans | 2 |
| Flow rate (ml · min−1) | 200 |
| Temperature (° C.) | 25 |
| Stability (° C. · min−1) | 0.2 |
| Sorption Time (hours) | 6 hour time out |

The sample was recovered after completion of the isotherm and re-analyzed by XRPD.

Crystalline Compound 1 (Pattern 1)

The free acid (Compound 1) is less hygroscopic than the sodium salt, with only a 0.45% mass gain between 0% and 90% relative humidity. The XRPD of the crystalline free acid was substantially the same after storage at 40° C./75% RH for one week.

Amorphous Compound 2

Amorphous Compound 2 exhibits hygroscopicity, increasing in mass by more than 20% upon raising the relative humidity from 0% to 90%. No change of form is observed during this process.

The material remains largely amorphous in nature after storage at 40° C./75% RH for one week.

Crystalline Compound 2 (Pattern 1)

Crystalline Compound 2 (Pattern 1) exhibits lower hygroscopicity than its amorphous counterpart and shows no loss of crystallinity after a week's storage at 40° C./75% RH or 25° C./95% RH.

Example 16

Thermodynamic Aqueous Solubility

Aqueous solubility was determined by suspending sufficient compound in water to give a maximum final concentration of ≥10 mg·ml-1 of the parent free-form of the compound. The suspension was equilibrated at 25° C. for 24 hours then the pH was measured. The suspension was then filtered through a glass fiber C filter into a 96 well plate unless stated otherwise. The filtrate was then diluted by a factor of 101. Quantification was by HPLC with reference to a standard solution of approximately 0.25 mg·ml$^{-1}$ in DMSO. Different volumes of the standard, diluted and undiluted sample solutions were injected. The solubility was calculated using the peak areas determined by integration of the peak found at the same retention time as the principal peak in the standard injection.

For solubility assessment at various pH levels sufficient material to produce a maximum concentration of 10 mg·ml$^{-1}$ of API was treated with 0.15M NaCl solution and then the pH adjusted with HCl or NaOH solutions to achieve the desired pH levels. The suspensions were allowed to equilibrate for 2 hours and the pH measured and adjusted if necessary. Suspensions were then filtered and the amount of dissolved API quantified by HPLC against a standard reference solution.

TABLE 10

HPLC Method Parameters for Solubility Measurements

| | | | |
| --- | --- | --- | --- |
| Type of method: | Reverse phase with gradient elution | | |
| Column: | Phenomenex Luna, C18(2) 5 μm 50 × 4.6 mm | | |
| Column Temperature (° C.): | 25 | | |
| Standard Injections (μl): | 1, 2, 3, 5, 7, 10 | | |
| Test Injections (μl): | 1, 2, 3, 10, 20, 50 | | |
| Detection Wavelength, Bandwidth (nm): | 260, 80 | | |
| Flow Rate (ml · min−1): | 2 | | |
| Phase A: | 0.1% TFA in water | | |
| Phase B: | 0.085% TFA in acetonitrile | | |
| | Time (min) | % Phase A | % Phase B |
| Timetable: | 0.0 | 95 | 5 |
| | 1.0 | 80 | 20 |
| | 2.3 | 5 | 95 |
| | 3.3 | 5 | 95 |
| | 3.5 | 95 | 5 |
| | 4.4 | 95 | 5 |

Analysis was performed on an Agilent HP1100 series system equipped with a diode array detector and using ChemStation software vB.02.01-SR1.

The thermodynamic aqueous solubility of both the free acid (Compound 1) and the sodium salt (Compound 2) were determined.

TABLE 11

Thermodynamic aqueous solubility

| Form | Solvent | pH of saturated solution | Appearance | Solubility (mg/ml, free form equivalent) |
|---|---|---|---|---|
| free acid | water | 7.07 | Suspension | 0.028 |
| free acid | water | 6.93 | Suspension | 0.031 |
| sodium salt | water | 8.90 | Clear Solution | >=20 |
| sodium salt | water | 9.07 | Clear Solution | >=10 |

The solubility of both the free acid and amorphous sodium salt was determined at a range of pH values. The results are shown in Tables 14 and 15.

TABLE 12

Solubility profile for Compound 2 (Amorphous)

| Target pH | Appearance after 2 hrs | pH after 2 hrs | Appearance after 24 hrs | pH after 24 hrs | Solubility (mg/mL) |
|---|---|---|---|---|---|
| pH3 | Residual Solid | 4.04 | Residual Solid | 2.90 | <0.001 |
| pH4 | Residual Solid | 4.29 | Residual Solid | 4.28 | <0.001 |
| pH5 | Residual Solid | 5.34 | Residual Solid | 5.11 | <0.001 |
| pH6 | Residual Solid | 6.42 | Residual Solid | 6.23 | 0.0017 |
| pH7 | Suspension | 7.18 | Suspension | 7.17 | 0.3 |
| pH8 | Fine Suspension | 8.08 | Fine Suspension | 8.01 | 5.6 |
| pH9 | Clear Solution | 9.09 | Clear Solution | 9.07 | 17 |
| pH11 | Clear Solution | 11.07 | Clear Solution | 11.01 | 16 |

TABLE 13

Solubility profile for Compound 1

| Target pH | Appearance after pH 2 hrs | pH after 2 hrs | Appearance after 24 hrs | pH after 24 hrs | Solubility (mg/mL) |
|---|---|---|---|---|---|
| pH3 | Residual Solid/ Solid on Surface | 3.04 | Residual Solid/ Solid on Surface | 3.04 | <0.001 |
| pH4 | Residual Solid/ Solid on Surface | 3.88 | Residual Solid/ Solid on Surface | 3.86 | <0.001 |
| pH5 | Residual Solid/ Solid on Surface | 4.81 | Residual Solid/ Solid on Surface | 4.81 | <0.001 |
| pH6 | Residual Solid/ Solid on Surface | 5.83 | Residual Solid/ Solid on Surface | 5.82 | <0.001 |
| pH7 | Residual Solid/ Solid on Surface | 6.92 | Suspension/ Residual Solid | 6.85 | 0.0033 |
| pH8 | Suspension | 7.95 | Suspension | 7.90 | 0.035 |
| pH9 | Suspension | 8.92 | Suspension | 8.90 | 0.93 |
| pH11 | Suspension | 8.84 | Clear Solution | 11.05 | 13 |

Example 17

Chemical Purity Determination

Purity analysis was performed by HPLC on an Agilent HP 1100 series system equipped with a diode array detector and using ChemStation software vB.02.01-SR1.

TABLE 14

| HPLC Method Parameters for Chemical Purity Determinations | |
|---|---|
| Sample Preparation: | ~0.5 mg/ml in acetonitrile:water 1:1 v/v |
| Column: | Supelco Ascentis Express C18, 100 × 4.6mm, 2.7 µm |
| Column Temperature (° C.): | 25 |
| Injection (µl): | 2-5 |
| Detection Wavelength, Bandwidth( nm): | 255, 90 |
| Flow Rate (ml · min$^{-1}$): | 2.0 |
| Phase A: | 0.1% TFA in water |
| Phase B: | 0.085% TFA in acetonitrile |

| | Time (min) | % Phase A | % Phase B |
|---|---|---|---|
| Timetable: | 0 | 95 | 5 |
| | 6 | 5 | 95 |
| | 6.2 | 95 | 5 |
| | 8 | 95 | 5 |

Samples of Compound 1 and Compound 2 were found to be greater than 90% pure. In some embodiments, samples of Compound 1 were found to be greater than 95% pure, greater than 96% pure, greater than 97% pure, greater than 98% pure, greater than 99% pure. In some embodiments, samples of Compound 2 were found to be greater than 94% pure, greater than 95% pure, greater than 96% pure, greater than 97% pure, greater than 98% pure, greater than 99% pure.

In some embodiments, samples of Compound 1 or Compound 2 include a detectable amount of a compound having one of the following structures:

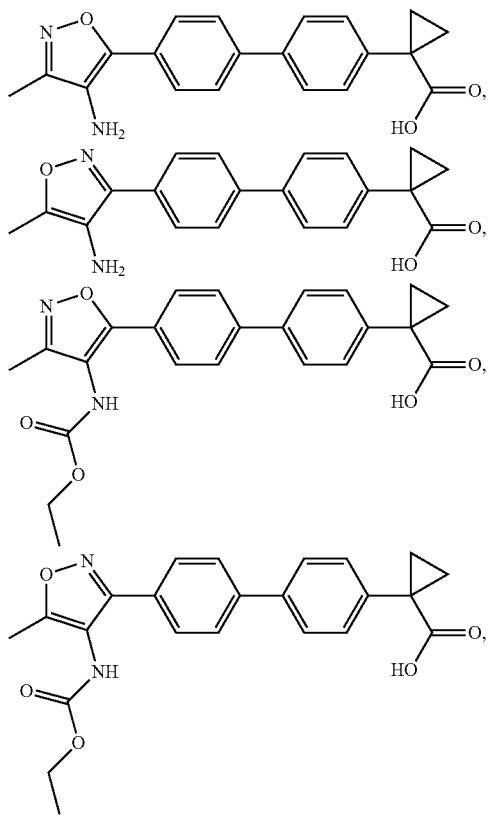

121
-continued
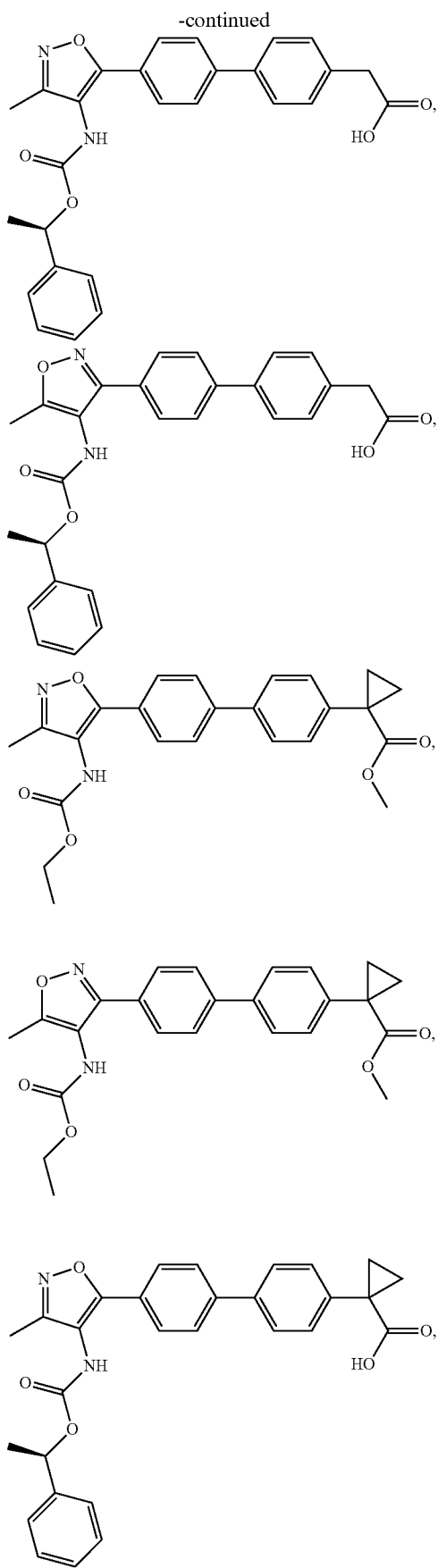
122
-continued
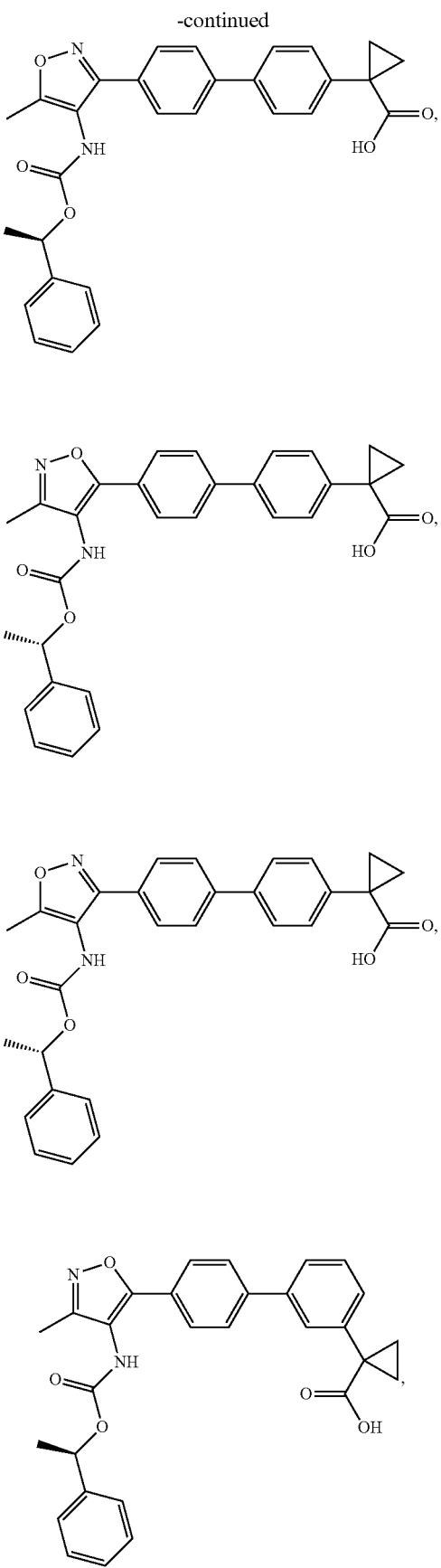

123
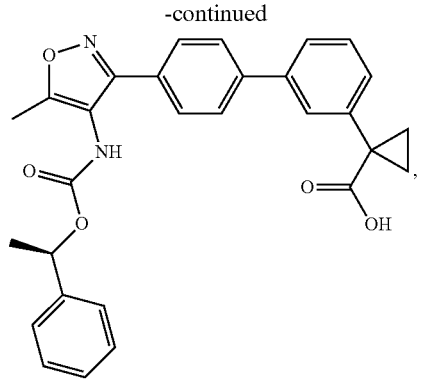
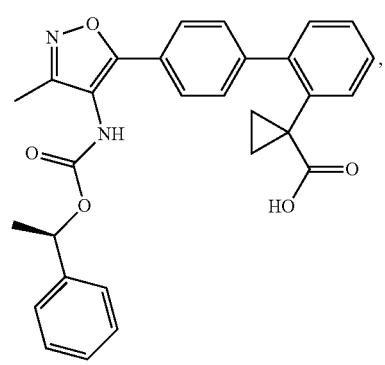
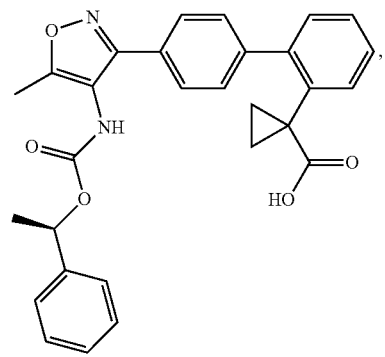
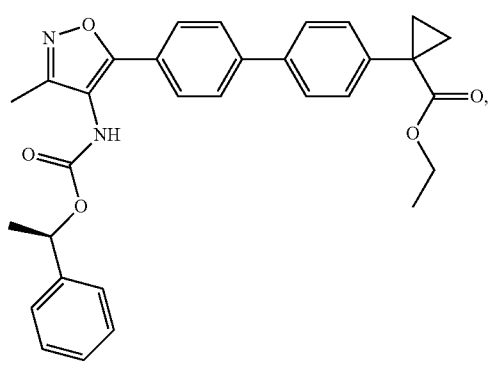
124
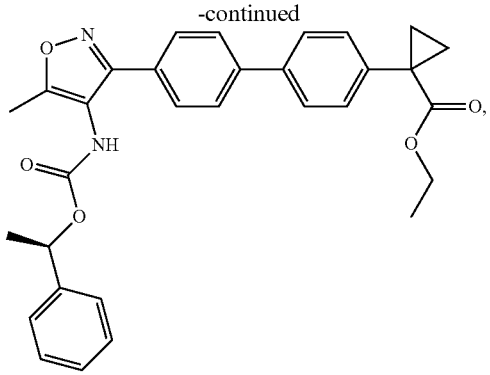
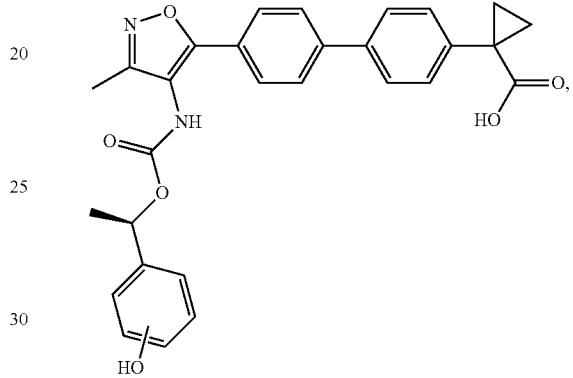
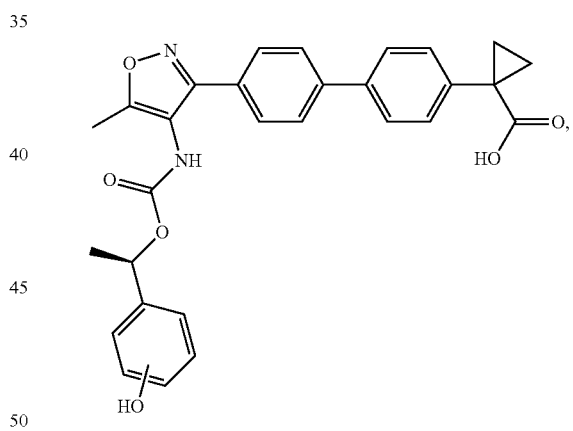
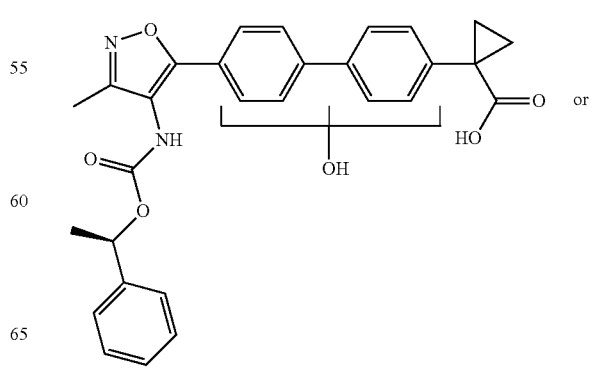
or

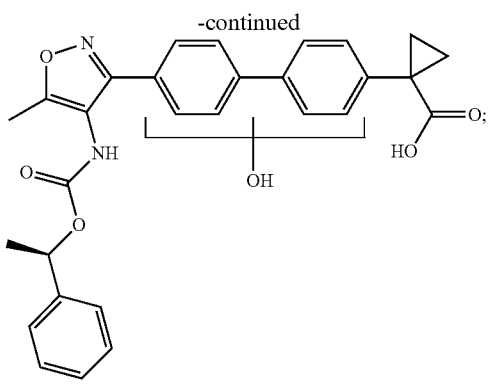

or combinations thereof.

Example 18

Chiral Purity

Chiral purity analysis was performed by HPLC on an Agilent HP 1100 series system equipped with a diode array detector and using ChemStation software vB.02.01-SR1.

TABLE 15

HPLC Method Parameters for Chemical Purity Determinations

| | |
|---|---|
| Sample Preparation: | ~0.5 mg/ml in methanol |
| Column: | Chiralpak AD-H, 5 μm, 250 × 4.6 mm |
| Column Temperature (° C.): | 35 |
| Injection (μl): | 5 |
| Detection: Wavelength, Bandwidth( nm): | 290 |
| Flow Rate (ml · min$^{-1}$): | 1.0 |
| Phase A: | Hexane (0.05% TFA) |
| Phase B: | Isopropanol |

| | Time (min) | % Phase A | % Phase B |
|---|---|---|---|
| Timetable: | 0 | 80 | 20 |
| | 35 | 80 | 20 |

Chiral purity (% enantiomeric excess; % e.e.) was determined. In some embodiments, samples of Compound 1 and Compound 2 were found to have a chiral purity greater than 98%. In some embodiments, samples of Compound 1 were found to have a chiral purity greater than 95%, greater than 96%, greater than 97%, greater than 98%, greater than 99%. In some embodiments, samples of Compound 2 were found to have a chiral purity greater than 94%, greater than 95%, greater than 96%, greater than 97%, greater than 98%, greater than 99%.

Example 19

Heavy Metals (Pd) by ICP-AES

Trace palladium (Pd) resulting from the use of catalytic amounts of Pd in the synthesis is assayed by inductively coupled plasma atomic emission spectrometry (ICP-AES). Pd content by ICP-AES is a detectable amount of palladium that is less than about 20 ppm. Pd content by ICP-AES is less than about 20 ppm. Pd content by ICP-AES is a detectable amount of palladium that is less than 20 ppm, less than 15 ppm, less than 10 ppm, or less than 5 ppm. Pd content by ICP-AES is less than 20 ppm, less than 15 ppm, less than 10 ppm, or less than 5 ppm. In some embodiments, samples or pharmaceutical compositions do not include a detectable amount of palladium.

Example 20

Heavy Metals (as Lead)

This test is performed according to USP<231> Method II.

Example 21

IR Spectroscopy of Crystalline Compound 2 (Pattern 1)

A sample of crystalline Compound 2 (Pattern 1; hydrate) was analyzed by infrared spectroscopy. The data was collected on a Perkin-Elmer Spectrum One instrument fitted with a universal Attenuated Total Reflectance (ATR) sampling accessory. Scan range=4000 cm−1 to 600 cm−1 with 64 scans and a resolution of 4 cm$^{-1}$. The data was analysed using Spectrum v5.0.1 software.

| Wavenumber (cm-$^1$) | Intensity (% T) |
|---|---|
| 3627 | 93 |
| 3345 | 94 |
| 3078 | 94 |
| 1707 | 80 |
| 1636 | 93 |
| 1574 | 75 |
| 1436 | 91 |
| 1376 | 78 |
| 1350 | 85 |
| 1325 | 85 |
| 1299 | 86 |
| 1194 | 91 |
| 1087 | 89 |
| 1059 | 89 |
| 1029 | 87 |
| 951 | 90 |
| 884 | 91 |
| 823 | 85 |
| 791 | 87 |
| 773 | 85 |
| 762 | 85 |
| 741 | 89 |
| 699 | 76 |
| 665 | 91 |

Pharmaceutical Compositions

Pharmaceutical compositions that include Compound 1, including pharmaceutically acceptable salts (e.g. Compound 2) and/or pharmaceutically acceptable solvates thereof include a variety of forms. In one aspect, pharmaceutical compositions are in the form of oral dosage forms. In some embodiments, pharmaceutical compositions are formulated as: oral solutions, oral suspensions, tablets, pills, capsules, ointments, creams or gels.

Example 22

Oral Solutions

In one aspect, an oral pharmaceutical composition in the form of an oral solution is prepared as outlined below.

An oral solution is prepared at 50 mg/mL of Compound 1 or Compound 2.

Oral Solution A:

In one embodiment, an oral pharmaceutical composition is prepared with the following ingredients:

50 mg/mL of Compound 1 or Compound 2
0.5% Methocel
0.5% Cherry flavor
0.5% sucralose
water, qs to The manufacturing process for the oral solutions of Compound 1 or Compound 2 described above is as follows: weigh the required amount of methocel and transfer to the container. Add the required amount of water to make a 0.5% solution and mix until dissolved. Weigh the required amount of cherry flavor and sucralose and add this to the solution and mix until homogenous. Weigh the required amount of Compound 1 or Compound 2 and slowly add to the solution. Mix until all Compound 1 or Compound 2 is dissolved (sonicate, warm, or stir if necessary).

Example 23

Capsule Formulations

Immediate Release Capsules

In one embodiment, a capsule formulation of Compound 1 or Compound 2 for administration to humans is prepared with the following ingredients:

| Component | Function | Quantity per Size 4 Capsule mg | Quantity per Size 1 Capsule mg |
|---|---|---|---|
| Compound 1 or Compound 2 | Active | 10 to 500 mg | 100 to 1000 mg |
| Hypromellose, USP | Capsule Shell | 1 capsule | 1 capsule |

The process to prepare Compound 1 or Compound 2 in a capsule is as follows: Weigh the required amount of Compound 1 or Compound 2, add into the appropriate size capsule, and close capsule. For example, 10-500 mg of Compound 1 or Compound 2 is placed into a Size 4 Capsule. In one embodiment, 100-500 mg of Compound 1 or Compound 2 is placed into a Size 1 Capsule.

Example 24

Immediate Release Tablets

Non-limiting examples of immediate release tables that include Compound 2 are presented below.

TABLE 16

Immediate release Tablets

| | Tablet 1 | | Tablet 2 | |
|---|---|---|---|---|
| Ingredients | % w/w | mg /unit | % w/w | mg / unit |
| Compound 2 | 35.05 | 262.85 | 7.07 | 53.0 |
| Anhydrous Dibasic Calcium Phosphate | 19.98 | 149.85 | 29.31 | 219.8 |
| Silicified Microcrystalline Cellulose | 39.96 | 299.70 | 58.62 | 439.7 |
| Sodium Starch Glycolate | 3.00 | 22.50 | 3.00 | 22.50 |
| Sodium Lauryl Sulfate | 1.00 | 7.50 | 1.00 | 7.50 |
| Magnesium Stearate | 1.00 | 3.75 | 1.00 | 7.5 |
| Total | 100.00 | 750.00 | 100.00 | 750.00 |

A non-limiting example for the preparation of immediate release tablets is described below. Other dose amounts are contemplated. In some cases, the tablets are coated with a thin film (e.g. opadry coating).

Manufacturing/analytical equipment typically used in the preparation of tablets include: formulation (U.S.A. standard testing sieve; V-shell blender; ERWEKA TBH300 MD hardness tester; Vanderkamp friability tester; Manesty beta press, sixteen station); analytical (Agilent 1100 series HPLC with variable wavelength detector; VanKel model VK7000 dissolution apparatus; VanKel model VK8000 dissolution autosampler).

To an appropriately-sized mixing vessel was add the following: ½ of the silicified microcrystalline cellulose HD90, ½ of the anhydrous dibasic Calcium phosphate, Compound 2, sodium lauryl sulfate, sodium starch glycolate (intra-granular portion), remaining ½ of the anhydrous dibasic calcium phosphate, remaining ½ of the silicified microcrystalline cellulose HD90. Blend ingredients. Pass blend through a sieve screen and transfer back to mixing vessel. Blend ingredients. Pre-screen ½ of magnesium stearate (intra-granular amount) through a sieve screen. Add to powder blend and blend ingredients. Perform roller compaction of the blend using a roller compactor and appropriate parameters to generate ribbons with suitable mechanical properties. Recycle the bypass (i.e. powder and loosely-compacted powder) through the roller compactor to achieve further densification. Pass the ribbons through a mill to achieve a granulation of suitable particle size distribution for tabletting. Transfer granulation to suitable mixing vessel. Blend granulation. Pre-screen ½ of magnesium stearate (extra-granular amount) through a sieve screen. Add to granulation and blend ingredients.

Transfer the final granulation to a tablet press and compress into tablets.

Dissolution Studies

In some embodiments, all tablets are tested for dissolution using the following parameters:

| Dissolution Parameters | |
|---|---|
| Apparatus: | USP2 Paddles |
| Speed: | 60 rpm |
| Dissolution Media: | $KH_2PO_4$ buffer, pH 7.4, 2% CTAB |
| Dissolution volume: | 900 mL |
| Medium temperature: | 37 ± 0.5° C. |
| Sampling volume: | 1.5 mL |

Immediate release tablets show release no less than (NLT) 75% of Compound 1 or Compound 2 within 45 minutes.

In some embodiments, tablets are optionally packaged in HDPE bottles, with CRC caps and heat induction seal.

Example 25

Enteric Coated Tablets

In some embodiments, enteric coated tablets are prepared with the ingredients listed in Table 17.

TABLE 17

Enteric Coated Tablets

| Ingredient | Tablet # 1 | Tablet # 2 | Tablet # 3 |
|---|---|---|---|
| | Amount per Tablet (mg) | | |
| Compound 1 or Compound 2 immediate release tablet (750 mg) | 750 | 750 | 750 |
| Eudragit L 100-55 | 20 | | |
| Eudragit S 100 | | 20 | |
| Eudragit L 100 | | | 20 |
| Triethyl Citrate | 5 | 5 | 5 |
| Acetone | | | |
| Purified Water | | | |
| Total | 775 | 775 | 775 |

The preparation of the enteric coated tablets is as follows: Weigh 388.0 g of acetone and 12.0 g of purified water and mix them in a beaker with an overhead stirrer. Weigh 40 g of the Eudragit and pour into the solvent mixture slowly in portions to prevent lump formation. Stir until a clear solution is made. Then weigh 6 g of triethyl citrate and add into the clear solution and keep stirring until a homogeneous solution is made. Mix around 60 g of placebo tablets with about 80 of the 750 mg immediate release tablets and coat with the coating mixture.

Example 26

Sustained Release Tablets

The blend of the formulation is prepared in the same manner as the immediate release tablets (e.g. sieving, blending, and compression). Other preparations are acceptable, such as wet granulation, fluidized bed, high shear granulation, etc. The formulation includes drug modifying release excipients. These excipients include but not limited to HPMC (hydroxy propyl methylcellulose or hypromellose), methacrylic polymers, polyvinyl acetate, and povidone. The amount of drug release modifying excipient ranges from about 10% to about 80% in the formulation. The drug release profile ranges from 0 to 4 hours, 0 to 6 hours, 0 to 8 hours, 0 to 12 hours, 0 to 24 hours, 2 to 4 hours, 2 to 6 hours, etc. In some embodiments, the formulations are coated with the Opadry coatings after direct compression. Example sustained release formulations are listed below.

TABLE 18

Sustained Release Tablet

| | Amount per tablet (mg) | %, w/w |
|---|---|---|
| Compound 1 or Compound 2 | 250.0 | 33.3 |
| Mannitol | 90.0 | 12.0 |
| Prosolv HD 90 | 177.5 | 23.7 |
| Sodium Stearyl Fumarate | 7.5 | 1.0 |
| Methocel K4M | 225.0 | 30.0 |
| Total | 750 | 100 |

TABLE 19

Sustained Release Tablet

| | Amount per tablet (mg) | %, w/w |
|---|---|---|
| Compound 1 or Compound 2 | 250.0 | 33.3 |
| Mannitol | 112.5 | 15.0 |
| Prosolv HD 90 | 230.0 | 30.7 |
| Sodium Stearyl Fumarate | 7.5 | 1.0 |
| Methocel K100 LV | 150.0 | 20.0 |
| Total | 750.0 | 100 |

Example 27

Ointment Compositions

A non-limiting example of an ointment composition is presented in Table 20.

TABLE 20

PEG Ointment Compositions

| | Formula # | | |
|---|---|---|---|
| Components (% w/w) | AA | BB | CC |
| Compound 1 or Compound 2 | 5 | 5 | 5 |
| Stearyl Alcohol | 4 | — | 1 |
| PEG 3350 | 40 | 40 | 36 |
| Butylated hydroxyl Toluene (BHT) | 0.1 | 0.1 | 0.1 |
| Dimethicone (Q7-9120 Silicone Fluid, 350CST) | — | — | 1 |
| Brij 721 | — | — | 3 |
| PEG 400 | 50.9 | 54.9 | 53.9 |

Example 28

Gel Compositions

A non-limiting example of a gel composition is presented in Table 21.

TABLE 21

| | Wt % | | |
|---|---|---|---|
| Components | 1 | 2 | 3 |
| Compound 1 or Compound 2 | 1 | 1.5 | 1 |
| Transcutol P | — | 10 | — |
| Propylene glycol | 10 | — | 10 |
| PEG 400 | 40 | 40 | 15 |
| Benzyl alcohol | 1 | 1.0 | 2 |
| Gelling agent | 1-2 | 1-2 | 1-2 |
| Glycerin | 10 | 10 | 10 |
| EDTA disodium | 0.5 | 0.5 | 0.5 |
| Methylparaben | 0.17 | 0.17 | 0.17 |
| Propylparaben | 0.03 | 0.03 | 0.03 |
| pH adjuster | pH adjusted to 7 | pH adjusted to 7 | pH adjusted to 7 |
| Purified water (or buffer) | q.s.a.d. | q.s.a.d. | q.s.a.d. |

Example 29

Cream Compositions

A non-limiting example of a cream composition is presented in Table 22.

TABLE 22

| Components | Formula # | | | |
|---|---|---|---|---|
| | A | B | C | D |
| Transcutol P | 25 | 25 | 25 | 25 |
| Propylene glycol | 20 | 20 | 20 | 20 |
| Mineral Oil | 5 | 5 | 5 | 5 |
| Dimethicone (Q7-9120 Silicon Fluid 100 CST) | 5 | 5 | 5 | 5 |
| BHT | 0.1 | 0.1 | 0.1 | 0.1 |
| Brij 72 | 1.0 | — | 1.2 | — |
| Brij 721 | 1.8 | — | 1.8 | — |
| Glycerul Monosterate SE | — | 10 | — | — |
| Sorbitan Monosterate | — | — | — | 2.5 |
| Pamulen TR1 | — | 0.3 | — | — |
| Stearyl Alcohol | 1.0 | — | 5 | 5 |
| Cetyl Alcohol | 0.5 | — | 3 | 3 |
| EDTA disodium | 0.05 | 0.05 | 0.05 | 0.05 |
| Methylparaben | 0.17 | 0.17 | 0.17 | 0.17 |
| Propylparaben | 0.03 | 0.03 | 0.03 | 0.03 |
| Carbopol Ultrez 10 | 0.4 | 0.2 | — | — |
| 4% NaOH | qs pH 7 | qs pH 7 | — | — |
| Purified Water | qsad | qsad | — | — |
| 20 mM Phosphate Buffer (pH7) | — | — | qsad | qsad |
| Compound 1 or Compound 2 | 3% (w/w) | 3% (w/w) | 3% (w/w) | 3% (w/w) |

Example 30

Identification of Metabolic Pathways

Compound 1 metabolites formed during incubation of Compound 1 with: rat, dog, monkey, and human liver microsomes; rat, dog, and human hepatocytes; as well as those generated in vivo and isolated from rat bile and rat and dog plasma were investigated.

Materials

Male Sprague-Dawley rats, male beagle dogs, and mixed pool human cryopreserved hepatocytes were purchased from Celsis (Woburn, Mass.). Fresh human hepatocyctes were purchased from Life Technologies (lot 00583558, male; Carlsbad, Calif.). KB media was from Celsis. UDPGA, β-NADPH and tryptophan blue was from Sigma Chemical.

Compound 2 (2 mg/kg) was administered intravenously (IV) to fasted rats as a solution in 0.9% saline via a bolus injection into the jugular vein (2 mg/mL; 2 mL/kg).

Microsomes

To determine the qualitative metabolic profile, 30 μM of Compound 1 was incubated aerobically with rat, dog, monkey, or human liver microsomes (1 mg/mL). The incubations were performed in phosphate buffer at pH 7.4, 37° C., with the reaction initiated by the addition of 13-NADPH, GSH and/or UDPGA (1, 5 and 2 mM mM final concentration, respectively). The reaction was terminated by the addition of 3 times incubation volume of acetonitrile after 60 minutes. The sample was centrifuged and the supernatant was transferred, nitrogen blow dried and reconstituted in 50% acetonitrile in water for LC/MS analysis.

Hepatocytes

Rat, dog, monkey, or human hepatocytes were thawed according to the supplier's instructions. Cells were counted using the Trypan Blue method, and then diluted to $1 \times 10^6$ viable cells/ml with KB medium. Compound 1 was tested at 30 μM and incubated for up to 2 hours in rat hepatocytes and 4 hours in dog, monkey or human hepatocytes at 37° C. Reactions were terminated with addition of 3 times incubation volume of acetonitrile, centrifuged, and supernatants were transferred, nitrogen blow dried and reconstituted in 50% acetonitrile in water for LC/MS analysis.

Rat Bile Duct Cannulation

Rats with surgically placed bile duct and jugular vein cannula were purchased from Charles River Laboratories and allowed to acclimate for 2 days. Compound 2 was intravenously dosed (2 mg/kg) to three rats as a solution in 0.9% saline (2 mg/mL; 1 mL/kg). Bile samples were collected at time-points 0-2, 2-5 and 5-8, and urine samples were collected at time-points 0-4 and 4-8 hrs post-dose in 8 mL scintillation vials and stored at −40° C. until analysis.

Plasma Extraction of Compound 1

Concentrations of Compound 1 in rat plasma were determined by LC-MS/MS after protein precipitation. Rat plasma (100 μL) was treated with 400 μL of internal standard solution (ISTD, buspirone in acetonitrile containing 1.5% acetic acid) to precipitate proteins. Samples were vortexed and then centrifuged for 10 min at approximately 4,000 rpm (3700×g) at 4° C. (Beckman centrifuge, Brea, Calif.).

Instruments

LC/MS/MS analysis was carried out with a Sciex API-4000Qtrap tandem mass spectrometer (Applied Biosystems/Life Technologies, Carlsbad, Calif.) interfaced to a high-performance liquid chromatography system consisting of an Agilent 1200 series pump (Foster City, Calif.) and a LEAP Technologies PAL autoinjector (Carrboro, N.C.).

LC-MS/MS Procedure

Parent/metabolite analysis was conducted in the positive ion mode (ESI) by multiple reaction monitoring of parent. The mobile phases contained 10 mM ammonium acetate in water with 0.05% formic acid (solvent A) and 10 mM ammonium acetate in 50% acetonitrile/50% methanol with 0.05% formic acid (solvent B). For Compound 1, the flow rate was maintained at 1 mL/min and the total run time was 2.5 min. Analytes were separated on a YMC ODS-AQ column (2.1×150 mm; 3 μm) and eluted with a linear gradient as follows:

1. mobile phase was held for 0.5 min at 5% B,
2. B was increased from 5% to 95% over the next 0.2 min,
3. B was held constant for 1.3 min at 95%, and
4. B was returned to the initial gradient conditions.

GSH adducts were investigated in microsomes, hepatocytes and rat bile using several methods including the neutral loss of pyroglutamate (129 Da) as well as a precursor ion scans of Compound 1 (105 Da, 318 Da and 438 Da).

For metabolite quantitation, the flow rate was maintained at 0.25 mL/min and the total run time was 60 min. Analytes were separated using a linear gradient as follows:

1. mobile phase was held for 5 min at 5% B,
2. B was increased from 5% to 95% over the next 45 min,
3. B was held constant for 5 min at 95%, and
4. B was returned to the initial gradient conditions Results The following metabolites were observed:

TABLE 23

Metabolites of Compound 1

| Metabolite | Structure | Metabolite Description |
| --- | --- | --- |
| M1 | 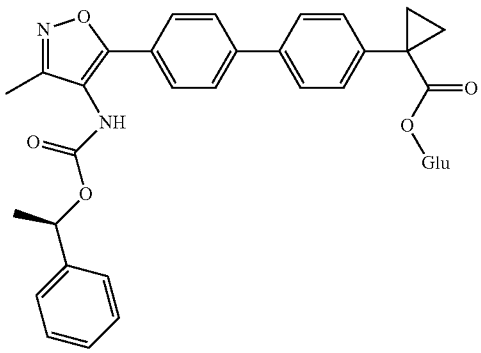 | Glucuronidation of Compound 1 |
| M2 | 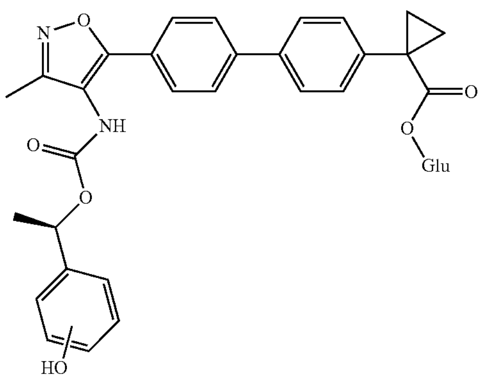 | Glucuronidation of Compound 1 plus oxidation |
| M3 | 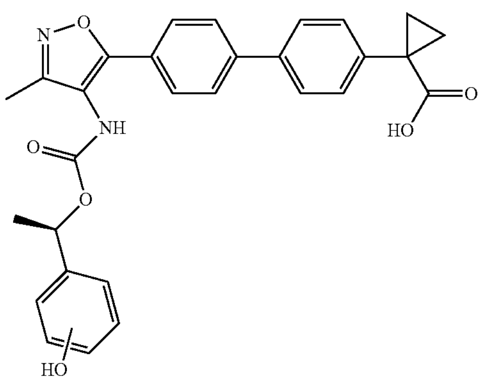 | Oxidation of phenyl ring of benzyl group. |
| M4 | 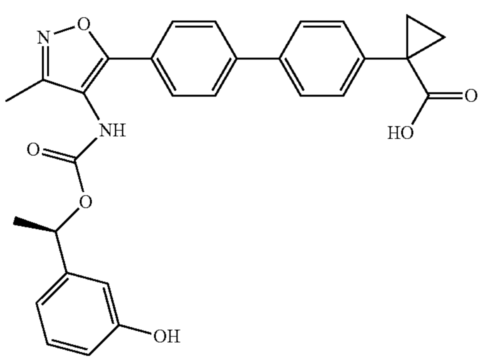 [SMILES: Cc1noc(-c2ccc(-c3ccc(C4(C(=O)O)CC4)cc3)cc2)c1NC(=O)O[C@H](C)c1cccc(O)c1] | Oxidation of phenyl ring of benzyl group. |

TABLE 23-continued

Metabolites of Compound 1

| Metabolite | Structure | Metabolite Description |
|---|---|---|
| M5 | 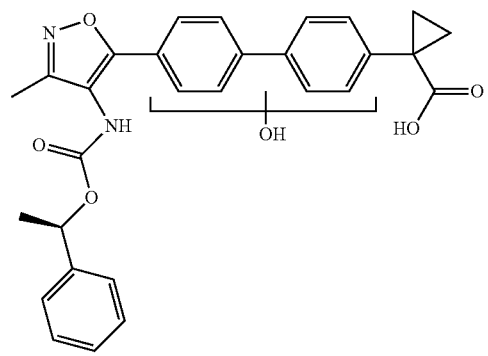 | Oxidation of biphenyl |

Glucuronides, including M1, are (direct and indirect) the major metabolites observed in liver microsomes, hepatocytes and rat bile. Mono-oxidation metabolites on the phenyl ring (M3 and M4) and the biphenyl ring are also observed in rat, dog and human liver microsomes, hepatocytes as well as in rat bile. An oxidated glucuronide (M2) was observed in liver microsomes (rat, dog & human), hepatocytes (dog) and bile (rat). Neither the primary amine (i.e. decarboxylation) nor its secondary metabolites (glycosylation or glucuronidation) are observed in plasma (rat & dog), rat bile or urine. No GSH adduct was observed in the in vitro screening assay, in rat, dog or human hepatocytes, and human microsomes. In vivo, there is neither GSH adduct is observed in rat bile, nor any metabolites in rat urine. In vivo, metabolites M1 and M4 AUC values are at less than 10% of the parent, Compound 1.

Example 31

Pharmacokinetics in Sprague-Dawley Rats

The pharmacokinetics of Compound 1 and Compound 2 was assessed in male and female Sprague-Dawley rats (225-300 g at 10 weeks).

Compound 2 (1 mg/kg) was administered intravenously (IV) to fasted rats (n=3) as a solution in purified water via a bolus injection into the jugular vein (1 mg/mL; 1 mL/kg). Compound 1 (10 mg/kg) was administered orally (PO), to fasted (for at least 12 hours) or non-fasted rats (n=2 or 3) as a solution in 0.5% methylcellulose unless otherwise noted via an oral gavage to the stomach (3.33 mg/mL; 3 mL/kg). Non-fasted animals were fasted for at least 12 hours and then were given food ad libitum for 1 hour prior to dosing. Fasted animals were dosed 1, 10, 30, 100 or 300 mg/kg Compound 1 as a solution in 0.5% methylcellulose via an oral gavage to the stomach (0.69 mg/mL, 10 mg/mL, 33.3 mg/mL or 100 mg/mL) (n=2 or 3 per dose group). In a gastrointestinal study, rats were anesthetized and Compound 1 was administered directly to the duodenum, jejunum or ileum at 1 mg/kg in 0.5% methylcellulose.

Capsules were also administered with Compound 2. Capsules were size 9 gelatin (Torpac, San Diego, Calif.).

TABLE 24

Capsule and Compound 2 weight.

| Capsule # | Capsule Weight (mg) | Compound 2 Weight (mg) |
|---|---|---|
| 1 | 9.86 | 3.21 |
| 2 | 10.53 | 3.05 |
| 3 | 10.2 | 3.18 |
| 4 | 9.38 | 3.06 |

Blood samples (approximately 300 µL total blood) were taken from each rat via the jugular vein cannula at pre-dose, and an initial time of 5 or 15 min and then various time points up to 24 hours post-dose (10-11 samples per animal). Samples were collected on wet ice in tubes containing potassium EDTA. After each blood draw, the cannula was flushed with an equivalent volume of heparinized saline (0.1 mL at 40 units/mL). Plasma samples, prepared by centrifugation of whole blood, were stored frozen (−80° C.) prior to analysis.

All other reagents were of analytical grade.

After intravenous (IV) administration (1 mg/kg), the clearance (5.1 to 5.2 µg·hr/mL) was low for both male and female rats; the volume of distribution was moderate and was approximately two-fold total body water. The half-life was 3.8 and 3.2 hours in males and females, respectively. No significant gender related PK differences were noted after intravenous dosing. In addition, Compound 1 suspension in methylcelluose was dosed as an oral gavage (PO) to fasted male/female animals at doses of 1, 10, 30, 100, and 300 mg/kg. Subsequent to a 1 mg/kg dose, the resulting maximal plasma concentrations were 0.4 and 0.3 µg/mL (Cmax) in male and female rats, respectively. The mean dose adjusted exposure ($AUC_{0-24}$/D) was 2.1 and 1.9 µg·hr/mL in males and females respectively, which resulted in an apparent bioavailability of 63% (male) and 58% (female) for Compound 1. As noted above (IV dosing at 1 mg/kg), no significant gender differences were observed after a PO administration. Upon oral administration at 10 mg/kg to fasted animals, the dose adjusted AUC value $_{(AUC0-24/D)}$ was 2.4 and 2.7 µg·hr/mL in male and female rats, respectively. These data suggest that between PO doses of 1 and 10 mg/kg, Compound 1 exposure is dose proportional when administered as a suspension. However, as the dose was increased to 30, 100 and 300 mg/kg, the resulting exposure increased in a greater than dose proportional manner. Upon oral administration at 1 mg/kg to fed animals, the exposure ($AUC_{0-24}$) was 1.6 and 1.4 µg·hr/mL in male and female rats, respectively. The trend of slightly lower exposure in fed animals vs. fasted was also observed at 10 mg/kg. Two additional studies were completed to assess the oral pharmacokinetics of Compound 2 formulated in capsule form, or as a free acid in suspension. The dose normalized exposure of the free acid, sodium salt and sodium salt in a gelatin capsule (10 mg/kg) was 5.1, 2.4 and 2.1 µg·hr/mL, respectively. Regional absorption of Compound 1 shows good oral bioavailability along the entire gastrointestinal tract.

Example 32

Pharmacokinetics in Male Beagle Dogs

The pharmacokinetics of Compound 1 and Compound 2 was assessed in male Beagle dogs.

Dosing of male Beagle dogs (n=3) was performed. Compound 1 or Compound 2 was dosed intravenously at 2 mg/kg (fasted) and orally (fasted or non-fasted) at 5 mg/kg. In fasted animals, food was withheld a minimum of 12 hours prior to dosing and then returned 4 hours post-dose. Non-fasted animals were allowed to feed 1 hour prior to dosing ad libitum. Compound 2 capsules were given by oral gavage in the fasted state. Plasma samples were collected by Perry Scientific study personnel.

The capsules are noted in Table 25 below. Capsules were size 0 gelatin (Capsugel, Peapack, N.J.). Tablet formulations are noted in Example 24.

TABLE 25

Capsule and Compound 2 weight.

| Capsule # | Capsule Weight (mg) | Compound 2 Weight (mg) |
|---|---|---|
| 1 | 90.64 | 55.24 |
| 2 | 88.41 | 55.31 |
| 3 | 91.55 | 64.91 |
| 4 | 87.57 | 60.26 |

For the clinical drug product oral solution of active agent (1.67 mg/mL), sucralose (0.5% w/w) and cherry flavor (0.5% w/w) is added to the formulation as a sweetener and taste masking agent, respectively to a 0.5% methocel aqueous solution.

Blood samples (approximately 1 mL total blood) were taken from each dog at pre-dose, and an initial time of 5 or 15 min and then various time points up to 24 hours post-dose (10-11 samples per animal). Samples were collected on wet ice in tubes containing potassium EDTA. After each blood draw, the cannula was flushed with an equivalent volume of heparinized saline (0.1 mL at 40 units/mL). Plasma samples, prepared by centrifugation of whole blood, were stored frozen (−80° C.) prior to analysis.

All other reagents were of analytical grade.

After intravenous administration of 2 mg/kg Compound 2, the compound showed a systemic clearance value of 10.5 mL/min/kg, an estimated volume of distribution value of 0.6 L/kg, and a 3.9 hr terminal half-life. Oral administration of 5 mg/kg Compound 2 in the fasted state showed an apparent oral bioavailability of 63%, with a C value of 5.5 µg/mL, while the fed state showed an apparent oral bioavailability of 60%. When Compound 2 was dosed as a capsule form, the AUC decreased 2.5-fold, and had an apparent oral bioavailability of 24%. When Compound 1 was dosed, it had reduced exposure, with an apparent oral bioavailability of 19%. Two different tablet formulations and a human dose solution were also investigated, and each showed similar AUC values and an apparent oral bioavailability of 100, 52 and 57%, respectively. The pharmacokinetic results suggest that Compound 2 has systemic exposure and food has little effect on the absorption in dog.

Example 33

Establishment of a CHO Cell Line Stably Expressing Human $LPA_1$

A 1.1 kb cDNA encoding the human $LPA_1$ receptor was cloned from human lung. Human lung RNA (Clontech Laboratories, Inc. USA) was reverse transcribed using the RETROscript kit (Ambion, Inc.) and the full-length cDNA for human $LPA_1$ was obtained by PCR of the reverse transcription reaction. The nucleotide sequence of the cloned human $LPA_1$ was determined by sequencing and confirmed to be identical to the published human $LPA_1$ sequence (An et al. *Biochem. Biophys. Res. Commun.* 231: 619 (1997). The cDNA was cloned into the pcDNA5/FRT expression plasmid and transfected in CHO cells using lipofectamine 2000 (Invitrogen Corp., USA). Clones stably expressing human $LPA_1$ were selected using hygromycin and identified as cells that show Ca-influx in response to LPA.

Example 34

Generation of Cells Transiently Expressing Human $LPA_2$

A vector containing the human $LPA_2$ receptor cDNA was obtained from the Missouri S&T cDNA Resource Center (www.cdna.org). The full-length cDNA fragment for human $LPA_2$ was obtained by PCR from the vector. The nucleotide sequence of the cloned human $LPA_2$ was determined by sequencing and confirmed to be identical to the published human $LPA_2$ sequence (NCBI accession number NM_004720). The cDNA was cloned into the pcDNA3.1 expression plasmid and transfected into B103 cells (Invitrogen Corp., USA) by seeding cells in a 96-well poly-D-lysine coated plate at 30,000-35,000 cells per well together with 0.2 µl lipofectamine 2000 and 0.2 µg of the $LPA_2$ expression vector. Cells were cultured overnight in complete media before being assayed for LPA-induced Ca-influx.

Example 35

Establishment of a CHO Cell Line Stably Expressing Human $LPA_3$

A vector containing the human $LPA_3$ receptor cDNA was obtained from the Missouri S&T cDNA Resource Center (www.cdna.org). The full-length cDNA fragment for human $LPA_3$ was obtained by PCR from the vector. The nucleotide sequence of the cloned human $LPA_3$ was determined by sequencing and confirmed to be identical to the published human $LPA_3$ sequence (NCBI accession number NM_012152). The cDNA was cloned into the pcDNA5/FRT expression plasmid and transfected in CHO cells using lipofectamine 2000 (Invitrogen Corp., USA). Clones stably expressing human $LPA_3$ were selected using hygromycin and identified as cells that show Ca-influx in response to LPA.

Example 36

LPA1 and LPA3 Calcium Flux Assays

Human $LPA_1$ or $LPA_3$ expressing CHO cells are seeded at 20,000-45,000 cells per well in a 96-well poly-D-lysine coated plate one or two days before the assay. Prior to the assay, the cells are washed once with PBS and then cultured in serum-free media overnight. On the day of the assay, a calcium indicator dye (Calcium 4, Molecular Devices) in assay buffer (HBSS with $Ca^{2+}$ and $Mg^{2+}$ and containing 20 mM Hepes and 0.3% fatty-acid free human serum albumin) is added to each well and incubation continued for 1 hour at 37° C. 10 µl of test compound in 2.5% DMSO are added to the cells and incubation continued at room temperature for 30 minutes. Cells are the stimulated by the addition of 10 nM LPA and intracellular $Ca^{2+}$ measured using the Flexstation 3 (Molecular Devices). $IC_{50}$s are determined using Graphpad prism analysis of drug titration curves.

Example 37

LPA2 Calcium Flux Assay

BT-20 human breast cancer cells are seeded at 25,000-35,000 cells per well in 150 µl complete media on Poly-D-Lysine coated black-wall clear-bottom plates. Following an overnight culture, cells are washed once with PBS then serum starved for 4-6 hours prior to the assay. On the day of the assay, a calcium indicator dye (Calcium 5, Molecular Devices) in assay buffer (HBSS with $Ca^{2+}$ and $Mg^{2+}$ and containing 20 mM Hepes and 0.3% fatty-acid free human serum albumin) is added to each well and incubation continued for 15 minutes at 37° C. 25 µl of test compounds in 2.5% DMSO are added to the cells and incubation continued at 37° C. for 15 minutes. Cells are the stimulated by the addition of 100 nM LPA and intracellular $Ca^{2+}$ measured using the Flexstation 3 (Molecular Devices). $IC_{50}$s are determined using Symyx Assay Explorer analysis of drug titration curves.

Illustrative in vitro biological data is presented in the Table below.

TABLE 26

Calcium Flux $IC_{50}$ Data

| | Ca Flux $IC_{50}$ (µM) | | | | |
|---|---|---|---|---|---|
| | $LPA_1$ | $LPA_2$ | $LPA_3$ | $LPA_4$ | $LPA_5$ |
| Compound 1 | A | C | C | C | C |
| S-enantiomer of Compound 1 | A | ND | C | ND | ND |
| Racemic Compound 1 | A | ND | C | ND | ND |

A = less than 0.2 uM,
B = 0.2-1.0 uM, and
C = greater than 1 uM;
ND = assay not performed

Example 38

LPA1 Chemotaxis Assay

Chemotaxis of the A2058 human melanoma cells was measured using the Neuroprobe ChemoTx® System plates (8 µm pore size, 5.7 mm diameter sites). The filter sites were coated with 0.001% fibronectin (Sigma) in 20 mM Hepes, pH 7.4 and allowed to dry. A2058 cells were serum-starved for 24 hours, then harvested with Cell Stripper and resuspended in DMEM containing 0.1% fatty-acid-free bovine serum albumin (BSA) to a concentration of $1 \times 10^6$/ml. Cells were mixed with an equal volume of test compound (2×) in DMEM containing 0.1% fatty-acid-free BSA and incubated at 37° C. for 15 minutes. LPA (100 nM in DMEM containing 0.1% fatty-acid-free BSA) or vehicle was added to each well of the lower chamber and 50 µl of the cell suspension/test compound mix was applied to the upper portion of the ChemoTx plate. Plates were incubated at 37° C. for three hours and then the cells removed from the upper portion by rinsing with PBS and scraping. The filter was dried then stained with HEMA 3 Staining System (Fisher Scientific). The absorbance of the filter was read at 590 nM and $IC_{50}$s were determined using Symyx Assay Explorer.

Compound 1, inhibited LPA-driven chemotaxis ($IC_{50}$ less than 100 nM) of human A2058 melanoma cells

Example 39

Bleomycin-Induced Lung Fibrosis Model in Mice

Female C57Bl/6 mice (Harlan, 25-30 g) are housed 4 per cage, given free access to food and water and allowed to acclimate for at least 7 days prior to test initiation. After the habituation phase, mice are lightly anesthetized with isoflurane (5% in 100% $O_2$) and administered with bleomycin sulfate (0.01-5 U/kg, Henry Schein) via intratracheal instillation (Cuzzocrea S et al. *Am J Physiol Lung Cell Mol Physiol*. 2007 May; 292(5):L1095-104. Epub 2007 Jan. 12.). Mice are returned to their cages and monitored daily for the duration of the experiment. Test compound or vehicle is delivered po, ip or sc daily. The route and frequency of dosing is based on previously determined pharmacokinetic properties. All animals are sacrificed using inhaled isoflurane 3, 7, 14, 21 or 28 days after bleomycin instillation. Following sacrifice, mice are intubated with a 20 gauge angiocatheter attached to a 1 ml syringe. Lungs are lavaged with saline to obtain bronchoalveolar lavage fluid (BALF) and then removed and fixed in 10% neutral buffered formalin for subsequent histopathological analysis. BALF is centrifuged for 10 min at 800×g to pellet the cells and the cell supernatant removed and frozen at −80° C. for subsequent protein analysis using the DC protein assay kit (Biorad, Hercules, Calif.) and soluble collagen analysis using Sircol (Biocolor Ltd, UK). BALF is analyzed for concentrations of inflammatory, pro-fibrotic and tissue injury biomarkers including transforming growth factor β1, hyaluronic acid, tissue inhibitor of metalloproteinase-1, matrix matelloproteinase-7, connective tissue growth factor and lactate dehydrogenase activity, using commercially available ELISA. The cell pellet is re-suspended in PBS. Total cell counts are then obtained using a Hemavet hematology system (Drew Scientific, Wayne, Pa.) and differential cells counts are determined using Shandon cytospin (Thermo Scientific, Waltham, Mass.). Lung tissue is stained using hematoxylin and eosin (H&E) and trichrome and lung fibrosis is determined by semiquantitative histopathological scoring (Ashcroft T. et al. *J. Clin. Path.* 1988; 41; 4, 467-470) using light microscopy (10× magnification) and quantitative, computer-assisted densitometry of collagen in lung tissue sections using light microscopy. The data are plotted using Graphpad prism and statistical differences between groups determined.

In the acute setting (3 day), Compound 1 significantly reduced total protein and collagen concentrations in broncheoalveolar lavage fluid (BALF). In a 7-day bleomycin model Compound 1 reduced BALF collagen, protein, TGFβ1, MMP-7, hyaluronan, and inflammatory cell influx. In the chronic setting (14 day bleomycin model), Compound 1 decreased total lung collagen when dosed either prophylactically (day 0-day 14) or therapeutically (day 3-day 14).

Example 40

Mouse Carbon Tetrachloride ($CCl_4$)-Induced Liver Fibrosis Model

Female C57BL/6 mice (Harlan, 20-25 g) housed 4/cage are given free access to food and water and allowed to acclimate for at least 7 days prior to test initiation. After the habituation phase, mice receive $CCl_4$ (1.0 ml/kg body weight) diluted in corn oil vehicle (100 μL volume) via i.p. injection twice a week for 8 weeks. (Higazi, A. A. et al., Clin Exp Immunol. 2008 April; 152(1):163-73. Epub 2008 Feb. 14.). Control mice receive an equivalent volume of corn oil vehicle only. Test compound or vehicle is delivered po, ip or sc daily. At the end of the study (8 weeks after first i.p. injection of $CCl_4$), mice are sacrificed using inhaled isoflurane and blood is drawn via cardiac puncture for subsequent analysis of ALT/AST levels. The liver is harvested, and one half of the liver is frozen at −80° C. and the other half is fixed in 10% neutral buffered formalin for histological assessment of liver fibrosis using light microscopy (10× magnification). Liver tissue homogenates are analyzed for collagen levels using Sircol (Biocolor Ltd, UK). Fixed Liver tissue is stained using hematoxylin and eosin (H&E) and trichrome and liver fibrosis is determined by quantitative, computer-assisted densitometry of collagen in liver tissue sections using light microscopy. Plasma and liver tissue lysates are also analyzed for concentrations of inflammatory, pro-fibrotic and tissue injury biomarkers including transforming growth factor β1, hyaluronic acid, tissue inhibitor of metalloproteinase-1, matrix matelloproteinase-7, connective tissue growth factor and lactate dehydrogenase activity, using commercially available ELISA. The resulting data are plotted using Graphpad prism and statistical differences between groups determined.

In this experiment, Compound 1 significantly reduced liver weight increase and collagen deposition in the liver as compared to the untreated group.

Example 41

Mouse Intravenous LPA-Induced Histamine Release

A mouse intravenous LPA-induced histamine release model is utilized to determine the in vivo potency of $LPA_1$ and $LPA_3$ receptor antagonists. Female CD-1 mice (weighing 25-35 grams) are administered compound (i.p., s.c. or p.o.) in a volume of 10 ml/kg 30 minutes to 24 hours prior to intravenous LPA challenge (300 μg/mouse in 0.1% FAF BSA) Immediately following LPA challenge mice are placed into an enclosed Plexiglas chamber and exposed to an isoflurane for a period of 2 minutes. They are removed, decapitated and trunk blood collected into tubes containing EDTA. Blood is then centrifuged at 10,000×g for 10 minutes at 4° C. Histamine concentrations in the plasma are determined by EIA. Drug concentrations in plasma are determined by mass spectrometry. The dose to achieve 50% inhibition of blood histamine release is calculated by non-linear regression (Graphpad Prism) and plotted as the $ED_{50}$. The plasma concentration associated with this dose is plotted as the $EC_{50}$.

Example 42

Mouse Dermal Vascular Leak Assay

Female BALB/c mice (Harlan) weighing 20-25 grams were given free access to standard mouse chow and water and were allowed to acclimate for two weeks prior to study initiation. Compound 1 was prepared in water vehicle at a concentration of 3 mg/ml and delivered by oral gavage at a volume of 10 ml/kg to yield a dose of 30 mg/kg. Three hours following dose, mice were placed into a restraining device and given Evan's blue dye intravenously by tail vein injection (0.2 ml of a 0.5% solution). Mice were then anesthetized using 3% isoflurane anaesthesia to allow for intradermal injection of LPA (30 μg in 20 μl 10.1% fatty acid free BSA). Thirty minutes after LPA injection mice were sacrificed by $CO_2$ inhalation and the skin removed from the challenge site and placed into 2 ml formamide for overnight extraction of Evan's blue dye.

Following extraction, a 150 μl aliquot of formamide for each tissue sample was placed into a 96 well plate and read at 610 nm using a photospectometer. The resulting data (OD units) were plotted using GraphPad Prizm. In this experiment Compound 1 reduced LPA-induced Evan's blue dye leak into the skin.

Example 43

Mouse Model of Bleomycin-Induced Scleroderma

A mouse model of bleomycin-induced scleroderma was used to evaluate the effect of Compound 1 in skin fibrosis. Methods were adapted from (Yamamoto, T et al. The Journal of Investigative Dermatology, 112: 456-462, 1999). Female C57Bl/6 mice were anesthetized with isoflurane (3.0-3.5% in 100% $O_2$) and two areas shaved bilaterally on the lower dorsolateral region. BLM (1-10 mg in 100 μl) prepared in sterile filtered PBS was administered subcutaneously to each shaved region once daily for 5 to 7 days per week for a total of 4 weeks (28 days).

Compound 1 was prepared in water vehicle and delivered orally twice a day on weekdays and once daily on weekends.

On day 28 all animals were sacrificed. The dorsolateral skin removed, trimmed of adherent subcutaneous fat and an 8 mm biopsy punch was used to collect two skin samples from each subject. One sample submerged in 10% neutral buffered formalin and submitted for histological analysis. The second sample was frozen at −80° C. for further processing of collagen content using either Sircol or hydroxyproline methods.

Figure 14:
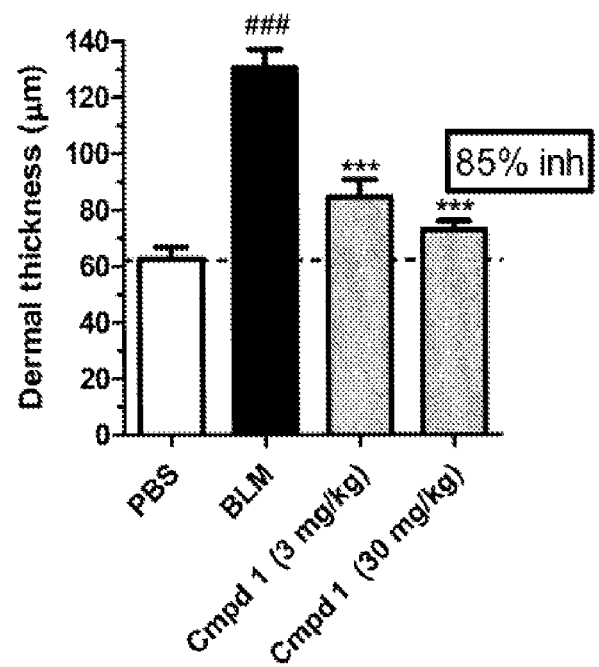
FIG. 14 illustrates the results of Compound 1 on dermal thickness in a mouse model of bleomycin-induced scleroderma.
Figure 15:
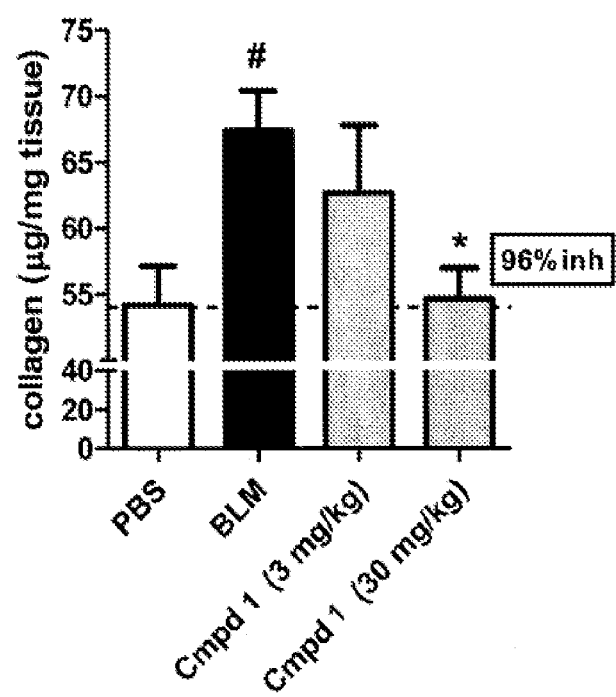
FIG. 15 illustrates the results of Compound 1 on collagen content in a mouse model of bleomycin-induced scleroderma.

FIGS. 14 and 15: Results of assay on mouse model of bleomycin-induced scleroderma using Compound 1. FIG. 14 shows dermal thickness. FIG. 15 shows collagen content. #P<0.05 versus PBS; *P<0.05 versus BLM; ANOVA. Compound 1 reduced both the dermal thickness and collagen content.

Example 44

Mouse Unilateral Ureteral Obstruction Kidney Fibrosis Model

Female C57BL/6 mice (Harlan, 20-25 g) housed 4/cage will be given free access to food and water and allowed to acclimate for at least 7 days prior to test initiation. After the habituation phase, mice undergo unilateral ureteral obstruction (UUO) surgery or sham to left kidney. Briefly, a longitudinal, upper left incision is performed to expose the left kidney. The renal artery is located and 6/0 silk thread is passed between the artery and the ureter. The thread is looped around the ureter and knotted 3 times insuring full ligation of ureter. The kidney is returned to abdomen, the abdominal muscle is sutured and the skin is stapled closed. Mice are returned to their cages and monitored daily for the duration of the experiment. Test compound or vehicle is delivered po, ip or sc daily. The route and frequency of dosing is based on previously determined pharmacokinetic properties. All animals are sacrificed using inhaled isoflurane 4, 8 or 14 days after UUO surgery. Following sacrifice blood is drawn via cardiac puncture, the kidneys are harvested and one half of the kidney is frozen at −80° C. and the other half is fixed in 10% neutral buffered formalin for histological assessment of kidney fibrosis using light microscopy (10× magnification). Kidney tissue homogenates are analyzed for collagen levels using Sircol (Biocolor Ltd, UK). Fixed kidney tissue is also stained using hematoxylin and eosin (H&E) and trichrome and kidney fibrosis is determined by quantitative, computer-assisted densitometry of collagen in liver tissue sections using light microscopy and collagen content in kidney lysate. Plasma and kidney tissue lysates are also analyzed for concentrations of inflammatory, pro-fibrotic and tissue injury biomarkers including transforming growth factor β1, hyaluronic acid, tissue inhibitor of metalloproteinase-1, and plasminogen activator inhibitor-1, using commercially available ELISA. The resulting data are plotted using Graphpad prism and statistical differences between groups determined.

In this experiment, Compound 1 reduced total kidney collagen, collagen Type 1, transforming growth factor β1, hyaluronic acid, tissue inhibitor of metalloproteinase-1 and plasminogen activator inhibitor-1 compared to untreated group.

Example 45

Clinical Trial in Humans with Idiopathic Pulmonary Fibrosis (IPF)

Purpose

The purposes of this study is to assess the efficacy of treatment with Compound 1, or a pharmaceutically acceptable salt thereof (e.g. Compound 2), compared with placebo in patients with idiopathic pulmonary fibrosis (IPF) and to assess the safety of treatment with Compound 1, or a pharmaceutically acceptable salt thereof (e.g. Compound 2), compared with placebo in patients with IPF.

The primary outcome variable is the absolute change in percent predicted forced vital capacity (FVC) from baseline to Week 72.

Secondary outcome measures include: composite outcomes of important IPF-related events; progression-free survival; categorical assessment of absolute change in percent predicted FVC from baseline to Week 72; change in Shortness-of-Breath from baseline to Week 72; change in percent predicted hemoglobin (Hb)-corrected carbon monoxide diffusing capacity (DLco) of the lungs from baseline to Week 72; change in oxygen saturation during the 6 minute walk test (6 MWT) from baseline to Week 72; change in high-resolution computed tomography (HRCT) assessment from baseline to Week 72; change in distance walked in the 6 MWT from baseline to Week 72.

Criteria

Patients eligible for this study include those patients that satisfy the following inclusion criteria: diagnosis of IPF; 40 to 80 years of age; FVC≥50% predicted value; DLco≥35% predicted value; either FVC or DLco≤90% predicted value; no improvement in past year; able to walk 150 meters in 6 minutes and maintain saturation ≥83% while on no more than 6 L/min supplemental oxygen.

Patients are excluded from this study if they satisfy any of the following criteria: unable to undergo pulmonary function testing; evidence of significant obstructive lung disease or airway hyper-responsiveness; in the clinical opinion of the investigator, the patient is expected to need and be eligible for a lung transplant within 72 weeks of randomization; active infection; liver disease; cancer or other medical condition likely to result in death within 2 years; diabetes; pregnancy or lactation; substance abuse; personal or family history of long QT syndrome; other IPF treatment; unable to take study medication; withdrawal from other IPF trials.

Patients are orally dosed with either placebo or an amount of Compound 1, or a pharmaceutically acceptable salt thereof (e.g. Compound 2), (1 mg/day-1000 mg/day). The primary outcome variable will be the absolute change in percent predicted FVC from Baseline to Week 72. Patients will receive blinded study treatment from the time of randomization until the last patient randomized has been treated for 72 weeks. A Data Monitoring Committee (DMC) will periodically review safety and efficacy data to ensure patient safety.

After week 72, patients who meet the Progression of Disease (POD) definition, which is a ≥10% absolute decrease in percent predicted FVC or a ≥15% absolute decrease in percent predicted DLco, will be eligible to receive permitted IPF therapies in addition to their blinded study drug. Permitted IPF therapies include corticosteroids, azathioprine, cyclophosphamide and N-acetyl-cysteine.

The examples and embodiments described herein are illustrative and various modifications or changes suggested to persons skilled in the art are to be included within this disclosure. As will be appreciated by those skilled in the art, the specific components listed in the above examples may be replaced with other functionally equivalent components, e.g., diluents, binders, lubricants, fillers, and the like.

What is claimed is:

1. A crystalline form of sodium salt of 1-{4'-[3-methyl-4-((R)-1-phenyl-ethoxycarbonylamino)-isoxazol-5-yl]-biphe-nyl-4-yl}-cyclopropanecarboxylic acid, wherein said crystalline form is a hydrate for use in a therapeutically effective amount in a pharmaceutical formulation wherein the crystalline form:

(a) has an X-ray powder diffraction (XRPD) pattern derived using Cu Kα radiation with characteristic peaks at 13.2° 2-Theta, 17.2° 2-Theta, 19.3° 2-Theta, 22.4° 2-Theta, and 25.6° 2-Theta;

(b) has an X-ray powder diffraction (XRPD) pattern substantially the same as shown in FIG. 4;

(c) has a DSC or a thermo-gravimetric analysis (TGA) substantially similar to the ones set forth in FIG. 5 and FIG. 6;

(d) has an infrared spectrum substantially similar to the one set forth in FIG. 7;

(e) was obtained from methyl ethyl ketone, acetonitrile, 1,4-dioxane/tert-butyl methyl ether, methyl ethyl ketone (MEK)/tert-butyl methyl, or ethanol/heptane;

(f) unit cell parameters substantially equal to the following at 25°:

| | |
|---|---|
| a(Å) | 13.8714(2) |
| b(Å) | 7.7379(2) |
| c(Å) | 25.5253(5) |
| α° | 90 |
| β° | 103.863(1) |
| γ° | 90 |
| V(Å3) | 2659.96(9) |
| Z | 4 |
| Calculated Density | 1.305 |
| Crystal System | Monoclinic |
| SG | $P2_1$ |
| R1 | 0.0301 |
| Sol. Sites | $1H_2O$ | or (g) combinations thereof.

2. A pharmaceutical composition comprising the crystalline form of claim 1, and at least one inactive ingredient selected from pharmaceutically acceptable carriers, diluents and excipients.

* * * * *